US012370179B1

(12) United States Patent
Malik et al.

(10) Patent No.: US 12,370,179 B1
(45) Date of Patent: *Jul. 29, 2025

(54) METHODS FOR TREATING HYPERTROPHIC CARDIOMYOPATHY

(71) Applicant: Cytokinetics, Inc., South San Francisco, CA (US)

(72) Inventors: Fady Malik, Burlingame, CA (US); Stuart Kupfer, Highland Park, IL (US); Stephen B. Heitner, Portland, OR (US); Laura Ann Robertson, San Francisco, CA (US); Lixin Meng, Cupertino, CA (US); Anna Osmukhina, Portland, OR (US); Qi Wohltman, Belmont, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/909,401

(22) Filed: Oct. 8, 2024

Related U.S. Application Data

(63) Continuation of application No. 17/812,994, filed on Jul. 15, 2022, now abandoned.

(60) Provisional application No. 63/203,333, filed on Jul. 16, 2021, provisional application No. 63/299,753, filed on Jan. 14, 2022, provisional application No. 63/305,609, filed on Feb. 1, 2022, provisional application No. 63/331,197, filed on Apr. 14, 2022, provisional application No. 63/343,975, filed on May 19, 2022.

(51) Int. Cl.
*A61K 31/4245* (2006.01)
*A61P 9/00* (2006.01)

(52) U.S. Cl.
CPC ............ *A61K 31/4245* (2013.01); *A61P 9/00* (2018.01)

(58) Field of Classification Search
CPC ................................................. A61K 31/4245
USPC ......................................................... 514/364
See application file for complete search history.

(56) References Cited

U.S. PATENT DOCUMENTS

| | | | |
|---|---|---|---|
| 10,836,755 B2 | 11/2020 | Chuang et al. | |
| 11,472,796 B2 | 10/2022 | Chuang et al. | |
| 11,932,631 B2 | 3/2024 | Andersen | |
| 12,065,436 B2 | 8/2024 | Chuang | |
| 12,247,024 B2 | 3/2025 | Andersen et al. | |
| 2006/0292695 A1 | 12/2006 | Clark et al. | |
| 2019/0256504 A1 | 8/2019 | Chuang | |
| 2022/0265612 A1 | 8/2022 | Qiao | |
| 2022/0313695 A1 | 10/2022 | Semigran et al. | |
| 2022/0315571 A1 | 10/2022 | Tom et al. | |
| 2023/0045450 A1 | 2/2023 | Andersen et al. | |
| 2023/0058927 A1* | 2/2023 | Malik | A61K 31/4245 |
| 2023/0119665 A1 | 4/2023 | Chuang et al. | |
| 2023/0158027 A1 | 5/2023 | Carlson et al. | |
| 2023/0338378 A1 | 10/2023 | Perera et al. | |
| 2024/0091203 A1 | 3/2024 | Heitner | |
| 2024/0115554 A1 | 4/2024 | Malik | |
| 2024/0150336 A1 | 5/2024 | Andersen | |
| 2025/0059173 A1 | 2/2025 | Chuang et al. | |

FOREIGN PATENT DOCUMENTS

| | | |
|---|---|---|
| CN | 114456163 A | 5/2022 |
| CN | 114516843 A | 5/2022 |
| CN | 114539229 A | 5/2022 |
| CN | 114539257 A | 5/2022 |
| WO | 2019144041 A1 | 7/2019 |
| WO | 2020257609 A1 | 12/2020 |
| WO | 2021011807 A1 | 1/2021 |
| WO | 2021011808 A1 | 1/2021 |
| WO | 2021092598 A1 | 5/2021 |
| WO | 2022047004 A1 | 3/2022 |
| WO | 2022105852 A1 | 5/2022 |
| WO | 2022111498 A1 | 6/2022 |
| WO | 2023288324 A1 | 1/2023 |
| WO | 2023211872 A1 | 11/2023 |
| WO | 2024020468 A1 | 1/2024 |
| WO | 2024031016 A1 | 2/2024 |
| WO | 2024050139 A1 | 3/2024 |
| WO | 2024086821 A1 | 4/2024 |
| WO | 2024097284 A1 | 5/2024 |
| WO | 2024134498 A1 | 6/2024 |
| WO | 2024173765 A1 | 8/2024 |
| WO | 2024179422 A1 | 9/2024 |
| WO | 2024182469 A1 | 9/2024 |
| WO | 2025096779 A2 | 5/2025 |

OTHER PUBLICATIONS

Zhao et al., Frontiers in Pharmacology, 2023, 14:1227470 (Year: 2023).*
Maron et al New England Journal of Medicine, 2024, 390(20), 1849-1861 (Year: 2024).*
Maron et al Supplementary appendix to New England Journal of Medicine, 2024, 390(20), 1849-1861 (Year: 2024).*
Abraham, T. et al. (Jun. 11, 2022). Early Cardiac Structural and Functional Reverse Remodeling in Obstructive Hypertrophic Cardiomyopathy After 10 Weeks of Aficamten Therapy: Analyses From Redwood-HCM, ASE20222, Seattle, Washington 1 page.

(Continued)

*Primary Examiner* — Yevgeny Valenrod
(74) *Attorney, Agent, or Firm* — MORRISON & FOERSTER LLP

(57) ABSTRACT

Methods for treating obstructive hypertrophic cardiomyopathy are described herein. The treatment methods include the administration of a cardiac myosin inhibitor (CK-3773274, also referred to as CK-274 or aficamten) and may include titrating an administered daily dose based on one or more components of an echocardiogram. The daily dose may be increased, maintained, decreased, or terminated, based on the echocardiogram.

21 Claims, 32 Drawing Sheets

(56) References Cited

OTHER PUBLICATIONS

Agarwal, P. et al (Nov. 12, 2020). "Abstract 14963: Accelerometer-measured Activity in Non-obstructive Hypertrophic Cardiomyopathy: Patient-generated Activity Measures Correlate With,and Are Convolutional Neural Network Predictors of, Clinical Parameters in the Maverick-HCM Study," Circulation 142: A1963., 8 pages.
American Heart Association (Date Unknown). "Classes and Stages of Heart Failure," retrieved from https://www.heartorg/en/health-topics/heart-failure/what-is-heart-failure/classes-of-heart-failure, last visited on Nov. 14, 2023, 2 pages.
Anonymous (Apr. 2022). "Camzyos Label," Camzyos, 27 pages.
Anonymous (Apr. 28, 2022). "U.S. Food and Drug Administration Approves Camzyos™ (mavacamten) for the Treatment of Adults With Symptomatic New York Heart Association Class II-III Obstructive Hypertrophic Cardiomyopathy (HCM) to Improve Functional Capacity and Symptoms," Bristol Myers Squibb, 10 pages.
Armstrong, A. (Apr. 2, 2022). "ACC: Bristol Myers Drug Helps Patients Avoid Heart Procedure Amid FDA Countdown," Fierce Biotech 6 pages . . . .
Benavente, K. et al. (Apr. 1, 2024. e-pub. Feb. 27, 2024). "Withdrawal Of Atrioventricular Nodal Blocking Agents in Patients Receiving Mavacamten: A Retrospective Single-Center Experience in A Predominantly Asian-American Cohort," The American Journal of Cardiology Brief Report 216:P63-P65.
Berge, S. et al. (Jan. 1977). "Pharmaceutical Salts," Journal of Pharmaceutical Sciences 66(1):1-19.
Braunwald, E. et al. (Nov. 21, 2023, e-pub. Oct. 7, 2023). "Mavacamten: A First-In-Class Myosin Inhibitor For Obstructive Hypertrophic Cardiomyopathy," European Heart Journal 44(44):4622-4633.
Campbell, S. et al. (Jan. 2024). "Classifying Pathogenicity of TPM1 Variants of Unknown Significance Using In Vitro and In Silico Approaches," Abstract No. 15, HCM Society 2023 Scientific, Journal of Cardiac Failure 30(Sup1):S3, 1 page.
Captur, G. et al. (Nov. 2021). "Maximal Wall Thickness Measurement in Hypertrophic Cardiomyopathy," JACC Cardiovasc. Imaging 14(11):2123-2134.
Chuang, C. et al. (Oct. 4, 2021). "Discovery of Aficamten (CK-274), A Next Generation Cardiac Myosin Inhibitor for the Treatment of Hypertrophic Cardiomyopathy," Journal of Medicinal Chemistry 64(19):14142-14152.
Chuang, G. (Apr. 9, 2021). "Discovery of CK-274: A Novel, Small Molecule, cardiac Myosin Inhibitor for the Treatment of Hypertrophic Cardiomyopathies (HCM)," ACS Spring 2021 National Meeting, 25 pages.
Clinical Data. (2022). "Bristol-Myers Squibb Mavacamten Myokardia ACC 2022," Clinical Data 5 pages.
Clinicaltrials. (version 1, Apr. 19, 2021). "CY 6022 is an Open Label Study to Collect Long-Term Safety and Tolerability Data for Aficamten (CK-3773274) (Redwood-OLE) NCT04848506," Clinical Trials NCT04848506 4 pages.
Clinicaltrials. (version 1, Jan. 11, 2022). "CY 6031 Study Will Evaluate the Effects of Treatment With Aficamten (CK-3773274(Over a 24-Week Period on Cardiopulmonary Exercise Capacity and Health Status in Patients With Symptomatic oHCM (Sequoia-HCM) NCT05186818," Clinical Trials NCT05186818, 5 pages.
Clinicaltrials. (version 1, Jan. 7, 2020). "NCT04219826—Redwood-HCM: Randomized Evaluation of Dosing with CK-3773274 in HCM," XP055964895 Clinical Trials, 9 pages.
Clinicaltrials. (version 1, Mar. 5, 2021). "Safety, Tolerability and Pharmacokinetics Study of CK-3773274, NCT04783766" Clinical Trials NCT04783766, 4 pages.
Clinicaltrials. (version 10, submitted Dec. 23, 2021). "CY 6022 is an Open Label Study to Collect Long-Term Safety and Tolerability Data for Aficamten (CK-3773274) (Redwood-OLE) NCT04848506," Clinical Trials NCT04848506, 3 pages.
Clinicaltrials. (version 5, submitted Sep. 3, 2021). "CY 6022 is an Open Label Study to Collect Long-Term Safety and Tolerability Data for Aficamten (CK-3773274) (Redwood-OLE) NCT04848506," Clinical Trials NCT04848506, 5 pages.
Clinicaltrials. (version 6, Jan. 29, 2020). "A Single and Multiple Ascending Dose Study of CK-3773274 in Healthy Adult Subjects NCT03767855," Clinical Trials NCT03767855, 9 pages.
Clinicialtrials. (version 23, submitted May 4, 2021). "Redwood-HCM: Randomized Evaluation of Dosing With CK-3773274 in HCM (Redwood-HCM, NCT04219826," Clinical Trials NCT04219826, 7 pages.
Clinicialtrials. (Version 25, submitted Mar. 4, 2022). "Redwood-HCM: Randomized Evaluation of Dosing With CK-3773274 in HCM (Redwood-HCM," Clinical Trials NCT04219826, 14 pages.
Coats, C.J. et al. (Jan. 2024). "Exercise Capacity In Patients With Obstructive Hypertrophic Cardiomyopathy," JACC Heart Fail. 12(1):199-215.
Coats, C.J. et al. (Sep. 15, 2015). "Cardiopulmonary Exercise Testing and Prognosis in Hypertrophic Cardiomyopathy," Circ. Heart Fail. 8(6):1022-1031.
Cytokinetics Inc. (Apr. 2, 2022). "Cytokinetics Announces Results From Cohort 3 Of Redwood-HCM Presented At American College Of Cardiology 71st Annual Scientific Session," Cytokinetics Inc. 9 pages.
Cytokinetics Inc. (Dec. 5, 2018). "Cytokinetics Announces Initiation of Phase 1 Clinical Trial of CK-3773274, A Cardiac Myosin Inhibitor," Cytokinetics Inc. 7 pages.
Cytokinetics Inc. (Dec. 9, 2020). "Cytokinetics Announces Progression of Redwood-HCM to Cohort 2," Cytokinetics Inc. 9 pages.
Cytokinetics Inc. (Feb. 1, 2022). "Cytokinetics Announces Positive Topline Results From Cohort 3 of Redwood-HCM," Cytokinetics Inc. 3 pages.
Cytokinetics Inc. (Feb. 23, 2022). "Cytokinetics Announces Start of Sequoia-HCM, A Phase 3 Clinical Trial of Aficamten in Patients With Symptomatic Obstructive Hypertrophic Cardiomyopathy," Cytokinetics Inc. 7 pages.
Cytokinetics Inc. (Jan. 11, 2021). "Cytokinetics Granted Orphan Drug Designation For CL-3773274 For the Treatment Of Hypertrophic Cardiomyopathy," Cytokinetics Inc. 8 pages.
Cytokinetics Inc. (Jan. 13, 2021). "Cytokinetics Announces First Patient Does in Cohort 2 of Redwood-HCM," Cytokinetics Inc. 7 pages.
Cytokinetics Inc. (Jan. 6, 2020). "Cytokinetics Announces Start of Redwood-HCM, A phase 2 Clinical Trail of CK-3773274," Cytokinetics Inc. 8 pages.
Cytokinetics Inc. (Jul. 18, 2022). "Empowering Muscle Empowering Lives. Sarcomere Directed Therapies. PowerPoint Presentation," Cytokinetics Inc. 57 pages.
Cytokinetics Inc. (Jul. 19, 2021). "Cytokinetics. Empowering Muscle Empowering Lives. Sarcomere Directed Therapies," Cytokinetics Inc. 16 pages.
Cytokinetics Inc. (Jul. 21, 2022). "Empowering Muscle Empowering Lives. Sarcomere Directed Therapies. PowerPoint Presentation," Cytokinetics Inc. 57 pages.
Cytokinetics Inc. (Jul. 22, 2022) "Empowering Muscle Empowering Lives. Sarcomere Directed Therapies. PowerPoint Presentation," Cytokinetics 57 pages.
Cytokinetics Inc. (Jun. 13, 2022). "Cytokinetics Announces Additional Data From Redwood-HCM Presented at the American Society of Echocardiography 33rd Annual Scientific Sessions," Cytokinetics Inc. 8 pages.
Cytokinetics Inc. (Mar. 2, 2022). "Cytokinetics Announces Cohort 4 of Redwood-HCM is Open to Enrollment," Cytokinetics Inc. 7 pages.
Cytokinetics Inc. (May 23, 2022). "Cytokinetics Announces Data From Redwood-Hcm Ole And Galactic-Hf Presented As Late Breaking Science Presentations At The European Society Of Cardiology Heart Failure 2022 Congress," Cytokinetics Inc. 11 pages.
Cytokinetics Inc. (May 4, 2021). "Cytokinetics Announces Cohort 3 of Redwood-HCM is Open to Enrollment," Cytokinetics Inc. 8 pages.
Cytokinetics Inc. (May 6, 2021). "Cytokinetics Announces Start of Open-Label Extension Study for Patients Completing Redwood-HCM," Cytokinetics Inc. 7 pages.
Cytokinetics Inc. (Press Release Dec. 27, 2023). "Cytokinetics Announces Positive Results From Sequoia-HCM, the Pivotal Phase

(56) References Cited

OTHER PUBLICATIONS

3 Clinical Trial of Aficamten in Patients With Obstructive Hypertrophic Cardiomyopathy," Cytokinetics Press Release, 3 pages.
Cytokinetics Inc. (Press Release Jan. 6, 2020). "Cytokinetics Announces Start of Redwood-HCM, A Phase 2 Clinical Trial of CK-3773274. Next Generation Cardiac Myosin Inhibitor Advances in Clinical Trail Designed to Assess Effects Using Two-week Dose Titration Schedule," Cytokinetics Press Release, 2 pages.
Cytokinetics Inc. (Sep. 12, 2021). "Cytokinetics Announces Results From Redwood-HCM and Galactic-HF Presented in Late Breaking Clinical Trial Session at the HFSA Annual Scientific Meeting," Cytokinetics Inc. 12 pages.
Cytokinetics Inc. (Sep. 16, 2019). "Cytokinetics Announces Data From Phase 1 Study of CK-3772374 At the HFSA 23rd Annual Scientific Meeting," Cytokinetics Inc. 8 pages.
Desai, M.Y. et al. (2023. e-pub Aug. 28, 2023) "Mavacamten in Patients with Hypertrophic Cardiomyopathy Referred for Septal Reduction: Week 56 Results From The Valor-HCM Randomized Clinical Trial," JAMA Cardiol 8:968-977.
Desai, M.Y. et al. (2024, e-pub. Feb. 13, 2024). "Real-world Experience With Mavacamten in Obstructive Hypertrophic Cardiomyopathy: Observations From a Tertiary Care Center," Prog. Cardiovasc. Dis.:1-7.
Devries, J. H. et al. (Oct. 1, 2023). "The European Medicines Agency Assessment of Mavacamten as Treatment of Symptomatic Obstructive Hypertrophic Cardiomyopathy in Adult Patients," European Heart Journal 44(37):3492-3494.
Dhakal, B. et al. (Mar. 2015). "Mechanisms Of Exercise Intolerance In Heart Failure With Preserved Ejection Fraction: The Role Of Abnormal Peripheral Oxygen Extraction," Circ. Heart Fail. 8(2):286-294, 23 pages.
Dybro, A.M. et al. (Dec. 2021). "Randomized Trials of Metoprolol in Patients with Obstructive Hypertrophic Cardiomyopathy," JACC 78(25): 2502-2517.
Fletcher G. (Jan. 15, 1995). "Exercise Standards: A Statement for Healthcare Professionals From the American Heart Association," Circulation 91(2): pp. 580-615.
Geske J.B. et al. (Jun. 2011). "Variability Of Left Ventricular Outflow Tract Gradient During Cardiac Catheterization In Patients With Hypertrophic Cardiomyopathy," JACC. Cardiovascular Interventions 4(6):704-709.
Ghazal, S.N. (2017. E-pub Aug. 11, 2016). "Valsalva Maneuver in Echocardiography," J. Echocardiogr. 15:1-5.
Green, E. M. et al. (Feb. 5, 2016). "A Small-Molecule Inhibitor of Sarcomere Contractility Suppresses Hypertrophic Cardiomyopathy in Mice," Science 351(6273):617-621, 7 pages.
Grillo, M.P. et al. (2019). "In Vitro and In Vivo Pharmacokinetic Characterization of Mavacamten, A First-In-Class Small Molecule Allosteric Modulator of Beta Cardiac Myosin," Xenobiotica 49(6):718-733.
Haykowsky, M.J. et al. (Jul. 12, 2011). "Determinants of Exercise Intolerance in Elderly Heart Failure Patients With Preserved Ejection Fraction," Journal of the American College of Cardiology 58(3):265-274.
Ho, C. Y. et al. (Jun. 2020). "EMJ 2 Safety and Efficacy of Mavacamten in Patients with Symptomatic Non-Obstructive Hypertrophic Cardiomyopathy: The Maverick-HCM Study," EMJ Cardiology 8 (Suppl 1): 2-4.
Ho, C.Y. et al. (Jun. 2, 2020). "Evaluation of Mavacamten in Symptomatic Patients With Nonobstructive Hypertrophic Cardiomyopathy," Journal of the America College of Cardiology 75(21):2649-2660.
Ho, C.Y. et al. (Jun. 2020). "Methods Paper. Study Design and Rationale of Explorer-HCM. Evaluation of Mavacamten in Adults with Symptomatic Obstructive Hypertrophic Cardiomyopathy," Circ. Heart Fail. 13: e006853:59-67.
International Preliminary Report on Patentability issued on Jan. 16, 2024, for Application No. PCT/US2022/073808, filed on Jul. 15, 2022, 9 pages.
International Search Report mailed on Oct. 30, 2023, for Application No. PCT/US2023/071610, filed on Aug. 3, 2023, 15 pages.
International Search Report mailed on Oct. 6, 2022, for Application No. PCT/US2022/073808, filed on Jul. 15, 2022, 18 pages.
International Search Report mailed on, Oct. 30, 2023, for Application No. PCT/US2023/070533, filed on Jul. 19, 2023, 16 pages.
Ionova, Y. et al. (Jun. 7, 2020). "CYP2C19 Allele Frequencies in Over 2.2 Million Direct-to-Consumer Genetics Research Participants and the Potential Implication for Prescriptions in a Large Health System," Clin. Transl. Sci. 13 (6):1298-1306.
Jacoby, D. et al. (Feb. 21. 2020). "Treatment of Hypertrophic Cardiomyopathy: What Every Cardiologist Needs to Know," American College of Cardiology Foundation, 6 pages.
Lakdawala, N. et al. (Nov. 9, 2023). "Changes In Standard Of Care (SOC) Medication During Long-Term Mavacamten Treatment For Obstructive Hypertrophic Cardiomyopathy (HCM): Results From The Explorer Cohort Of Mava-Long-Term Extension (LTE)," European Heart Journal 44(Supplement_2): 3 pages.
Lewis, G.D. et al. (May 2022, E-pub Mar. 3, 2022). "Developments in Exercise Capacity Assessment in Heart Failure Clinical Trials and the Rationale for the Design of Meteoric-HF," Circ. Heart Fail. 15(5):510-524.
Malik, F.I. et al. (2022). "A Phase 1 Does-Escalation Study of the cardiac Myosin Inhibitor Aficamten Healthy Participants," JACC Basic to Translation Science 7(8):763-775.
Maron, M. (Sep. 12, 2021). "Redwood HCM. Randomized Evaluation of Doing With Aficamten in Obstructive Outflow Disease-HCM," HFSA 2021 Denver Colorado, 18 pages.
Maron, M. S. et al. (Jan. 3-10, 2023). "Phase 2 Study of Aficamten in Patients With Obstructive Hypertrophic Cardiomyopathy," J Am Coll. Cardiol. 81(1):34-45.
Maron, M.S. et al. (Jan. 2024). "Baseline Characteristics of Patients in Sequioa-HCM: A Phase 3 Trial of Aficamten in Obstructive Hypertrophic Cardiomyopathy," Poster, Abstract No. 9, Journal of Cardiac Failure 30(Sup1): S3, 1 page.
Maron, M.S. et al. (May 13, 2024). "Aficamten for Symptomatic Obstructive Hypertrophic Cardiomyopathy," N Engl J Med. 390(20):1849-1861.
Masri, A. et al. (May 23, 2022). "Efficacy and Safety of Aficamten in Patients With Symptomatic Obstructive Hypertrophic Cardiomyopathy," Heart Failure 12 pages.
Morelli, C. et al. (May 6, 2022). Sarcomere Protein Modulation: The New Frontier in Cardiovascular Medicine and Beyond, European Journal of Internal Medicine 102:1-7.
Myokardia, Inc. (May 11, 2020). "Myokarida Announces Primary and All Secondary Endpoints Met in Phase 3 Explorer Clinical Trial of Mavacamten for the Treatment of Obstructive Hypertrophic Cardiomyopathy," Myokardia, Inc. 6 pages.
Nayor, M. et al. (May 2022. E-pub May 4, 2022). "Clinical and Hemodynamic Associations and Prognostic Implications of Ventilatory Efficiency in Patients With Preserved Left Ventricular Systolic Function," Circ. Heart Fail. 13 (5):1-11.
Olivotto, I. et al. (2020, e-pub. Aug. 29, 2020). "Mavacamten for Treatment of Symptomatic Obstructive Hypertrophic Cardiomyopathy (Explorer-HCM): a Randomised, Double-Blind, Placebo-Controlled, Phase 3 Trial," The Lancet 396:759-769.
Ommen, S. et al. (Dec. 22, 2020. E-pub Nov. 20, 2020). "AHA/ACC Guideline for the Diagnosis and Treatment of Patients With Hypertrophic Cardiomyopathy: Executive Summary," Circulation 142(25):e533-e557.
Ostrominski, J.W. et al. (Jul. 2023). "Cardiac Myosin Inhibitors For Managing Obstructive Hypertrophic Cardiomyopathy," JACC Heart Fail.11(7):735-748.
Owens, A. et al. (Jan. 2024). "Cumulative Long Term Efficacy and Safety of Mavacamten Treatment in Nonobstructive Hypertrophic Cardiomyopathy: Updated Interim Analysis from the Maverick Cohort of the MAVA-Long-Term Extension (LTE) Study up to 120 Weeks," Abstract No. 6, HCM Society 2023 Scientific, Journal of Cardiac Failure 32(Sup1), 1 page.
Owens, A. et al. (Nov. 8, 2021). "Abstract 9685: Long-Term Efficacy and Safety of Mavacamten in Patients with Non-

(56) References Cited

OTHER PUBLICATIONS

Obstructive Hypertrophic Cardiomyopathy: Interim Results from the Maverick-LTE Cohort of the MAVA-LTE Study," Circulation 144: A9685, 8 pages.
Owens, A.T. et al. (Apr. 2, 2021). "Efficacy and Safety of Aficamten and Disopyramide Coadministration in Obstructive Hypertrophic Cardiomyopathy: Results from Redwood-HCM Cohort," ACC22 Cytokinetics 1 page.
Owens, A.T. et al. (Mar. 8, 2022). "Efficacy and Safety of Aficamten and Disopyramide Coadministration in Obstructive Hypertrophic Cardiomyopathy: Results From Redwood-HCM Cohort 3," JACC 79(9)(Supp. A):244.
Owens, A.T. et al. (Nov. 11, 2023). "Aficamten For Drug-Refractory Severe Obstructive Hypertrophic Cardiomyopathy In Patients Receiving Disopyramide: Redwood-HCM Cohort 3," J. Card. Fail. 29(11):1576-1582.
Palau, P. et al. (2020). "Beta-blockers Withdrawal In Patients With Heart Failure With Preserved Ejection Fraction And Chronotropic Incompetence: Effect On Functional Capacity Rationale And Study Design Of A Prospective, Randomized, Controlled Trial (The Preserve-HR trial)," Clinical Cardiology 43:423-429.
Prasad, M. Et al. (Nov. 8, 2022). "Abstract 13045: Increased Recognition of Transthyretin Amyloid Cardiomyopathy as a Cause of Heart Failure in Women," Circulation 246: A13045, 1 page.
Prasad, S.B. et al. (May 15, 2021). "Editorial. Quality First in Obstructive Hypertrophic Cardiomyopathy," The Lancet 2 pages.
Rader, F. et al. (Jan. 2024). "Mavacamten Treatment for Symptomatic Obstructive Hypertrophic Cardiomyopathy: Interim Results From the MAVA-LTE Study, Explorer-LTE Cohort," JACC. Heart Fail. 12(1):164-177.
Robertson, L.A. et al. (Sep. 14, 2019). "210. A First in Human Study of the Selective Cardiac Myosin Inhibitor, CK-3773274," Cytokinetics, Inc. 1 page.
Spertus, J.A. et al. (May 15, 2021). "Mavacamten for Treatment of Symptomatic Obstructive Hypertrophic Cardiomyopathy (Explorer-HCM): Health Status Analysis of A Randomized, Double-Blind, Placebo-Controlled, Phase 3 Trial," The Lancet, 9 pages.
US Food and Drug Administration (Apr. 26, 2022). "Camzyos (Mavacamten): Clinical and Statistical Review(s)," last visited Mar. 21, 2024, 153 pages.
US Food and Drug Administration Apr. 28, 2022). "Camzyos (Mavacamten): Risk Assessment and Risk Mitigation Review(s)," last visited on Feb. 23, 2024, 107 pages.
Weyman Young, A. E. (Jul. 1, 2022). "2022 Arthur E. Weyman Young Investigator's Award Competition Finalists," Journal of the American Society of Echocardiography 35(7):e1-e103.
Wheeler, M.T. et al. (Mar. 1, 2023. e-pub Jan. 18, 2023). "Effects of Mavacamten on Measures of Cardiopulmonary Exercise Testing Beyond Peak Oxygen Consumption: A Secondary Analysis of the Explorer-HCM Randomized Trial," JAMA Cardiology 8(3):240-247.
Wilcox, J.E. et al. (2020). "Lessons From Maverick-HCM. The Need for Less Speed," Journal of the American College of Cardiology 75(21):2661-2663.
Zampieri, M. et al. (Jun. 20, 2021). "Pathophysiology and Treatment of Hypertrophic Cardiomyopathy: New Perspectives," Current Heart Failure Reports 18(4):169-179.
Cremin, P. et al. (Oct. 25, 2022). "In Vivo Pharmacokinetic Characterization of CK-3773274, a Novel Cardiac Myosin Inhibitor," American Association of Pharmaceutical Scientists ePoster Library [Online], 1 page.
U.S. Appl. No. 18/916,215, filed Oct. 15, 2024, for Fady Malik et al.
U.S. Appl. No. 18/762,390, filed Jul. 2, 2024, for Chuang Chihyuan et al.
U.S. Appl. No. 19/002,411, filed Dec. 26, 2024, for Fady Malik et al.
Abdelfattah, O.M. et al. (Dec. 2023). "Mavacamten Short-Term Hemodynamic, Functional, and Electrocardiogrames: Initial Real-World Post-Trial Experience," JACC Adv. 2(10):1-4.
Abella, L.M.R. et al. (Mar. 2023, e-pub. Nov. 18, 2022). "Effects Of Omecamtiv Mecarbil And Mavacamten In Isolated Human Atrium," Naunyn-Schmiedebergs Arch Pharmacol. 396(3):499-511.
Abood, Z. et al. (2025, e-pub. Aug. 13, 2024). "Mavacamten In Real-Life Practice: Initial Experience At A Hypertrophic Cardiomyopathy Centre," ESC Heart Failure 12(1):672-676.
Abood, Z. et al. (Aug. 21, 2024). "Mavacamten Safety and Efficacy in a Heart Transplant Patient Exhibiting Obstructive Hypertrophic Cardiomyopathy Phenotype," JACC Case Rep. 29(16):1-5.
Afsar, M.N.A. et al. (Nov. 2024). "Quantification of Sarcoplasmic Reticulum Ca2+ Release in Primary Ventricular Cardiomyocytes," Current Protocols 4(11):1-18.
Aguiar, T. et al. (Aug. 2022, e-pub. Jul. 19, 2022). "Mavacamten, A Novel Revolutionizing Therapy In Hypertrophic Obstructive Cardiomyopathy: A Literature Review," Rev Port Cardiol. 41(8):693-703.
Aimo, A. et al. (2025, e-pub. Nov. 9, 2024). "Diagnosis and Management of Hypertrophic Cardiomyopathy: European vs. American Guidelines," Heart Failure Reviews 30:315-325.
Akhtar, H. et al. (Jul. 7, 2022). "Effects of Renin-Angiotensin-Aldosterone System Inhibition on Left Ventricular Hypertrophy, Diastolic Function, and Functional Status in Patients With Hypertrophic Cardiomyopathy: A Systematic Review," Cureus 14(7):1-10.
Alharbi, T.Y. et al. (Sep. 30, 2024). "Safety and Effectiveness of Mavacamten Use in Hypertrophic Obstructive Cardiomyopathy: A Systematic Review and Meta-Analysis," Cureus 16(9):1-13.
Almansouri, N.E. et al. (2024, e-pub. Aug. 22, 2024). "Efficacy And Safety Of Mavacamten For The Treatment Of Hypertrophic Cardiomyopathy: An Updated Systematic Review And Meta-Analysis Of Randomized Controlled Trials," Ann Med Surg. 86(10):6097-6104.
Alsidawi, S. A et al. (Nov. 2024). "The Impact of Mavacamten Dosing on Wall Thickness Regression: An Insight From Longer Term Follow-up Based on Genetic Profile," American Heart Journal 277:138-141.
Alsulami, K. et al. (Dec. 16, 2020). "Small Molecules Acting on Myofilaments as Treatments for Heart and Skeletal Muscle Diseases," International Journal of Molecular Sciences 21(24):1-30.
Altibi, A. et al. (2023, e-pub. Apr. 27, 2023). "Baseline and Longitudinal Imaging of Hypertrophic Cardiomyopathy in the Era of Emerging Therapeutics," Current Cardiology Reports 25:583-595.
Amesz, J.H. et al. (Jan. 2024, e-pub. Dec. 21, 2023). "Biomechanical Response Of Ultrathin Slices Of Hypertrophic Cardiomyopathy Tissue To Myosin Modulator Mavacamten," Biomedicine & Pharmacotherapy 170:1-8.
Ammirati, E. et al. (Jan. 2024). "Mavacamten: Practical Answers for the Clinician and New Questions From the MAVA-Long-Term Extension Study," JACC 12(1):178-181.
Amr, A. et al. (Jun. 20, 2024). "Assessing the Applicability of Cardiac Myosin Inhibitors for Hypertrophic Cardiomyopathy Management in a Large Single Center Cohort," Rev Cardiovasc Med. 25(6):1-6.
Anderson, R.L. (Aug. 28, 2018, e-pub. Aug. 13, 2018). "Deciphering The Super Relaxed State of Human β-cardiac Myosin And The Mode of Action of Mavacamten From Myosin Molecules to Muscle Fibers," PNAS 115(35):E8143-E8152.
Anonymous (May 13, 2024). "Sequoia-HCM Trial Meets Primary Endpoint In Obstructive Hypertrophic Cardiomyopathy," European Society of Cardiology Press Release, retrieved online from https://www.escardio.org/The-ESC/Press-Office/Press-releases/SEQUOIA-HCM-trial-meets-primary-endpoint-in-obstructive-hypertrophic-cardiomyopathy, 5 pages.
Arefin, A. et al. (Jul. 4, 2023). "Reproducibility Of Drug-Induced Effects On The Contractility Of An Engineered Heart Tissue Derived From Human Pluripotent Stem Cells," Frontiers in Pharmacology 14:1-15.
Argiro, A. et al. (Mar. 1, 2021). "Emerging Medical Treatment for Hypertrophic Cardiomyopathy," J. Clin. Med. 10 (951):1-14.
Asbeutah, A.A.A. et al. (Sep. 2024, e-pub. Apr. 12, 2024). "Novel Therapies for the Treatment of Cardiovascular Disease," Med Clin N Am. 108(5):953-964.

(56) References Cited

OTHER PUBLICATIONS

Auguin, D. et al. (2024, e-pub. Jun. 7, 2024). "Omecamtiv Mecarbil And Mavacamten Target The Same Myosin Pocket Despite Opposite Effects In Heart Contraction," Nature Communications 15(4885):1-14.

Auguin, D. et al. (Nov. 15, 2023). "Omecamtiv Mecarbil and Mavacamten Target The Same Myosin Pocket Despite Antagonistic Effects In Heart Contraction," bioRxiv, 45 pages.

Austin, M.A. et al. (Oct. 2, 2024). "Riding the Waves of Novel Therapies in Hypertrophic Cardiomyopathy," JACC 29(19):1-3.

Awinda, P.O. et al. (Dec. 2020, e-pub. Oct. 21, 2020). "Effects of Mavacamten on Ca(2+) Sensitivity of Contraction as Sarcomere Length Varied in Human Myocardium," Br J Pharmacol. 177(24):5609-5621.

Awinda, P.O. et al. (Feb. 1, 2021, e-pub. Dec. 18, 2020). "Mavacamten Decreases Maximal Force and Ca (2+) Sensitivity in the N47K-Myosin Regulatory Light Chain Mouse Model of Hypertrophic Cardiomyopathy," Am J Physiol Heart Circ Physiol. 320(2):H881-H890.

Becker, F. et al. (2024, e-pub. Oct. 8, 2024). "Real-World Experience In Initiation Of Treatment With The Selective Cardiomyosin Inhibitor Mavacamten In An Outpatient Clinic Cohort During The 12-Week Titration Period," Clinical Research in Cardiology, 7 pages.

Beghini, A. et al. (2025, e-pub. May 28, 2024). "2024 Update in Heart Failure," ESC Heart Failure 12:8-42.

Beinfeld, M. et al. (Mar. 2022). "Mavacamten For Hypertrophic Cardiomyopathy: Effectiveness And Value," J Manage Care Spec Pharm. 28(3):369-375.

Bello, J. et al. (Jan. 2025, e-pub. Aug. 21, 2024). "Mavacamten," StatPearls, 10 pages.

Bertero, E. et al. (2024, e-pub. Jan. 2, 2024). "Real-World Candidacy To Mavacamten In A Contemporary Hypertrophic Obstructive Cardiomyopathy Population," Eur J Heart Fail. 26(1):59-64.

Bhagwan, J.R. et al. (Aug. 2020, e-pub. Jun. 10, 2020). "Isogenic Models of Hypertrophic Cardiomyopathy Unveil Differential Phenotypes and Mechanism-Driven Therapeutics," J. Mol. Cell Cardiol. 145:43-53.

Bishev, D. et al. (2023, e-pub. Jul. 14, 2023). "Efficacy and Safety of Mavacamten in the Treatment of Hypertrophic Cardiomyopathy: A Systematic Review," Heart, Lung, and Circulation 32:1049-1056.

Blair, J.M. et al. (Mar. 1, 2025). "Painful Diplopia Associated With Mavacamten Use: A Case Report," J Neuro-Ophthalmology 45(1):e29-e30.

Bogomolovas, J. et al. (May 2024). "A Therapeutic Leap: How Myosin Inhibitors Moved From Cardiac Interventions To Skeletal Muscle Myopathy Solutions," J Clin Invest. 134(9):1-3.

Butzner, M. et al. (Jan.-Dec. 2024, e-pub. Jul. 1, 2024). "The Prognostic Value of Peak Oxygen Uptake in Obstructive Hypertrophic Cardiomyopathy: A Literature Review to Inform Economic Model Development," J Med Econ. 27(1):817-825.

Capilupi, M.J. et al. (Jan./Feb. 2023). "Mavacamten: A Novel Disease-Specific Treatment for Hypertrophic Cardiomyopathy," Cardiology in Review 31(1):45-51.

Castrichini, M. et al. (Oct. 2024). "Incidence of Newly Recognized Atrial Fibrillation in Patients With Obstructive Hypertrophic Cardiomyopathy Treated with Mavacamten," Heart Rhythm 21(10):2066-2067.

Chakraborti, A. et al. (May 6, 2024). "Myosin-Catalyzed ATP Hydrolysis in the Presence of Disease-Causing Mutations: Mavacamten as a Way to Repair Mechanism," J Phys Chem B. 128:4716-4727.

Chang, P. et al. (Aug. 13, 2024). "Characterization Of Mavacamten Pharmacokinetics In Patients With Hypertrophic Cardiomyopathy To Inform Dose Titration," CPT Pharmacometrics Syst Pharmacol. 13(9):1462-1475.

Chatur, S. et al. (Sep. 2023). "Monitoring Treatment with Cardiac Myosin Inhibitors in Symptomatic Obstructive Hypertrophic Cardiomyopathy," Curr Opin Cardiol. 38(5):424-432.

Chen, L. et al. (2024). "Structure Of Mavacamten-Free Human Cardiac Thick Filaments Within The Sarcomere By Cryoelectron Tomography," Proc Natl Acad Sci. 121(9):1-10.

Chen, M. et al. (Jun. 25, 2023). Aficamten is Associated with Improvements in Cardiac Mechanics in Obstructive Hypertrophic Cardiomyopathy: Results from the Forest-HCM Trial, accessed online at https://cytokinetics.com/wp-content/uploads/2023/10/Chen_2023_ASE_FOREST-HCM-Aficamten-Improvements-in-Cardiac-Mechanics-in-oHCM.pdf on May 21, 2025, 1 page.

Chiang, M. et al. (Nov. 2023). "Drug-Drug Interaction Potential of Mavacamten with Oral Contraceptives: Results from a Clinical Pharmacokinetic Study and a Physiologically Based Pharmacokinetic Model," The Journal of Clinical Pharmacology 63(11):1275-1282.

Chiang, M. et al. (Oct. 2023, e-pub. Aug. 6, 2023). "Physiologically Based Pharmacokinetic Modeling and Simulation of Mavacamten Exposure with Drug-Drug Interactions from CYP Inducers and Inhibitors by CYP2C19 Phenotype," 114(4):922-932.

Chin, A.C. et al. (Jul. 2022). "Myosin Modulators Move Forward with FDA Approval of Mavacamten," Nature Cardiovascular Research 1:595-596.

Chu, S. et al. (Sep. 2, 2021). "Direct Detection Of The Myosin Super-Relaxed State And Interacting-Heads Motif In Solution," J Biol Chem. 297(4):1-7.

Chuang, G. (Apr. 9, 2021). Discovery of CK-274: A Novel, Small Molecule, Cardiac Myosin Inhibitor For The Treatment Of Hypertrophic Cardiomyopathies (HCM), accessed online at https://cytokinetics.com/wp-content/uploads/2021/04/CK-274_ACS-Spring-2021-FINAL.pdf on May 21, 2025, 25 pages.

Chuang, G. (May 8, 2024). Discovery of Aficamten (CK-274): Next-in-class Cardiac myosin inhibitor (CMI) for obstructive Hypertrophic Cardiomyopathy (oHCM), accessed online at https://cytokinetics.com/wp-content/uploads/2024/05/Chuang_2024_DDN_Discovery-of-Aficamten.pdf on May 21, 2025, 20 pages.

Clinicaltrials. (Apr. 12, 2018). "Extension Study of Mavacamten (MYK-461) in Adults With Symptomatic Obstructive Hypertrophic Cardiomyopathy Previously Enrolled in Pioneer" Clinical Trials NCT03496168, accessed online https://clinicaltrials.gov/study/NCT03496168 on May 15, 2025, 16 pages.

Clinicaltrials. (Apr. 16, 2020). "A Study to Evaluate Mavacamten in Adults With Symptomatic Obstructive HCM Who Are Eligible for Septal Reduction Therapy," Clinical Trials NCT04349072, accessed online https://clinicaltrials.gov/study/NCT04349072 on May 15, 2025, 13 pages.

Clinicaltrials. (Apr. 18, 2024). "Colligo-HCM: A Multinational Observational Study of the Real-World Effectiveness of Mavacamten Among Patients With Symptomatic Obstructive Hypertrophic Cardiomyopathy (oHCM)," Clinical Trials NCT06372457 accessed online https://clinicaltrials.gov/study/NCT06372457 on May 15, 2025, 20 pages.

Clinicaltrials. (Apr. 4, 2024). "A Study of EDG-7500 in Adults With Hypertrophic Cardiomyopathy (Cirrus-HCM)" Clinical Trials NCT06347159, accessed online at https://clinicaltrials.gov/study/NCT06347159 on May 15, 2025, 13 pages.

Clinicaltrials. (Aug. 12, 2024). "A Retrospective Cohort Study of Mavacamten Patient Support Program in Canada," Clinical Trials NCT06549608 accessed online https://clinicaltrials.gov/study/NCT06549608 on May 15, 2025, 8 pages.

Clinicaltrials. (Aug. 13, 2024). "Real-world Patient Reported Outcomes Among Patients Treated With Camzyos," Clinical Trials NCT06551129 accessed online https://clinicaltrials.gov/study/NCT06551129 May 15, 2025, 10 pages.

Clinicaltrials. (Aug. 5, 2022). "A Prospective Registry Study to Assess Real-world Patient Characteristics, Treatment Patterns, and Longitudinal Outcomes in Patients Receiving Mavacamten and Other Treatments for Symptomatic Obstructive Hypertrophic Cardiomyopathy (Obstructive-HCM)," Clinical Trials NCT05489705 accessed online https://clinicaltrials.gov/study/NCT05489705 May 15, 2025, 29 sheets.

Clinicaltrials. (Dec. 30, 2021). "A Study to Evaluate the Efficacy and Safety of Mavacamten in Chinese Adults With Symptomatic Obstructive HCM," Clinical Trials NCT05174416, accessed online https://clinicaltrials.gov/study/NCT05174416 on May 15, 2025, 11 pages.

(56) References Cited

OTHER PUBLICATIONS

Clinicaltrials. (Dec. 31, 2014). "Study Evaluating the Safety, Tolerability and Preliminary Pharmacokinetics and Pharmacodynamics of MYK-461" Clinical Trials NCT02329184, accessed online https://clinicaltrials.gov/study/NCT02329184 on May 15, 2025, 8 pages.

Clinicaltrials. (Feb. 12, 2024). "A Study to Evaluate Mavacamten in Adolescents With Symptomatic Obstructive Hypertrophic Cardiomyopathy," Clinical Trials NCT06253221 accessed online https://clinicaltrials.gov/study/NCT06253221 on May 15, 2025, 21 pages.

Clinicaltrials. (Feb. 22, 2018). "A Phase 2 Study of Mavacamten in Adults With Symptomatic Non-Obstructive Hypertrophic Cardiomyopathy (nHCM)" Clinical Trials NCT03442764, accessed online https://clinicaltrials.gov/study/NCT03442764 on May 15, 2025, 13 pages.

Clinicaltrials. (Feb. 5, 2015). "Single Ascending Dose Study of MYK-461 in Healthy Volunteers" Clinical Trials NCT02356289, accessed online at https://clinicaltrials.gov/study/NCT02356289 on May 15, 2025, 7 pages.

Clinicaltrials. (Feb. 9, 2023). "A Study to Evaluate the Effects of Mavacamten in Healthy Participants" Clinical Trials NCT05719805, accessed online https://clinicaltrials.gov/study/NCT05719805 on May 15, 2025, 10 pages.

Clinicaltrials. (Jul. 11, 2023). "Mavacamten Pregnancy Surveillance Program," Clinical Trials NCT05939700 accessed online https://clinicaltrials.gov/study/NCT05939700 May 15, 2025, 7 pages.

Clinicaltrials. (Jul. 22, 2016). "A Phase 2 Open-label Pilot Study Evaluating MYK-461 in Subjects With Symptomatic Hypertrophic Cardiomyopathy and Left Ventricular Outflow Tract Obstruction" Clinical Trials NCT02842242, accessed online https://clinicaltrials.gov/study/NCT02842242 on May 15, 2025, 12 pages.

Clinicaltrials. (Jun. 10, 2022). "A Study of Mavacamten in Obstructive Hypertrophic Cardiomyopathy," Clinical Trials NCT05414175 accessed online https://clinicaltrials.gov/study/NCT05414175 on May 15, 2025, 12 pages.

Clinicaltrials. (Mar. 20, 2018). "Clinical Study to Evaluate Mavacamten (MYK-461) in Adults With Symptomatic Obstructive Hypertrophic Cardiomyopathy," Clinical Trials NCT03470545, accessed online https://clinicaltrials.gov/study/NCT03470545 on May 15, 2025, 18 pages.

Clinicaltrials. (Mar. 29, 2024). "Real-World Effectiveness of Mavacamten in Canada," Clinical Trials NCT06338202 accessed online https://clinicaltrials.gov/study/NCT06338202 on May 15, 2025, 11 pages.

Clinicaltrials. (May 5, 2022). "A Study to Evaluate the Effects on the Single-Dose Drug Levels of Mavacamten in Healthy Participants" Clinical Trials NCT05362045, accessed online https://clinicaltrials.gov/study/NCT05362045 on May 15, 2025, 10 pages.

Clinicaltrials. (Nov. 1, 2023). "A Study to Evaluate Mavacamten Impact on Myocardial Structure in Participants With Symptomatic Obstructive Hypertrophic Cardiomyopathy," Clinical Trials NCT06112743 accessed online https://clinicaltrials.gov/study/NCT06112743 May 15, 2025, 22 pages.

Clinicaltrials. (Nov. 26, 2021). "Study Evaluating the Pharmacokinetics of Mavacamten in Healthy Adult Chinese Subjects" Clinical Trials NCT05135871, accessed online https://clinicaltrials.gov/study/NCT05135871 on May 15, 2025, 13 pages.

Clinicaltrials. (Nov. 27, 2023). "A Study to Assess the Safety of Mavacamten in Korean Patients With Symptomatic Obstructive Hypertrophic Cardiomyopathy," Clinical Trials NCT06146660 accessed online https://clinicaltrials.gov/study/NCT06146660 May 15, 2025, 7 pages.

Clinicaltrials. (Oct. 17, 2022). "A Study of Mavacamten in Non-Obstructive Hypertrophic Cardiomyopathy," Clinical Trials NCT05582395, accessed online https://clinicaltrials.gov/study/NCT05582395 on May 15, 2025, 29 pages.

Clinicaltrials. (Oct. 29, 2018). "A Long-Term Safety Extension Study of Mavacamten in Adults Who Have Completed Maverick-HCM or Explorer-HCM," Clinical Trials NCT03723655, accessed online https://clinicaltrials.gov/study/NCT03723655 on May 15, 2025, 13 pages.

Clinicaltrials. (Sep. 27, 2022). "A Study to Evaluate the Efficacy, Safety, and Tolerability of MYK-224 in Participants With Symptomatic Obstructive Hypertrophic Cardiomyopathy" Clinical Trials NCT05556343, accessed online at https://clinicaltrials.gov/study/NCT05556343 on May 15, 2025, 15 pages.

Clinicaltrials. (Sep. 5, 2023). "Effect of Mavacamten Treatment on Coronary Flow Reserve in oHCM," Clinical Trials NCT06023186 accessed online https://clinicaltrials.gov/study/NCT06023186 May 15, 2025, 9 pages.

Clinicaltrials. (version 1, Jun. 29, 2023). "Study to Evaluate the Effect of Aficamten Administration on QT/QTc Interval" Clinical Trials NCT05924815, accessed online at https://clinicaltrials.gov/study/NCT05924815?tab=history&a=1#version-content-panel on Apr. 28, 2025, 10 pages.

Clinicaltrials. (version 10, Jan. 12, 2022). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=10#version-content-panel on Apr. 28, 2025, 12 pages.

Clinicaltrials. (version 10, Mar. 12, 2024). "Phase 3 Trial to Evaluate the Efficacy and Safety of Aficamten Compared to Placebo in Adults With Symptomatic nHCM (Acacia-HCM)," Clinical Trials NCT06081894, accessed online at https://clinicaltrials.gov/study/NCT06081894?tab=history&a=10#version-content-panel on Apr. 28, 2025, 15 pages.

Clinicaltrials. (version 12, Jul. 6, 2022). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=12#version-content-panel on Apr. 28, 2025, 16 pages.

Clinicaltrials. (version 14, Aug. 2, 2022). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=14#version-content-panel on Apr. 28, 2025, 17 pages.

Clinicaltrials. (version 16, Jun. 22, 2022). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=16#version-content-panel on Apr. 28, 2025, 12 pages.

Clinicaltrials. (version 19, Mar. 18, 2024). "Phase 3 Trial to Evaluate the Efficacy and Safety of Aficamten Compared to Metoprolol Succinate in Adults With Symptomatic oHCM (Maple-HCM)" Clinical Trials NCT05767346, accessed online at https://clinicaltrials.gov/study/NCT05767346?tab=history&a=19#version-content-panel on Apr. 28, 2025, 19 pages.

Clinicaltrials. (version 19, Nov. 8, 2022). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=19#version-content-panel on Apr. 28, 2025, 12 pages.

Clinicaltrials. (version 2, Apr. 27, 2021). "Safety, Tolerability and Pharmacokinetics Study of CK-3773274," Clinical Trials NCT04783766, accessed online at https://clinicaltrials.gov/study/NCT04783766?tab=history&a=2#version-content-panel on Apr. 28, 2025, 10 pages.

Clinicaltrials. (version 2, Mar. 6, 2024). "An Open-Label Study of Aficamten for Chinese Patients With Symptomatic Ohcm," Clinical Trials NCT06116968, accessed online at https://clinicaltrials.gov/study/NCT06116968?tab=history&a=2#version-content-panel on Apr. 28, 2025, 10 pages.

Clinicaltrials. (version 2, May 11, 2021). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=2#version-content-panel on Apr. 28, 2025, 13 pages.

Clinicaltrials. (version 2, Sep. 21, 2023). "Study to Evaluate the Effect of Aficamten Administration on QT/QTc Interval," Clinical

(56) References Cited

OTHER PUBLICATIONS

Trials NCT05924815, accessed online at https://clinicaltrials.gov/study/NCT05924815?tab=history&a=2#version-content-panel on Apr. 28, 2025, 10 pages.
Clinicaltrials. (version 23, May 7, 2021). "Dose-finding Study to Evaluate the Safety, Tolerability, PK, and PD of CK-3773274 in Adults With HCM (Redwood-HCM)," Clinical Trials NCT04219826, accessed online at https://clinicaltrials.gov/study/NCT04219826?tab=history&a=23#version-content-panel on Apr. 28, 2025, 17 pages.
Clinicaltrials. (version 24, Jun. 5, 2023). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=24#version-content-panel on Apr. 28, 2025, 13 pages.
Clinicaltrials. (version 25, Dec. 4, 2024). "Phase 3 Trial to Evaluate the Efficacy and Safety of Aficamten Compared to Placebo in Adults With Symptomatic nHCM (Acacia-HCM)," Clinical Trials NCT06081894, accessed online at https://clinicaltrials.gov/study/NCT06081894?tab=history&a=25#version-content-panel on Apr. 28, 2025, 30 pages.
Clinicaltrials. (version 25, Jul. 3, 2023). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=25#version-content-panel on Apr. 28, 2025, 14 pages.
Clinicaltrials. (version 25, Mar. 21, 2022). "Dose-finding Study to Evaluate the Safety, Tolerability, PK, and PD of CK-3773274 in Adults With HCM (Redwood-HCM)," Clinical Trials NCT04219826, accessed online at https://clinicaltrials.gov/study/NCT04219826?tab=history&a=25#version-content-panel on Apr. 28, 2025, 18 pages.
Clinicaltrials. (version 26, Aug. 1, 2021). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=26#version-content-panel on Apr. 28, 2025, 15 pages.
Clinicaltrials. (version 26, Nov. 7, 2022). "Dose-finding Study to Evaluate the Safety, Tolerability, PK, and PD of CK-3773274 in Adults With HCM (Redwood-HCM)" Clinical Trials NCT04219826, accessed online at https://clinicaltrials.gov/study/NCT04219826?tab=history&a=26#version-content-panel on Apr. 28, 2025, 16 pages.
Clinicaltrials. (version 27, Aug. 1, 2023). "Dose-finding Study to Evaluate the Safety, Tolerability, PK, and PD of CK-3773274 in Adults With HCM (Redwood-HCM)," Clinical Trials NCT04219826, accessed online at https://clinicaltrials.gov/study/NCT04219826?tab=history&a=27#version-content-panel on Apr. 28, 2025, 16 pages.
Clinicaltrials. (version 28, Apr. 14, 2023). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=28#version-content-panel on Apr. 28, 2025, 29 pages.
Clinicaltrials. (version 29, Apr. 26, 2023). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=29#version-content-panel on Apr. 28, 2025, 29 pages.
Clinicaltrials. (version 29, Jan. 10, 2024). "Dose-finding Study to Evaluate the Safety, Tolerability, PK, and PD of CK-3773274 in Adults With HCM (Redwood-HCM)," Clinical Trials NCT04219826, accessed online at https://clinicaltrials.gov/study/NCT04219826?tab=history&a=29#version-content-panel on Apr. 28, 2025, 16 pages.
Clinicaltrials. (version 3, Jul. 17, 2023). "Phase 3 Trial to Evaluate the Efficacy and Safety of Aficamten Compared to Metoprolol Succinate in Adults With Symptomatic oHCM (Maple-HCM)," Clinical Trials NCT05767346, accessed online at https://clinicaltrials.gov/study/NCT05767346?tab=history&a=3#version-content-panel on Apr. 28, 2025, 14 pages.
Clinicaltrials. (version 3, Oct. 8, 2024). "A Study to Evaluate the Effect of Aficamten in Pediatric Patients With Symptomatic Obstructive Hypertrophic Cardiomyopathy (oHCM). (Cedar-HCM)," Clinical Trials NCT06412666, accessed online at https://clinicaltrials.gov/study/NCT06412666?tab=history&a=3#version-content-panel on Apr. 28, 2025, 13 pages.
Clinicaltrials. (version 3, Sep. 17, 2021). "Safety, Tolerability and Pharmacokinetics Study of CK-3773274," Clinical Trials NCT04783766, accessed online at https://clinicaltrials.gov/study/NCT04783766?tab=history&a=3#version-content-panel on Apr. 28, 2025, 10 pages.
Clinicaltrials. (version 30, Feb. 26, 2024). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=30#version-content-panel on Apr. 28, 2025, 16 pages.
Clinicaltrials. (version 30, Jul. 24, 2023). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=30#version-content-panel on Apr. 28, 2025, 22 pages.
Clinicaltrials. (version 32, Jan. 8, 2024). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=32#version-content-panel on Apr. 28, 2025, 22 pages.
Clinicaltrials. (version 33, Dec. 2, 2024). "Aficamten vs Placebo in Adults With Symptomatic Obstructive Hypertrophic Cardiomyopathy (Sequoia-HCM) (Sequoia-HCM)," Clinical Trials NCT05186818, accessed online at https://clinicaltrials.gov/study/NCT05186818?tab=history&a=33#version-content-panel on Apr. 28, 2025, 22 pages.
Clinicaltrials. (version 34, Aug. 12, 2024). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=34#version-content-panel on Apr. 28, 2025, 17 pages.
Clinicaltrials. (version 35, Sep. 20, 2024). "Phase 3 Trial to Evaluate the Efficacy and Safety of Aficamten Compared to Metoprolol Succinate in Adults With Symptomatic oHCM (Maple-HCM)," Clinical Trials NCT05767346, accessed online at https://clinicaltrials.gov/study/NCT05767346?tab=history&a=35#version-content-panel on Apr. 28, 2025, 29 pages.
Clinicaltrials. (version 38, Dec. 4, 2024). "Open-label Extension Study to Evaluate the Long-term Safety and Tolerability of Aficamten in Adults With HCM (Forest-HCM)," Clinical Trials NCT04848506, accessed online at https://clinicaltrials.gov/study/NCT04848506?tab=history&a=38#version-content-panel on Apr. 28, 2025, 18 pages.
Clinicaltrials. (version 4, Oct. 22, 2024). "A Study to Evaluate the Effect of Aficamten in Pediatric Patients With Symptomatic Obstructive Hypertrophic Cardiomyopathy (oHCM). (Cedar-HCM)," Clinical Trials NCT06412666, accessed online at https://clinicaltrials.gov/study/NCT06412666?tab=history&a=4#version-content-panel on Apr. 28, 2025, 13 pages.
Coats, C. et al. (Oct. 1, 2022). Safety, Efficacy, and Quantitative Understanding of Obstruction, Impact of Aficamten in Hypertrophic Cardiomyopathy (Sequoia-HCM) Study Design: A Phase 3 Study, accessed online at https://cytokinetics.com/wp-content/uploads/2022/10/HFSA-2022-SEQUOIA-HCM-poster-23Sep2022_FINAL.pdf on May 21, 2025, 1 page.
Coats, C.J. et al. (Aug. 6, 2024, e-pub. Jul. 26, 2024). "Dosing and Safety Profile of Aficamten in Symptomatic Obstructive Hypertrophic Cardiomyopathy: Results From Sequoia-HCM," Journal of the American Heart Association 13(15):23 pages.
Coats, C.J. et al. (May 13, 2024). Sequoia-HCM: Dosing and Safety Profile of Aficamten in Symptomatic Obstructive Hypertrophic Cardiomyopathy, accessed online at https://cytokinetics.com/wp-content/uploads/2024/05/ESC-HF.24-SEQUOIA-HCM-Dosing-and-Safety_Coats_Final_For-Upload.pdf on May 21, 2025, 16 pages.
Coats, C.J. et al. (May 18, 2025). Effect of Aficamten Treatment on Patients with Hypertrophic Obstructive Cardiomyopathy by Geographical Region, accessed online at https://cytokinetics.com/wp-content/uploads/2025/05/Coats_2025_ESC-HFA_SEQUOIA-HCM-Geographical-Analysis.pdf on May 21, 2025, 11 pages.

(56) References Cited

OTHER PUBLICATIONS

Coats, C.J. et al. (Nov. 7, 2024, e-pub. Sep. 1, 2024). "Cardiac Biomarkers And Effects Of Aficamten In Obstructive Hypertrophic Cardiomyopathy: The Sequoia-HCM Trial," European Heart Journal 45(42):4464-4478.
Coats, C.J. et al. (Sep. 1, 2024). Clinical Application of Biomarkers in Obstructive HCM: Insights from Sequoia-HCM, accessed online at https://cytokinetics.com/wp-content/uploads/2024/09/ESC24-SEQUOIA-Biomarkers-Oral-FINAL.pdf on May 21, 2025, 22 pages.
Cole, C.J. et al. (Apr. 2024, e-pub. Mar. 19, 2024). "Mavacamten: A Novel Agent for Hypertrophic Cardiomyopathy," Clinical Therapeutics 46(4):368-373.
Cremer, P.C. et al. (Dec. 2022, e-pub. Nov. 6, 2022). "Myosin Inhibition and Left Ventricular Diastolic Function in Patients With Obstructive Hypertrophic Cardiomyopathy Referred for Septal Reduction Therapy: Insights From the Valor-HCM Study," Circ Cardiovasc Imaging. 15(12):865-875.
Cresci, S. et al. (Feb. 13, 2024, e-pub. Nov. 14, 2023). "Effect of Mavacamten in Women Compared With Men With Obstructive Hypertrophic Cardiomyopathy: Insights From Explorer-HCM," Circulation 149(7):498-509.
Cui, H. et al. (2024, E-pub. May 28, 2022). "Cardiopulmonary Exercise Test in Patients with Obstructive Hypertrophic Cardiomyopathy," The Journal of Thoracic and Cardiovascular Surgery 167(2):701-710.
Cytokinetics Inc. (Jul. 16, 2024). "Empowering Muscle Empowering Lives." Cytokinetics Inc. 52 pages.
Cytokinetics Inc. (May 16, 2024). "Empowering Muscle Empowering Lives." Cytokinetics Inc. 62 pages.
Cytokinetics Inc. (Nov. 10, 2023). "Empowering Muscle Empowering Lives. Sarcomere Directed Therapies," Cytokinetics Inc. 54 pages.
Cytokinetics Inc. (Sep. 12, 2023). "Empowering Muscle Empowering Lives. Sarcomere Directed Therapies," Cytokinetics Inc. 45 pages.
Cytokinetics, Inc. (Jul. 19, 2021). "Empowering Muscle Empowering Lives," accessed online at https://cytokinetics.com/wp-content/uploads/2021/07/REDWOOD-HCM-Investor-Slides-Updated-071821-For-Website.pdf on May 21, 2025, 16 pages.
Dalo, J.D. et al. (Nov. 21, 2023). "Mavacamten, a First-in-Class Cardiac Myosin Inhibitor for Obstructive Hypertrophic Cardiomyopathy," Annals of Pharmacotherapy 44(44):4622-4633.
Daniels, M.J. et al. (Sep. 7, 2021). "Myosin Modulation in Hypertrophic Cardiomyopathy and Systolic Heart Failure: Getting Inside the Engine," Circulation 144(10):759-762.
Day, S.M et al. (Oct. 1, 2023, e-pub. Aug. 28, 2023). "Long-Term Efficacy and Safety of Mavacamten in Symptomatic Patients With Obstructive Hypertrophic Cardiomyopathy," JAMA Cardiology 8(10):E1.
Day, S.M. et al. (Mar. 1, 2022). "Myosin Modulators: Emerging Approaches For The Treatment of Cardiomyopathies And Heart Failure," J Clin Invest. 132(5):1-11.
Del Franco, A. et al. (Mar. 2024, e-pub. Feb. 27, 2024). "Long-Term Effects of Mavacamten on Electromechanical Dispersion and Deformation in Obstructive Hypertrophic Cardiomyopathy," Circ Heart Fail. 17:281-283.
Del Vecchio, K. et al. (2024, e-pub. Sep. 19, 2024). "How Effective Is Disopyramide In Treating Pediatric Hypertrophic Cardiomyopathy? State Of The Art And Future Directions," Monaldi Arch Chest Dis. 94(3085):8 pages.
Desai, D. et al. (May 30, 2024). "MYBPC3 D389V Variant Induces Hypercontractility in Cardiac Organoids," bioRxiv, 31 pages.
Desai, D.A. et al. (2024, e-pub. Apr. 4, 2024). "Roles of cMyBP-C Phosphorylation On Cardiac Contractile Dysfunction In db/db Mice," J Mol Cell Cardiol Plus 8:1-13.
Desai, M.Y et al. (2023, e-pub. Aug. 22, 2023). "Medical Therapies for Hypertrophic Cardiomyopathy: Current State of the Art," Progress Cardiovasc Disc. 80:32-37.
Desai, M.Y. (Jul. 12, 2024). "Two Cardiac Myosin Inhibitors in the Treatment of Obstructive Hypertrophic Cardiomyopathy," Med. 5(7):655-659.
Desai, M.Y. et al. (2021). "Study Design and Rationale of Valor-HCM: Evaluation of Mavacamten in Adults with Symptomatic Obstructive Hypertrophic Cardiomyopathy Who Are Eligible for Septal Reduction Therapy," American Heart Journal 239:80-89.
Desai, M.Y. et al. (2023, e-pub. Jun. 13, 2023). "Mavacamten, an Alternative to Septal Reduction Therapy for Patients with Hypertrophic Cardiomyopathy," Heart International 17(1):2-4.
Desai, M.Y. et al. (Apr. 1, 2025). "Risk Evaluation And Mitigation Strategy For Mavacamten: An Example Demonstrating Appropriate Safety Oversight," Am J Health Syst Pharm 82(7):e324-e325.
Desai, M.Y. et al. (Aug. 2024). "Right Treatment for the Right Patient: Mavacamten Cannot Fix Everything," JACC Cardiovascular Imaging 17(8):989-993.
Desai, M.Y. et al. (Jan. 2025, e-pub. Nov. 11, 2024). "Mavacamten: Real-World Experience from 22 Months of the Risk Evaluation and Mitigation Strategy (REMS) Program," Circ Heart Fail. 18(1):1-10.
Desai, M.Y. et al. (Jul. 12, 2022). "Myosin Inhibition in Patients with Obstructive Hypertrophic Cardiomyopathy Referred for Septal Reduction Therapy," Journal of the American Cardiology 80(2):95-108.
Desai, M.Y. et al. (Mar. 14, 2023). "Dose-Blinded Myosin Inhibition in Patients With Obstructive Hypertrophic Cardiomyopathy Referred for Septal Reduction Therapy: Outcomes Through 32 Weeks," Circulation 147(11):850-863.
Desai, M.Y. et al. (Mar. 2025, e-pub Sep. 2, 2024). "Mavacamten-Associated Temporal Changes in Left Atrial Function in Obstructive HCM: Insights From the Valor-HCM Trial," JACC Cardiovasc Imaging 18(3):251-262.
Desai, M.Y. et al. (Nov. 18, 2024). "Mavacamten in Patients With Hypertrophic Cardiomyopathy Referred for Septal Reduction: Week 128 Results from Valor-HCM," Circulation:1-13.
Desai, M.Y. et al. (Oct. 2023). "Mavacamten for Obstructive Hypertrophic Cardiomyopathy in China," JAMA Cardiology 8(10):966-967.
Desai, M.Y. et al. (Sep. 10, 2024). "Mavacamten in Obstructive Hypertrophic Cardiomyopathy Patients Referred for Septal Reduction: Health Status Analysis Through Week 56 in Valor-HCM Trial," J Am Coll Cardiol. 84 (11):1041-1045.
Desai, M.Y. et al. (Sep. 2024). "Serial Changes in Ventricular Strain in Symptomatic Obstructive Hypertrophic Cardiomyopathy Treated With Mavacamten: Insights From the Valor-HCM Trial," Circ. Cardiovasc Imaging 17:735-745.
Desai, N. et al. (Jan. 2022). "Projecting the Long-term Clinical Value of Mavacamten for the Treatment of Obstructive Hypertrophic Cardiomyopathy in the United States: An Assessment of Net Health Benefit," Clin Ther. 44 (1):52-66.
Dhingra, L.S. (Feb. 15, 2025, e-pub. Nov. 23, 2024). "A Multicenter Evaluation of the Impact of Therapies on Deep Learning-Based Electrocardiogramtrophic Cardiomyopathy Markers," Am J Cardiol. 237:35-40.
Dominguez, F. et al. (Feb. 2023, e-pub. Jan. 11, 2023) "Mavacamten In Obstructive Hypertrophic Cardiomyopathy—Are Beta-Blockers Blocking Part Of Its Shine?" European Journal Of Heart Failure 25(2):271-273.
Dong, T. et al. (Apr. 8, 2023). "Review of Mavacamten for Obstructive Hypertrophic Cardiomyopathy and Future Directions," Drug Des Devel Ther. 17:1097-1106.
Dong, T. et al. (Jan. 2023, e-pub. Dec. 22, 2022). "An Evaluation of Mavacamten for the Treatment of Symptomatic Obstructive Hypertrophic Cardiomyopathy in Adults," Expert Rev Cardiovasc Ther. 21(1):5-13.
Dong, T. et al. (Sep./Oct. 2023, e-pub. Aug. 14, 2023). "Multimodality Imaging Of Hypertrophic Cardiomyopathy," Prog Cardiovasc Dis. 80:14-24.
Donkervoort, S. et al. (Apr. 3, 2024). "Pathogenic TNNI1 Variants Disrupt Sarcomere Contractility Resulting in Hypo- and Hypercontractile Muscle Disease," Sci Transl Med. 16(741):1-13.

(56) References Cited

OTHER PUBLICATIONS

Dvornikov, A.V. (Mar. 6, 2023, e-pub. Jan. 12, 2023). "Fluorescence Lifetime-Based Assay Reports Structural Changes In Cardiac Muscle Mediated By Effectors Of Contractile Regulation," J. Gen Physiol. 155(3):1-14.
Edelberg, J.M. et al. (2022, e-pub. Apr. 18, 2022). "The Impact of Mavacamten on the Pathophysiology of Hypertrophic Cardiomyopathy: A Narrative Review," Am J. Cardiovasc Drugs 22(5):497-510.
Eiswirth, C. et al. (2024, e-pub. Aug. 15, 2024). "Reflections on Community Experience with Mavacamten," Progress in Cardiovascular Diseases 86:69-72.
Elliot, P.M. (Nov. 2020). "The End Of The Beginning For Drug Therapy In Obstructive Hypertrophic Cardiomyopathy With Explorer-HCM," Cardiovascular Research 116(13):e175-e178.
Farrant, J. P. et al. (2025, e-pub. Oct. 27, 2024). "Considerations for Drug Trials in Hypertrophiccardiomyopathy," ESC Heart Failure 12(2):1095-1112.
Forouzandehmehr, M. et al. (Oct. 31, 2022). "Altered Contractility in Mutation-Specific Hypertrophic Cardiomyopathy: A Mechano-Energetic in Silico Study with Pharmacological Insights," Front Physiol. 13:1-15.
Frye, C. et al. (Jan. 2025). "The Efficacy of Goal-Directed Valsalva to Elicit Clinically Significant Gradients in Patients With Obstructive Hypertrophic Cardiomyopathy Taking Mavacamten Therapy," J Am Soc Echocardiogr. 38 (1):51-52.
Fumagalli, C. et al. (2020, e-pub. Jan. 28, 2020). "Targeted Medical Therapies for Hypertrophic Cardiomyopathy," Current Cardiology Reports 22(10):1-13.
Gaballa, A. et al. (2024, e-pub. May 30, 2024). "Promising Therapies for Adults with Symptomatic Obstructive Hypertrophic Cardiomyopathy: 2023 and Beyond," Expert Opinion on Pharmacotherapy 25(7):915-924.
Garcia-Pavia, P. et al. (Dec. 16, 2024). "Long-Term Effect Of Mavacamten In Obstructive Hypertrophic Cardiomyopathy," Eur Heart J. 45(47):5071-5083.
Garcia-Pavia, P. et al. (Feb. 2025). "Aficamten vs Metoprolol for Obstructive Hypertrophic Cardiomyopathy: Maple-HCM Rationale, Study Design, and Baseline Characteristics," Journal of The American College of Cardiology 13(2):346-357.
Garcia-Pavia, P. et al. (Oct. 7, 2023). A Phase 3 Randomized Controlled Trial Comparing Aficamten Vs Metoprolol In Patients With Symptomatic Hypertrophic Cardiomyopathy And Left Ventricular Outflow Tract Obstruction, accessed online at https://cytokinetics.com/wp-content/uploads/2023/10/HFSA23-MAPLE-HCM-Study-Design-poster_jp16-UPLOAD.pdf on May 21, 2025, 1 page.
George, T. G. et al. (Jun. 9, 2023). "Dystrophic Cardiomyopathy: Role Of The Cardiac Myofilaments," Frontiers in Physiology 14:1-11.
Gill, R. (Sep. 18, 2024). "Advancements in the Diagnosis and Treatment of Hypertrophic Cardiomyopathy: A Comprehensive Review," J Cardiovasc Dev Dis. 11(290):1-17.
Giudicessi, J.R. (Feb. 2024). "Genotype Influences Mavacamten Responsiveness in Obstructive Hypertrophic Cardiomyopathy," Mayo Clin Proc. 99(2):341-343.
Golla, V.M. (2024). "Discerning The Stability Behaviour Of Mavacamten Availing Liquid Chromatography-Mass Spectrometry And Nuclear Magnetic Resonance Spectroscopy: In Silico Toxicity And Mutagenicity Prediction Of Degradation Products," Journal of Mass Spectrometry 59:1-11.
Gollapudi, S.K. et al. (Jan-Jun. 2021, e-pub. Dec. 3, 2020). "Synthetic Thick Filaments: A New Avenue For Better Understanding The Myosin Super-Relaxed State In Healthy, Diseased, And Mavacamten-Treated Cardiac Systems," J Biol Chem. 296:1-14.
Gollapudi, S.K. et al. (Nov. 19, 2021). "Two Classes of Myosin Inhibitors, Para-nitroblebbistatin and Mavacamten, Stabilize β-Cardiac Myosin in Different Structural and Functional States," J Mol Biol. 433(23):167295, 17 pages.
Grillo, M.P. (Sep. 2024, e-pub. Aug. 7, 2024). "Pharmacokinetics, Mass Balance, Tissue Distribution, Metabolism, and Excretion of [14C]Aficamten Following Single Oral Dose Administration to Rats," Xenobiotica 52 (9):670-685.
Guo, G. et al. (Jan. 2024, e-pub. Nov. 8, 2023). "Enhanced Myofilament Calcium Sensitivity Aggravates Abnormal Calcium Handling And Diastolic Dysfunction In Patient-Specific Induced Pluripotent Stem Cell-Derived Cardiomyocytes With MYH7 Mutation," Cell Calcium 117:1-13.
Hajj, A. A. et al. (2023, e-pub. Oct. 13, 2023). "Hypertrophic Cardiomyopathy: Investigational Drugs Inhibiting Myosin And Upcoming Agents," Expert Opinion on Investigational Drugs 32(9):849-853.
Halas, M. et al. (May 2022). "Effects of Sarcomere Activators and Inhibitors Targeting Myosin Cross-Bridges on Ca(2+)-Activation of Mature and Immature Mouse Cardiac Myofilaments," Mol Pharmacol. 101:286-299.
Hameed, I. et al. (Feb. 2023). "Mavacamten: A Door That Has Opened In The Treatment Of Hypertrophic Cardiomyopathy," J Pak Med Assoc. 73(2):446-447.
Hartman, J.J. et al. (Feb. 19, 2020). Characterization of the Cardiac Myosin Inhibitor CK-3773274: a Potential Therapeutic Approach for Hypertrophic Cardiomyopathy, accessed online at https://cytokinetics.com/wp-content/uploads/2020/02/CY008-20CG-BPS20-CK-274-MOA-Encore-Poster_MT16_FINAL_PRESS.pdf on May 21, 2025, 1 page.
Hegde, S. et al. (Nov. 5, 2024, e-pub. Sep. 1, 2024). "Impact of Aficamten on Echocardiographic Cardiac Structure and Function in Symptomatic Obstructive Hypertrophic Cardiomyopathy," Journal of The American College of Cardiology 84(19):1789-1802.
Hegde, S. et al. (Sep. 1, 2024). Impact of Aficamten on Echocardiographic Cardiac Structure and Function in Adults with Symptomatic Obstructive Hypertrophic Cardiomyopathy, accessed online at https://cytokinetics.com/wp-content/uploads/2024/09/ESC24-SEQUOIA-Echo-LBCT-FINAL.pdf on May 21, 2025, 22 pages.
Hegde, S.M. et al. (Dec. 21/28, 2021). "Effect of Mavacamten on Echocardiographic Features in Symptomatic Patients With Obstructive Hypertrophic Cardiomyopathy," J Am Coll Cardiol. 78(25):2518-2532.
Hei, B. et al. (Sep. 17, 2024). "Human Cardiac β-myosin Powerstroke Energetics: Thin Filament, Pi Displacement, And Mutation Effects," Biophysical Journal 123:3133-3142.
Heitner, S.B. (2019, e-pub. Apr. 30, 2019). "Mavacamten Treatment for Obstructive Hypertrophic Cardiomyopathy: A Clinical Trial," Annals of Internal Medicine 170:741-748.
Hwee, D. T. et al. (Jul. 30, 2019). The Cardiac Myosin Inhibitor, CK-3773274, Reduces Contractility in the R403Q Mouse Model of Hypertrophic Cardiomyopathy, accessed online at https://cytokinetics.com/wp-content/uploads/2019/08/CY006-19C-BCVS19-CK274-R403Q-HCM-poster_MT15_FINAL_PRESS.pdf on May 21, 2025, 1 page.
Hwee, D.T. et al. (Jul. 29, 2019). Pharmacologic Characterization of the Cardiac Myosin Inhibitor, CK-3773274: A Potential Therapeutic Approach for Hypertrophic Cardiomyopathy, accessed online at https://cytokinetics.com/wp-content/uploads/2019/08/CY006-19C-BCVS19-CK247-MOA-poster_MT12_FINAL_PRESS.pdf on May 21, 2025, 1 page.
Iavarone, M. et al. (Oct. 2022, e-pub. Sep. 2, 2022). "Medical Treatment of Patients with Hypertrophic Cardiomyopathy: An Overview of Current and Emerging Therapy," Arch Cardiovasc Dis. 115(10):529-537.
Ingelman-Sundberg, M. et al. (2024). "Precision Medicine In Cardiovascular Therapeutics: Evaluating The Role Of Pharmacogenetic Analysis Prior To Drug Treatment," J Intern Med. 295:583-598.
International Preliminary Report on Patentability issued on Dec. 18, 2024, for Application No. PCT/US2023/070533, filed on Jul. 19, 2023, 9 pages.
International Preliminary Report on Patentability issued on Feb. 4, 2025, for PCT Application No. PCT/U2023/071610, filed on Aug. 3, 2023, 8 pages.
International Search Report mailed on Apr. 4, 2025, for Application No. PCT/US2024/061908, filed on Dec. 26, 2024, 16 pages.
Iorga, B. et al. (Jun. 9, 2021). "Why Make a Strong Muscle Weaker?" J Gen Physiol. 153(7):1-4.

(56) References Cited

OTHER PUBLICATIONS

Ismayl, M. et al. (Jan. 2023). "Mavacamten Treatment for Hypertrophic Cardiomyopathy: A Systematic Review and Meta-Analysis of Randomized Controlled Trials," Curr Probl Cardiol. 48:1-16.
Jacoby, D. et al. (Jan. 30, 2021). "Mavacamten For Hypertrophic Obstructive Cardiomyopathy—Authors' Reply," Lancet 397(10272):369-370.
Kaplan, J.L. et al. (Nov. 2023, E-pub. Jul. 4, 2023). "Advancing Treatments for Feline Hypertrophic Cardiomyopathy: The Role of Animal Models and Targeted Therapeutics," Veterinary Clinics of North America: Small Animal Practice 53(6):1293-1308, 34 pages.
Kawana, M. et al. (Sep. 26, 2022). "Hypertrophic Cardiomyopathy: Mutations to Mechanisms to Therapies," Front Physiol 13:1-21.
Kawas, R.F. et al. (Aug. 11, 2017). "A Small-Molecule Modulator of Cardiac Myosin Acts on Multiple Stages of the Myosin Chemomechanical Cycle," J. Biol. Chem. 292(40):16571-16577.
Keam, S.J. (Jul. 2022, e-pub. Jul. 8, 2022). "Mavacamten: First Approval," Drugs 82:1127-1135.
Kearney, A. et al. (May 2021, e-pub. Apr. 12, 2021). "Advances in Clinical Cardiology 2020: A Summary of Key Clinical Trials," Adv Ther. 38(5):2170-2200.
Kelly, C. et al. (Mar. 14, 2024). "Myosin Folding Boosts Solubility In Cardiac Muscle Sarcomeres," JCI Insight 9 (8):1-16.
Khalilimeybodi, A. (2024, Apr. 24, 2024). "Modeling Cardiomyocyte Signaling And Metabolism Predicts Genotype-To-Phenotype Mechanisms In Hypertrophic Cardiomyopathy," Comput Biol Med. 175(108499):1-18.
Kim, D.S. et al. (Aug. 30, 2024). "One-Year Real-World Experience With Mavacamten And Its Physiologic Effects On Obstructive Hypertrophic Cardiomyopathy," Frontiers in Cardiovascular Medicine 11:1-6.
Kitaoka, H. et al. (Jan. 2025, e-pub. Nov. 7, 2024). "Phase 3 Open-Label Study Evaluating the Efficacy and Safety of Mavacamten in Japanese Adults With Obstructive Hypertrophic Cardiomyopathy— The Horizon-HCM Study," Circ J. 89(1):130-138.
Kogut, J. et al. (2020, e-pub. Oct. 6, 2022). "Hypertrophic Cardiomyopathy 2020," Curr Cardiol Rep. 22 (154):1-11.
Lairez, O. et al. (2024, e-pub. Feb. 2, 2024). "Towards Etiological Treatments in Cardiomyopathies," Presse Med 53(1):1-9.
Laitila, J. et al. (Oct. 2024, E-pub. Aug. 31, 2024). "Myosin ATPase Inhibition Fails To Rescue The Metabolically Dysregulated Proteome Of Nebulin-Deficient Muscle," J Physiol. 602(20):5229-5245.
Lancellotti, P. et al. (2023). "New Guidelines On The Diagnostic And Therapeutic Management Of Hypertrophic Cardiomyopathy," Rev Med. Liege 78(11):619-625. (English Abstract Only).
Lancellotti, P. et al. (2024). "Mavacamten (Camzyos®): First Myosin Modulator for Obstructive Hypertrophic Cardiomyopathy Treatment," Rev Med Liege 79(2):120-128. (English Abstract Only).
Lander, B.S. (2021, e-pub. May 25, 2021). "Hypertrophic Cardiomyopathy: Updates Through the Lens of Sports Cardiology," Curr Treat Options Cardiovasc Med. 23(53):20 pages.
Langley, P. (2022). "Concerns with Patient Reported Outcome Measurement and Value Claims for Therapy Response: The Case of Mavacamten and Symptomatic Hypertrophic Cardiomyopathy (SHCM)," Innovations in Pharmacy 13(2):1-7.
Lee, H-J. et al. (Aug. 2022, E-pub. Jun. 30, 2022). "Major Clinical Issues in Hypertrophic Cardiomyopathy," Korean Circ J. 52(8):563-575.
Lee, M.M.Y et al. (Nov. 1, 2024, e-pub. Sep. 4, 2024). "Aficamten and Cardiopulmonary Exercise Test Performance: A Substudy of the Sequoia-HCM Randomized Clinical Trial," JAMA Cardiology 9(11):990-1000.
Lehman, S. L. et al. (Jun. 2022). "Targeting The Sarcomere in Inherited Cardiomyopathies," Nat Rev Cardiol. 19 (6):353-363, 23 pages.
Lekaditi, D. et al. (May 2021). "Myosin Modulators: The New Era of Medical Therapy for Systolic Heart Failure and Hypertrophic Cardiomyopathy," Cardiol Res. 12(3):146-148.

Lewalle, A. et al. (Sep. 17, 2024). "Cardiac Length-Dependent Activation Driven By Force-Dependent Thick-Filament Dynamics," Biophysical Journal 123:2996-3009.
Lewis, G. et al. (May 13, 2024). Sequoia-HCM: Enhancing Exercise Response in Obstructive Hypertrophic Cardiomyopathy, accessed online at https://cytokinetics.com/wp-content/uploads/2024/05/ESC-HF.24-SEQUOIA-HCM-CPET_Lewis_Final_Upload.pdf on May 21, 2025, 12 pages.
Li, M. et al. (Feb. 20, 2023). "Development And Prevention Of Ischemic Contracture ("Stone Heart") In The Pig Heart," Frontiers in Cardiovascular Medicine 10:1-11.
Li, Q. et al. (2023, e-pub. May 6, 2023). "Effects of CYP2C19 Inhibitors On Mavacamten Pharmacokinetics In Rats Based On UPLC-MS/MS," Chem Biol Interact. 380(110531):1-6.
Liang, L. et al. (2024, e-pub. Jul. 31, 2024). "Incidence And Recurrence Of Atrial Fibrillation Among Patients With Obstructive Hypertrophic Cardiomyopathy Treated With Mavacamten: A Single-Center Experience," Clinical Research in Cardiology:5 pages.
Liang, L. et al. (Sep. 2024). "Evolving Strategies for the Management of Obstructive Hypertrophic Cardiomyopathy," J Card Fail. 30(9):1136-1153.
Liao, H-L. et al. (2024). "Evaluation Of Mavacamten In Patients With Hypertrophic Cardiomyopathy," J Cardiovasc Med. 25:1-8.
Litt, M.J. et al. (Apr. 6, 2023). "Familial Hypertrophic Cardiomyopathy: Diagnosis and Management," Vascular Health and Risk Management 19:211-221.
Liu, T. et al. (2023). "Computational Modeling Of Electromechanical Coupling In Human Cardiomyocyte Applied To Study Hypertrophic Cardiomyopathy And Its Drug Response," Comput Methods Programs Biomed. 231(107372):1-28.
Lu, T. (2024). "Bibliometrics Analysis of Studies on Hypertrophic Cardiomyopathy From 2018 to 2022," Acta Academiae Medicinae Sinicae 46(3):377-383. (English Abstract Only).
Ma, W. et al. (Aug. 28, 2023). "Myosin in Autoinhibited Off State(s), Stabilized By Mavacamten, Can Be Recruited Via Inotropic Effectors," bioRxiv, 33 pages.
Ma, W. et al. (Feb. 12, 2024). "Myosin In Autoinhibited Off State(s), Stabilized By Mavacamten, Can Be Recruited In Response To Inotropic Interventions," Proc Natl Acad Sci. 121(8):1-8.
Magavern, E.F. et al. (Oct. 4, 2024). "CYP2C19 Genetic Testing For Mavacamten And Ischaemic Stroke Treatment: What Does The Result Mean For Cardiovascular Prescribers In The UK And Europe?," Eur Heart J Cardiovasc Pharmacother 10(6):481-483.
Magnusson, P. et al. (Aug. 5, 2021). "Mavacamten—New Treatment For Hypertrophic Cardiomyopathy: First Disease-Specific Drug—Expected To Be A Valuable Part Of Treatment In Selected Cases," Lakartidningen 118:21054, 2 pages. (English Abstract Only).
Maharao, N. et al. (Apr. 8, 2025). "Clinical Evaluation of the Effect of Aficamten on QT/QT Interval in Healthy Participants," Clinical and Translational Science 18:1-9.
Maharao, N. et al. (Mar. 29, 2025). Evaluation of Cytochrome P450 2C9, 2C19, and 2D6 Inhibition on the Pharmacokinetics of Aficamten in Healthy Participants, accessed online at https://cytokinetics.com/wp-content/uploads/2025/04/ACC.25_DDI_Poster_FINAL_3.24.25.pdf on May 21, 2025, 1 page.
Maharao, N. et al. (Sep. 8, 2024). Clinical Evaluation of the Effect of Aficamten on QT/QTc Interval in Healthy Participants, accessed online at https://cytokinetics.com/wp-content/uploads/2024/12/Maharao_2024_ACCP_Aficamten-TQT-1.pdf on May 21, 2025, 1 page.
Malhi, J.K. et al. (Jul. 17, 2024). "Mavacamten in Right Ventricular Outflow Tract Obstruction," JACC 29(14):1-6.
Mamidi, R. et al. (Sep. 4, 2018, e-pub. Sep. 1, 2018). "Impact of the Myosin Modulator Mavacamten on Force Generation and Cross-Bridge Behavior in a Murine Model of Hypercontractility," 7(17):e009627, 15 pages.
Margara, F. et al. (Dec. 28, 2022). "Mechanism Based Therapies Enable Personalised Treatment of Hypertrophic Cardiomyopathy," Sci Rep. 12:22501, 17 pages.
Marian, A.J. (May 14, 2021). "Molecular Genetic Basis of Hypertrophic Cardiomyopathy," Circ Res. 128 (10):1533-1553.
Maron, B.J. et al. (May 15, 2021). "Is Regression of Left Ventricular Hypertrophy Really a Good Thing for Patients With Hypertrophic

(56) References Cited

OTHER PUBLICATIONS

Cardiomyopathy?: The Emerging Mavacamten Story," The American Journal of Cardiology 147:145-146.

Maron, B.J. et al. (May 3, 2022). "Future Role of New Negative Inotropic Agents in the Era of Established Surgical Myectomy for Symptomatic Obstructive Hypertrophic Cardiomyopathy," J Am Heart Assoc. 11(9):e024566, 6 pages.

Maron, M.S. (Mar. 23, 2021). "Exploring New and Old Therapies for Obstructive Hypertrophic Cardiomyopathy: Mavacamten in Perspective," Circulation 143(12):1181-1183.

Maron, M.S. et al. (Jan. 2022, e-pub. Jan. 24, 2022). "Is Surgical Myectomy Challenged By Emergence Of Novel Drug Therapy With Mavacamten?" Asian Cardiovasc Thorac Ann. 30(1):11-18.

Maron, M.S. et al. (May 13, 2024). Sequoia-HCM: Aficamten for the Treatment of Symptomatic Obstructive Hypertrophic Cardiomyopathy, accessed online at https://cytokinetics.com/wp-content/uploads/2024/05/ESC-HF.24-SEQUOIA-HCM-Primary-Results_Maron_Final_Upload.pdf on May 21, 2025, 22 pages.

Maron, M.S. et al. (May 17, 2025). "Efficacy of Aficamten in Patients with Obstructive Hypertrophic Cardiomyopathy and Mild Symptoms: Results from the Sequioa-HCM Trial," European Heart Journal, 34 pages.

Maron, M.S. et al. (Nov. 5, 2024, e-pub. Sep. 30, 2024). "Impact of Aficamten on Disease and Symptom Burden in Obstructive Hypertrophic Cardiomyopathy: Results From Sequoia-HCM," Journal of The American College of Cardiology 84(19):1821-1831.

Maron, M.S. et al. (Oct. 6, 2023). Baseline Characteristics of Patients in Sequoia-HCM: A Phase 3 Trial of Aficamten in Obstructive Hypertrophic Cardiomyopathy, accessed online at https://cytokinetics.com/wp-content/uploads/2023/10/CYTK-18787-HCMS23-SEQUOIA-HCM-Baseline-Characteristics.pdf on May 21, 2025, 1 page.

Maron, M.S. et al. (Sep. 30, 2024). Impact of Aficamten on Disease and Symptom Burden in Obstructive Hypertrophic Cardiomyopathy: Results From Sequoia-HCM, accessed online at https://cytokinetics.com/wp-content/uploads/2024/09/Maron_2024_HFSA_SEQUOIA-HCM-Global-Efficacy.pdf on May 21, 2025, 15 pages.

Masri, A, et al. (Oct. 7, 2023). A Phase 3, Multicenter, Randomized, Double-blind Trial To Evaluate The Efficacy And Safety Of Aficamten Compared To Placebo In Adults With Symptomatic Non-obstructive Hypertrophic Cardiomyopathy, accessed online at https://cytokinetics.com/wp-content/uploads/2023/10/Masri_HFSA23-ACACIA-HCM-Trial_poster_dk10-UPLOAD.pdf on May 21, 2025, 1 page.

Masri, A. (May 9, 2022). "Cardiac Myosin Inhibitors as a Novel Treatment Option for Obstructive Hypertrophic Cardiomyopathy: Addressing the Core of the Matter," J Am Heart Assoc. 11(9):e024656, 8 pages.

Masri, A. et al. (2025, e-pub. Apr. 2, 2025). "Concomitant Aficamten and Disopyramide in Symptomatic Obstructive Hypertrophic Cardiomyopathy," JACC:1-14.

Masri, A. et al. (Apr. 2024, e-pub. Apr. 9, 2024). "Long-Term Safety and Efficacy of Mavacamten in Symptomatic Obstructive Hypertrophic Cardiomyopathy: Interim Results of the Pioneer-OLE Study," J Am Heart Assoc. 13(8): e030607, 11 pages.

Masri, A. et al. (Jan. 2025, e-pub. Nov. 11, 2024). "Stop Dreaming: Mavacamten REMS Data Are Here," Circ Heart Fail. 18:11-13.

Masri, A. et al. (Jan. 25, 2024). Effect of Aficamten on Structure and Function in Patients with Obstructive Hypertrophic Cardiomyopathy: The Forest-HCM CMR Sub-study, accessed online at https://cytokinetics.com/wp-content/uploads/2024/01/FOREST-HCM-MRI-Data-Rapid-Fire_FINAL_1.25.24. pdf on May 21, 2025, 8 pages.

Masri, A. et al. (Mar. 30, 2025). Effect of Aficamten Treatment for Up to 72 Weeks on Cardiac Structure and Function in Patients with Obstructive Hypertrophic Cardiomyopathy: The Sequoia-HCM and Forest-HCM CMR Sub-studies, accessed online at https://cytokinetics.com/wp-content/uploads/2025/04/2025-SEQUOIA-FOREST-HCM-MRI-poster_3.21.25-_SS131.07_v4.3.pdf on May 21, 2025, 1 page.

Masri, A. et al. (Mar. 31, 2025). Concomitant Aficamten and Disopyramide in Patients with Symptomatic Obstructive Hypertrophic Cardiomyopathy, accessed online at https://cytokinetics.com/wp-content/uploads/2025/04/ACC25-FOREST-HCM-Disopyramide_Oral-Presentation_FINAL_3.26.25.pdf on May 21, 2025, 14 pages.

Masri, A. et al. (Mar. 4, 2023). Aficamten in Patients with Symptomatic Non-Obstructive Hypertrophic Cardiomyopathy (Redwood-HCM Cohort 4), accessed online at https://cytokinetics.com/wp-content/uploads/2023/03/Masri-ACC23-REDWOOD-HCM-C4-UPLOAD-REVISED-6_MARCH_2023.pdf on May 21, 2025, 1 page.

Masri, A. et al. (Mar. 7, 2023). "Aficamten In Patients With Symptomatic Non-Obstructive Hypertrophic Cardiomyopathy (Redwood-HCM Cohort 4)", Journal Of The American College Of Cardiology 81(8):609.

Masri, A. et al. (May 20, 2023). Evaluation of Aficamten in Patients with Symptomatic Non-obstructive Hypertrophic Cardiomyopathy: Redwood HCM Cohort 4, accessed online at https://cytokinetics.com/wp-content/uploads/2023/05/REDWOOD-HCM-Cohort-4_ESC-HFA-LBCT_052023_Final.pdf on May 21, 2025, 14 pages.

Masri, A. et al. (May 2015). "Predictors Of Long-Term Outcomes In Patients With Hypertrophic Cardiomyopathy Undergoing Cardiopulmonary Stress Testing And Echocardiography," Am Heart J. 169(5):684-692.

Masri, A. et al. (Nov. 17, 2024). Efficacy and Safety of Aficamten in Patients Guideline—Eligible for Septal Reduction Therapy in the Forest-HCM Trial, accessed online at https://cytokinetics.com/wp-content/uploads/2024/11/Masri_2024_AHA_FOREST-HCM-SRT.pdf on May 21, 2025, 11 pages.

Masri, A. et al. (Nov. 2024, e-pub. Mar. 15, 2024). "Efficacy and Safety of Aficamten in Symptomatic Non-Obstructive Hypertrophic Cardiomyopathy: Results From the Redwood-HCM Trial, Cohort 4," Journal of Cardiac Failure 30(11):1439-1448.

Masri, A. et al. (Nov. 5, 2024). "Standard-of-Care Medication Withdrawal in Patients With Obstructive Hypertrophic Cardiomyopathy Receiving Aficamten in Forest-HCM," Journal of The American College of Cardiology 84(19):1839-1849.

Masri, A. et al. (Nov. 5, 2024, e-pub. Sep. 1, 2024). "Effect of Aficamten on Cardiac Structure and Function in Obstructive Hypertrophic Cardiomyopathy: Sequoia-HCM CMR Substudy," Journal of The American College of Cardiology 84(19):1806-1817.

Masri, A. et al. (Oct. 1, 2022). Efficacy and Safety of Aficamten in Patients with Symptomatic Obstructive Hypertrophic Cardiomyopathy: Interim Results from the Randomized Evaluation of Dosing with CK-3773274 in Hypertrophic Cardiomyopathy (Redwood-HCM) Open-Label Extension Study, accessed online at https://cytokinetics.com/wp-content/uploads/2022/10/HFSA22-REDWOOD-HCM-OLE-poster_9Sept_FINAL.pdf on May 21, 2025, 1 page.

Masri, A. et al. (Sep. 1, 2024). Aficamten in Patients with Obstructive Hypertrophic Cardiomyopathy: An Integrated Safety Analysis, accessed online at https://cytokinetics.com/wp-content/uploads/2024/09/ESC24-FOREST-Integrated-Safety-FINAL.pdf on May 21, 2025, 14 pages.

Masri, A. et al. (Sep. 1, 2024). Effect of Aficamten on Cardiac Structure and Function in Patients with Obstructive Hypertrophic Cardiomyopathy: The Sequoia-HCM CMR Trial, accessed online at https://cytokinetics.com/wp-content/uploads/2024/09/ESC24_SEQUOIA-CMR-LBCT-FINAL.pdf on May 21, 2025, 14 pages.

Masri, A. et al. (Sep. 1, 2024). Safety and Outcomes of Standard of Care Medications Withdrawal in Patients with Obstructive Hypertrophic Cardiomyopathy Treated with Aficamten in Forest-HCM Trial, accessed online at https://cytokinetics.com/wp-content/uploads/2024/09/ESC24-FOREST-HCM-SoC-Withdrawal-FNAL.pdf on May 21, 2025, 17 pages.

Masri, A. et al. (Sep. 2024, e-pub. Jul. 18, 2024). "Safety and Efficacy of Aficamten in Patients With Non-obstructive Hypertrophic Cardiomyopathy: A 36-week Analysis From Forest-HCM," European Journal of Heart Failure 26:1993-1998.

Masri, A. et al. (Sep. 30, 2022). Withdrawal of Background Standard of Care Medical Therapy in Patients with Obstructive Hypertrophic Cardiomyopathy Treated with Aficamten in Redwood HCM OLE, accessed online at https://cytokinetics.com/wp-content/uploads/2022/09/BTW_HCM-Med-Society_9.29.2022_FINAL.pdf on May 21, 2025, 16 pages.

(56) References Cited

OTHER PUBLICATIONS

Massera, D. et al. (Oct. 2024). "Unmasking Obstruction in Hypertrophic Cardiomyopathy With Postprandial Resting and Treadmill Stress Echocardiography," J Am Soc Echocardiogr 37:971-980.

Mathai, S. et al. (Nov. 15, 2022). "Left Ventricular Outflow Tract Obstruction In Hypertrophic Cardiomyopathy And The Impact Of Mavacamten," Ther Adv Chronic Dis. 13:1-11.

Maurizi, N. et al. (Aug. 26, 2024). "Accelerated Hypertension Following Mavacamten Introduction In Severe Obstructive Hypertrophic Cardiomyopathy With Hypertension: A Case Report," Eur Heart J Case Rep. 8(9):1-5.

Mavacamten (Camzyos). (Jun. 2023). "CADTH Reimbursement Review: Therapeutic Area: Obstructive Hypertrophic Cardiomyopathy," Canadian Journal of Health Technologies 3(6):176 pages.

Mavacamten (Camzyos). (May 2023). "CADTH Reimbursement Recommendations: Indication: For The Treatment of Symptomatic Obstructive Hypertrophic Cardiomyopathy of New York Heart Association Class II to III in Adult Patients," Canadian Journal of Health Technologies 3(5):21 pages.

Mazur, M. et al. (2024, e-pub. Jul. 11, 2024). "Hypertrophic Cardiomyopathy: From Medical Treatment to Advanced Heart Failure Therapies," Current Cardiology Reports 26:985-994.

McGurk, K.A. et al. (Jun. 4, 2024). "Pharmacogenetic Influences Over Mavacamten Pharmacokinetics: Considerations for the Treatment of Individuals With Hypertrophic Cardiomyopathy," Circulation 149(23):1786-1788, 5 pages.

Mehra, N. et al. (Oct. 2023, e-pub. Nov. 7, 2023). "Obstructive Hypertrophic Cardiomyopathy: A Review Of New Therapies," Future Cardiol. 19(13):661-670.

Memon, A. et al. (2023, e-pub. Sep. 19, 2023). "Efficacy And Safety Of Mavacamten In Treatment Of Hypertrophic Cardiomyopathy: A Systematic Review And Meta-Analysis," Future Science OA 9(10):13 pages.

Memon, A.A.Q. et al. (Apr. 5, 2024). "Mavacamten: A Review of a Novel Therapeutic Approach for Hypertrophic Cardiomyopathy," Cardiovasc Hematol Agents Med Chem. 23(2):77-86, 10 pages.

Merali, S. et al. (2024, e-pub. Jun. 26, 2024). "Effect of Activated Charcoal on Mavacamten Pharmacokinetics in Healthy Participants," Am J Cardiovasc Drugs 24(4):569-575.

Merali, S. et al. (Sep. 2024, E-pub. May 2, 2024). "Recommendation Of Mavacamten Posology By Model-Based Analyses In Adults With Obstructive Hypertrophic Cardiomyopathy," CPT Pharmacometrics Syst Pharmacol. 13 (9):1448-1461.

Mi, K. et al. (Aug. 14, 2023). "Comparing The Efficacy And Safety Of Medications In Adults With Hypertrophic Cardiomyopathy: A Systematic Review And Network Meta-Analysis," Front Cardiovasc Med.10:1-9.

Mohran, S. et al. (Dec. 14, 2023). "The Biochemically Defined Super Relaxed State Of Myosin—A Paradox," J Biol Chem. 300(1):1-12.

Monte, E. et al. (May 14, 2024). "Personalized Transcriptome Signatures In A Cardiomyopathy Stem Cell Biobank," bioRxiv, 29 pages.

Mozzini, C. et al. (Sep. 2023, e-pub. May 26, 2023). "The Heart Failure Knights," Curr Probl Cardiol. 48 (9):1-14.

Mobius-Winkler, M.N. et al. (2024). "The Diagnosis and Treatment of Hypertrophic Cardiomyopathy," Dtsch Arztebl Int. 121(24):805-811.

Nag, S. (Feb. 10, 2021). "To Lie or Not To Lie: Super-relaxing With Myosins," eLife 10:e63703, 21 pages.

Nag, S. et al. (Jul. 28, 2023). "Mavacamten, A Precision Medicine For Hypertrophiccardiomyopathy: From A Motor Protein To Patients," Science Advances 9:1-18.

Nassif, M. et al. (Aug. 2022). "Validation of the Kansas City Cardiomyopathy Questionnaire in Symptomatic Obstructive Hypertrophic Cardiomyopathy," JACC Heart Fail. 10(8):531-539.

Nelson, S. et al. (Sep. 15, 2020, e-pub. Aug. 15, 2020). "Imaging ATP Consumption in Resting Skeletal Muscle: One Molecule at a Time," Biophysical Journal 119(6):1050-1055.

Newlands, C. et al. (Nov. 17, 2024). Modifiability of Post-Exercise Oxygen Uptake Recovery Patterns: A Substudy of the Sequoia-HCM Randomized Trial, accessed online at https://cytokinetics.com/wp-content/uploads/2024/11/AHA24_VO2-Recovery_MDP_Final.pdf on May 21, 2025, 9 pages.

O'Malley, P.A. (May-Jun. 2024). "Mavacamten (Camzyos) First-in-Class Small-Molecule Myosin Inhibitor for Treatment of Obstructive Hypertrophic Cardiomyopathy," Clin Nurse Spec. 38(3):119-121.

Oldach, M.S. et al. (Nov. 16, 2020). Pharmacodynamic Effects of a Single Dose of CK-3773274 in Cats with Hypertrophic Cardiomyopathy, accessed online at https://cytokinetics.com/wp-content/uploads/2020/11/Poster_AHA_2020_CK-274-Cats-HCM_Oldach.pdf on May 21, 2025, 1 page.

Olivotto, I. et al. (May 17, 2025). Efficacy and Safety of Aficamten in Patients with Obstructive Hypertrophic Cardiomyopathy and Mild Symptoms, accessed online at https://cytokinetics.com/wp-content/uploads/2025/05/Olivotto_2025_ESC-HFA_SEQUOIA-HCM-Mild-Symptoms.pdf on May 21, 2025, 12 pages.

Ottaviani, A. et al. (Sep. 1, 2023). "Revisiting Diagnosis and Treatment of Hypertrophic Cardiomyopathy: Current Practice and Novel Perspectives," Journal of Clinical Medicine 12(5710):1-32.

Owens A.T. et al. (Apr. 2, 2022). Redwood-HCM Cohort 3: Evidence for Clinical Efficacy of Aficamten in Patients with Obstructive HCM and HF Symptoms Refractory to Maximal Medical Therapy, Including Disopyramide, accessed online at https://cytokinetics.com/wp-content/uploads/2022/04/ACC-1005-17-REDWOOD-Cohort-3-Poster-Final.pdf on May 21, 2025, 1 page.

Owens, A.T. (Sep. 3, 2024, e-pub. Aug. 29, 2024). "Mavacamten for Obstructive Hypertrophic Cardiomyopathy: Rationale for Clinically Guided Dose Titration to Optimize Individual Response," J Am Heart Assoc. 13(17):e033767, 14 pages.

Owens, A.T. et al. (Sep. 27, 2024). Global Remodeling Changes with Aficamten in Patients with Obstructive Hypertrophic Cardiomyopathy: An Analysis of the Sequoia-HCM Trial, accessed online at https://cytokinetics.com/wp-content/uploads/2024/09/HCMS24-SEQUOIA-HCM-Global-Remodeling-LB-Oral_27SEPT2024.pdf on May 21, 2025, 14 pages.

Packard, E. et al. (Dec. 2022, E-Pub. Oct. 15, 2022). "Contemporary Therapies and Future Directions in the Management of Hypertrophic Cardiomyopathy," Cardiol Ther. 11(4):491-507.

Palandri, C. et al. (Jun. 2022, e-pub. Jun. 13, 2022). "Pharmacological Management of Hypertrophic Cardiomyopathy: From Bench to Bedside," Drugs 82(8):889-912.

Papadakis, M. et al. (Sep. 12, 2020, e-pub. Aug. 29, 2020). "Mavacamten: Treatment Aspirations In Hypertrophic Cardiomyopathy," The Lancet 396:736-737.

Papp, Z. (Aug. 2022). "Moderating the Myosin Motor to Treat Hypertrophic Cardiomyopathy," JACC Basic Transl Sci. 7(8):776-778.

Pardon, G. et al. (2024, e-pub. Jun. 26, 2024). "Tracking Single hiPSC-Derived Cardiomyocyte Contractile Function Using CONTRAX An Efficient Pipeline For Traction Force Measurement," Nature Communications 15(5427):1-19.

Parodi, A. et al. (Jun.-Jul. 2024, e-pub. May 7, 2024). "Target Population For A Selective Cardiac Myosin Inhibitor In Hypertrophic Obstructive Cardiomyopathy: Real-Life Estimation From The French Register Of Hypertrophic Cardiomyopathy (REMY)," Arch Cardiovasc Dis. 117(6-7):427-432.

Patel, J. et al. (Oct. 25, 2023). "Aficamten—A Second in Class Cardiac Myosin Inhibitor for Hypertrophic Cardiomyopathy," Cardiol Rev:1-4.

Patil, D. et al. (Nov. 2023, e-pub. Sep. 5, 2023). "Novel Therapeutic Avenues for Hypertrophic Cardiomyopathy," Am J Cardiovasc Drugs 23(6):623-640.

Perera, V. et al. (Dec. 2023, E-pub Sep. 28, 2023). "Effects of Omeprazole and Verapamil on the Pharmacokinetics, Safety, and Tolerability of Mavacamten: Two Drug-Drug Interaction Studies in Healthy Participants," Clin Pharmacol Drug Dev. 12(12):1241-1251.

(56) References Cited

OTHER PUBLICATIONS

Pilagov, M. (Jan. 2, 2023, e-pub. Nov. 17, 2022). "Single-Molecule Imaging Reveals How Mavacamten And PKA Modulate ATP Turnover In Skeletal Muscle Myofibrils," Journal of General Physiology 155(1):1-11, 16 pages.

Pugsley, M.K. et al. (2025, e-pub. Mar. 20, 2025). "A Characterization of the Nonclinical Pharmacology and Toxicology of Aficamten, a Reversible Allosteric Inhibitor of Cardiac Myosin," Int J. Toxicology:1-24.

Pysz, P. et al. (2021, e-pub. Jul. 9, 2021). "Mavacamten—A New Disease-Specific Option For Pharmacological Treatment Of Symptomatic Patients With Hypertrophic Cardiomyopathy," Kardiol Pol. 79(9):949-954.

Quintana, E. et al. (Jan. 30, 2021). "Mavacamten For Hypertrophic Obstructive Cardiomyopathy," Lancet 397 (10272):369-370.

Rabiee Rad, M. et al. (Jan. 12, 2023). "Safety And Efficacy Of Mavacamten For Treatment Of Hypertrophic Cardiomyopathy: A Systematic Review And Meta-Analysis Of Randomized Clinical Trials," Egypt Heart J. 75(4):1-7.

Rabiee Rad, M. et al. (Sep. 2023). "Novel Treatments of Hypertrophic Cardiomyopathy in GDMT for Heart Failure: A State-of-art Review," Current Problems in Cardiology 48(9):1-22.

Ramonfaur, D. (Aug. 2024, e-pub. Jul. 31, 2024). "Eighteen-Month Real-World Experience Using Mavacamten for Treatment of Obstructive Hypertrophic Cardiomyopathy in a Racially Diverse Population," J Am Heart Assoc. 13 (15):e034069, 12 pages.

Rangwala, H.S. et al. (Dec. 2, 2023). "Analyzing Safety And Effectiveness Of Mavacamten In Comparison With Placebo For Managing Hypertrophic Cardiomyopathy: A Systemic Review And Meta-Analysis," Egypt Heart J. 75 (99):1-10.

Rao Gajula, S.N. et al. (Jun. 2023, e-pub. May 31, 2023). "Effect Of Chronopharmacology And Food On In Vivo Pharmacokinetic Profile Of Mavacamten," Bioanalysis 15(12):695-706.

Rao, S.J. et al. (2023, e-pub. Jan. 10, 2023). "Multi-Modality Management Of Hypertrophic Cardiomyopathy," Hospital Practice 51(1):2-11.

Rapezzi, C. (2021). "Explorer-HCM: Mavacamten For The Treatment Of Symptomatic Obstructive Hypertrophic Cardiomyopathy," G. Ital Cardiol. 22(2):30-32, 4 pages. (English Machine Translation of Abstract Only).

Rehan, S. et al. (Jul.-Aug. 2024, e-pub. Mar. 12, 2024). "Effects of Mavacamten Concomitant With Beta-Blockers on Patients With Hypertrophic Cardiomyopathy: A Meta-Analysis of Randomized Controlled Trials," Am J Ther. 31(4):e491-e494.

Reyes, K.L.R. et al. (Dec. 21, 2022, e-Pub. Oct. 5, 2022). "Mavacamten: A First-in-class Oral Modulator of Cardiac Myosin for the Treatment of Symptomatic Hypertrophic Obstructive Cardiomyopathy," Heart International 16 (2):91-98.

Reza, N. (Nov. 5, 2024). "Trusting the True Experts Through Patient-Reported Health Status in Hypertrophic Cardiomyopathy," J Am Coll Cardiol. 84(19):1786-1788.

Reza, N. et al. (Jun. 2024). "Real-World Experience and 36-Week Outcomes of Patients With Symptomatic Obstructive Hypertrophic Cardiomyopathy Treated With Mavacamten," JACC 12(6):1123-1125.

Robinson, P. et al. (Jul. 2023, e-pub. Apr. 29, 2023). "Comparing The Effects Of Chemical Ca(2+) Dyes And R-GECO On Contractility And Ca(2+) Transients In Adult And Human iPSC Cardiomyocytes," Journal of Molecular and Cellular Cardiology 180:44-57.

Roehl, K. et al. (May 2024). "Effect of Mavacamten on Hypertrophic Cardiomyopathy Patients With Left Ventricular Outflow Tract Obstruction Provoked Only Postexercise or With Amyl Nitrite," Journal of the American Society of Echocardiography 37(5):566-568, 9 Pages.

Rohde, J.A. (Aug. 7, 2018, e-pub. Jul. 17, 2018). "Mavacamten Stabilizes An Autoinhibited State Of Two-Headed Cardiac Myosin," PNAS 115(32):E7486-E7494.

Rosenzveig, A. et al. (May-Aug. 2023, e-pub. Jun. 4, 2023). "Current And Emerging Pharmacotherapy For The Management Of Hypertrophic Cardiomyopathy," Expert Opinion on Pharmacotherapy 24(12):1349-1360.

Rupert, C. et al. (Nov. 11, 2023). Acute Treatment With Aficamten Rescues Contractile Function in a Myopod® Engineered Heart Tissue Model of Hypertrophic Cardiomyopathy, accessed online at https://cytokinetics.com/wp-content/uploads/2023/11/AHA-SS-2023_Propria-Cytokinetics-Poster_FINAL.pdf on May 21, 2025, 1 page.

Saberi S, et al. (Mar. 4, 2023). Long-Term Efficacy and Safety of Aficamten in Patients with Symptomatic Obstructive Hypertrophic Cardiomyopathy, accessed online at https://cytokinetics.com/wp-content/uploads/2023/03/ACC23-FOREST-HCM-Poster-FINAL-V2.pdf on May 21, 2025, 1 page.

Saberi, S. et al. (Apr. 5, 2024). Efficacy and Safety of Aficamten in the First Cohort of Patients With Symptomatic Obstructive Hypertrophic Cardiomyopathy Completing 48-Week Follow-up: Findings From Forest-HCM, accessed online at https://cytokinetics.com/wp-content/uploads/2024/04/Saberi_2024_ACC_FOREST-HCM-48-Week-Efficacy-and-Safety.pdf on May 21, 2025, 1 page.

Saberi, S. et al. (Feb. 9, 2021). "Mavacamten Favorably Impacts Cardiac Structure in Obstructive Hypertrophic Cardiomyopathy," Circulation 143(6):606-608.

Saberi, S. et al. (Oct. 2, 2022). Improvement in KCCQ Scores in Patients with Obstructive Hypertrophic Cardiomyopathy Treated with Aficamten in the Redwood HCM OLE Study, accessed online at https://cytokinetics.com/wp-content/uploads/2022/10/REDWOOD-HCM-OLE-HFSA-KCCQ_09202022_FINAL.pdf on May 21, 2025, 21 pages.

Sakellaropoulos, S.G. et al. (Aug. 2023, e-pub. Jul. 12, 2023). "Hypertrophic Cardiomyopathy: A Cardiovascular Challenge Becoming a Contemporary Treatable Disease," Cardiol Res. 14(4):243-249.

Sarkar, S.S. et al. (Jun. 26, 2022). Aficamten, a Selective Small-Molecule Cardiac Myosin Inhibitor for the Potential Treatment of Hypertrophic Cardiomyopathy, accessed online at https://cytokinetics.com/wp-content/uploads/2022/08/Cyto-GRC22-HCM-Aficamten-Pre-Clin-poster.pdf on May 21, 2025, 1 page.

Savage, P. et al. (2022, e-pub Apr. 28, 2022). "Advances in Clinical Cardiology 2021: A Summary of Key Clinical Trials," Adv Ther. 39:2398-2437.

Sawan, M.A. et al. (Jan. 3, 2024). "A Systematic Review Of Present And Future Pharmaco-Structural Therapies For Hypertrophic Cardiomyopathy," Clin Cardiol. 47:1-15.

Scellini, B. et al. (Jul. 5, 2021). "Mavacamten Has A Differential Impact On Force Generation In Myofibrils From Rabbit Psoas And Human Cardiac Muscle," J Gen Physiol. 153(7):1-14.

Schenk, A. et al. (May 2023). "Mavacamten—A Targeted Therapy for Hypertrophic Cardiomyopathy," J Cardiovasc Pharmacol. 81(5):317-326.

Scholtz, S. et al. (Oct. 19, 2023). "Alcohol Septal Ablation or Mavacamten for Obstructive Hypertrophic Cardiomyopathy," Journal of Clinical Medicine 12(6628):1-17.

Schulze, C. et al. (Nov. 18, 2024). Changes in EQ-5D-5L with Aficamten in Obstructive Hypertrophic Cardiomyopathy (oHCM): the Sequoia-HCM Trial, accessed online at https://cytokinetics.com/wp-content/uploads/2024/11/CYTK-24760-1-AHA24-EQ-5D-5L-poster-Print-and-Ship_jp01-UPLOAD.pdf on May 21, 2025, 1 page.

Sebastian, S.A. (2023, e-pub. Aug. 1, 2023). "Aficamten: A Breakthrough Therapy for Symptomatic Obstructive Hypertrophic Cardiomyopathy," Am J Cardiovasc Drugs 23:519-532.

Seo, K. et al. (Nov. 21, 2023, e-pub. Oct. 18, 2023). "Improved Cardiac Performance and Decreased Arrhythmia in Hypertrophic Cardiomyopathy With Non-B-Blocking R-Enantiomer Carvedilol," Circulation 148 (21):1691-1704.

Sewanan, L.R. et al. (Jan. 15, 2021). "Mavacamten Preserves Length-Dependent Contractility and Improves Diastolic Function in Human Engineered Heart Tissue," Am J Physiol Heart Circ Physiol 320(3):H1112-H1123.

Sewanan, L.R. et al. (Jul. 28, 2021). "Loss Of Crossbridge Inhibition Drives Pathological Cardiac Hypertrophy In Patients Harboring The TPM1 E192K Mutation," J Gen Physiol. 153(9):1-21.

(56) References Cited

OTHER PUBLICATIONS

Sewanan, L.R. et al. (Oct. 18, 2022). "Prospects for Remodeling the Hypertrophic Heart With Myosin Modulators," Front Cardiovasc Med. 9:1-8.
Shang, E. et al. (2024). "Comparison of Drug Therapy Efficacy in Patients With Hypertrophic Cardiomyopathy: A Network Meta-Analysis," The American Journal of Cardiology 226:97-107.
Sharpe, A.N. et al. (Jan. 2023). "Effects of Aficamten On Cardiac Contractility In A Feline Translational Model Of Hypertrophic Cardiomyopathy," Scientific Reports 13(32):1-11.
Sharpe, A.N. et al. (Jan. 2023, e-pub. Nov. 16, 2022). "Pharmacokinetics Of A Single Dose Of Aficamten (CK-274) On Cardiac Contractility In A A31P MYBPC3 Hypertrophic Cardiomyopathy Cat Model," J Vet Pharmacol Ther. 46(1):52-61.
Sherrod, C.F. et al. (Nov. 5, 2024, e-pub. Sep. 1, 2024). "Effect of Aficamten on Health Status Outcomes in Obstructive Hypertrophic Cardiomyopathy: Results From Sequoia-HCM," J Am Coll Cardiol. 84 (19):1773-1785.
Sikand, N. et al. (Mar. 2024). "Are Cardiac Myosin Inhibitors Useful in Patients With Hypertrophic Obstructive Cardiomyopathy and Comorbid Hypertension?" JACC 12(3):580-582.
Siontis, K.C. et al. (Oct. 2023, e-pub. Sep. 13, 2023). "Patient-Level Artificial Intelligence-Enhanced Electrocardiogram Hypertrophic Cardiomyopathy: Longitudinal Treatment and Clinical Biomarker Correlations," JACC Adv. 2(8):1-11.
Solis, C. et al. (Nov. 2023, e-pub. Aug. 17, 2023). "Cardiomyocyte External Mechanical Unloading Activates Modifications Of $\alpha$-actinin Differently From Sarcomere-Originated Unloading," The FEBS Journal 290:5322-5339.
Sparrow, A.J. et al. (Apr. 12, 2019). "Measurement of Myofilament-Localized Calcium Dynamics in Adult Cardiomyocytes and the Effect of Hypertrophic Cardiomyopathy Mutations," Circulation Research 124(8):1228-1239.
Sparrow, A.J. et al. (Feb. 21, 2020). "Mavacamten Rescues Increased Myofilament Calcium Sensitivity and Dysregulation of Ca(2+) Flux Caused by Thin Filament Hypertrophic Cardiomyopathy Mutations," Am J Physiol Heart Circ Physiol. 318(3):H715-H722.
Spertus, J. et al. (Sep. 1, 2024). Effect of Aficamten on Patient-Reported Health Status in Obstructive Hypertrophic Cardiomyopathy: Results from Sequoia-HCM, accessed online at https://cytokinetics.com/wp-content/uploads/2024/09/ESC24-SEQUOIA-KCCQ-LBCT-FINAL.pdf on May 21, 2025, 17 pages.
Spertus, J.A. et al. (2024, e-pub. Mar. 6, 2024). "Comment On: European Heart Journal Global Spotlight On European Medicines Agency Evaluation Of Mavacamten," Eur Heart J Open 4(2):1.
Spudich, J.A. (Oct. 28, 2024). "From Amoeboid Myosin To Unique Targeted Medicines For A Genetic Cardiac Disease," Front Physiol. 15:1-17.
Statescu, C. et al. (Jul. 5, 2021). "Pushing the Limits of Medical Management in HCM: A Review of Current Pharmacological Therapy Options," Int J Mol Sci. 22(13):1-13.
Stern, J. et al. (Dec. 14, 2016). "A Small Molecule Inhibitor of Sarcomere Contractility Acutely Relieves Left Ventricular Outflow Tract Obstruction in Feline Hypertrophic Cardiomyopathy," PLOS One 11(12):1-13.
Sukaina, M. (2022, e-pub. Aug. 21, 2022). "Efficacy and Safety Of Mavacamten: A New Era In The Treatment Of Hypertrophic Cardiomyopathy," Eur J Intern Med 106:144-146.
Sukhun, R. et al. (Oct. 22, 2023). Pharmacokinetics, Excretion, and Metabolism of [14C]Aficamten Following Single Oral Dose Administration to Rats, accessed online at https://cytokinetics.com/wp-content/uploads/2024/03/Sukhun_2023_AAPS_PK-Excretion-and-Metabolism-of-14C-Aficamten-in-Rats.pdf on May 21, 2025, 1 page.
Sukhun, R. et al. (Sep. 15, 2024). Cytochrome P450 (CYP) Phenotyping of Aficamten, a Next-in-class Inhibitor of Cardiac Myosin, Using Human Liver Microsomes and Human Recombinant CYP Enzymes, accessed online at https://cytokinetics.com/wp-content/uploads/2024/10/Sukhun_2024_ISSX_Cytochrome-P450-Phenotyping-of-Aficamten.pdf on May 21, 2025, 1 page.
Sukhun, R. et al. (Sep. 2024, e-pub. Aug. 9, 2024). "In Vitro and In Vivo Pharmacokinetic Preclinical Characterization of Aficamten, a Small Molecule Cardiac Myosin Inhibitor," Xenobiotica 54(9):686-700.
Sulaiman, S.A. (2024, e-pub. Aug. 8, 2024). "Mavacamten In Hypertrophic Obstructive Cardiomyopathy: Prospects For AI Integration And Mitigating Healthcare Disparities," Curr Probl Cardiol. 49(102786):1-8.
Suppah, M. et al. (Jan. 2025, e-pub. Oct. 9, 2024). "Sustained Benefits of Mavacamten in Patients With Obstructive Hypertrophic Cardiomyopathy: Long-Term Assessment Using Artificial Intelligence—Electrocardiogram and Echocardiographic Data," Journal of the American Society of Echocardiography 38(1):47-49, 10 pages.
Sykuta, A. et al. (Mar. 2024, e-pub. Jun. 16, 2023). "Cardiac Myosin Inhibitors: Expanding the Horizon for Hypertrophic Cardiomyopathy Management," Annals of Pharmacotherapy 58(3):273-285.
Taddei-Allen, P. (Mar. 2022). "Considerations For Managed Care Pharmacy In Evaluating Mavacamten, A Novel Agent For Obstructive Hypertrophic Cardiomyopathy," J Manag Care Spec Pharm. 28(3):376-378.
Tamargo, J. et al. (2023, e-pub. May 11, 2023). "New Pharmacological Agents And Novel Cardiovascular Pharmacotherapy Strategies In 2022," European Heart Journal 9:353-370.
Tamargo, J. et al. (Oct. 2022, e-pub. Sep. 5, 2022). "Hypertrophic Cardiomyopathy: An Up-To-Date Snapshot Of The Clinical Drug Development Pipeline," Expert Opinion On Investigational Drugs, Expert Opin Investig Drugs. 31(10):1027-1052.
Tian, Z. et al. (Dec. 28, 2023, e-pub. Aug. 28, 2023). "Effect of Mavacamten on Chinese Patients With Symptomatic Obstructive Hypertrophic Cardiomyopathy," JAMA Cardiol. 8(10):957-965.
Tian, Z. et al. (Jun. 19, 2023). "Study Design And Rationale Of Explorer-CN: A Phase III, Randomised, Double-Blind, Placebo-Controlled Clinical Study To Evaluate The Efficacy And Safety Of Mavacamten In Chinese Adults With Symptomatic Obstructive Hypertrophic Cardiomyopathy," BMJ Open 13(6):1-8.
Toepfer, C.N. et al. (Apr. 2019.) "SarcTrack: An Adaptable Software Tool for Efficient Large-Scale Analysis of Sarcomere Function in hiPSC-Cardiomyocytes," Circ Res. 124(8):1172-1183.
Toepfer, C.N. et al. (Jan. 23, 2019). "Hypertrophic Cardiomyopathy Mutations in MYBPC3 Dysregulate Myosin," Sci Transl Med. 11(476):20 pages.
Tomasevic, S. et al. (Feb. 28, 2023). "Computational Modeling on Drugs Effects for Left Ventricle in Cardiomyopathy Disease," Pharmaceutics 15(3):1-18.
Tower-Rader, A. et al. (2020, Sep. 20, 2020). "Mavacamten: A Novel Small Molecule Modulator Of $\beta$-Cardiac Myosin For Treatment Of Hypertrophic Cardiomyopathy," Expert Opin Investig Drugs. 29(11):1171-1178.
Tuohy, C.V. et al. (Feb. 2020, e-pub. Jan. 9, 2020). "Hypertrophic Cardiomyopathy: The Future of Treatment," Eur J. Heart Failure 22(2):228-240.
Ullah, I. et al. (2024). "Efficacy And Safety Of Mavacamten For Symptomatic Hypertrophic Cardiomyopathy—An Updated Meta-Analysis Of Randomized Controlled Trials," Int J Cardiol Heart Vasc. 53:1-7.
Van Der Linden, L. et al. (Nov. 14, 2024). "Pharmacogenetic Testing To Broaden Patient Eligibility For Mavacamten," European Heart Journal—Cardiovascular Pharmacotherapy 11(1):92-93.
Vanhaecke, P. et al. (Aug. 7, 2024). "Usefulness of Mavacamten in the Challenging Association of Aortic Stenosis and Obstructive Hypertrophic Cardiomyopathy," JACC 29(15):1-5.
Varian, K. et al. (Aug. 2017). "Therapeutic Strategies Targeting Inherited Cardiomyopathies," Curr Heart Fail Rep. 14(4):321-330, 17 pages.
Vyas, R. et al. (Apr. 18, 2024). "Evaluating The Efficacy And Safety Of Mavacamten In Hypertrophic Cardiomyopathy: A Systematic Review And Meta-Analysis Focusing On Qualitative Assessment, Biomarkers, And Cardiac Imaging," PLoS One 19(4):1-14.
Waldman, C.B. et al. (Oct. 2021, e-pub. May 21, 2021). "A Plain Language Summary Of The Explorer-HCM study: Mavacamten For Obstructive Hypertrophic Cardiomyopathy," Future Cardiol. 17(7):1269-1275.

(56) References Cited

OTHER PUBLICATIONS

Walklate, J. et al. (Jan. 25, 2022). "Exploring The Super-Relaxed State Of Myosin In Myofibrils From Fast-Twitch, Slow-Twitch, And Cardiac Muscle," J Biol Chem. 298(3):101640, 13 pages.

Wang, A. et al. (Mar. 2024). "Mavacamten for Obstructive Hypertrophic Cardiomyopathy With or Without Hypertension: Post-Hoc Analysis of the Explorer-HCM Trial," JACC 12(3):567-579.

Wang, K. et al. (Sep. 8, 2023). "Human Engineered Cardiac Tissue Model Of Hypertrophic Cardiomyopathy Recapitulates Key Hallmarks Of The Disease And The Effect Of Chronic Mavacamten Treatment," Front Bioeng Biotechnol. 11:1-17.

Wessly, P. et al. (Dec. 2023). "Early Observations on Effects of Mavacamten on Left Atrial Function in Obstructive Hypertrophic Cardiomyopathy Patients," JACC Cardiovascular Imaging 16(12):1633-1634.

Wheeler, M.T. et al. (2023, E-pub. Feb. 1, 2023). "Effect of Beta-Blocker Therapy on The Response To Mavacameten in Patients With Symptomatic Obstructive Hypertrophic Cardiomyopathy," European Journal of Heart Failure 25:260-270.

Willeford, A. et al. (Dec. 2023, e-pub. Sep. 9, 2023). "Transitioning Disopyramide To Mavacamten In Obstructive Hypertrophic Cardiomyopathy: A Case Series And Clinical Guide," Pharmacotherapy 43(12):1397-1404.

Woodland, M. et al. (2023). "New Era: Mavacamten for Obstructive Hypertrophic Cardiomyopathy," Cardiovasc Hematol Agents Med Chem. 21(2):78-83, 10 pages.

Wu, X. et al. (Jul. 2024). "Pharmacokinetics And Safety Of Mavacamten In Healthy Chinese Participants With Different CYP2C19 Phenotypes," Clincal Transl Sci. 17(7):1-11.

Xie, J. et al. (2022, e-pub. Dec. 22, 2021). "Assessing Health-Related Quality-Of-Life In Patients With Symptomatic Obstructive Hypertrophic Cardiomyopathy: EQ-5D-based Utilities In The Explorer-HCM trial," J Med Econ. 25(1):51-58.

Xu, D. et al. (2025, Feb. 5, 2025). "Effect of Hepatic Impairment or Renal Impairment on the Pharmacokinetics of Aficamten," Clinical Pharmacokinetics 64:397-406.

Xu, D. et al. (Mar. 28, 2024). Drug-Drug Interaction Study to Evaluate the Effect of Strong CYP3A Inhibition and P450 Induction on the Pharmacokinetics of Aficamten and the Effect of Aficamten on P-Glycoprotein in Healthy Participants, accessed online at https://cytokinetics.com/wp-content/uploads/2024/04/ASCPT24-Aficamten-Drug-Drug-Interaction-Study-Poster-jp19-UPLOAD_RS-3.20.24.pdf on May 21, 2025, 1 page.

Xu, D. et al. (Mar. 28, 2024). Effect of Moderate Hepatic Impairment on the Pharmacokinetics of Aficamten and its Metabolites, accessed online at https://cytokinetics.com/wp-content/uploads/2024/03/CYTK-24812-Cyto-ASCPT24-Aficamten-Hepatic-Impairment-Study-Poster-jp18-UPLOAD.pdf on May 21, 2025, 1 page.

Xu, D. et al. (Oct. 2024, e-pub. Sep. 10, 2024). "Pharmacokinetics, Disposition, And Biotransformation Of The Cardiac Myosin Inhibitor Aficamten In Humans," Pharmacol Res Perspect. 12(5):1-12.

Xu, D. et al. (Oct. 22, 2023). Disposition and Metabolism of the Cardiac Myosin Inhibitor Aficamten in Humans, accessed online at https://cytokinetics.com/wp-content/uploads/2024/03/Xu_2023_AAPS_Disposition-and-Metabolism-of-Aficamten-in-Humans.pdf on May 21, 2025, 1 page.

Xu, W. (Jun. 3, 2024). "An Overview Of The Treatments for Hypertrophic Cardiomyopathy," Front Cardiovasc Med. 11:1-9.

Yacoub, M.S. et al. (2024, e-pub. Dec. 19, 2023). "A Systematic Review And Meta Analysis Of The Efficacy And Safety Of Mavacamten Therapy In International Cohort Of 524 Patients With Hypertrophic Cardiomyopathy," Heart Failure Reviews 29:479-496.

Yashirogi, S. et al. (Jan. 7, 2021, e-pub. Nov. 29, 2020). "AMPK Regulates Cell Shape Of Cardiomyocytes By Modulating Turnover Of Microtubules Through CLIP-170," EMBO Reports 22(1):1-17.

Yassen, M. et al. (2024). "The Efficacy of Cardiac Myosin Inhibitors Versus Placebo in Patients With Symptomatic Hypertrophic Cardiomyopathy: A Meta-Analysis and Systematic Review," Am J Cardiol 210:219-224.

Yu, J. et al. (Jun. 2024, e-pub. May 10, 2024). "Risk of Enzyme- and Transporter-mediated Drug Interactions With Drugs Approved by the US Food and Drug Administration in 2022: A Detailed Analysis of In Vitro and Clinical Data Available in New Drug Application Reviews," Clin. Ther. 46(6):499-508.

Yukselen, Z. (2024, e-pub. Aug. 21, 2024). "A Real-World Pharmacovigilance Study of FDA Adverse Event Reporting System (FAERS) for Mavacamten," Am J Cardiovasc Drugs 24:791-799.

Zampieri, M. (2021, e-pub. Jun. 3, 2021). "Mavacamten, a Novel Therapeutic Strategy for Obstructive Hypertrophic Cardiomyopathy," Curr Cardiol Rep. 23(79):1-8.

Zatorski, N. et al (May 2023). "Mavacamten Improves Symptoms in Obstructive Hypertrophic Cardiomyopathy Patients," Trends Pharmacol Sci. 44(5):318-319, 5 pages.

Zawadzka, M.M. et al. (Oct. 2022). "Phenotyping in Heart Failure with Preserved Ejection Fraction: A Key to Find Effective Treatment," Adv Clin Exp Med. 31(10):1163-1172.

Zhang, H. et al. (Jun. 21, 2023). "Clinical Trials in Hypertrophic Cardiomyopathy Therapy: A Comprehensive Analysis of Trials Registered in Global Clinical Databases," Drug Des Devel Ther. 17:1863-1877.

Zhang, S. et al. (May 14, 2024). "Deconvolution Of Polygenic Risk Score In Single Cells Unravels Cellular And Molecular Heterogeneity Of Complex Human Diseases," bioRxiv, 57 pages.

Zhang, Y. P. et al. (Apr. 24, 2021). "Mavacamten: A Promising New Target Drug For The Treatment Of Hypertrophic Cardiomyopathy," Zhonghua Xin Xue Guan Bing Za Zhi 49(4):310-313. (English Abstract Only).

Zheng, L. et al. (Oct. 23, 2024). "A Systematic Review and Meta-analysis of Efficacy and Safety of Mavacamten for the Treatment of Hypertrophic Cardiomyopathy," Rev Cardiovasc Med. 25(10):1-10.

Zheng, X. et al. (Feb. 2, 2023). "Global Research Trends Of Hypertrophic Cardiomyopathy From 2000 To 2022: Insights From Bibliometric Analysis," Front Cardiovasc Med 10:1-10.

\* cited by examiner

METHODS FOR TREATING HYPERTROPHIC CARDIOMYOPATHY

CROSS REFERENCE TO RELATED APPLICATIONS

This application is a continuation of U.S. application Ser. No. 17/812,994, filed Jul. 15, 2022, which claims priority to U.S. Provisional Application No. 63/203,333, filed Jul. 16, 2021; U.S. Provisional Application No. 63/299,753, filed Jan. 14, 2022; U.S. Provisional Application No. 63/305,609, filed Feb. 1, 2022; U.S. Provisional Application No. 63/331,197, filed Apr. 14, 2022; and U.S. Provisional Application No. 63/343,975, filed May 19, 2022; the contents of which are hereby incorporated by reference in their entirety for all purposes.

FIELD

The disclosure herein relates to the treatment of obstructive hypertrophic cardiomyopathy, and compounds and compositions that may be used for treating hypertrophic cardiomyopathy.

BACKGROUND

Hypertrophic cardiomyopathy (HCM) is a disease in which the heart muscle (myocardium) becomes abnormally thick (hypertrophied). The thickening of cardiac muscle leads to the inside of the left ventricle becoming smaller and stiffer, and thus the ventricle becomes less able to relax and fill with blood. Patients with obstructive hypertrophic cardiomyopathy may therefore suffer from abnormalities in diastology and mitral regurgitation (MR). This ultimately limits the heart's pumping function, resulting in symptoms including chest pain, dizziness, shortness of breath, or fainting during physical activity. A subset of patients with HCM are at high risk of progressive disease which can lead to atrial fibrillation, stroke and death due to arrhythmias. Adverse cardiac remodeling in oHCM is a known risk factor for progression toward arrhythmias and heart failure. Thus, there is a need for therapies that address this condition.

BRIEF SUMMARY

Methods and compositions for treating hypertrophic cardiomyopathy are described herein. A cardiac myosin inhibitor (CK-3773274, also referred to as CK-274 or aficamten, and herein as Compound 1), or a pharmaceutically acceptable salt thereof) can be used to treat hypertrophic cardiomyopathy, reduce resting left ventricular outflow tract pressure gradient (LVOT-G) to less than 30 mmHg in a patient with obstructive hypertrophic cardiomyopathy (oHCM), and/or reduce post-Valsalva left ventricular outflow tract pressure gradient (LVOT-G) to less than 50 mmHg in a patient with obstructive hypertrophic cardiomyopathy (oHCM). As further, described herein, the daily dose of Compound 1 may be titrated based on the results of an echocardiogram.

In an example, a method of reducing resting left ventricular outflow tract pressure gradient (LVOT-G) to less than 30 mmHg in a patient with obstructive hypertrophic cardiomyopathy (oHCM) includes administering to the patient a therapeutically effective amount of Compound 1, or a pharmaceutically acceptable salt thereof. The reduction in resting LVOT-G to less than 30 mmHg may occur within ten weeks of initiating treatment with Compound 1, or a pharmaceutically acceptable salt thereof. The reduction in resting LVOT-G to less than 30 mmHg may occur within two weeks of initiating treatment with Compound 1, or a pharmaceutically acceptable salt thereof. In some implementations, reduction in resting LVOT-G is sustained for at least 10 weeks of treatment. In some embodiments, the reduction in resting LVOT-G occurs within two to six weeks of the end of a dose titration. In some embodiments, the reduction in resting LVOT-G peaks within two to six weeks of the end of a dose titration.

In some implementations, a method of reducing post-Valsalva left ventricular outflow tract pressure gradient (LVOT-G) to less than 50 mmHg in a patient with obstructive hypertrophic cardiomyopathy (oHCM) includes administering to the patient a therapeutically effective amount of Compound 1, or a pharmaceutically acceptable salt thereof. The reduction in post-Valsalva LVOT-G to less than 50 mmHg may occur within two weeks of initiating treatment with Compound 1, or a pharmaceutically acceptable salt thereof. The reduction in post-Valsalva LVOT-G may be sustained for at least 10 weeks of treatment. In some embodiments, the reduction in post-Valsalva LVOT-G occurs within two to six weeks of the end of dose titration. In some embodiments, the reduction in post-Valsalva LVOT-G peaks within two to six weeks of the end of dose titration.

A method of treating obstructive hypertrophic cardiomyopathy (oHCM) in a patient in need thereof, can include administering to the patient a therapeutically effective amount of Compound 1, or a pharmaceutically acceptable salt thereof, wherein the therapeutically effective amount of Compound 1, or a pharmaceutically acceptable salt thereof, is selected by titrating a daily dose of Compound 1, or a pharmaceutically acceptable salt thereof, administered to the patient. In some embodiments, the dose is titrated once during a course of treatment. In some embodiments, the dose is titrated two or more times during a course of treatment. The daily dose may be administered to a patient at a constant amount for about two weeks before the daily dose amount is titrated.

In some implementations of the above methods, Compound 1, or a pharmaceutically acceptable salt thereof is administered at a daily dose of about 5 mg to about 30 mg. In some embodiments, the daily dose is about 5 mg. In some embodiments, the daily dose is about 10 mg. In some embodiments, the daily dose is about 15 mg. In some embodiments, the daily dose is about 20 mg. In some embodiments, the daily dose is about 30 mg.

In some implementations, the daily dose is administered as a single dose each day. In some implementations, the daily dose is administered in 2 divided doses.

In some embodiments, a method of treating obstructive hypertrophic cardiomyopathy (oHCM) in a patient in need thereof, comprises: administering to the patient a first daily dose of Compound 1, or a pharmaceutically acceptable salt thereof, for a first time period; and based on one or more components of a first echocardiogram for the patient acquired after the first time period, administering to the patient a second daily dose of Compound 1, or a pharmaceutically acceptable salt thereof, for a second time period or terminating the administering of Compound 1, or a pharmaceutically acceptable salt thereof, to the patient. The method may include selecting the second daily dose of Compound 1, or a pharmaceutically acceptable salt thereof, based on the one or more components of the first echocardiogram. In some embodiments, the one or more components of the first echocardiogram comprises a biplane LVEF, a post-Valsalva LVOT-G, or a resting LVOT-G. In some embodiments, the one or more components of the first echocardiogram comprises a biplane LVEF, a post-Valsalva LVOT-G, and a resting LVOT-G. In some embodiments, the one or more components of the first echocardiogram comprises a biplane LVEF and a post-Valsalva LVOT-G.

In some implementations of the above method, the one or more components of the first echocardiogram comprises a biplane LVEF, and the second daily dose of Compound 1, or a pharmaceutically acceptable salt thereof, is lower than the first daily dose of Compound 1, or a pharmaceutically acceptable salt thereof, when the biplane LVEF of the first echocardiogram is below a predetermined biplane LVEF threshold. For example, the predetermined biplane LVEF threshold may be 50%.

In some implementations of the above method, the one or more components of the first echocardiogram comprises a biplane LVEF, and the administering of Compound 1, or a pharmaceutically acceptable salt thereof, to the patient is terminated when the biplane LVEF of the first echocardiogram is below a predetermined biplane LVEF threshold. For example, the predetermined biplane LVEF threshold may be 50%.

In some implementations of the above method, the one or more components of the first echocardiogram comprises a biplane LVEF, a resting LVOT-G, and a post-Valsalva LVOT-G, and wherein the second daily dose of Compound 1, or a pharmaceutically acceptable salt thereof, is the same as the first daily dose of Compound 1, or a pharmaceutically acceptable salt thereof, when the biplane LVEF of the first echocardiogram is at or above the predetermined biplane LVEF threshold, the resting LVOT-G of the first echocardiogram is below a predetermined resting LVOT-G threshold, and the post-Valsalva LVOT-G of the first echocardiogram is below a predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some implementations of the above method, the one or more components of the first echocardiogram comprises a biplane LVEF, a resting LVOT-G, and a post-Valsalva LVOT-G, and wherein the second daily dose of Compound 1, or a pharmaceutically acceptable salt thereof, is greater than the first daily dose of Compound 1, or a pharmaceutically acceptable salt thereof, when either of the following conditions are met on the first echocardiogram: (1) the biplane LVEF is at or above the predetermined biplane LVEF threshold and the resting LVOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some implementations of the above method, the one or more components of the first echocardiogram comprises a biplane LVEF and a post-Valsalva LVOT-G, and wherein the second daily dose of Compound 1, or a pharmaceutically acceptable salt thereof, is the same as the first daily dose of Compound 1, or a pharmaceutically acceptable salt thereof, when either of the following conditions are met on the first echocardiogram: (1) the biplane LVEF is at or above the predetermined biplane LVEF threshold and below a second predetermined biplane LVEF threshold; or (2) the biplane LVEF is at or above the second predetermined biplane LVEF threshold and the post-Valsalva LVOT-G of the first echocardiogram is below a second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some implementations of the above method, the one or more components of the first echocardiogram comprises a biplane LVEF and a post-Valsalva LVOT-G, and wherein the second daily dose of Compound 1, or a pharmaceutically acceptable salt thereof, is greater than the first daily dose of Compound 1 when the biplane LVEF of the first echocardiogram is above the second predetermined biplane LVEF threshold and the post-Valsalva LVOT-G of the first echocardiogram is at or above the second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some implementations of the above method, the first daily dose of Compound 1, or a pharmaceutically acceptable salt thereof, is about 5 mg of Compound 1. In some embodiments, the second daily dose of Compound 1, or a pharmaceutically acceptable salt thereof, is about 5 mg or about 10 mg of Compound 1.

In some implementations of the above method, the method further comprises measuring the one or more components of the first echocardiogram.

In some implementations of the above method, first time period is about 2 weeks. In some embodiments, the second time period is about 2 weeks.

In some implementations of the above method, the second daily dose of Compound 1, or a pharmaceutically acceptable salt thereof, is administered to the patient for the second time period, and the method further comprises, based on one or more components of a second echocardiogram for the patient acquired after the second time period and the second daily dose of Compound 1, or a pharmaceutically acceptable salt thereof, administering to the patient a third daily dose of Compound 1, or a pharmaceutically acceptable salt thereof for a third time period or terminating the administering of Compound 1, or a pharmaceutically acceptable salt thereof to the patient. In some embodiments, the method comprises selecting the third daily dose of Compound 1, or a pharmaceutically acceptable salt thereof, based on the one or more components of the second echocardiogram and the second daily dose. In some embodiments, the one or more components of the second echocardiogram comprises a biplane LVEF, a post-Valsalva LVOT-G, or a resting LVOT-G. In some embodiments, the one or more components of the second echocardiogram comprises a biplane LVEF, a post-Valsalva LVOT-G, and a resting LVOT-G. In some embodiments, the one or more components of the second echocardiogram comprises a biplane LVEF and a post-Valsalva LVOT-G.

In some embodiments of the above method, the one or more components of the second echocardiogram comprises a biplane LVEF, and the third daily dose of Compound 1, or a pharmaceutically acceptable salt thereof, is lower than the second daily dose of Compound 1, or a pharmaceutically acceptable salt thereof, or the administering of Compound 1, or a pharmaceutically acceptable salt thereof, to the patient is terminated, when the biplane LVEF of the second echocardiogram is below the predetermined biplane LVEF threshold. In some embodiments, the predetermined biplane LVEF threshold is 50%.

In some embodiments of the above method, the administering of Compound 1, or a pharmaceutically acceptable salt thereof, to the patient is terminated when the biplane LVEF of the second echocardiogram is below the predetermined biplane LVEF threshold and the second daily dose of Compound 1, or a pharmaceutically acceptable salt thereof is the same as the first daily dose of Compound 1 or lower. In some embodiments, the predetermined biplane LVEF threshold is 50%.

In some embodiments of the above method, the third daily dose of Compound 1, or a pharmaceutically acceptable salt thereof, is the same as the first daily dose of Compound 1, or a pharmaceutically acceptable salt thereof, when the second daily dose of Compound 1, or a pharmaceutically acceptable salt thereof, is higher than the first daily dose of Compound 1, or a pharmaceutically acceptable salt thereof, and the biplane LVEF of the second echocardiogram is below the predetermined biplane LVEF threshold. In some embodiments, the predetermined biplane LVEF threshold is 50%.

In some embodiments of the above method, the one or more components of the second echocardiogram comprises a biplane LVEF, a resting LVOT-G, and a post-Valsalva LVOT-G, and wherein the third daily dose of Compound 1, or a pharmaceutically acceptable salt thereof, is the same as the second daily dose of Compound 1, or a pharmaceutically acceptable salt thereof when the biplane LVEF of the second echocardiogram is at or above the predetermined biplane LVEF threshold, the resting LVEOT-G of the second echocardiogram is below the predetermined resting LVOT-G threshold, and the post-Valsalva LVOT-G of the second echocardiogram is below the predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some embodiments of the above method, the one or more components of the second echocardiogram comprises a biplane LVEF, a resting LVOT-G, and a post-Valsalva LVOT-G, and wherein the third daily dose of Compound 1, or a pharmaceutically acceptable salt thereof, is greater than the second daily dose of Compound 1, or a pharmaceutically acceptable salt thereof, when either of the following conditions are met on the second echocardiogram: (1) the biplane LVEF is at or above the predetermined biplane LVEF threshold and the resting LVEOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some embodiments of the above method, the one or more components of the second echocardiogram comprises a biplane LVEF and a post-Valsalva LVOT-G, and wherein the third daily dose of Compound 1, or a pharmaceutically acceptable salt thereof, is the same as the second daily dose of Compound 1, or a pharmaceutically acceptable salt thereof, when either of the following conditions are met on the second echocardiogram: (1) the biplane LVEF is at or above the predetermined biplane LVEF threshold and below the second predetermined biplane LVEF threshold; or (2) the biplane LVEF is at or above the second predetermined biplane LVEF threshold and the post-Valsalva LVOT-G is below the second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some embodiments of the above method, the one or more components of the second echocardiogram comprises a biplane LVEF and a post-Valsalva LVOT-G, and wherein the third daily dose of Compound 1, or a pharmaceutically acceptable salt thereof, is greater than the second daily dose of Compound 1, or a pharmaceutically acceptable salt thereof, when the biplane LVEF of the second echocardiogram is above the second predetermined biplane LVEF threshold and the post-Valsalva LVOT-G of the second echocardiogram is at or above the second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some embodiments of the above method, the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, and the third daily dose of Compound 1, or a pharmaceutically acceptable salt thereof, is about 5 mg, about 10 mg, or about 15 mg of Compound 1.

In some embodiments of the above method, the method further comprises measuring the one or more components of the second echocardiogram.

In some embodiments of the above method, the third time period is about 2 weeks.

In some embodiments of the above method, the third daily dose of Compound 1, or a pharmaceutically acceptable salt thereof, is administered to the patient for the third time period, the method further comprising, based on one or more components of a third echocardiogram for the patient acquired after the third time period and the third daily dose of Compound, or a pharmaceutically acceptable salt thereof, administering to the patient a fourth daily dose of Compound 1, or a pharmaceutically acceptable salt thereof, for a fourth time period or terminating the administering of Compound 1, or a pharmaceutically acceptable salt thereof, to the patient. In some embodiments, the method further comprises selecting the fourth daily dose of Compound 1, or a pharmaceutically acceptable salt thereof, based on the one or more components of the third echocardiogram and the third daily dose. In some embodiments, the one or more components of the third echocardiogram comprises a biplane LVEF, a post-Valsalva LVOT-G, or a resting LVOT-G. In some embodiments, the one or more components of the third echocardiogram comprises a biplane LVEF, a post-Valsalva LVOT-G, and a resting LVOT-G. In some embodiments, the one or more components of the third echocardiogram comprises a biplane LVEF and a post-Valsalva LVOT-G.

In some embodiments of the above method, the one or more components of the third echocardiogram comprises a biplane LVEF, and the fourth daily dose of Compound 1, or a pharmaceutically acceptable salt thereof, is lower than the third daily dose of Compound 1, or a pharmaceutically acceptable salt thereof, or the administering of Compound 1, or a pharmaceutically acceptable salt thereof, to the patient is terminated, when the biplane LVEF of the third echocardiogram is below the predetermined biplane LVEF threshold. In some embodiments, the administering of Compound 1, or a pharmaceutically acceptable salt thereof, to the patient is terminated when the biplane LVEF of the third echocardiogram is below the predetermined biplane LVEF threshold and the third daily dose of Compound 1, or a pharmaceutically acceptable salt thereof, is the same as the first daily dose of Compound 1, or a pharmaceutically acceptable salt thereof, or lower. In some embodiments, the predetermined biplane LVEF threshold is 50%.

In some embodiments of the above method, the fourth daily dose of Compound 1, or a pharmaceutically acceptable salt thereof, is the same as the second daily dose of Compound 1, or a pharmaceutically acceptable salt thereof, when the third daily dose of Compound 1, or a pharmaceutically acceptable salt thereof, is higher than the second daily dose of Compound 1, or a pharmaceutically acceptable salt thereof, and the biplane LVEF of the third echocardiogram is below the predetermined biplane LVEF threshold; or the fourth daily dose of Compound 1, or a pharmaceutically acceptable salt thereof, is the same as the first daily dose of Compound 1, or a pharmaceutically acceptable salt thereof, when the third daily dose of Compound 1, or a pharmaceutically acceptable salt thereof, is the same as the second daily dose of Compound 1, or a pharmaceutically acceptable salt thereof, and the biplane LVEF of the third echocardiogram is below the predetermined biplane LVEF threshold. In some embodiments, the predetermined biplane LVEF threshold is 50%.

In some embodiments of the above method, the one or more components of the third echocardiogram comprises a biplane LVEF, a resting LVOT-G, and a post-Valsalva LVOT-G, and wherein the fourth daily dose of Compound 1, or a pharmaceutically acceptable salt thereof, is the same as the third daily dose of Compound 1, or a pharmaceutically acceptable salt thereof, when the biplane LVEF of the third echocardiogram is at or above the predetermined biplane LVEF threshold, the resting LVEOT-G of the third echocardiogram is below the predetermined resting LVOT-G threshold, and the post-Valsalva LVOT-G of the third echocardiogram is below the predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some embodiments of the above method, the one or more components of the third echocardiogram comprises a biplane LVEF, a resting LVOT-G, and a post-Valsalva LVOT-G, and wherein the fourth daily dose of Compound 1, or a pharmaceutically acceptable salt thereof, is greater than the third daily dose of Compound 1, or a pharmaceutically acceptable salt thereof, when either of the following conditions are met on the third echocardiogram: (1) the biplane LVEF is at or above the predetermined biplane LVEF threshold and the resting LVEOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold. In some embodiments, the predetermined biplane LVEF threshold is 50%, the predetermined resting LVOT-G threshold is 30 mmHg, and the post-Valsalva LVOT-G threshold is 50 mmHg.

In some embodiments of the above method, the one or more components of the third echocardiogram comprises a biplane LVEF and a post-Valsalva LVOT-G, and wherein the fourth daily dose of Compound 1, or a pharmaceutically acceptable salt thereof, is the same as the third daily dose of Compound 1, or a pharmaceutically acceptable salt thereof, when either of the following conditions are met on the third echocardiogram: (1) the biplane LVEF is at or above the predetermined biplane LVEF threshold and below the second predetermined biplane LVEF threshold; or (2) the biplane LVEF is at or above the second predetermined biplane LVEF threshold and the post-Valsalva LVOT-G is below the second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some embodiments of the above method, the one or more components of the third echocardiogram comprises a biplane LVEF and a post-Valsalva LVOT-G, and wherein the fourth daily dose of Compound 1, or a pharmaceutically acceptable salt thereof, is greater than the third daily dose of Compound 1, or a pharmaceutically acceptable salt thereof, when the biplane LVEF of the third echocardiogram is above the second predetermined biplane LVEF threshold and the post-Valsalva LVOT-G of the third echocardiogram is at or above the second predetermined post-Valsalva LVOT-G threshold. In some embodiments, the predetermined biplane LVEF threshold is 50%, the second predetermined biplane LVEF threshold is 55%, and the second predetermined post-Valsalva LVOT-G threshold is 30 mmHg.

In some embodiments of the above method, the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, the third daily dose of Compound 1, or a pharmaceutically acceptable salt thereof, is about 5 mg, about 10 mg, or about 15 mg of Compound 1, and the fourth daily dose of Compound 1, or a pharmaceutically acceptable salt thereof, is about 5 mg, about 10 mg, about 15 mg, or about 20 mg of Compound 1.

In some embodiments of the above method, the method further comprises measuring the one or more components of the third echocardiogram.

In some embodiments of the above method, the fourth time period is about 2 weeks.

In some implementation, a method of treating obstructive hypertrophic cardiomyopathy (oHCM) in a patient in need thereof, comprises: administering to the patient a first daily dose of Compound 1, or a pharmaceutically acceptable salt thereof, for a first time period; and based on a first echocardiogram comprising a biplane LVEF and a post-Valsalva LVOT-G for the patient acquired after the first time period, administering to the patient a second daily dose of Compound 1, or a pharmaceutically acceptable salt thereof, for a second time period or terminating the administering of Compound 1 to the patient, wherein: the administering of Compound 1, or a pharmaceutically acceptable salt thereof, to the patient is terminated if the biplane LVEF of the first echocardiogram is below a first predetermined biplane LVEF threshold; the second daily dose of Compound 1, or a pharmaceutically acceptable salt thereof, is the same as the first daily dose of Compound 1, or a pharmaceutically acceptable salt thereof, if either of the following conditions are met on the first echocardiogram: (1) the biplane LVEF is at or above the first predetermined biplane LVEF threshold and below a second predetermined biplane LVEF threshold; or (2) the biplane LVEF is at or above the second predetermined biplane LVEF threshold and the post-Valsalva LVOT-G is below a predetermined post-Valsalva LVOT-G threshold; and the second daily dose of Compound 1, or a pharmaceutically acceptable salt thereof, is greater than the first daily dose of Compound 1, or a pharmaceutically acceptable salt thereof, if the biplane LVEF of the first echocardiogram is above the second predetermined biplane LVEF threshold and the post-Valsalva LVOT-G of the first echocardiogram is at or above the predetermined post-Valsalva LVOT-G threshold.

In some embodiments of the above method, the first daily dose of Compound 1, or a pharmaceutically acceptable salt thereof, is about 5 mg of Compound 1 and the second daily dose of Compound 1, or a pharmaceutically acceptable salt thereof, is about 5 mg or about 10 mg of Compound 1.

In some embodiments of the above method, the method further comprises measuring the biplane LVEF and the post-Valsalva LVOT-G for the first echocardiogram.

In some embodiments of the above method, the first time period is about 2 weeks.

In some embodiments of the above method, the second time period is about 2 weeks.

In some embodiments of the above method, the second daily dose of Compound 1, or a pharmaceutically acceptable salt thereof, is administered to the patient for the second time period, the method further comprising, based on a second echocardiogram comprising a biplane LVEF and a post-Valsalva LVOT-G for the patient acquired after the second time period and the second daily dose of Compound 1, or a pharmaceutically acceptable salt thereof, administering to the patient a third daily dose of Compound 1, or a pharmaceutically acceptable salt thereof, for a third time period or terminating the administering of Compound 1, or a pharmaceutically acceptable salt thereof, to the patient, wherein: the administering of Compound 1, or a pharmaceutically acceptable salt thereof, to the patient is terminated if the biplane LVEF of the second echocardiogram is below the first predetermined biplane LVEF threshold and the second daily dose of Compound 1, or a pharmaceutically acceptable salt thereof, is the same as the first daily dose of Compound 1, or a pharmaceutically acceptable salt thereof; the third daily dose of Compound 1, or a pharmaceutically acceptable salt thereof, is lower than the second daily dose of Compound 1, or a pharmaceutically acceptable salt thereof, if the biplane LVEF of the second echocardiogram is below the first predetermined biplane LVEF threshold and the second daily dose of Compound 1, or a pharmaceutically acceptable salt thereof, is higher than the first daily dose of Compound 1, or a pharmaceutically acceptable salt thereof; the third daily dose of Compound 1, or a pharmaceutically acceptable salt thereof, is the same as the second daily dose of Compound 1, or a pharmaceutically acceptable salt thereof, if either of the following conditions are met on the second echocardiogram: (1) the biplane LVEF is at or above the first predetermined biplane LVEF threshold and below the second predetermined biplane LVEF threshold; or (2) the biplane LVEF is at or above the second predetermined biplane LVEF threshold and the post-Valsalva LVOT-G is below the predetermined post-Valsalva LVOT-G threshold; and the third daily dose of Compound 1, or a pharmaceutically acceptable salt thereof, is greater than the second daily dose of Compound 1, or a pharmaceutically acceptable salt thereof, if the biplane LVEF of the second echocardiogram is above the second predetermined biplane LVEF threshold and the post-Valsalva LVOT-G of the second echocardiogram is at or above the predetermined post-Valsalva LVOT-G threshold.

In some embodiments of the above method, the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, and the third daily dose of Compound 1, or a pharmaceutically acceptable salt thereof, is about 5 mg, about 10 mg, or about 15 mg of Compound 1.

In some embodiments of the above method, the method further comprises measuring the biplane LVEF and the post-Valsalva LVOT-G for the second echocardiogram.

In some embodiments of the above method, the third time period is about 2 weeks.

In some embodiments of the above method, the third daily dose of Compound 1, or a pharmaceutically acceptable salt thereof, is administered to the patient for the third time period, the method further comprising, based on a third echocardiogram comprising a biplane LVEF and a post-Valsalva LVOT-G for the patient acquired after the third time period and the second third dose of Compound 1, or a pharmaceutically acceptable salt thereof, administering to the patient a fourth daily dose of Compound 1, or a pharmaceutically acceptable salt thereof, for a fourth time period or terminating the administering of Compound 1 to the patient, wherein: the administering of Compound 1, or a pharmaceutically acceptable salt thereof, to the patient is terminated if the biplane LVEF of the third echocardiogram is below the first predetermined biplane LVEF threshold and the third daily dose of Compound 1, or a pharmaceutically acceptable salt thereof, is the same as the first daily dose of Compound 1, or a pharmaceutically acceptable salt thereof; the fourth daily dose of Compound 1, or a pharmaceutically acceptable salt thereof, is lower than the third daily dose of Compound 1, or a pharmaceutically acceptable salt thereof, if the biplane LVEF of the third echocardiogram is below the first predetermined biplane LVEF threshold and the third daily dose of Compound 1, or a pharmaceutically acceptable salt thereof, is higher than the first daily dose of Compound 1, or a pharmaceutically acceptable salt thereof; the fourth daily dose of Compound 1, or a pharmaceutically acceptable salt thereof, is the same as the third daily dose of Compound 1, or a pharmaceutically acceptable salt thereof, if either of the following conditions are met on the third echocardiogram: (1) the biplane LVEF is at or above the first predetermined biplane LVEF threshold and below the second predetermined biplane LVEF threshold; or (2) the biplane LVEF is at or above the second predetermined biplane LVEF threshold and the post-Valsalva LVOT-G is below the predetermined post-Valsalva LVOT-G threshold; and the fourth daily dose of Compound 1, or a pharmaceutically acceptable salt thereof, is greater than the third daily dose of Compound 1, or a pharmaceutically acceptable salt thereof, if the biplane LVEF of the third echocardiogram is above the second predetermined biplane LVEF threshold and the post-Valsalva LVOT-G of the third echocardiogram is at or above the predetermined post-Valsalva LVOT-G threshold. In some embodiments, the first daily dose of Compound 1, or a pharmaceutically acceptable salt thereof is about 5 mg of Compound 1, the second daily dose of Compound 1, or a pharmaceutically acceptable salt thereof, is about 5 mg or about 10 mg of Compound 1, the third daily dose of Compound 1, or a pharmaceutically acceptable salt thereof, is about 5 mg, about 10 mg, or about 15 mg of Compound 1, and the fourth daily dose of Compound 1, or a pharmaceutically acceptable salt thereof, is about 5 mg, about 10 mg, about 15 mg, or about 20 mg of Compound 1. In some embodiments, the method further comprises measuring the biplane LVEF and the post-Valsalva LVOT-G for the second echocardiogram. In some embodiments, the third time period is about 2 weeks.

In some embodiments of the above method, the first predetermined biplane LVEF threshold is 50%, the second predetermined biplane LVEF threshold is 55%, and the predetermined post-Valsalva LVOT-G threshold is 30 mmHg.

In some embodiments of any of the above methods, prior to administration of Compound 1, or a pharmaceutically acceptable salt thereof, the patient has (i) resting LVOT-G ≥50 mmHg; or (ii) resting LVOT-G ≥30 mmHg and <50 mmHg with post-Valsalva LVOT-G ≥50 mmHg.

In some embodiments of any of the above methods, prior to administration of Compound 1, or a pharmaceutically acceptable salt thereof, the patient has left ventricular ejection fraction (LVEF) ≥60%.

In some embodiments of any of the above methods, the patient is not administered disopyramide during treatment with Compound 1, or a pharmaceutically acceptable salt thereof.

In some embodiments of any of the above methods, the patient is administered disopyramide during the treatment with Compound 1, or a pharmaceutically acceptable salt thereof.

In some embodiments of any of the above methods, the patient has not been treated with disopyramide or an antiarrhythmic drug that has negative inotropic activity within 4 weeks prior to treatment with Compound 1, or a pharmaceutically acceptable salt thereof.

In some embodiments of any of the above methods, the patient is administered an antiarrhythmic medication during the treatment with Compound 1, or a pharmaceutically acceptable salt thereof.

In some embodiments of any of the above methods, the patient is a CYP2D6 poor metabolizer.

In some embodiments of any of the above methods, the patient is fasting when administered Compound 1, or a pharmaceutically acceptable salt thereof.

In some embodiments of any of the above methods, the patient is fed when administered Compound 1, or a pharmaceutically acceptable salt thereof.

In some embodiments of any of the above methods, the method does not include taking a blood sample of the patient.

In some embodiments of any of the above methods, the method does not include analyzing a blood sample of the patient.

In some embodiments of any of the above methods, the patient is administered a beta-blocker during the treatment with Compound 1, or a pharmaceutically acceptable salt thereof.

Also provided herein is a method of treating obstructive hypertrophic cardiomyopathy (oHCM) in a patient in need thereof, comprising administering to the patient a therapeutically effective amount of Compound 1, or a pharmaceutically acceptable salt thereof.

In some embodiments of any of the above methods, the method results in one or more of the following: improvement in mitral regurgitation, improvement in cardiac relaxation, beneficial cardiac remodeling, reverse cardiac remodeling, beneficial cardiac structural remodeling, beneficial cardiac functional remodeling, reversal of adverse cardiac remodeling, reduction in mean left ventricular mass index (LVMI), improvement in left ventricular (LV) filling pressures, reduction in left atrial volume index (LAVI), reduction in the categorical assessment of systolic anterior motion of the mitral valve leaflet, reduction in systolic anterior motion of the mitral valve leaflet, reduction in the frequency of eccentric mitral regurgitation, reduction in mitral regurgitation, reduction in lateral E/e', reduction in lateral E/E, reduction in brain natriuretic peptide (BNP) and reduction in N-terminal prohormone of brain natriuretic peptide (NT-proBNP).

In some embodiments, the one or more results of the treatment occur within 1, 2, 3, 4, 5, 6, 7, 8, 9, or 10 weeks of initiating treatment with Compound 1, or a pharmaceutically acceptable salt thereof.

In some embodiments of any of the above methods, a left ventricle mass index (LVMI) for the patient is reduced.

In some embodiments of any of the above methods, a left arterial volume index (LAVI) for the patient is reduced.

In some embodiments of any of the above methods, an e' for the patient is reduced.

In some embodiments of any of the above methods, a lateral E/e' for the patient is reduced.

In some embodiments of any of the above methods, a likelihood systolic anterior motion of the mitral valve leaflet is reduced.

In some embodiments of any of the above methods, a likelihood of mitral regurgitation is reduced.

In some embodiments of any of the above methods, a level of brain natriuretic peptide or N-terminal prohormone of brain natriuretic peptide (NT-proBNP) in the patient is decreased.

In some embodiments of any of the above methods, a level of cardiac troponin I in the patient is decreased.

In some embodiments of any of the above methods, left ventricular wall stress in the patient is decreased.

In some embodiments of any of the above methods, myocardial injury in the patient is decreased.

In some embodiments of any of the above methods, heart failure symptoms in the patient are reduced, for instance, the methods result in the reduction in the patient's NYHA classification.

In some embodiments of any of the above methods, the method results in sustained effect(s) for at least 10 weeks, 12 weeks, 6 months, 1 year, 2 years, 3 years, 4 years, or 5 years.

In some embodiments of any of the above methods, administration for the second time period, third time period, or fourth time period may be, for example, administration for about 2 weeks, about 10 weeks, about 12 weeks, about 6 months, about 1 year, about 2 years, about 3 years, about 4 years, or about 5 years, or indefinite. As used herein, administration for an indefinite time period may indicate: administration until the patient is no longer in need of treatment; administration until there is no further effect of treatment; or administration until there is no further reason for treatment.

DETAILED DESCRIPTION

Figure 1:
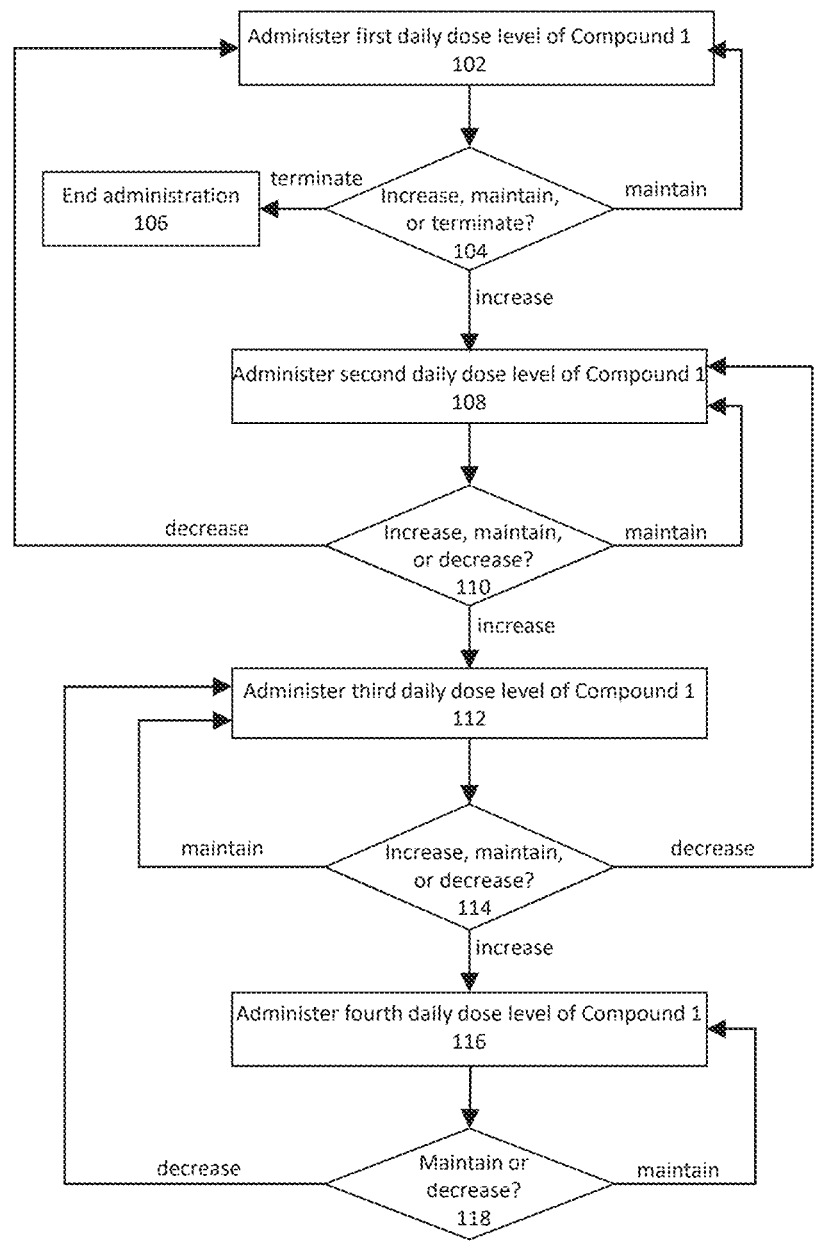
FIG. 1 illustrates and exemplary method for treating obstructive hypertrophic cardiomyopathy (oHCM) in a patient that included titrating the daily dose of CK-274, or a pharmaceutically acceptable salt thereof.

Described herein is a cardiac myosin inhibitor (CK-3773274, also referred to as CK-274 or aficamten) and methods for treating hypertrophic cardiomyopathy using the cardiac myosin inhibitor. Treatment methods may include adjusting a dose, for example to increase, decrease or maintain a dose, based on the results of one or more measured left ventricular outflow tract pressure gradient (LVOT-G), biplane left ventricular ejection fraction (LVEF) measurement, and/or post-Valsalva LVOT-G measurements. These measurements may be taken, for example, using an echocardiogram.

CK-3773274 (Compound 1) is a small molecule cardiac myosin inhibitor having the structure shown below.

Compound 1

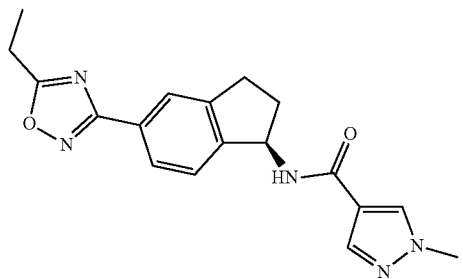

The chemical name of CK-274 is (R)—N-(5-(5-ethyl-1,2,4-oxadiazol-3-yl)-2,3-dihydro-1H-inden-1-yl)-1-methyl-1H-pyrazole-4-carboxamide. The small molecule inhibitor may be, for example, orally administered to a patient for the treatment of hypertrophic cardiomyopathy.

CK-274 has been described in WO 2019/144041, which is incorporated by reference herein. CK-274, or a pharmaceutically acceptable salt thereof, may be obtained following the methods described therein. CK-274 used in the disclosed methods can be present as a pharmaceutically acceptable salt, solvate, hydrate, polymorph, or combination thereof, and can be formulated into any suitable pharmaceutical formulation. Polymorphs of CK-274 have been described in WO 2021/011807, which is incorporated by reference herein. Formulations of CK-274 have been described in WO 2021/011808, which is incorporated by reference herein. CK-274 was designed to reduce the hypercontractility that is associated with hypertrophic cardiomyopathy (HCM). Without being bound by theory, in preclinical models, CK-274 reduces myocardial contractility by binding directly to cardiac myosin at a distinct and selective allosteric binding site, thereby preventing myosin from entering a force producing state. CK-274 reduces the number of active actin-myosin cross bridges during each cardiac cycle and consequently reduces myocardial contractility. This mechanism of action may be therapeutically effective in conditions characterized by excessive hypercontractility, such as HCM (e.g., obstructive HCM, also referred to as oHCM).

Definitions

As used in the present specification, the following words and phrases are generally intended to have the meanings as set forth below, except to the extent that the context in which they are used indicates otherwise.

Reference to "about" a value or parameter herein includes (and describes) that value or parameter per se, and any value or parameter 5% above or 5% below said parameter. For example, description to "about X" includes description of "X" and "X+/−5%".

"NYHA classification" or "NYHA class" refers to the New York Heart Association functional classification of heart failure symptoms. Descriptions of each of NYHA classes I, II, III, and IV can be found in "Classes of Heart Failure", American Heart Association, https://www.heart.org/en/health-topics/heart-failure/what-is-heart-failure/classes-of-heart-failure, adapted from: 1) Dolgin M, Association NYH, Fox A C, Gorlin R, Levin R I, New York Heart Association. Criteria Committee. "Nomenclature and criteria for diagnosis of diseases of the heart and great vessels". 9th ed. Boston, MA: Lippincott Williams and Wilkins; Mar. 1, 1994; and 2) Criteria Committee, New York Heart Association, Inc. Diseases of the Heart and Blood Vessels. Nomenclature and Criteria for diagnosis, 6th edition Boston, Little, Brown and Co. 1964, p 114. Briefly, NYHA class I indicates that the patient has no limitation of physical activity; ordinary physical activity does not cause undue fatigue, palpitation, dyspnea (shortness of breath). NYHA class II indicates that the patient has slight limitation of physical activity; comfortable at rest; ordinary physical activity results in fatigue, palpitation, dyspnea (shortness of breath). NYHA class III indicates that the patient has marked limitation of physical activity; comfortable at rest; less than ordinary physical activity causes fatigue, palpitation, or dyspnea. NYHA class IV indicates that the patient is unable to carry on any physical activity without discomfort; symptoms of heart failure at rest; if any physical activity is undertaken, discomfort increases.

The term "pharmaceutically acceptable salt" refers to a salt of any of the compounds herein that are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, J. Pharmaceutical Sciences, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, J. Pharmaceutical Sciences, January 1977, 66(1), 1-19). Those skilled in the art will recognize various synthetic methodologies that may be used to prepare pharmaceutically acceptable addition salts.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

Reference to any dose amount of a compound or pharmaceutically acceptable salt thereof described herein (e.g., 5 mg, 10 mg, 20 mg, etc. of Compound 1) refers to the amount (i.e., equivalent mass) of said compound without any salt.

Treatment of Hypertrophic Cardiomyopathy

As further described herein a therapeutically effective amount of CK-274 may be administered to a patient for the treatment of hypertrophic cardiomyopathy. CK-274 may be administered at a constant dose level. CK-274 may be administered at a titrated dose level. For example, the dose of CK-274 may be adjusted depending on the patient's response to the drug. That is, the dose of the CK-274 may be periodically increased, decreased, or maintained depending on the measurement of a drug response, such as one or more of a left ventricular outflow tract pressure gradient (LVOT-G), biplane left ventricular ejection fraction (LVEF), and/or post-Valsalva LVOT-G measurements.

Results of a recent clinical trial (see Example 1) demonstrated that treatment with CK-274 for 10 weeks resulted in substantial and statistically significant reductions from baseline compared to placebo in the average resting left ventricular outflow tract pressure gradient (LVOT-G) (p=0.0003, p=0.0004, Cohort 1 and Cohort 2, respectively) and the average post-Valsalva LVOT-G (p=0.001, p<0.0001, Cohort 1 and Cohort 2, respectively). The majority of patients treated with CK-274 (78.6% in Cohort 1 and 92.9% in Cohort 2) achieved the target goal of treatment, defined as resting gradient <30 mmHg and post-Valsalva gradient <50 mmHg at Week 10 compared to placebo (7.7%). Reductions in LVOT-G occurred within two weeks of initiating treatment with CK-274, peaked within two to six weeks of the end of dose titration, and were sustained until the end of treatment at 10 weeks. The observed reductions in LVOT-G were dose dependent, with patients achieving greater reductions of LVOT-G with increasing doses of CK-274.

Treatment with CK-274 in in the clinical trial was well tolerated. Overall, the incidence of adverse events was similar between treatment arms. No serious adverse events were attributed to CK-274 and no treatment interruptions occurred on CK-274. No new cases of atrial fibrillation were reported by the investigators. In this dose-range finding trial, one patient experienced a transient decrease in left ventricular ejection fraction (LVEF) that required dose adjustment but not dose interruption. LVEF returned towards baseline within two weeks after the end of treatment in both cohorts, confirming the reversibility of effect with CK-274 as was similarly observed in healthy participants in the Phase 1 study of CK-274.

CK-274 is administered at a therapeutically effective dosage, e.g., a dosage sufficient to provide treatment for the disease state. For a human, the daily dose may be between about 1 mg and about 50 mg. For example, the daily dose may be about 5 mg, about 10 mg, about 15 mg, about 20 mg, or about 30 mg, or any amount therebetween. A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

In one example, a patient is treated for hypertrophic cardiomyopathy by administering to the patient a daily dose of about 5 mg to about 30 mg of CK-274. In one example, a patient is treated for hypertrophic cardiomyopathy by administering to the patient a daily dose of about 5 mg CK-274. In one example, a patient is treated for hypertrophic cardiomyopathy by administering to the patient a daily dose of about 10 mg CK-274. In one example, a patient is treated for hypertrophic cardiomyopathy by administering to the patient a daily dose of about 15 mg CK-274. In one example, a patient is treated for hypertrophic cardiomyopathy by administering to the patient a daily dose of about 20 mg CK-274. In one example, a patient is treated for hypertrophic cardiomyopathy by administering to the patient a daily dose of about 25 mg CK-274. In one example, a patient is treated for hypertrophic cardiomyopathy by administering to the patient a daily dose of about 30 mg CK-274. In some embodiments of any of the foregoing, the treatment for hypertrophic cardiomyopathy further comprises administering disopyramide to the patient.

In some embodiments, provided are methods for the treatment for hypertrophic cardiomyopathy comprising administration of CK-274, or a pharmaceutically acceptable salt thereof, or a pharmaceutical composition containing CK-274, or a pharmaceutically acceptable salt thereof, in combination with a second therapeutic agent, wherein the second therapeutic agent is disopyramide. In some embodiments, the hypertrophic cardiomyopathy is obstructive hypertrophic cardiomyopathy and/or treatment refractory hypertrophic cardiomyopathy. In some embodiments, provided are methods for the treatment for obstructive hypertrophic cardiomyopathy, treatment refractory hypertrophic cardiomyopathy, or treatment refractive obstructive hypertrophic cardiomyopathy, comprising administration of CK-274, or a pharmaceutically acceptable salt thereof, or a pharmaceutical composition containing CK-274, or a pharmaceutically acceptable salt thereof, in combination with a second therapeutic agent, wherein the second therapeutic agent is disopyramide. In some embodiments, the combination of CK-274, or a pharmaceutically acceptable salt thereof, and disopyramide comprises simultaneous administration of CK-274, or a pharmaceutically acceptable salt thereof, and disopyramide. In some embodiments, the combination of CK-274 and disopyramide comprises sequential administration of CK-274, or a pharmaceutically acceptable salt thereof, and disopyramide. In some embodiments, the combination of CK-274, or a pharmaceutically acceptable salt thereof, and disopyramide comprises administration of CK-274, or a pharmaceutically acceptable salt thereof, to a patient already undergoing treatment with disopyramide.

During the course of treatment for hypertrophic cardiomyopathy, the dose of CK-274 administered to the patient may be titrated, for example by increasing, decreasing, or maintaining the dose. Titration may occur once during treatment, or may be performed iteratively separated by a period of time. For example, in some implementations, the dose of CK-274 is titrated two or more times (e.g., 3, 4, 5 or more) during the course of treatment. In some embodiments, a new daily dose amount is administered to the patient at a constant amount for about 1 week to about 8 weeks (or about 2 weeks to about 6 weeks, or about 4 weeks) before the daily dose amount is titrated. In some embodiments, a new daily dose amount is administered to the patient at a constant amount for about 2 weeks before being titrated. For example, a first daily dose may be administered to the patient for about 2 weeks before a first titration, wherein the daily dose amount is increased, decreased or maintained. The second titration may then occur approximately 2 weeks after the first titration. Titration of the dose allows the dose to be personalized to the patient's response to the drug, thus maximizing the potential treatment effect for patients.

Titration of the dose can be based on one or more of a left ventricular outflow tract pressure gradient (LVOT-G), biplane left ventricular ejection fraction (LVEF), and/or post-Valsalva LVOT-G measured in the patient. The measurement or measurements may be determined, for example, using an echocardiogram. The echocardiogram is taken following administration of the daily dose, for example about 1 hour to about 3 hours following administration of the dose. In some embodiments, the echocardiogram is taken about 2 hours following administration of the daily dose.

In some embodiments, an initial daily dose of about 5 mg, about 10 mg, about 15 mg, about 20 mg, or about 30 mg CK-274, or any amount therebetween, is administered to the patient. After a period of time (e.g., about 2 weeks), resting LVOT-G, biplane LVEF, and/or post-Valsalva LVOT-G is measured, for example by echocardiography, following the administration of the dose (for example, about 1-3 hours, or about 2 hours following the administration of the dose). If the resting LVOT-G at or above a predetermined resting LVOT-G threshold (e.g., about 25 mmHg or more, about 30 mmHg or more, or about 35 mmHg or more) and the biplane LVEF is at or above a predetermined biplane LVEF threshold (e.g., about 40% or more, about 45% or more, about 50% or more, about 55% or more, or about 60% or more), the daily dose is increased. Alternatively, if the resting LVOT-G is not at or above the predetermined resting LVOT-G threshold, the dose may still be increased if the post-Valsalva LVOT-G is at or above a predetermined post-Valsalva LVOT-G threshold (e.g., about 40 mmHg or more, about 45 mmHg or more, about 50 mmHg or more, about 55 mmHg or more, or about 60 mmHg or more) and the biplane LVEF is at or above the predetermined biplane LVEF threshold. The dose may be maintained if the biplane LVEF is at or above the predetermined threshold, but the resting LVOT-G is below the resting LVOT-G threshold and the post-Valsalva LVOT-G is below the post-Valsalva LVOT-G threshold. The dose may be decreased or terminated if the biplane LVEF is below the biplane LVEF threshold. For example, the dose may be decreased if the biplane LVEF is below the biplane LVEF threshold and the current dose is not the lowest (e.g., first) dose. The dose may be terminated if the biplane LVEF is below the biplane LVEF threshold and the current dose is the lowest (e.g., first) dose. In some embodiments, the resting LVOT-G threshold is about 30 mmHg, the biplane LVEF threshold is about 50%, and the post-Valsalva LVOT-G threshold is about 50 mmHg. In some embodiments, titration of the dose of CK-274 comprises maintaining the dose at the current dose; increasing the dose by about 1 mg, about 2 mg, about 3 mg, about 4 mg, about 5 mg, or about 10 mg, or any amount therebetween; decreasing the dose by about 1 mg, about 2 mg, about 3 mg, about 4 mg, about 5 mg, or about 10 mg, or any amount therebetween; or terminating administration. In some embodiments, titration of the dose comprises maintaining the dose at the current dose; increasing the dose by about 1 mg, about 2 mg, about 3 mg, about 4 mg, about 5 mg, or about 10 mg, or any amount therebetween; or decreasing the dose by about 1 mg, about 2 mg, about 3 mg, about 4 mg, about 5 mg, or about 10 mg, or any amount therebetween.

After a period of time (e.g., about 2 weeks) of the patient being administered the first titrated dose, the dose may be again titrated (i.e., increased, decreased, or maintained) based on the resting LVOT-G, biplane LVEF, and/or post-Valsalva LVOT-G of the patient, for example using the same threshold parameters as discussed above. An exemplary dose titration schedule includes: administration of a first titrated dose for about 2 weeks, about 3 weeks, about 4 weeks, about 5 weeks, about 6 weeks, about 8 weeks, about 10 weeks, or about 12 weeks, or any amount of time therebetween, followed by dose titration based on the resting LVOT-G, biplane LVEF, and/or post-Valsalva LVOT-G of the patient, for example using the same threshold parameters as discussed above. Further iterations of administration and dose titration may be conducted accordingly.

In some embodiments, the method results in a reduction of the resting left ventricular outflow tract pressure gradient (LVOT-G) to less than a particular value in the patient. The reduction in resting LVOT-G to less than the particular value may occur within ten weeks of initiating treatment with Compound 1, or a pharmaceutically acceptable salt thereof. The reduction in resting LVOT-G to less than the particular value may occur within one week, two weeks, three weeks, four weeks, one month, five weeks, six week, seven weeks, eight weeks, two months, nine weeks, or ten weeks of initiating treatment with Compound 1, or a pharmaceutically acceptable salt thereof. In some embodiments, reduction in resting LVOT-G is sustained for at least 10 weeks of treatment. In some embodiments, the reduction in resting LVOT-G occurs within two to six weeks of the end of a dose titration. In some embodiments, the reduction in resting LVOT-G peaks within two to six weeks of the end of a dose titration. In some embodiments, the particular resting LVOT-G value is: 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, or 25 mmHg.

In some embodiments, the method results in a reduction of the post-Valsalva left ventricular outflow tract pressure gradient (LVOT-G) to less than a particular value in the patient. The reduction in post-Valsalva LVOT-G to less than the particular value may occur within one week, two weeks, three weeks, four weeks, one month, five weeks, six week, seven weeks, eight weeks, two months, nine weeks, or ten weeks of initiating treatment with Compound 1, or a pharmaceutically acceptable salt thereof. The reduction in post-Valsalva LVOT-G may be sustained for at least 10 weeks of treatment. In some embodiments, the reduction in post-Valsalva LVOT-G occurs within two to six weeks of the end of dose titration. In some embodiments, the reduction in post-Valsalva LVOT-G peaks within two to six weeks of the end of dose titration. In some embodiments, the particular post-Valsalva LVOT-G value is: 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 mmHg.

Provided herein is a method of reducing resting left ventricular outflow tract pressure gradient (LVOT-G) to less than a particular value in a patient with obstructive hypertrophic cardiomyopathy (oHCM) comprises administering to the patient a therapeutically effective amount of Compound 1, or a pharmaceutically acceptable salt thereof. The reduction in resting LVOT-G to less than the particular value may occur within one week, two weeks, three weeks, four weeks, one month, five weeks, six week, seven weeks, eight weeks, two months, nine weeks, or ten weeks of initiating treatment with Compound 1, or a pharmaceutically acceptable salt thereof. The reduction in resting LVOT-G to less than the particular value may occur within two weeks of initiating treatment with Compound 1, or a pharmaceutically acceptable salt thereof. In some implementations, reduction in resting LVOT-G is sustained for at least 10 weeks of treatment. In some embodiments, the reduction in resting LVOT-G occurs within two to six weeks of the end of a dose titration. In some embodiments, the reduction in resting LVOT-G peaks within two to six weeks of the end of a dose titration. In some embodiments, the particular resting LVOT-G value is: 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, or 25 mmHg.

Provided herein is a method of reducing post-Valsalva left ventricular outflow tract pressure gradient (LVOT-G) to less than a particular value in a patient with obstructive hypertrophic cardiomyopathy (oHCM) which comprises administering to the patient a therapeutically effective amount of Compound 1, or a pharmaceutically acceptable salt thereof. The reduction in post-Valsalva LVOT-G to less than the particular value may occur within one week, two weeks, three weeks, four weeks, one month, five weeks, six week, seven weeks, eight weeks, two months, nine weeks, or ten weeks of initiating treatment with Compound 1, or a pharmaceutically acceptable salt thereof. The reduction in post-Valsalva LVOT-G may be sustained for at least 10 weeks of treatment. In some embodiments, the reduction in post-Valsalva LVOT-G occurs within two to six weeks of the end of dose titration. In some embodiments, the reduction in post-Valsalva LVOT-G peaks within two to six weeks of the end of dose titration. In some embodiments, the particular post-Valsalva LVOT-G value is: 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 mmHg.

Provided herein is a method of reducing resting left ventricular outflow tract pressure gradient (LVOT-G) to less than a particular value and reducing post-Valsalva left ventricular outflow tract pressure gradient (LVOT-G) to less than a particular value in a patient with obstructive hypertrophic cardiomyopathy (oHCM) which comprises administering to the patient a therapeutically effective amount of Compound 1, or a pharmaceutically acceptable salt thereof. The reduction in resting LVOT-G to less than the particular value and the reduction in post-Valsalva LVOT-G to less than the particular value may occur within one week, two weeks, three weeks, four weeks, one month, five weeks, six week, seven weeks, eight weeks, two months, nine weeks, or ten weeks of initiating treatment with Compound 1, or a pharmaceutically acceptable salt thereof. The reduction in resting LVOT-G to less than the particular value and the reduction in post-Valsalva LVOT-G to less than the particular value may occur within two weeks of initiating treatment with Compound 1, or a pharmaceutically acceptable salt thereof. In some implementations, reduction in resting LVOT-G and reduction in post-Valsalva LVOT-G is sustained for at least 10 weeks of treatment. In some embodiments, both the reduction in resting LVOT-G and the reduction in post-Valsalva LVOT-G may occur within two to six weeks of the end of a dose titration. In some embodiments, both the reduction in resting LVOT-G and the reduction in post-Valsalva LVOT-G peak within two to six weeks of the end of a dose titration. In some embodiments, the particular resting LVOT-G value is: 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, or 25 mmHg. In some embodiments, the particular post-Valsalva LVOT-G value is: 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 mmHg. In some embodiments, the particular resting LVOT-G value is 30 mm Hg, and the particular post-Valsalva LVOT-G value is 50 mmHg.

Provided herein is a method of treating obstructive hypertrophic cardiomyopathy (oHCM) in a patient eligible for septal reduction therapy (SRT), which comprises administering to the patient a therapeutically effective amount of Compound 1, or a pharmaceutically acceptable salt thereof. Also provided herein is a method of treating oHCM in a patient in need of SRT, which comprises administering to the patient a therapeutically effective amount of Compound 1, or a pharmaceutically acceptable salt thereof, wherein the method precludes the need for SRT in the patient. In some embodiments, the SRT is myectomy. In some embodiments, the SRT is alcohol septal ablation.

Further provided herein is a method of treating obstructive hypertrophic cardiomyopathy (oHCM) in a patient with heart failure symptoms, comprising administering to the patient a therapeutically effective amount of Compound 1, or a pharmaceutically acceptable salt thereof, wherein the method results in a reduction of heart failure symptoms as assessed by NYHA classification. In some embodiments of the foregoing, the methods improve heart failure symptoms by at least one NYHA class in the patient, for instance, by one or two NYHA class(es). In some embodiments of the foregoing, the methods convert patients from NYHA class III to class II or class I. In some embodiments of the foregoing, the methods convert patients from NYHA class III to class II. In some embodiments of the foregoing, the methods convert patients from NYHA class III to class I. In some embodiments of the foregoing, the methods convert patients from NYHA class II to class I. In some embodiments of the foregoing, reduction of heart failure symptoms occurs within ten weeks of initiating treatment with Compound 1, or a pharmaceutically acceptable salt thereof.

In some embodiments, titration of the daily dose of CK-274, or a pharmaceutically acceptable salt thereof, is based on the results of an echocardiogram that includes a biplane LVEF and a post-Valsalva LVOT-G. For example, based on the results of the biplane LVEF and/or post-Valsalva LVOT-G, the daily dose of CK-274, or a pharmaceutically acceptable salt thereof, may be increased, maintained, or decreased (or terminated, for example if the subject is already receiving the lowest (e.g., first) daily dose). For example, based on the results of the biplane LVEF and/or post-Valsalva LVOT-G, the daily dose of CK-274, or a pharmaceutically acceptable salt thereof, may be increased, maintained, or decreased (or terminated, for example if the subject is already receiving the first daily dose). A first daily dose of CK-274, or a pharmaceutically acceptable salt thereof, is administered to the patient for a first time period (e.g., about two weeks). A second daily dose for the subject, or termination of administration of CK-274 or the pharmaceutically acceptable salt thereof, is then selected based on a biplane LVEF and post-Valsalva LVOT-G for the patient acquired after the first time period. The administration of CK-274 or the pharmaceutically acceptable salt thereof may be terminated if the biplane LVEF of the echocardiogram is below a first predetermined biplane LVEF threshold (e.g., 50%). The administration of CK-274 or the pharmaceutically acceptable salt thereof may be terminated if the biplane LVEF of the echocardiogram is below a first predetermined biplane LVEF threshold (e.g., 50%) and the patient is already receiving the lowest (e.g., first) daily dose.

If the biplane LVEF of the echocardiogram is below a first predetermined biplane LVEF threshold (e.g., 50%) and the patient is not already receiving the lowest daily dose, then the daily dose may be decreased (i.e., the second daily dose is lesser than the first daily dose). If the biplane LVEF is at or above the first predetermined biplane threshold and below a second predetermined biplane LVEF threshold (e.g., 55%), or if the biplane LVVEF is at or above the second predetermined biplane LVEF threshold and the post-Valsalva LVOT-G is below a predetermined post-Valsalva LVOT-G threshold (e.g., 30 mmHg), then the daily dose is maintained (i.e., the second daily dose is the same as the first daily dose). If the biplane LVEF is at or above the second predetermined biplane threshold and the post-Valsalva LVOT-G is above the predetermined post-Valsalva LVOT-G threshold, the daily dose may be increased (i.e., the second daily dose is greater than the first daily dose).

The second daily dose may be administered to the patient for a second time period (e.g., about two weeks) before again being titrated based on the results of a second echocardiogram that includes a biplane LVEF and a post-Valsalva LVOT-G for the patient acquired after the second time period. For example, a third daily dose, or termination of the administration, may be selected or the administration terminated based on the second echocardiogram and the second daily dose. If the second daily dose is the same as (or lower than) the first daily dose and the biplane LVEF of the second echocardiogram is below the first predetermined biplane LVEF threshold, the administration may be terminated. If the second daily dose is higher than the first daily dose and the biplane LVEF of the second echocardiogram is below the first predetermined biplane LVEF threshold, the third daily dose may be decreased relative to the second daily dose, for example to the amount of the first daily dose. If the second daily dose is the same as (or lower than) the first daily dose (e.g., if the second daily dose is the lowest dose) and the biplane LVEF of the second echocardiogram is below the first predetermined biplane LVEF threshold, the administration may be terminated. If the second daily dose is higher than the lowest (e.g., first) daily dose and the biplane LVEF of the second echocardiogram is below the first predetermined biplane LVEF threshold, the third daily dose may be decreased relative to the second daily dose, for example to the amount of the first daily dose. If the biplane LVEF is at or above the first predetermined biplane LVEF threshold and below the second predetermined biplane LVEF threshold, or if the biplane LVEF is at or above the second predetermined biplane LVEF threshold and the post-Valsalva LVOT-G is below the predetermined post-Valsalva LVOT-G threshold, the daily dose may be maintained (i.e., the third daily dose is the same as the second daily dose). The third daily dose may be increased relative to the second daily dose if the biplane LVEF of the second echocardiogram is above the second predetermined biplane LVEF threshold and the post-Valsalva LVOT-G of the second echocardiogram is at or above the predetermined post-Valsalva LVOT-G threshold. The third daily dose is then administered to the patient for a third time period (e.g., two weeks).

Titration of the daily dose may be repeated for additional rounds, if desired, to select a fourth daily dose of CK-274, or a pharmaceutically acceptable salt thereof or termination of administration. For example, a third echocardiogram comprising a biplane LVEF and a post-Valsalva LVOT-G may be acquired for the patient after the third time period, and a fourth daily dose of CK-274, or a pharmaceutically acceptable salt thereof, may be selected based on the third echocardiogram and the third daily dose. If the biplane LVEF of the third echocardiogram is below the first predetermined biplane LVEF threshold and the third daily dose is the same as (or lower than) the first daily dose, the administration of CK-274, or a pharmaceutically acceptable salt thereof, may be terminated. If the third daily dose is higher than the first daily dose, and the biplane LVEF of the third echocardiogram is below the first predetermined biplane LVEF threshold, then the fourth daily dose is decreased relative to the third daily dose. If the biplane LVEF of the third echocardiogram is below the first predetermined biplane LVEF threshold and the third daily dose is the same as (or lower than) the first daily dose (e.g., if the third daily dose is the lowest dose), the administration of CK-274, or a pharmaceutically acceptable salt thereof, may be terminated. If the third daily dose is higher than the lowest (e.g., first) daily dose, and the biplane LVEF of the third echocardiogram is below the first predetermined biplane LVEF threshold, then the fourth daily dose is decreased relative to the third daily dose. If the biplane LVEF of the third echocardiogram is at or above the predetermined biplane LVEF threshold and below the second predetermined biplane LVEF threshold, or the biplane LVEF of the third echocardiogram is at or above the second predetermined biplane LVEF threshold and the post-Valsalva LVOT-G of the third echocardiogram is below the predetermined post-Valsalva LVOT-G threshold, then the fourth daily dose may be the same as the third daily dose. If the biplane LVEF of the third echocardiogram is above the second predetermined biplane LVEF threshold and the post-Valsalva LVOT-G of the third echocardiogram is at or above the predetermined post-Valsalva LVOT-G threshold, then the fourth daily dose may be increased relative to the third daily dose.

FIG. 1 illustrates and exemplary method for treating obstructive hypertrophic cardiomyopathy (oHCM) in a patient that included titrating the daily dose of CK-274, or a pharmaceutically acceptable salt thereof. The exemplary method shown in FIG. 1 provides four daily dose levels, with a first daily dose level being the lowest daily dose level, but may be readily modified to include additional or fewer dose levels. The exemplary method shown in FIG. 1 may be further modified such that the first daily dose level is not the lowest daily dose level. At 102, the first daily dose level (e.g., about 5 mg) of CK-274, or a pharmaceutically acceptable salt thereof, is administered to a patient. After a first time period, the daily dose level is increased or maintained, or the administration is terminated, at 104. The selection may be based on a first echocardiogram acquired for the patient after the first time period. Termination of administration 106 may be selected if the biplane LVEF of the first echocardiogram is below a predetermined biplane LVEF threshold (e.g., 50%), wherein the no further dose of CK-274 or pharmaceutically acceptable salt thereof is administered to the patient. Maintenance of the first daily dose level (e.g., about 5 mg) may be selected when either of the following conditions are met on the first echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the first echocardiogram is below a predetermined post-Valsalva LVOT-G threshold (e.g., 30 mmHg). Alternatively, maintenance of the first daily dose level (e.g., about 5 mg) may be selected when the biplane LVEF of the first echocardiogram is at or above the predetermined biplane LVEF threshold (e.g., 50%), the resting LVOT-G of the first echocardiogram is below a predetermined resting LVOT-G threshold (e.g., 30 mmHg), and the post-Valsalva LVOT-G of the first echocardiogram is below a predetermined post-Valsalva LVOT-G threshold (e.g., 50 mmHg). If maintenance is selected, the first daily dose level of CK-274, or a pharmaceutically acceptable salt thereof, is administered to the patient at 102 for a second time period, and, optionally, the daily dose may be re-titrated at 104 after a second time period. The daily dose level may be increased to a second daily dose level (e.g., 10 mg) when either of the following conditions are met on the first echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the first echocardiogram is below a second predetermined post-Valsalva LVOT-G threshold (e.g., 30 mmHg). Alternatively, the daily dose level may be increased to a second daily dose level (e.g., 10 mg) when either of the following conditions are met on the first echocardiogram: (1) the biplane LVEF is at or above the predetermined biplane LVEF threshold (e.g., 50%) and the resting LVOT-G is at or above the predetermined resting LVOT-G threshold (e.g., 30 mmHg), or (2) the biplane LVEF is at or above the predetermined biplane LVEF threshold (e.g., 50%), the resting LVOT-G is below the predetermined resting LVOT-G threshold (e.g., 30 mmHg), and the post-Valsalva LVOT-G is at or above the predetermined post-Valsalva LVOT-G threshold (e.g., 50 mmHg). If an increase in the daily dose level is selected, the second daily dose level of CK-274, or a pharmaceutically acceptable salt thereof, is administered to the patient for the second time period at 108.

If the second daily dose level of CK-274, or a pharmaceutically acceptable salt thereof, (e.g., 10 mg) is administered to the patient at 108, the daily dose may be re-titrated (i.e., select an increase, decrease, or maintenance of the daily dose) based on an echocardiogram at 110. The daily dose may be decreased to the first daily dose level (e.g., from 10 mg to 5 mg) if the biplane LVEF of the echocardiogram is below a predetermined biplane LVEF threshold (e.g., 50%). If the daily dose is decreased to the first daily dose level, the first daily dose level is administered to the patient at 102. Maintenance of the second daily dose level (e.g., about 10 mg) may be selected when either of the following conditions are met on the echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the echocardiogram is below a predetermined post-Valsalva LVOT-G threshold (e.g., 30 mmHg). Alternatively, maintenance of the second daily dose level (e.g., about 10 mg) may be selected when the biplane LVEF of the echocardiogram is at or above the predetermined biplane LVEF threshold (e.g., 50%), the resting LVOT-G of the echocardiogram is below a predetermined resting LVOT-G threshold (e.g., 30 mmHg), and the post-Valsalva LVOT-G of the second echocardiogram is below a predetermined post-Valsalva LVOT-G threshold (e.g., 50 mmHg). If maintenance is selected, the second daily dose level of CK-274, or a pharmaceutically acceptable salt thereof, is administered to the patient at 108 for a further time period, and, optionally, the daily dose may be re-titrated at 110 after said time period. The daily dose level may be increased to a third daily dose level (e.g., 15 mg) when either of the following conditions are met on the echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the echocardiogram is below a second predetermined post-Valsalva LVOT-G threshold (e.g., 30 mmHg). Alternatively, the daily dose level may be increased to a third daily dose level (e.g., 15 mg) when either of the following conditions are met on the echocardiogram: (1) the biplane LVEF is at or above the predetermined biplane LVEF threshold (e.g., 50%) and the resting LVOT-G is at or above the predetermined resting LVOT-G threshold (e.g., 30 mmHg), or (2) the biplane LVEF is at or above the predetermined biplane LVEF threshold (e.g., 50%), the resting LVOT-G is below the predetermined resting LVOT-G threshold (e.g., 30 mmHg), and the post-Valsalva LVOT-G is at or above the predetermined post-Valsalva LVOT-G threshold (e.g., 50 mmHg). If an increase in the daily dose level is selected, the second daily dose level of CK-274, or a pharmaceutically acceptable salt thereof, is administered to the patient for the time period at 112.

If the third daily dose level of CK-274, or a pharmaceutically acceptable salt thereof, (e.g., 10 mg) is administered to the patient at 112, the daily dose may be re-titrated (i.e., select an increase, decrease, or maintenance of the daily dose) based on an echocardiogram at 114. The daily dose may be decreased to the second daily dose level (e.g., from 15 mg to 10 mg) if the biplane LVEF of the echocardiogram is below a predetermined biplane LVEF threshold (e.g., 50%). If the daily dose is decreased to the second daily dose level, the second daily dose level is administered to the patient at 108. Maintenance of the third daily dose level (e.g., about 15 mg) may be selected when either of the following conditions are met on the echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the echocardiogram is below a predetermined post-Valsalva LVOT-G threshold (e.g., 30 mmHg). Alternatively, maintenance of the third daily dose level (e.g., about 15 mg) may be selected when the biplane LVEF of the echocardiogram is at or above the predetermined biplane LVEF threshold (e.g., 50%), the resting LVOT-G of the echocardiogram is below a predetermined resting LVOT-G threshold (e.g., 30 mmHg), and the post-Valsalva LVOT-G of the echocardiogram is below a predetermined post-Valsalva LVOT-G threshold (e.g., 50 mmHg). If maintenance is selected, the third daily dose level of CK-274, or a pharmaceutically acceptable salt thereof, is administered to the patient at 112 for a further time period, and, optionally, the daily dose may be re-titrated at 114 after said time period. The daily dose level may be increased to a fourth daily dose level (e.g., 20 mg) when either of the following conditions are met on the echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the echocardiogram is below a second predetermined post-Valsalva LVOT-G threshold (e.g., 30 mmHg). Alternatively, the daily dose level may be increased to a fourth daily dose level (e.g., 20 mg) when either of the following conditions are met on the echocardiogram: (1) the biplane LVEF is at or above the predetermined biplane LVEF threshold (e.g., 50%) and the resting LVOT-G is at or above the predetermined resting LVOT-G threshold (e.g., 30 mmHg), or (2) the biplane LVEF is at or above the predetermined biplane LVEF threshold (e.g., 50%), the resting LVOT-G is below the predetermined resting LVOT-G threshold (e.g., 30 mmHg), and the post-Valsalva LVOT-G is at or above the predetermined post-Valsalva LVOT-G threshold (e.g., 50 mmHg). If an increase in the daily dose level is selected, the fourth daily dose level of CK-274, or a pharmaceutically acceptable salt thereof, is administered to the patient for the second time period at 116.

In the exemplary method shown in FIG. 1, the first daily dose level is the minimum dose, and therefore may not be further decreased. Nevertheless, in other embodiments, the first daily dose level may be other than the minimum dose, and therefore may be decreased to a lower dose level (e.g., from 10 mg to 5 mg) if the biplane LVEF of the echocardiogram is below a predetermined biplane LVEF threshold (e.g., 50%).

In the exemplary method shown in FIG. 1, the fourth daily dose level is the maximum dose, and therefore may not be further increased. Nevertheless, in other embodiments, additional dose levels may be available and the daily dose may be further increased at 118. The method shown in FIG. 1, at 118 a selection is made to maintain the fourth daily dose level or decrease the daily dose level based on an echocardiogram. The daily dose may be decreased to the third daily dose level (e.g., from 20 mg to 15 mg) if the biplane LVEF of the echocardiogram is below a predetermined biplane LVEF threshold (e.g., 50%). If the daily dose is decreased to the third daily dose level, the second daily dose level is administered to the patient at 112. Maintenance of the third daily dose level (e.g., about 20 mg) may be selected when either of the following conditions are met on the echocardiogram: (1) the biplane LVEF is at or above the predetermined biplane LVEF threshold (e.g., 50%) and below a second predetermined biplane LVEF threshold (e.g., 55%); or (2) the biplane LVEF is at or above the second predetermined biplane LVEF threshold (e.g., 55%) and the post-Valsalva LVOT-G of the echocardiogram is below a predetermined post-Valsalva LVOT-G threshold (e.g., 30 mmHg). Alternatively, maintenance of the third daily dose level (e.g., about 15 mg) may be selected when the biplane LVEF of the echocardiogram is at or above the predetermined biplane LVEF threshold (e.g., 50%), the resting LVOT-G of the echocardiogram is below a predetermined resting LVOT-G threshold (e.g., 30 mmHg), and the post-Valsalva LVOT-G of the echocardiogram is below a predetermined post-Valsalva LVOT-G threshold (e.g., 50 mmHg). If maintenance is selected, the third daily dose level of CK-274, or a pharmaceutically acceptable salt thereof, is administered to the patient at 116 for a further time period, and, optionally, the daily dose may be re-titrated at 118 after said time period.

Exemplary daily dose increases include an increase from about 5 mg to about 10 mg CK-274, about 10 mg to about 15 mg CK-274, about 10 mg to about 20 mg CK-274, or about 20 mg to about 30 mg. Other dose increases may be readily envisioned, for instance, increasing a given initial daily dose by about 1 mg, about 2 mg, about 3 mg, about 4 mg, about 5 mg, or about 10 mg, or any amount therebetween. Exemplary daily dose decreases include a decrease from about 30 mg to about 20 mg, about 20 mg to about 10 mg, about 15 mg to about 10 mg, or about 10 mg to about 5 mg. Other dose decreases may be readily envisioned, for instance, decreasing a given initial daily dose by about 1 mg, about 2 mg, about 3 mg, about 4 mg, about 5 mg, or about 10 mg, or any amount therebetween.

Exemplary embodiments of the methods described herein comprise administering a first daily dose (e.g., a first daily dose of between about 1 mg and about 20 mg, such as 1 mg, 2 mg, 3 mg, 4 mg, 5 mg, 6 mg, 7 mg, 8 mg, 9 mg, 10 mg, 15 mg, or 20 mg) or any amount therebetween) of CK-274, or a pharmaceutically acceptable salt thereof, for a first period (e.g., about one week, two weeks, three weeks, four weeks, five weeks, six weeks, seven weeks, eight weeks, nine weeks, ten weeks, twelve weeks, or any length of time therebetween), followed by maintaining the daily dose, decreasing the daily dose (e.g., decreasing the daily dose by between about 1 mg and about 10 mg, such as decreasing the daily dose by 1 mg, 2 mg, 3 mg, 4 mg, 5 mg 6 mg, 7 mg, 8 mg, 9 mg, or 10 mg, or any amount therebetween), increasing the daily dose (e.g., increasing the daily dose by between about 1 mg and about 10 mg, such as increasing the daily dose by 1 mg, 2 mg, 3 mg, 4 mg, 5 mg 6 mg, 7 mg, 8 mg, 9 mg, or 10 mg, or any amount therebetween), or terminating administration based on the resting LVOT-G, biplane LVEF, and/or post-Valsalva LVOT-G of the patient to arrive at a second daily dose. Another exemplary embodiment of the methods described herein comprises administering a first daily dose of CK-274, or a pharmaceutically acceptable salt thereof, for about two weeks, followed by maintaining the daily dose, decreasing the daily dose by about 5 mg, increasing the daily dose by about 5 mg, or terminating administration based on the resting LVOT-G, biplane LVEF, and/or post-Valsalva LVOT-G of the patient to arrive at a second daily dose. Another exemplary embodiment of the methods described herein comprises administering a first daily dose of CK-274, or a pharmaceutically acceptable salt thereof, for about three weeks, followed by maintaining the daily dose, decreasing the daily dose by about 5 mg, increasing the daily dose by about 5 mg, or terminating administration based on the resting LVOT-G, biplane LVEF, and/or post-Valsalva LVOT-G of the patient to arrive at a second daily dose. Another exemplary embodiment of the methods described herein comprises administering a first daily dose of CK-274, or a pharmaceutically acceptable salt thereof, for about two weeks, followed by maintaining the daily dose, decreasing the daily dose by about 10 mg, increasing the daily dose by about 10 mg, or terminating administration based on the resting LVOT-G, biplane LVEF, and/or post-Valsalva LVOT-G of the patient to arrive at a second daily dose. Another exemplary embodiment of the methods described herein comprises administering a first daily dose of CK-274, or a pharmaceutically acceptable salt thereof, for about three weeks, followed by maintaining the daily dose, decreasing the daily dose by about 10 mg, increasing the daily dose by about 10 mg, or terminating administration based on the resting LVOT-G, biplane LVEF, and/or post-Valsalva LVOT-G of the patient to arrive at a second daily dose. Another exemplary embodiment of the methods described herein comprises administering a first daily dose of CK-274, or a pharmaceutically acceptable salt thereof, for between about 2 and about 12 weeks, followed by maintaining the daily dose, decreasing the daily dose by about 10 mg, increasing the daily dose by about 10 mg, or terminating administration based on the resting LVOT-G, biplane LVEF, and/or post-Valsalva LVOT-G of the patient to arrive at a second daily dose.

Treatment for hypertrophic cardiomyopathy can result in improved exercise capacity and/or relieve symptoms in patients with hyperdynamic ventricular contraction resulting from hypertrophic cardiomyopathy. In some embodiments, the method includes administering a therapeutically effective daily dose of CK-274, or a pharmaceutically acceptable salt thereof, to an individual with hypertrophic cardiomyopathy, thereby improving the exercise capacity of the individual. In some embodiments, the method includes administering a therapeutically effective daily dose of CK-274, or a pharmaceutically acceptable salt thereof, to an individual with hypertrophic cardiomyopathy, thereby relieving one or more symptoms of hyperdynamic ventricular contraction. In some embodiments, the method includes administering a therapeutically effective daily dose of CK-274, or a pharmaceutically acceptable salt thereof, in combination with disopyramide to an individual with hypertrophic cardiomyopathy, thereby improving the exercise capacity of the individual. In some embodiments, the method includes administering a therapeutically effective daily dose of CK-274, or a pharmaceutically acceptable salt thereof, in combination with disopyramide to an individual with hypertrophic cardiomyopathy, thereby relieving one or more symptoms of hyperdynamic ventricular contraction.

In some embodiments, a therapeutically effective amount of CK-274, or a pharmaceutically acceptable salt thereof, is administered to a patient with hypertrophic cardiomyopathy, thereby decreasing resting LVOT-G in the patient. In some embodiments, the patient has a baseline resting LVOT-G of about 30 mmHg or more, about 40 mmHg or more, or about 50 mmHg or more. In response to administration of the therapeutically effective amount of CK-274, or a pharmaceutically acceptable salt thereof, the resting LVOT-G can decrease to less than 30 mmHg, for example to about 25 mmHg or less, about 20 mmHg or less, or about 15 mmHg or less. In some embodiments, in response to administration of the therapeutically effective amount of CK-274, or a pharmaceutically acceptable salt thereof, the resting LVOT-G decreases by about 10 mmHg or more, about 15 mmHg or more, about 20 mmHg or more, about 25 mmHg or more, about 30 mmHg or more, or about 35 mmHg or more. In some embodiments, in response to administration of the therapeutically effective amount of CK-274, or a pharmaceutically acceptable salt thereof, the resting LVOT-G decreases by about 10 mmHg to about 40 mmHg. The decrease in resting LVOT-G may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy, thereby decreasing post-Valsalva LVOT-G in the patient. In some embodiments, a therapeutically effective amount of CK-274, or a pharmaceutically acceptable salt thereof, is administered in combination with disopyramide to a patient with hypertrophic cardiomyopathy, thereby decreasing post-Valsalva LVOT-G in the patient. In some embodiments, the patient has a baseline post-Valsalva LVOT-G of about 30 mmHg or more, about 40 mmHg or more, 50 mmHg or more, about 60 mmHg or more, or about 70 mmHg or more. In response to administration of the therapeutically effective amount of CK-274, or a pharmaceutically acceptable salt thereof, the post-Valsalva LVOT-G can decrease to less than 50 mmHg, for example to about 45 mmHg or less, about 40 mmHg or less, about 35 mmHg or less, or about 30 mmHg or less. In some embodiments, in response to administration of the therapeutically effective amount of CK-274, or a pharmaceutically acceptable salt thereof, the post-Valsalva LVOT-G decreases by about 10 mmHg or more, about 15 mmHg or more, about 20 mmHg or more, about 25 mmHg or more, about 30 mmHg or more, or about 35 mmHg or more. In some embodiments, in response to administration of the therapeutically effective amount of CK-274, or a pharmaceutically acceptable salt thereof, the post-Valsalva LVOT-G decreases by about 10 mmHg to about 40 mmHg. The decrease in post-Valsalva LVOT-G may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy to treat the hypertrophic cardiomyopathy, wherein the biplane LVEF is maintained at or above 50%. In some embodiments, a therapeutically effective amount of CK-274, or a pharmaceutically acceptable salt thereof, is administered in combination with disopyramide to a patient with hypertrophic cardiomyopathy to treat the hypertrophic cardiomyopathy, wherein the biplane LVEF is maintained at or above 50%. In some embodiments, in response to administration of the therapeutically effective amount of CK-274, or a pharmaceutically acceptable salt thereof, the biplane LVEF decreases by less than about 20%, less than about 15%, less than about 10%, or less than about 5%. The maintenance interval of the biplane LVEF may be about 1 week or longer, about 2 weeks or longer, about 3 weeks or longer, about 4 weeks or longer, about 5 weeks or longer, about 6 weeks or longer, about 8 weeks or longer, or about 10 weeks or longer of daily dose administration.

In some embodiments, a therapeutically effective amount of CK-274, or a pharmaceutically acceptable salt thereof, is administered to a patient with hypertrophic cardiomyopathy, thereby decreasing a left ventricle mass index (LVMI) for the patient. In response to administration of the therapeutically effective amount of CK-274, or a pharmaceutically acceptable salt thereof, the LVMI can decrease by about 1 $g/m^2$ or more, by about 1.5 $g/m^2$ or more, by about 2 $g/m^2$ or more, by about 2.5 $g/m^2$ or more, by about 3 $g/m^2$ or more, by about 3.5 $g/m^2$ or more, or by about 4 $g/m^2$ or more. In some embodiments, in response to administration of the therapeutically effective amount of CK-274, or a pharmaceutically acceptable salt thereof, the LVMI decreases by about 1 $g/m^2$ to about 10 $g/m^2$ mmHg, such as by about 1 $g/m^2$ to about 6 $g/m^2$, or about 2 $g/m^2$ to about 5 $g/m^2$. The decrease in LVMI may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy, thereby decreasing a left arterial volume index (LAVI) for the patient. In response to administration of the therapeutically effective amount of CK-274, or a pharmaceutically acceptable salt thereof, the LAVI can decrease by about 0.5 $mL/m^2$ or more, by about 1 $mL/m^2$ or more, by about 1.5 $mL/m^2$ or more, by about 2 $mL/m^2$ or more, or by about 2.5 $mL/m^2$ or more. In some embodiments, in response to administration of the therapeutically effective amount of CK-274, or a pharmaceutically acceptable salt thereof, the LAVI decreases by about 0.5 $mL/m^2$ to about 5 $mL/m^2$ mmHg, such as by about 0.5 $mL/m^2$ to about 4 $g/m^2$, or about 1 $mL/m^2$ to about 3 $mL/m^2$. The decrease in LAVI may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy, thereby decreasing an e' value for the patient. In response to administration of the therapeutically effective amount of CK-274, or a pharmaceutically acceptable salt thereof, the e' value can decrease by about 0.1 cm/s or more, by about 0.15 cm/s or more, by about 0.2 cm/s or more, or by about 0.25 cm/s or more. In some embodiments, in response to administration of the therapeutically effective amount of CK-274, or a pharmaceutically acceptable salt thereof, the e' value decreases by about 0.05 cm/s to about 0.3 cm/s, such as by about 0.1 cm/s to about 0.25 cm/s, or about 0.15 cm/s to about 0.25 cm/s. The decrease in e' value may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy, thereby decreasing a lateral E/e' ratio for the patient. In response to administration of the therapeutically effective amount of CK-274, or a pharmaceutically acceptable salt thereof, the lateral E/e' ratio can decrease by about 0.5 or more, by 1 or more, by about 1.2 or more, by about 1.5 or more, or by about 1.8 or more. In some embodiments, in response to administration of the therapeutically effective amount of CK-274, or a pharmaceutically acceptable salt thereof, the lateral E/e' ratio decreases by about 0.5 to about 2, such as by about 1 to about 1.8, or about 1.5 to about 1.8. The decrease in lateral E/e' ratio may occur after about 1 week, after about 2 weeks, after about 3 weeks, after about 4 weeks, after about 5 weeks, after about 6 weeks, after about 8 weeks, or after about 10 weeks of daily dose administration.

In some embodiments, a therapeutically effective amount of CK-274, or a pharmaceutically acceptable salt thereof, is administered to a patient with hypertrophic cardiomyopathy, thereby decreasing a likelihood of systolic anterior motion (SAM) of the mitral valve leaflet for the patient.

In some embodiments, a therapeutically effective amount of CK-274, or a pharmaceutically acceptable salt thereof, is administered to a patient with hypertrophic cardiomyopathy, thereby decreasing a likelihood of mitral regurgitation or eccentric mitral regurgitation for the patient.

In some embodiments, a therapeutically effective amount of CK-274, or a pharmaceutically acceptable salt thereof, is administered to a patient with hypertrophic cardiomyopathy, thereby decreasing a level of brain natriuretic peptide or N-terminal prohormone of brain natriuretic peptide (NT-proBNP) in the patient. The decrease in a level of brain natriuretic peptide or N-terminal prohormone of brain natriuretic peptide (NT-proBNP) in the patient may occur after about 1 week, after about 2 weeks, after about 3 weeks, after about 4 weeks, after about 5 weeks, after about 6 weeks, after about 8 weeks, or after about 10 weeks of daily dose administration. In some embodiments of the foregoing, the hypertrophic cardiomyopathy is obstructive hypertrophic cardiomyopathy (oHCM).

In some embodiments, a therapeutically effective amount of CK-274, or a pharmaceutically acceptable salt thereof, is administered to a patient with hypertrophic cardiomyopathy, thereby decreasing a level of cardiac troponin I. The decrease in a level of cardiac troponin I in the patient may occur after about 1 week, after about 2 weeks, after about 3 weeks, after about 4 weeks, after about 5 weeks, after about 6 weeks, after about 8 weeks, or after about 10 weeks of daily dose administration. In some embodiments of the foregoing, the hypertrophic cardiomyopathy is obstructive hypertrophic cardiomyopathy (oHCM).

In some embodiments of any of the foregoing, the patient with hypertrophic cardiomyopathy is classified as NYHA class III when administration with CK-274, or a pharmaceutically acceptable salt thereof, is initiated. In some embodiments, the patient with hypertrophic cardiomyopathy is classified as NYHA class II when administration with CK-274, or a pharmaceutically acceptable salt thereof, is initiated.

In some embodiments of any of the foregoing, administration of CK-274, or a pharmaceutically acceptable salt thereof, to a patient with hypertrophic cardiomyopathy further results in decreased left ventricular wall stress and/or decreased myocardial injury in the patient. Reductions in left ventricular wall stress may be measured by reductions in serum NT-proBNP levels. Decreases in myocardial injury may be measured by changes in hs-troponin. The decrease in left ventricular wall stress and/or the decrease in myocardial injury in the patient may occur after about 1 week, after about 2 weeks, after about 3 weeks, after about 4 weeks, after about 5 weeks, after about 6 weeks, after about 8 weeks, or after about 10 weeks of daily dose administration. In some embodiments of the foregoing, the hypertrophic cardiomyopathy is obstructive hypertrophic cardiomyopathy (oHCM).

In some embodiments of any of the foregoing, administration of CK-274, or a pharmaceutically acceptable salt thereof, to a patient with obstructive hypertrophic cardiomyopathy results in an improvement in exercise capacity in the patient. In some embodiments of any of the foregoing, administration of CK-274, or a pharmaceutically acceptable salt thereof, to a patient with obstructive hypertrophic cardiomyopathy results in an improvement in exercise capacity in the patient, for example as measured by change in peak oxygen uptake ($pVO_2$) or change in peak oxygen uptake ($pVO_2$) by cardiopulmonary exercise testing (CPET).

In some embodiments of any of the foregoing, administration of CK-274, or a pharmaceutically acceptable salt thereof, to a patient with obstructive hypertrophic cardiomyopathy results in an improvement in total workload during CPET.

In some embodiments of any of the foregoing, administration of CK-274, or a pharmaceutically acceptable salt thereof, to a patient with obstructive hypertrophic cardiomyopathy results in an improvement in other CPET parameters, including but not limited to one or more of: (1) ventilator efficiency ($VE/VCO_2$ slope); (2) circulatory power ($VO_2$×systolic BP); and (3) ventilator anaerobic threshold (VAT).

In some embodiments of any of the foregoing, administration of CK-274, or a pharmaceutically acceptable salt thereof, to a patient with obstructive hypertrophic cardiomyopathy results in an improvement in patient health status. In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-Overall Summary Score (KCCQ-OSS). In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-Clinical Summary Score (KCCQ-CSS). In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-Total Symptom Score (KCCQ-TSS). In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-Physical Limitation Score (KCCQ-PLS). In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-Social Limitation Score (KCCQ-SLS). In some embodiments of any of the foregoing, administration of CK-274, or a pharmaceutically acceptable salt thereof, to a patient with obstructive hypertrophic cardiomyopathy results in an improvement in patient health status as determined by changes in the Kansas City Cardiomyopathy Questionnaire-quality of live (KCCQ-QoL). In some embodiments, administration of CK-274, or a pharmaceutically acceptable salt thereof, to a patient with obstructive hypertrophic cardiomyopathy results in improvement in one or more KCCQ domain scores (such as KCCQ-OSS, KCCQ-CSS, KCCQ-TSS, KCCQ-PLS, KCCQ-SLS, or KCCQ-QoL) by at least about 5 points, at least about 10 points, or at least about 20 points. In some embodiments, administration of CK-274, or a pharmaceutically acceptable salt thereof, to a patient with obstructive hypertrophic cardiomyopathy results in improvement in one or more KCCQ score (such as KCCQ-OSS, KCCQ-CSS, KCCQ-TSS, KCCQ-PLS, KCCQ-SLS, or KCCQ-QoL) by between about 5 points and less than 10 points, between about 10 points and less than 20 points, or by at least 20 points. In some such embodiments, the improvement in the one or more KCCQ domain scores is an improvement in KCCQ-OSS. In some embodiments, the improvement in the one or more KCCQ domain scores is sustained for about 6 months. In some embodiments, administration of CK-274, or a pharmaceutically acceptable salt thereof, to a patient with obstructive hypertrophic cardiomyopathy results in improvement in KCCQ-CSS by 1 point, 2 points, 3 points, 4 points, 5 points, or more than 5 points. In some embodiments of any of the foregoing, administration of CK-274, or a pharmaceutically acceptable salt thereof, to a patient with obstructive hypertrophic cardiomyopathy results in an improvement in patient health status and health-related quality of life as measured by PRO questionnaire, as determined by changes from responses to the EuroQol 5-dimension 5-level instrument (EQ-5D-5L).

Combinations of the foregoing are also contemplated. In some embodiments of any of the foregoing, administration of CK-274, or a pharmaceutically acceptable salt thereof, to a patient with obstructive hypertrophic cardiomyopathy results in an improvement in exercise capacity and functional class, for instance, as determined by (1) change from baseline of ≥1.5 mL/kg/min in $pVO_2$ and ≥1 class improvement in NYHA Functional Class; or (2) change from baseline of ≥3.0 mL/kg/min in $pVO_2$ and no worsening of NYHA Functional Class. In some embodiments of any of the foregoing, administration of CK-274, or a pharmaceutically acceptable salt thereof, to a patient with obstructive hypertrophic cardiomyopathy results in resting LVOT-G<30 mmHg, post-Valsalva LVOT-G<50 mmHg, and NYHA Functional Class I in the patient. In some embodiments of any of the foregoing, administration of CK-274, or a pharmaceutically acceptable salt thereof, to a patient with obstructive hypertrophic cardiomyopathy results in resting LVOT-G<30 mmHg, post-Valsalva LVOT-G<50 mmHg, and ≥1 class improvement in NYHA Functional Class in the patient.

In some embodiments, administration with CK-274, or a pharmaceutically acceptable salt thereof, to a patient with hypertrophic cardiomyopathy results in a sustained effect for at least 10 weeks, 12 weeks, 6 months, 1 year, 2 years, 3 years, 4 years, or 5 years. In some embodiments, administration with CK-274, or a pharmaceutically acceptable salt thereof, to a patient with hypertrophic cardiomyopathy results in a sustained effect for at least 6 months. In some embodiments, administration with CK-274, or a pharmaceutically acceptable salt thereof, to a patient with hypertrophic cardiomyopathy results in a sustained effect for at least 1 year. In some embodiments, administration with CK-274, or a pharmaceutically acceptable salt thereof, to a patient with hypertrophic cardiomyopathy results in a sustained effect for at least 5 years. Sustained effects include, for example, one or more effects selected from the group consisting of: reduction in resting LVOT-G to less than 30 mmHg; reduction in post-Valsalva LVOT-G to less than 50 mmHg; improvement in mitral regurgitation; improvement in cardiac relaxation; beneficial cardiac remodeling; reverse cardiac remodeling; beneficial cardiac structural remodeling; beneficial cardiac functional remodeling; reversal of adverse cardiac remodeling; reduction in mean left ventricular mass index (LVMI); improvement in left ventricular (LV) filling pressures; reduction in left atrial volume index (LAVI); reduction in the categorical assessment of systolic anterior motion of the mitral valve leaflet; reduction in systolic anterior motion of the mitral valve leaflet; reduction in the frequency of eccentric mitral regurgitation; reduction in mitral regurgitation; reduction in lateral E/e'; reduction in lateral E/E; reduction in brain natriuretic peptide (BNP) levels; reduction in N-terminal prohormone of brain natriuretic peptide (NT-proBNP) levels; reduction in cardiac troponin I levels; decreased left ventricular wall stress; decreased myocardial injury; and reduction in heart failure symptoms, for example, reduction in NYHA classification.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

CK-274 can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see Remington's Pharmaceutical Sciences, Mack Publishing Company, Easton, Pennsylvania.

In some embodiments, CK-274 or pharmaceutical composition containing CK-274 will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

ENUMERATED EMBODIMENTS

Embodiment 1. A method of reducing resting left ventricular outflow tract pressure gradient (LVOT-G) to less than 30 mmHg in a patient with obstructive hypertrophic cardiomyopathy (oHCM) comprising administering to the patient a therapeutically effective amount of Compound 1, or a pharmaceutically acceptable salt thereof.

Embodiment 2. The method of embodiment 1, wherein the reduction in resting LVOT-G to less than 30 mmHg occurs within ten weeks of initiating treatment with Compound 1, or a pharmaceutically acceptable salt thereof.

Embodiment 3. The method of embodiment 1, wherein the reduction in resting LVOT-G to less than 30 mmHg occurs within two weeks of initiating treatment with Compound 1, or a pharmaceutically acceptable salt thereof.

Embodiment 4. The method of any one of embodiments 1-3, wherein the reduction in resting LVOT-G is sustained for at least 10 weeks of treatment.

Embodiment 5. The method of any one of embodiments 1-4, wherein the reduction in resting LVOT-G peaks within two to six weeks of the end of a dose titration.

Embodiment 6. A method of reducing post-Valsalva left ventricular outflow tract pressure gradient (LVOT-G) to less than 50 mmHg in a patient with obstructive hypertrophic cardiomyopathy (oHCM) comprising administering to the patient a therapeutically effective amount of Compound 1, or a pharmaceutically acceptable salt thereof.

Embodiment 7. The method of embodiment 6, wherein the reduction in post-Valsalva LVOT-G to less than 50 mmHg occurs within two weeks of initiating treatment with Compound 1, or a pharmaceutically acceptable salt thereof.

Embodiment 8. The method of embodiment 6 or 7, wherein the reduction in post-Valsalva LVOT-G is sustained for at least 10 weeks of treatment.

Embodiment 9. The method of any one of embodiments 6-8, wherein the reduction in post-Valsalva LVOT-G peaks within two to six weeks of the end of a dose titration.

Embodiment 10. A method of treating obstructive hypertrophic cardiomyopathy (oHCM) in a patient in need thereof, comprising administering to the patient a therapeutically effective amount of Compound 1, or a pharmaceutically acceptable salt thereof, wherein the therapeutically effective amount of Compound 1, or a pharmaceutically acceptable salt thereof, is selected by titrating a daily dose of Compound 1, or a pharmaceutically acceptable salt thereof, administered to the patient.

Embodiment 11. The method of embodiment 10, wherein the dose is titrated once during a course of treatment.

Embodiment 12. The method of embodiment 10, wherein the dose is titrated two or more times during a course of treatment.

Embodiment 13. The method of any one of embodiments 10-12, wherein a daily dose is administered to a patient at a constant amount for about two weeks before the daily dose amount is titrated.

Embodiment 14. The method of any one of embodiments 1-13, wherein Compound 1, or a pharmaceutically acceptable salt thereof is administered at a daily dose of about 5 mg to about 30 mg.

Embodiment 15. The method of embodiment 14, wherein the daily dose is about 5 mg.

Embodiment 16. The method of embodiment 14, wherein the daily dose is about 10 mg.

Embodiment 17. The method of embodiment 14, wherein the daily dose is about 15 mg.

Embodiment 18. The method of embodiment 14, wherein the daily dose is about 20 mg.

Embodiment 19. The method of embodiment 14, wherein the daily dose is about 30 mg.

Embodiment 20. The method of any one of embodiments 10-19, wherein the daily dose is administered as a single dose each day.

Embodiment 21. The method of any one of embodiments 10-19, wherein the daily dose is administered in 2 divided doses.

Embodiment 22. A method of treating obstructive hypertrophic cardiomyopathy (oHCM) in a patient in need thereof, comprising:
  administering to the patient a first daily dose of Compound 1, or a pharmaceutically acceptable salt thereof, for a first time period; and
  based on one or more components of a first echocardiogram for the patient acquired after the first time period, administering to the patient a second daily dose of Compound 1, or a pharmaceutically acceptable salt thereof, for a second time period or terminating the administering of Compound 1, or a pharmaceutically acceptable salt thereof, to the patient.

Embodiment 23. The method of embodiment 22, comprising selecting the second daily dose of Compound 1, or a pharmaceutically acceptable salt thereof, based on the one or more components of the first echocardiogram.

Embodiment 24. The method of embodiment 22 or 23, wherein the one or more components of the first echocardiogram comprises a biplane LVEF, a post-Valsalva LVOT-G, or a resting LVOT-G.

Embodiment 25. The method of embodiment 22 or 23, wherein the one or more components of the first echocardiogram comprises a biplane LVEF, a post-Valsalva LVOT-G, and a resting LVOT-G.

Embodiment 26. The method of embodiment 22 or 23, wherein the one or more components of the first echocardiogram comprises a biplane LVEF and a post-Valsalva LVOT-G.

Embodiment 27. The method of any one of embodiments 22-26, wherein the one or more components of the first echocardiogram comprises a biplane LVEF, and the second daily dose of Compound 1, or a pharmaceutically acceptable salt thereof, is lower than the first daily dose of Compound 1, or a pharmaceutically acceptable salt thereof, when the biplane LVEF of the first echocardiogram is below a predetermined biplane LVEF threshold.

Embodiment 28. The method of any one of embodiments 22-26, wherein the one or more components of the first echocardiogram comprises a biplane LVEF, and the administering of Compound 1, or a pharmaceutically acceptable salt thereof, to the patient is terminated when the biplane LVEF of the first echocardiogram is below a predetermined biplane LVEF threshold.

Embodiment 29. The method of embodiment 27 or 28, wherein the predetermined biplane LVEF threshold is 50%.

Embodiment 30. The method of any one of embodiments 22-29, wherein the one or more components of the first echocardiogram comprises a biplane LVEF, a resting LVOT-G, and a post-Valsalva LVOT-G, and wherein the second daily dose of Compound 1, or a pharmaceutically acceptable salt thereof, is the same as the first daily dose of Compound 1, or a pharmaceutically acceptable salt thereof, when the biplane LVEF of the first echocardiogram is at or above the predetermined biplane LVEF threshold, the resting LVOT-G of the first echocardiogram is below a predetermined resting LVOT-G threshold, and the post-Valsalva LVOT-G of the first echocardiogram is below a predetermined post-Valsalva LVOT-G threshold.

Embodiment 31. The method of any one of embodiments 22-30, wherein the one or more components of the first echocardiogram comprises a biplane LVEF, a resting LVOT-G, and a post-Valsalva LVOT-G, and wherein the second daily dose of Compound 1, or a pharmaceutically acceptable salt thereof, is greater than the first daily dose of Compound 1, or a pharmaceutically acceptable salt thereof, when either of the following conditions are met on the first echocardiogram: (1) the biplane LVEF is at or above the predetermined biplane LVEF threshold and the resting LVOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold.

Embodiment 32. The method of embodiment 30 or 31, wherein the predetermined biplane LVEF threshold is 50%, the predetermined resting LVOT-G threshold is 30 mmHg, and the post-Valsalva LVOT-G threshold is 50 mmHg.

Embodiment 33. The method of any one of embodiments 22-29, wherein the one or more components of the first echocardiogram comprises a biplane LVEF and a post-Valsalva LVOT-G, and wherein the second daily dose of Compound 1, or a pharmaceutically acceptable salt thereof, is the same as the first daily dose of Compound 1, or a pharmaceutically acceptable salt thereof, when either of the following conditions are met on the first echocardiogram: (1) the biplane LVEF is at or above the predetermined biplane LVEF threshold and below a second predetermined biplane LVEF threshold; or (2) the biplane LVEF is at or above the second predetermined biplane LVEF threshold and the post-Valsalva LVOT-G of the first echocardiogram is below a second predetermined post-Valsalva LVOT-G threshold.

Embodiment 34. The method of any one of embodiments 22-29 and 33, wherein the one or more components of the first echocardiogram comprises a biplane LVEF and a post-Valsalva LVOT-G, and wherein the second daily dose of Compound 1, or a pharmaceutically acceptable salt thereof, is greater than the first daily dose of Compound 1 when the biplane LVEF of the first echocardiogram is above the second predetermined biplane LVEF threshold and the post-Valsalva LVOT-G of the first echocardiogram is at or above the second predetermined post-Valsalva LVOT-G threshold.

Embodiment 35. The method of embodiment 33 or 34, wherein the predetermined biplane LVEF threshold is 50%, the second predetermined biplane LVEF threshold is 55%, and the second predetermined post-Valsalva LVOT-G threshold is 30 mmHg.

Embodiment 36. The method of any one of embodiments 22-35, wherein the first daily dose of Compound 1, or a pharmaceutically acceptable salt thereof, is about 5 mg of Compound 1.

Embodiment 37. The method of embodiment 36, wherein the second daily dose of Compound 1, or a pharmaceutically acceptable salt thereof, is about 5 mg or about 10 mg of Compound 1.

Embodiment 38. The method of any one of embodiments 22-37, further comprising measuring the one or more components of the first echocardiogram.

Embodiment 39. The method of any one of embodiments 22-38, wherein the first time period is about 2 weeks.

Embodiment 40. The method of any one of embodiments 22-39, wherein the second time period is about 2 weeks.

Embodiment 41. The method of any one of embodiments 22-40, wherein the second daily dose of Compound 1, or a pharmaceutically acceptable salt thereof, is administered to the patient for the second time period, the method further comprising, based on one or more components of a second echocardiogram for the patient acquired after the second time period and the second daily dose of Compound 1, or a pharmaceutically acceptable salt thereof, administering to the patient a third daily dose of Compound 1, or a pharmaceutically acceptable salt thereof for a third time period or terminating the administering of Compound 1, or a pharmaceutically acceptable salt thereof to the patient.

Embodiment 42. The method of embodiment 41, comprising selecting the third daily dose of Compound 1, or a pharmaceutically acceptable salt thereof, based on the one or more components of the second echocardiogram and the second daily dose.

Embodiment 43. The method of embodiment 41 or 42, wherein the one or more components of the second echocardiogram comprises a biplane LVEF, a post-Valsalva LVOT-G, or a resting LVOT-G.

Embodiment 44. The method of embodiment 41 or 42, wherein the one or more components of the second echocardiogram comprises a biplane LVEF, a post-Valsalva LVOT-G, and a resting LVOT-G.

Embodiment 45. The method of embodiment 41 or 42, wherein the one or more components of the second echocardiogram comprises a biplane LVEF and a post-Valsalva LVOT-G.

Embodiment 46. The method of any one of embodiments 41-45, wherein the one or more components of the second echocardiogram comprises a biplane LVEF, and the third daily dose of Compound 1, or a pharmaceutically acceptable salt thereof, is lower than the second daily dose of Compound 1, or a pharmaceutically acceptable salt thereof, or the administering of Compound 1, or a pharmaceutically acceptable salt thereof, to the patient is terminated, when the biplane LVEF of the second echocardiogram is below the predetermined biplane LVEF threshold.

Embodiment 47. The method of embodiment 46, wherein the administering of Compound 1, or a pharmaceutically acceptable salt thereof, to the patient is terminated when the biplane LVEF of the second echocardiogram is below the predetermined biplane LVEF threshold and the second daily dose of Compound 1, or a pharmaceutically acceptable salt thereof is the same as the first daily dose of Compound 1 or lower.

Embodiment 48. The method of embodiment 46, wherein the third daily dose of Compound 1, or a pharmaceutically acceptable salt thereof, is the same as the first daily dose of Compound 1, or a pharmaceutically acceptable salt thereof, when the second daily dose of Compound 1, or a pharmaceutically acceptable salt thereof, is higher than the first daily dose of Compound 1, or a pharmaceutically acceptable salt thereof, and the biplane LVEF of the second echocardiogram is below the predetermined biplane LVEF threshold.

Embodiment 49. The method of any one of embodiments 46-48, wherein the predetermined biplane LVEF threshold is 50%.

Embodiment 50. The method of any one of embodiments 41-49, wherein the one or more components of the second echocardiogram comprises a biplane LVEF, a resting LVOT-G, and a post-Valsalva LVOT-G, and wherein the third daily dose of Compound 1, or a pharmaceutically acceptable salt thereof, is the same as the second daily dose of Compound 1, or a pharmaceutically acceptable salt thereof when the biplane LVEF of the second echocardiogram is at or above the predetermined biplane LVEF threshold, the resting LVEOT-G of the second echocardiogram is below the predetermined resting LVOT-G threshold, and the post-Valsalva LVOT-G of the second echocardiogram is below the predetermined post-Valsalva LVOT-G threshold.

Embodiment 51. The method of any one of embodiments 41-50, wherein the one or more components of the second echocardiogram comprises a biplane LVEF, a resting LVOT-G, and a post-Valsalva LVOT-G, and wherein the third daily dose of Compound 1, or a pharmaceutically acceptable salt thereof, is greater than the second daily dose of Compound 1, or a pharmaceutically acceptable salt thereof, when either of the following conditions are met on the second echocardiogram: (1) the biplane LVEF is at or above the predetermined biplane LVEF threshold and the resting LVEOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold.

Embodiment 52. The method of embodiment 50 or 51, wherein the predetermined biplane LVEF threshold is 50%, the predetermined resting LVOT-G threshold is 30 mmHg, and the post-Valsalva LVOT-G threshold is 50 mmHg.

Embodiment 53. The method of any one of embodiments 41-49, wherein the one or more components of the second echocardiogram comprises a biplane LVEF and a post-Valsalva LVOT-G, and wherein the third daily dose of Compound 1, or a pharmaceutically acceptable salt thereof, is the same as the second daily dose of Compound 1, or a pharmaceutically acceptable salt thereof, when either of the following conditions are met on the second echocardiogram: (1) the biplane LVEF is at or above the predetermined biplane LVEF threshold and below the second predetermined biplane LVEF threshold; or (2) the biplane LVEF is at or above the second predetermined biplane LVEF threshold and the post-Valsalva LVOT-G is below the second predetermined post-Valsalva LVOT-G threshold.

Embodiment 54. The method of any one of embodiments 41-49 and 53, wherein the one or more components of the second echocardiogram comprises a biplane LVEF and a post-Valsalva LVOT-G, and wherein the third daily dose of Compound 1, or a pharmaceutically acceptable salt thereof, is greater than the second daily dose of Compound 1, or a pharmaceutically acceptable salt thereof, when the biplane LVEF of the second echocardiogram is above the second predetermined biplane LVEF threshold and the post-Valsalva LVOT-G of the second echocardiogram is at or above the second predetermined post-Valsalva LVOT-G threshold.

Embodiment 55. The method of embodiment 53 or 54, wherein the predetermined biplane LVEF threshold is 50%, the second predetermined biplane LVEF threshold is 55%, and the second predetermined post-Valsalva LVOT-G threshold is 30 mmHg.

Embodiment 56. The method of any one of embodiments 41-55, wherein the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, and the third daily dose of Compound 1, or a pharmaceutically acceptable salt thereof, is about 5 mg, about 10 mg, or about 15 mg of Compound 1.

Embodiment 57. The method of any one of embodiments 41-56, further comprising measuring the one or more components of the second echocardiogram.

Embodiment 58. The method of any one of embodiments 41-57, wherein the third time period is about 2 weeks.

Embodiment 59. The method of any one of embodiments 41-58, wherein the third daily dose of Compound 1, or a pharmaceutically acceptable salt thereof, is administered to the patient for the third time period, the method further comprising, based on one or more components of a third echocardiogram for the patient acquired after the third time period and the third daily dose of Compound, or a pharmaceutically acceptable salt thereof, administering to the patient a fourth daily dose of Compound 1, or a pharmaceutically acceptable salt thereof, for a fourth time period or terminating the administering of Compound 1, or a pharmaceutically acceptable salt thereof, to the patient.

Embodiment 60. The method of embodiment 59, comprising selecting the fourth daily dose of Compound 1, or a pharmaceutically acceptable salt thereof, based on the one or more components of the third echocardiogram and the third daily dose.

Embodiment 61. The method of embodiment 59 or 60, wherein the one or more components of the third echocardiogram comprises a biplane LVEF, a post-Valsalva LVOT-G, or a resting LVOT-G.

Embodiment 62. The method of embodiment 59 or 60, wherein the one or more components of the third echocardiogram comprises a biplane LVEF, a post-Valsalva LVOT-G, and a resting LVOT-G.

Embodiment 63. The method of embodiment 59 or 60, wherein the one or more components of the third echocardiogram comprises a biplane LVEF and a post-Valsalva LVOT-G Embodiment 64. The method of any one of embodiments 59-63, wherein the one or more components of the third echocardiogram comprises a biplane LVEF, and the fourth daily dose of Compound 1, or a pharmaceutically acceptable salt thereof, is lower than the third daily dose of Compound 1, or a pharmaceutically acceptable salt thereof, or the administering of Compound 1, or a pharmaceutically acceptable salt thereof, to the patient is terminated, when the biplane LVEF of the third echocardiogram is below the predetermined biplane LVEF threshold.

Embodiment 65. The method of embodiment 64, wherein the administering of Compound 1, or a pharmaceutically acceptable salt thereof, to the patient is terminated when the biplane LVEF of the third echocardiogram is below the predetermined biplane LVEF threshold and the third daily dose of Compound 1, or a pharmaceutically acceptable salt thereof, is the same as the first daily dose of Compound 1, or a pharmaceutically acceptable salt thereof, or lower.

Embodiment 66. The method of embodiment 64 or 65, wherein:
the fourth daily dose of Compound 1, or a pharmaceutically acceptable salt thereof, is the same as the second daily dose of Compound 1, or a pharmaceutically acceptable salt thereof, when the third daily dose of Compound 1, or a pharmaceutically acceptable salt thereof, is higher than the second daily dose of Compound 1, or a pharmaceutically acceptable salt thereof, and the biplane LVEF of the third echocardiogram is below the predetermined biplane LVEF threshold; or
the fourth daily dose of Compound 1, or a pharmaceutically acceptable salt thereof, is the same as the first daily dose of Compound 1, or a pharmaceutically acceptable salt thereof, when the third daily dose of Compound 1, or a pharmaceutically acceptable salt thereof, is the same as the second daily dose of Compound 1, or a pharmaceutically acceptable salt thereof, and the biplane LVEF of the third echocardiogram is below the predetermined biplane LVEF threshold.

Embodiment 67. The method of any one of embodiments 64-66, wherein the predetermined biplane LVEF threshold is 50%.

Embodiment 68. The method of any one of embodiments 59-67, wherein the one or more components of the third echocardiogram comprises a biplane LVEF, a resting LVOT-G, and a post-Valsalva LVOT-G, and wherein the fourth daily dose of Compound 1, or a pharmaceutically acceptable salt thereof, is the same as the third daily dose of Compound 1, or a pharmaceutically acceptable salt thereof, when the biplane LVEF of the third echocardiogram is at or above the predetermined biplane LVEF threshold, the resting LVEOT-G of the third echocardiogram is below the predetermined resting LVOT-G threshold, and the post-Valsalva LVOT-G of the third echocardiogram is below the predetermined post-Valsalva LVOT-G threshold.

Embodiment 69. The method of any one of embodiments 59-68, wherein the one or more components of the third echocardiogram comprises a biplane LVEF, a resting LVOT-G, and a post-Valsalva LVOT-G, and wherein the fourth daily dose of Compound 1, or a pharmaceutically acceptable salt thereof, is greater than the third daily dose of Compound 1, or a pharmaceutically acceptable salt thereof, when either of the following conditions are met on the third echocardiogram: (1) the biplane LVEF is at or above the predetermined biplane LVEF threshold and the resting LVEOT-G is at or above the predetermined resting LVOT-G threshold, or (2) the biplane LVEF is at or above the predetermined biplane LVEF threshold, the resting LVOT-G is below the predetermined resting LVOT-G threshold, and the post-Valsalva LVOT-G is at or above the predetermined post-Valsalva LVOT-G threshold.

Embodiment 70. The method of embodiment 68 or 69, wherein the predetermined biplane LVEF threshold is 50%, the predetermined resting LVOT-G threshold is 30 mmHg, and the post-Valsalva LVOT-G threshold is 50 mmHg.

Embodiment 71. The method of any one of embodiments 59-67, wherein the one or more components of the third echocardiogram comprises a biplane LVEF and a post-Valsalva LVOT-G, and wherein the fourth daily dose of Compound 1, or a pharmaceutically acceptable salt thereof, is the same as the third daily dose of Compound 1, or a pharmaceutically acceptable salt thereof, when either of the following conditions are met on the third echocardiogram: (1) the biplane LVEF is at or above the predetermined biplane LVEF threshold and below the second predetermined biplane LVEF threshold; or (2) the biplane LVEF is at or above the second predetermined biplane LVEF threshold and the post-Valsalva LVOT-G is below the second predetermined post-Valsalva LVOT-G threshold.

Embodiment 72. The method of any one of embodiments 59-67 and 71, wherein the one or more components of the third echocardiogram comprises a biplane LVEF and a post-Valsalva LVOT-G, and wherein the fourth daily dose of Compound 1, or a pharmaceutically acceptable salt thereof, is greater than the third daily dose of Compound 1, or a pharmaceutically acceptable salt thereof, when the biplane LVEF of the third echocardiogram is above the second predetermined biplane LVEF threshold and the post-Valsalva LVOT-G of the third echocardiogram is at or above the second predetermined post-Valsalva LVOT-G threshold.

Embodiment 73. The method of embodiment 71 or 72, wherein the predetermined biplane LVEF threshold is 50%, the second predetermined biplane LVEF threshold is 55%, and the second predetermined post-Valsalva LVOT-G threshold is 30 mmHg.

Embodiment 74. The method of any one of embodiments 59-73, wherein the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, the third daily dose of Compound 1, or a pharmaceutically acceptable salt thereof, is about 5 mg, about 10 mg, or about 15 mg of Compound 1, and the fourth daily dose of Compound 1, or a pharmaceutically acceptable salt thereof, is about 5 mg, about 10 mg, about 15 mg, or about 20 mg of Compound 1

Embodiment 75. The method of any one of embodiments 59-74, further comprising measuring the one or more components of the third echocardiogram Embodiment 76. The method of any one of embodiments 59-75, wherein the fourth time period is about 2 weeks.

Embodiment 77. A method of treating obstructive hypertrophic cardiomyopathy (oHCM) in a patient in need thereof, comprising:
administering to the patient a first daily dose of Compound 1, or a pharmaceutically acceptable salt thereof, for a first time period; and
based on a first echocardiogram comprising a biplane LVEF and a post-Valsalva LVOT-G for the patient acquired after the first time period, administering to the patient a second daily dose of Compound 1, or a pharmaceutically acceptable salt thereof, for a second time period or terminating the administering of Compound 1 to the patient, wherein:
  the administering of Compound 1, or a pharmaceutically acceptable salt thereof, to the patient is terminated if the biplane LVEF of the first echocardiogram is below a first predetermined biplane LVEF threshold;
  the second daily dose of Compound 1, or a pharmaceutically acceptable salt thereof, is the same as the first daily dose of Compound 1, or a pharmaceutically acceptable salt thereof, if either of the following conditions are met on the first echocardiogram: (1) the biplane LVEF is at or above the first predetermined biplane LVEF threshold and below a second predetermined biplane LVEF threshold; or (2) the biplane LVEF is at or above the second predetermined biplane LVEF threshold and the post-Valsalva LVOT-G is below a predetermined post-Valsalva LVOT-G threshold; and
  the second daily dose of Compound 1, or a pharmaceutically acceptable salt thereof, is greater than the first daily dose of Compound 1, or a pharmaceutically acceptable salt thereof, if the biplane LVEF of the first echocardiogram is above the second predetermined biplane LVEF threshold and the post-Valsalva LVOT-G of the first echocardiogram is at or above the predetermined post-Valsalva LVOT-G threshold.

Embodiment 78. The method of embodiment 77, wherein the first daily dose of Compound 1, or a pharmaceutically acceptable salt thereof, is about 5 mg of Compound 1 and the second daily dose of Compound 1, or a pharmaceutically acceptable salt thereof, is about 5 mg or about 10 mg of Compound 1.

Embodiment 79. The method of embodiment 77 or 78, further comprising measuring the biplane LVEF and the post-Valsalva LVOT-G for the first echocardiogram Embodiment 80. The method of any one of embodiments 77-79, wherein the first time period is about 2 weeks.

Embodiment 81. The method of any one of embodiments 79-80, wherein the second time period is about 2 weeks.

Embodiment 82. The method of embodiment 77-81, wherein the second daily dose of Compound 1, or a pharmaceutically acceptable salt thereof, is administered to the patient for the second time period, the method further comprising, based on a second echocardiogram comprising a biplane LVEF and a post-Valsalva LVOT-G for the patient acquired after the second time period and the second daily dose of Compound 1, or a pharmaceutically acceptable salt thereof, administering to the patient a third daily dose of Compound 1, or a pharmaceutically acceptable salt thereof, for a third time period or terminating the administering of Compound 1, or a pharmaceutically acceptable salt thereof, to the patient, wherein:
  the administering of Compound 1, or a pharmaceutically acceptable salt thereof, to the patient is terminated if the biplane LVEF of the second echocardiogram is below the first predetermined biplane LVEF threshold and the second daily dose of Compound 1, or a pharmaceutically acceptable salt thereof, is the same as the first daily dose of Compound 1, or a pharmaceutically acceptable salt thereof;
  the third daily dose of Compound 1, or a pharmaceutically acceptable salt thereof, is lower than the second daily dose of Compound 1, or a pharmaceutically acceptable salt thereof, if the biplane LVEF of the second echocardiogram is below the first predetermined biplane LVEF threshold and the second daily dose of Compound 1, or a pharmaceutically acceptable salt thereof, is higher than the first daily dose of Compound 1, or a pharmaceutically acceptable salt thereof;
  the third daily dose of Compound 1, or a pharmaceutically acceptable salt thereof, is the same as the second daily dose of Compound 1, or a pharmaceutically acceptable salt thereof, if either of the following conditions are met on the second echocardiogram: (1) the biplane LVEF is at or above the first predetermined biplane LVEF threshold and below the second predetermined biplane LVEF threshold; or (2) the biplane LVEF is at or above the second predetermined biplane LVEF threshold and the post-Valsalva LVOT-G is below the predetermined post-Valsalva LVOT-G threshold; and
  the third daily dose of Compound 1, or a pharmaceutically acceptable salt thereof, is greater than the second daily dose of Compound 1, or a pharmaceutically acceptable salt thereof, if the biplane LVEF of the second echocardiogram is above the second predetermined biplane LVEF threshold and the post-Valsalva LVOT-G of the second echocardiogram is at or above the predetermined post-Valsalva LVOT-G threshold.

Embodiment 83. The method of embodiment 82, wherein the first daily dose of Compound 1, or a pharmaceutically acceptable salt thereof, is about 5 mg of Compound 1, the second daily dose of Compound 1, or a pharmaceutically acceptable salt thereof, is about 5 mg or about 10 mg of Compound 1, and the third daily dose of Compound 1, or a pharmaceutically acceptable salt thereof, is about 5 mg, about 10 mg, or about 15 mg of Compound 1.

Embodiment 84. The method of embodiment 82 or 83, further comprising measuring the biplane LVEF and the post-Valsalva LVOT-G for the second echocardiogram.

Embodiment 85. The method of any one of embodiments 82-84, wherein the third time period is about 2 weeks.

Embodiment 86. The method of any one of embodiments 82-85, wherein the third daily dose of Compound 1, or a pharmaceutically acceptable salt thereof, is administered to the patient for the third time period, the method further comprising, based on a third echocardiogram comprising a biplane LVEF and a post-Valsalva LVOT-G for the patient acquired after the third time period and the second third dose of Compound 1, or a pharmaceutically acceptable salt thereof, administering to the patient a fourth daily dose of Compound 1, or a pharmaceutically acceptable salt thereof, for a fourth time period or terminating the administering of Compound 1 to the patient, wherein:
  the administering of Compound 1, or a pharmaceutically acceptable salt thereof, to the patient is terminated if the biplane LVEF of the third echocardiogram is below the first predetermined biplane LVEF threshold and the third daily dose of Compound 1, or a pharmaceutically acceptable salt thereof, is the same as the first daily dose of Compound 1, or a pharmaceutically acceptable salt thereof;
  the fourth daily dose of Compound 1, or a pharmaceutically acceptable salt thereof, is lower than the third daily dose of Compound 1, or a pharmaceutically acceptable salt thereof, if the biplane LVEF of the third echocardiogram is below the first predetermined biplane LVEF threshold and the third daily dose of Compound 1, or a pharmaceutically acceptable salt thereof, is higher than the first daily dose of Compound 1, or a pharmaceutically acceptable salt thereof;

the fourth daily dose of Compound 1, or a pharmaceutically acceptable salt thereof, is the same as the third daily dose of Compound 1, or a pharmaceutically acceptable salt thereof, if either of the following conditions are met on the third echocardiogram: (1) the biplane LVEF is at or above the first predetermined biplane LVEF threshold and below the second predetermined biplane LVEF threshold; or (2) the biplane LVEF is at or above the second predetermined biplane LVEF threshold and the post-Valsalva LVOT-G is below the predetermined post-Valsalva LVOT-G threshold; and the fourth daily dose of Compound 1, or a pharmaceutically acceptable salt thereof, is greater than the third daily dose of Compound 1, or a pharmaceutically acceptable salt thereof, if the biplane LVEF of the third echocardiogram is above the second predetermined biplane LVEF threshold and the post-Valsalva LVOT-G of the third echocardiogram is at or above the predetermined post-Valsalva LVOT-G threshold.

Embodiment 87. The method of embodiment 86, wherein the first daily dose of Compound 1, or a pharmaceutically acceptable salt thereof is about 5 mg of Compound 1, the second daily dose of Compound 1, or a pharmaceutically acceptable salt thereof, is about 5 mg or about 10 mg of Compound 1, the third daily dose of Compound 1, or a pharmaceutically acceptable salt thereof, is about 5 mg, about 10 mg, or about 15 mg of Compound 1, and the fourth daily dose of Compound 1, or a pharmaceutically acceptable salt thereof, is about 5 mg, about 10 mg, about 15 mg, or about 20 mg of Compound 1.

Embodiment 88. The method of embodiment 86 or 87, further comprising measuring the biplane LVEF and the post-Valsalva LVOT-G for the third echocardiogram.

Embodiment 89. The method of any one of embodiments 86-88, wherein the third time period is about 2 weeks.

Embodiment 90. The method of any one of embodiments 77-89, wherein the first predetermined biplane LVEF threshold is 50%, the second predetermined biplane LVEF threshold is 55%, and the predetermined post-Valsalva LVOT-G threshold is 30 mmHg.

Embodiment 91. The method of any one of embodiments 1-90, wherein, prior to administration of Compound 1, or a pharmaceutically acceptable salt thereof, the patient has (i) resting LVOT-G ≥50 mmHg; or (ii) resting LVOT-G ≥30 mmHg and <50 mmHg with post-Valsalva LVOT-G ≥50 mmHg.

Embodiment 92. The method of any one of embodiments 1-91, wherein prior to administration of Compound 1, or a pharmaceutically acceptable salt thereof, the patient has left ventricular ejection fraction (LVEF) ≥60%.

Embodiment 93. The method of any one of embodiments 1-92, wherein the patient is not administered disopyramide during treatment with Compound 1, or a pharmaceutically acceptable salt thereof.

Embodiment 94. The method of any one of embodiments 1-92, wherein the patient is administered disopyramide during the treatment with Compound 1, or a pharmaceutically acceptable salt thereof.

Embodiment 95. The method of any one of embodiments 1-92, wherein the patient has not been treated with disopyramide or an antiarrhythmic drug that has negative inotropic activity within 4 weeks prior to treatment with Compound 1, or a pharmaceutically acceptable salt thereof.

Embodiment 96. The method of any one of embodiments 1-94, wherein the patient is administered an antiarrhythmic medication during the treatment with Compound 1, or a pharmaceutically acceptable salt thereof.

Embodiment 97. The method of any one of embodiments 1-96, wherein the patient is a CYP2D6 poor metabolizer.

Embodiment 98. The method of any one of embodiments 1-97, wherein the patient is fasting when administered Compound 1, or a pharmaceutically acceptable salt thereof Embodiment 99. The method of any one of embodiments 1-97, wherein the patient is fed when administered Compound 1, or a pharmaceutically acceptable salt thereof.

Embodiment 100. The method of any one of embodiments 1-99, wherein the method does not include taking a blood sample of the patient.

Embodiment 101. The method of any one of embodiments 1-100, wherein the method does not include analyzing a blood sample of the patient.

Embodiment 102. The method of any one of embodiments 1-101, wherein the patient is administered a beta-blocker during the treatment with Compound 1, or a pharmaceutically acceptable salt thereof Embodiment 103. A method of treating obstructive hypertrophic cardiomyopathy (oHCM) in a patient in need thereof, comprising administering to the patient a therapeutically effective amount of Compound 1, or a pharmaceutically acceptable salt thereof.

Embodiment 104. The method of any one of embodiments 1-103, wherein the method results in one or more of the following: improvement in mitral regurgitation, improvement in cardiac relaxation, beneficial cardiac remodeling, reverse cardiac remodeling, beneficial cardiac structural remodeling, beneficial cardiac functional remodeling, reversal of adverse cardiac remodeling, reduction in mean left ventricular mass index (LVMI), improvement in left ventricular (LV) filling pressures, reduction in left atrial volume index (LAVI), reduction in the categorical assessment of systolic anterior motion of the mitral valve leaflet, reduction in systolic anterior motion of the mitral valve leaflet, reduction in the frequency of eccentric mitral regurgitation, reduction in mitral regurgitation, reduction in lateral E/e', reduction in lateral E/E, reduction in brain natriuretic peptide (BNP) and reduction in N-terminal prohormone of brain natriuretic peptide (NT-proBNP).

Embodiment 105. The method of any one of embodiments 1-103, wherein the method results in one or more of the following: improvement in peak oxygen uptake (pVO$_2$) by cardiopulmonary exercise testing (CPET), improvement in Kansas City Cardiomyopathy Questionnaire Clinical Summary Score (KCCQ-CSS), improvement in NYHA Functional Classification by one or more class(es), improvement in post-Valsalva left ventricular outflow tract gradient (LVOT-G), and improvement in total workload during CPET.

Embodiment 106. The method of embodiment 105, wherein the method results in change from baseline of ≥1.5 mL/kg/min in pVO$_2$ and improvement in NYHA Functional Class by one or more class(es)

Embodiment 107. The method of embodiment 105, wherein the method results in change from baseline of ≥3.0 mL/kg/min in pVO$_2$ and no worsening of NYHA Functional Class.

Embodiment 108. The method of embodiment 105, wherein the method results in improvement in KCCQ-CSS by 5 or more points.

Embodiment 109. The method of embodiment 105, wherein the method results in resting LVOT-G<30 mmHg, post-Valsalva LVOT-G<50 mmHg, and NYHA Functional Class I.

Embodiment 110. The method of embodiment 105, wherein the method results in resting LVOT-G<30 mmHg, post-Valsalva LVOT-G<50 mmHg, and improvement in NYHA Functional Class by one or more class(es).

Embodiment 111. The method of any one of embodiments 104-110, wherein the one or more results of the treatment occur within 1, 2, 3, 4, 5, 6, 7, 8, 9, or 10 weeks of initiating treatment with Compound 1, or a pharmaceutically acceptable salt thereof.

Embodiment 112. A method of reducing resting left ventricular outflow tract pressure gradient (LVOT-G) to less than 30 mmHg, and reducing post-Valsalva left ventricular outflow tract pressure gradient (LVOT-G) to less than 50 mmHg, in a patient with obstructive hypertrophic cardiomyopathy (oHCM), comprising administering to the patient a therapeutically effective amount of Compound 1, or a pharmaceutically acceptable salt thereof.

Embodiment 113. The method of embodiment 112, wherein the reduction of resting left ventricular outflow tract pressure gradient (LVOT-G) to less than 30 mmHg and reduction of post-Valsalva left ventricular outflow tract pressure gradient (LVOT-G) to less than 50 mmHg occurs within ten weeks of initiating treatment with Compound 1, or a pharmaceutically acceptable salt thereof.

Embodiment 114. The method of embodiment 113, wherein the reduction of resting left ventricular outflow tract pressure gradient (LVOT-G) to less than 30 mmHg and reduction of post-Valsalva left ventricular outflow tract pressure gradient (LVOT-G) to less than 50 mmHg occurs within two weeks of initiating treatment with Compound 1, or a pharmaceutically acceptable salt thereof.

Embodiment 115. The method of any one of embodiments 112-114, wherein the reduction in resting LVOT-G and post-Valsalva LVOT-G is sustained for at least 10 weeks of treatment.

Embodiment 116. The method of any one of embodiments 112-114, wherein the therapeutically effective amount of Compound 1, or a pharmaceutically acceptable salt thereof, is selected by titrating a daily dose of Compound 1, or a pharmaceutically acceptable salt thereof, administered to the patient.

Embodiment 117. The method of embodiment 116, wherein the dose is titrated once during a course of treatment.

Embodiment 118. The method of embodiment 116, wherein the dose is titrated two or more times during a course of treatment.

Embodiment 119. The method of any one of embodiments 116-118, wherein a daily dose is administered to a patient at a constant amount for about two weeks before the daily dose amount is titrated.

Embodiment 120. The method of any one of embodiments 116-118, wherein Compound 1, or a pharmaceutically acceptable salt thereof is administered at a daily dose of about 5 mg to about 30 mg.

Embodiment 121. The method of embodiment 120, wherein the daily dose is about 5 mg.

Embodiment 122. The method of embodiment 120, wherein the daily dose is about 10 mg.

Embodiment 123. The method of embodiment 120, wherein the daily dose is about 15 mg.

Embodiment 124. The method of embodiment 120, wherein the daily dose is about 20 mg.

Embodiment 125. The method of embodiment 120, wherein the daily dose is about 30 mg.

Embodiment 126. The method of any one of embodiments 116-125, wherein the daily dose is administered as a single dose each day.

Embodiment 127. The method of any one of embodiments 116-125, wherein the daily dose is administered in 2 divided doses.

Embodiment 128. The method of any one of embodiments 116-127, wherein the reduction in resting LVOT-G and post-Valsalva LVOT-G peaks within two to six weeks of the end of a dose titration.

Embodiment 129. A method of treating obstructive hypertrophic cardiomyopathy (oHCM) in a patient in need thereof, comprising administering to the patient a therapeutically effective amount of Compound 1, or a pharmaceutically acceptable salt thereof, wherein said patient has a resting left ventricular outflow tract pressure gradient (LVOT-G) of at least 50 mmHg prior to administering Compound 1 or a pharmaceutically acceptable salt thereof.

Embodiment 130. A method of treating obstructive hypertrophic cardiomyopathy (oHCM) in a patient in need thereof, comprising administering to the patient a therapeutically effective amount of Compound 1, or a pharmaceutically acceptable salt thereof, wherein said patient has a resting left ventricular outflow tract pressure gradient (LVOT-G) of at least 30 mmHg and less than 50 mmHg, and a post-Valsalva left ventricular outflow tract pressure gradient (LVOT-G) of at least 50 mmHg prior to administering Compound 1 or a pharmaceutically acceptable salt thereof.

Embodiment 131. A method of treating obstructive hypertrophic cardiomyopathy (oHCM) in a patient in need thereof, comprising administering to the patient a therapeutically effective amount of Compound 1, or a pharmaceutically acceptable salt thereof, wherein said patient is eligible for septal reduction therapy (SRT).

Embodiment 132. The method of embodiment 131, wherein the method precludes the need of septal reduction therapy in the patient.

Embodiment 133. The method of embodiment 131 or 132, wherein the septal reduction therapy is myectomy.

Embodiment 134. The method of embodiment 131 or 132, wherein the septal reduction therapy is alcohol septal ablation.

Embodiment 135. A method of treating obstructive hypertrophic cardiomyopathy (oHCM) in a patient with heart failure symptoms, comprising administering to the patient a therapeutically effective amount of Compound 1, or a pharmaceutically acceptable salt thereof, wherein the method results in a reduction of heart failure symptoms as assessed by NYHA classification.

Embodiment 136. The method of embodiment 135, wherein the method converts patients from NYHA class III to class II or class I.

Embodiment 137. The method of embodiment 135, wherein the method converts patients from NYHA class II to class I.

Embodiment 138. The method of embodiment 135, wherein the method converts patients from NYHA class III to class I.

Embodiment 139. The method of embodiment 135, wherein the method converts patients from NYHA class III to class II.

Embodiment 140. The method of any one of embodiments 135-139, wherein the reduction of heart failure symptoms occurs within ten weeks of initiating treatment with Compound 1, or a pharmaceutically acceptable salt thereof.

Embodiment 141. The method of embodiment 135, wherein the method results in improvement by at least one NYHA class in the patient.

Embodiment 142. The method of embodiment 141, wherein the method results in improvement by one NYHA class.

Embodiment 143. The method of embodiment 141, wherein the method results in improvement by two NYHA classes.

Embodiment 144. The method of any one of embodiments 135-143, wherein the reduction of heart failure symptoms occurs within ten weeks of initiating treatment with Compound 1, or a pharmaceutically acceptable salt thereof.

Embodiment 145. A method of reducing NT-proBNP levels in a patient, comprising administering to the patient a therapeutically effective amount of Compound 1, or a pharmaceutically acceptable salt thereof.

Embodiment 146. The method of embodiment 145, wherein the patient has obstructive hypertrophic cardiomyopathy (oHCM).

Embodiment 147. A method of reducing cardiac troponin I levels in a patient, comprising administering to the patient a therapeutically effective amount of Compound 1, or a pharmaceutically acceptable salt thereof.

Embodiment 148. The method of embodiment 147, wherein the patient has obstructive hypertrophic cardiomyopathy (oHCM).

Embodiment 149. The method of any one of embodiments 129-148, wherein the therapeutically effective amount of Compound 1, or a pharmaceutically acceptable salt thereof, is selected by titrating a daily dose of Compound 1, or a pharmaceutically acceptable salt thereof, administered to the patient.

Embodiment 150. The method of embodiment 149, wherein the dose is titrated once during a course of treatment.

Embodiment 151. The method of embodiment 149, wherein the dose is titrated two or more times during a course of treatment.

Embodiment 152. The method of any one of embodiments 149-151, wherein a daily dose is administered to a patient at a constant amount for about two weeks before the daily dose amount is titrated.

Embodiment 153. The method of any one of embodiments 149-152, wherein Compound 1, or a pharmaceutically acceptable salt thereof is administered at a daily dose of about 5 mg to about 30 mg.

Embodiment 154. The method of embodiment 153, wherein the daily dose is about 5 mg.

Embodiment 155. The method of embodiment 153, wherein the daily dose is about 10 mg.

Embodiment 156. The method of embodiment 153, wherein the daily dose is about 15 mg.

Embodiment 157. The method of embodiment 153, wherein the daily dose is about 20 mg.

Embodiment 158. The method of embodiment 153, wherein the daily dose is about 30 mg.

Embodiment 159. The method of any one of embodiments 154-158, wherein the daily dose is administered as a single dose each day.

Embodiment 160. The method of any one of embodiments 154-158, wherein the daily dose is administered in 2 divided doses.

Embodiment 161. The method of any one of embodiments 1-160, wherein the patient is classified as NYHA class III, when administration of Compound 1, or a pharmaceutically acceptable salt thereof, is initiated.

Embodiment 162. The method of any one of embodiments 1-160, wherein the patient is classified as NYHA class II, when administration of Compound 1, or a pharmaceutically acceptable salt thereof, is initiated.

Embodiment 163. The method of any one of embodiments 1-162, wherein the method decreases left ventricular wall stress in the patient.

Embodiment 164. The method of any one of embodiments 1-163, wherein the method decreases myocardial injury in the patient.

Embodiment 165. The method of any one of embodiments 1-164, wherein administration of Compound 1, or a pharmaceutically acceptable salt thereof, has a sustained effect for at least 6 months.

Embodiment 166. The method of any one of embodiments 1-164, wherein administration of Compound 1, or a pharmaceutically acceptable salt thereof, has a sustained effect for at least 5 years.

Embodiment 167. The method of any one of embodiments 1-164, wherein administration of Compound 1, or a pharmaceutically acceptable salt thereof, has a sustained effect for at least 10 weeks, 12 weeks, 1 year, 2 years, 3 years, or 4 years.

Embodiment 168. A method of decreasing left ventricular wall stress in a patient, comprising administering to the patient a therapeutically effective amount of Compound 1, or a pharmaceutically acceptable salt thereof, wherein the patient has obstructive hypertrophic cardiomyopathy (oHCM).

Embodiment 169. The method of embodiment 168, wherein the therapeutically effective amount of Compound 1, or a pharmaceutically acceptable salt thereof, is selected by titrating a daily dose of Compound 1, or a pharmaceutically acceptable salt thereof, administered to the patient.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1

This first-in-human study of aficamten (also referred to as CK-274) was undertaken to evaluate its safety, pharmacokinetic, and pharmacodynamic profile, including effects of food or a CYP2D6 poor metabolizer (CYP2D6-PM) phenotype. Aficamten, a selective cardiac myosin inhibitor, reduced measures of left ventricular contractility preclinically in vitro and in vivo, and therefore, may have therapeutic potential for the management of hypertrophic cardiomyopathy.

This phase 1, double-blind, randomized, placebo-controlled study enrolled healthy adults, aged 18 to 55 years, to receive single-ascending doses or multiple-ascending doses (14 or 17 days) of aficamten or placebo. In addition to standard safety and pharmacokinetic assessments, pharmacodynamic effects were assessed by echocardiography. The study enrolled 102 participants (57 in single-dose, 24 in multiple-dose, 9 in CYP2D6-PM, and 12 in food-effect cohorts). At single doses of aficamten <50 mg and multiple doses <10 mg, adverse events were generally mild and no more frequent than with placebo. In single-ascending dose cohorts, plasma concentrations of aficamten increased in a dose-proportional manner; the half-life of aficamten was 75 to 85 h. Neither food nor CYP2D6-PM phenotype had a clinically meaningful impact on pharmacokinetics. With a single 50-mg dose, mean left ventricular ejection fraction (LVEF) decreased from baseline by 5.5% (p=0.0001). With multiple doses, a mean reduction in LVEF of 5.0% was observed after 14 days of 10 mg of aficamten once daily. Aficamten appears safe and well tolerated at doses evaluated. A pharmacodynamic effect on LVEF was demonstrated, providing support for further clinical investigations of aficamten.

Methods

Figure 2:
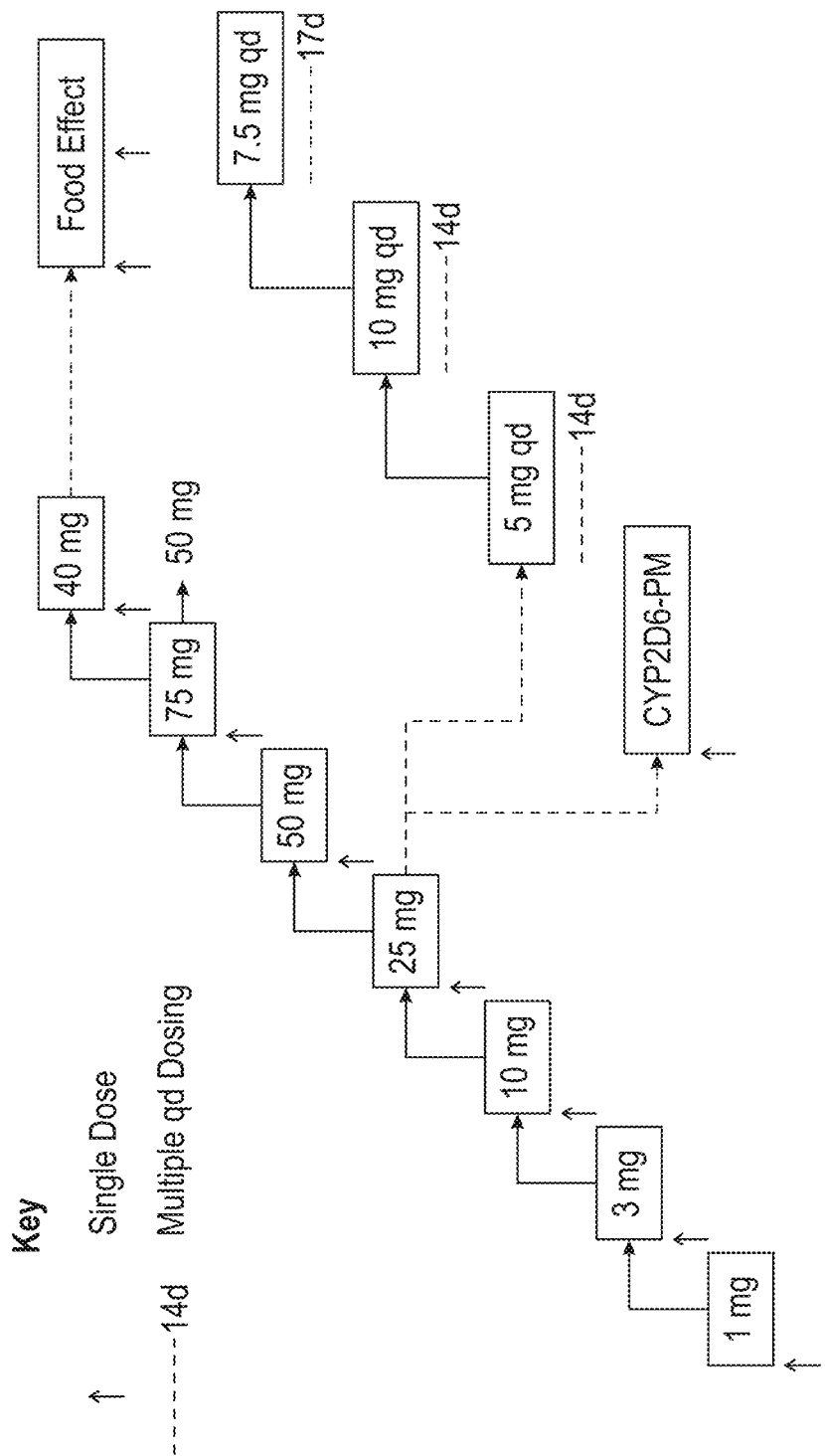
FIG. 2 shows a schematic overview of a phase 1 clinical study for CK-274 (also referred to as aficamten). The study included SAD cohorts, MAD cohorts, a CYP2D6-PM cohort, and a food-effect cohort. The MAD and CYP2D6-PM cohorts began when a tolerated, pharmacologically active dose (reduction in LVEF of approximately 5%) was identified in the SAD cohorts. The food-effect cohort began following completion of the last SAD cohort. Criteria to stop dose escalation were met in the SAD 75-mg dose cohort, and remaining patients in this cohort received 50 mg. Subsequently, the final SAD cohort was completed using 40 mg of aficamten. CYP2D6-PM=cytochrome P450 2D6 poor metabolizer phenotype; d=day; LVEF=left ventricular ejection fraction; MAD=multiple-ascending dose; qd=once daily; SAD=single-ascending dose.

Study Overview and Ethics. The study used a randomized, placebo-controlled, single-ascending dose (SAD) and multiple-ascending dose (MAD) design (FIG. 2). The study was not designed to identify a maximum tolerated dose, but rather to identify a pharmacologically active dose range, defined as giving an absolute reduction in left ventricular ejection fraction (LVEF) from baseline in the range of 5% to 15% (such as, a baseline LVEF value of 70% reduced to between 55% to 65%). Dose escalation was to be stopped when this range was achieved, or when a non-tolerated dose was identified, if earlier.

Participants and Treatments. To be eligible for this study, participants were to be healthy adults aged 18 to 55 years, with body mass index of 18.0 to 32.0 kg/m², normal electrocardiogram (ECG) and clinical laboratory values, or only minor abnormalities that were deemed not clinically significant. Participants also had to have normal cardiac structure and function, with LVEF ≥60% for the first 4 SAD cohorts, ≥65% for subsequent SAD cohorts, all MAD cohorts, and the food-effect cohort, and ≥55% for the CYP2D6-PM cohort. Before the study, participants were not allowed to use any prescription medication within 14 days, over-the-counter medication within 7 days (except acetaminophen), or tobacco or nicotine within 3 months; in addition, they were not permitted to consume alcohol, caffeine, or grapefruit within 48 h before study check-in.

A randomization schedule was centrally generated for each cohort and treatment period. In all cohorts, aficamten or matching placebo was administered in granule form in a capsule with ~240 ml of water. Study drug was administered following an overnight fast, except during the fed period in the food-effect cohort.

Single-ascending dose (SAD) cohorts. The SAD portion of the study used a randomized, double-blind, placebo-controlled, sequential, escalating-dose design, in which participants received single-ascending oral doses of the study drug. Seven cohorts were dosed in sequence (FIG. 2). Of the 8 participants within each cohort, the first 2 were randomly assigned (1:1) to aficamten or placebo and followed for a minimum of 2 days before the remainder of the group was dosed. The remaining 6 participants were then randomly assigned (5:1) to receive either oral single doses of aficamten (1, 3, 10, 25, 40, 50, or 75 mg) or placebo.

The initial dose of aficamten was selected using criteria from the United States Food and Drug Administration guidance based on prior animal studies and employing a safety margin of 10-fold. Dose escalation would stop when results identified a pharmacologically active dose range that reduced LVEF by 5% to 15% or a non-tolerated dose, whichever occurred first.

Recommendations regarding dose escalation in the SAD cohorts- and in the MAD cohorts described below-were made by the treating investigator (who was blinded to treatment group) and endorsed or not by the Dose Level Review Committee (DLRC), who were unblinded. Decisions were made when ≥6 participants had been treated and followed for ≥3 days, including collection of clinical, laboratory, ECG, and telemetry data, and echocardiograms suitable for assessing LV function around the time of maximum plasma drug concentration ($C_{max}$). Criteria for escalation included that no more than 2 participants in a dose group developed an LVEF <50% and no individual developed an LVEF <45%. Dose escalation criteria were as follows: (1) no individual had sustained a cardiac serious adverse event related to the study drug; (2) no 2 individuals had experienced similar, non-cardiac serious adverse events in the same organ system that seemed to be related to the study drug; (3) no 2 individuals treated with aficamten experienced a decrease in left ventricular ejection fraction (LVEF) >15% in comparison with the last pre-dose value (determined by the Dose Level Review Committee [DLRC]); (4) no individual developed an LVEF <45% (unless determined not to be related to the study drug by the DLRC and the treating investigator); and (5) both the treating investigator and DLRC approved the escalation and next level dose based on their clinical judgment.

Multiple-ascending dose (MAD) cohorts. The MAD cohorts also used a randomized, double-blind, placebo-controlled, sequential design. Enrollment in the MAD cohorts began when the SAD cohorts identified a single oral dose that was well tolerated and associated with an observed PD effect. Each of the 3 MAD cohorts included 8 participants, randomized (6:2) to aficamten or placebo. Participants received oral doses of the study drug once daily for 14 days (in the cohorts comparing 5 or 10 mg of aficamten vs. placebo) or 17 days (for the cohort comparing 7.5 mg of aficamten vs. placebo).

CYP2D6 poor metabolizer cohort. A separate cohort was enrolled to evaluate the potential impact of CYP2D6 genetic variants on the PK properties of aficamten. The CYP2D6 gene encodes the cytochrome P450 2D6 enzyme, described as the most extensively characterized polymorphic drug-metabolizing enzyme, and prior in vitro studies had implicated CYP2D6 as a potential metabolizing enzyme of aficamten.

CYP2D6 genotypes were determined at screening for all study participants; those identified as CYP2D6-PMs were excluded from the SAD and MAD cohorts but were invited to participate in the CYP2D6-PM cohort. The first individual in the CYP2D6-PM cohort was dosed after the SAD 25-mg cohort (FIG. 2). Each participant received a single dose of aficamten (10 mg) or placebo. Nine participants were randomized (7:2) with a sentinel dosing group consisting of the first 2 participants treated.

Food-effect cohort. To assess the effect of food on the PK of aficamten, a separate cohort was enrolled after completion of the last SAD cohort, with enrollment of 8 to 12 participants planned. In an open-label, 2-way crossover design, participants were to receive 2 single doses of 10 mg of aficamten, separated by ≥14 days. Participants were randomized in a 1:1 ratio to 1 of 2 sequences: fasted/fed or fed/fasted. In the fasted period, aficamten was administered after an overnight fast; in the fed period, aficamten was administered 30 minutes after the start of a high-fat breakfast.

Assessment

Safety and tolerability. Safety was assessed by the incidence of adverse events (AEs) and by incidence of reduced LVEF. Treatment-emergent AEs (TEAE) were defined as AEs that began or increased after study drug administration. All AEs were coded using the Medical Dictionary for Regulatory Activities version 21.1 and graded using the National Cancer Institute Common Terminology Criteria for AEs (version 4.03) 5-point severity scale. Each AE was judged as either related or unrelated to the study drug by the treating investigator. Clinical laboratory tests were obtained at regular intervals in all cohorts.

For safety monitoring, participants in all cohorts had periodic echocardiograms, which were assessed by a cardiologist. In the SAD and MAD cohorts, echocardiograms were also reviewed by an echocardiography core laboratory for PD assessments, as described below. In addition, participants in all cohorts were monitored with continuous 12-lead ECG recording using Holter monitors. For safety monitoring, a single 12-lead ECG was extracted at screening, pre-dose, and periodically throughout follow-up, and interpreted by the investigator. In the SAD, MAD, and CYP2D6-PM cohorts, cardiodynamic ECGs (triplicate 10-second, 12-lead ECG recordings) were obtained prior to the corresponding PK blood and ECG intervals quantitated by qualified readers.

Pharmacokinetic analyses. For all study groups, blood samples for PK assessment were obtained pre-dose, up to 12 times daily on day 1, and then at regular intervals throughout the study. Blood samples were collected according to the following schedule: SAD Cohorts: Day 1: pre-dose and 0.25, 0.5, 1, 1.5, 2, 2.5, 3, 4, 6, 8, 12, 16, 24, 36, 48, 72, 96, and 216 h post dose. MAD Cohorts (14-day Dosing): Day 1: pre-dose and 0.25, 0.5, 1, 1.5, 2, 2.5, 3, 4, 6, 8, and 12 h post dose; Days 2, 4, 5, 6, and 9: pre-dose (corresponding to trough samples following dosing on days 1, 3, 4, 5, and 8) and 1.5 h post dose; Days 3, 7, 8, 10, 11, 12, and 13: pre-dose (corresponding to trough samples following dosing on days 2, 6, 7, 9, 10, 11, and 12); Day 14: pre-dose and 0.25, 0.5, 1.5, 2, 2.5, 3, 4, 6, 8, 12, 16, 24, 36, 48, 72, and 168 h post dose. MAD Cohort (17-Day Dosing): Day 1: pre-dose and 0.25, 0.5, 1, 1.5, 2, 2.5, 3, 4, 6, 8, and 12 h post dose; Days 2, 4, 5, 6, and 9: pre-dose (corresponding to trough samples following dosing on days 1, 3, 4, 5, and 8) and 1.5 h post dose; Days 3, 7, 8, 10, 11, 12, 13, 14, 15, and 16: pre-dose (corresponding to trough samples following dosing on days 2, 6, 7, 9, 10, 11, and 12); Day 17: pre-dose and 0.25, 0.5, 1.5, 2, 2.5, 3, 5, 7, 9, 12, 24, 36, 48, 72, and 168 h post dose. CYPD6-PM Cohort: Day 1: pre-dose and 0.25, 0.5, 1, 1.5, 2, 2.5, 3, 4, 6, 8, 12, 16, 24, 36, 48, 72, 96, 216, 312, and 552 h post dose. Food-Effect Cohort: Day 1: pre-dose and 0.25, 0.5, 1, 1.5, 2, 2.5, 3, 4, 6, 8, 12, 16, 24, 36, 48, 72, 96, 144, and 216 h post dose. Standard non-compartmental methods were used to calculate PK parameters using Phoenix® WinNonlin® Version 7.0; actual sample collection times were utilized.

Plasma concentrations of aficamten were measured utilizing high performance liquid chromatography-tandem mass spectrometry methods validated for accuracy, precision, linearity, sensitivity, and specificity at Celerion (Lincoln, Nebraska). The analytical range (the lower to upper limits of quantitation) for aficamten was 1.00 to 500 ng/ml.

Echocardiography. For PD assessments of LVEF, echocardiograms for the SAD and MAD cohorts were interpreted by the echocardiography core laboratory and used for all data analysis and dose level review decisions while immediate local interpretation of the echocardiograms was performed for safety monitoring. In the SAD cohorts receiving 1, 3, or 10 mg of aficamten, echocardiograms were obtained on day −1, pre-dose on day 1, and at 1.5, 4, and 24 h post dose. For SAD cohorts receiving 25, 40, 50, or 75 mg of aficamten, echocardiograms were obtained on day −1, pre-dose on day 1, and at 1.5, 6, and 24 h post dose. Echocardiograms on day 3 (48 h after dosing) were obtained only if the 24 h LVEF had not returned to near or above baseline, as determined by the investigator. In the MAD cohorts, echocardiograms were obtained on day −1, pre-dose on day 1, and at 1.5 h post dose on days 2, 4, and 9, and at 1.5, 24, and 72 h post dose on day 14 (for the 5-mg and 10-mg cohorts) or on day 17 (for the 7.5-mg cohort). Echocardiograms were obtained 3 days after the last dose (on day 17 or 20) only if the participant's prior LVEF was not near or above baseline, as determined by the investigator.

Statistical Analysis. The sample size chosen for this study was based upon precedent set by other first-in-human PK studies of similar nature and was not based on power calculations. All participants who received ≥1 dose of the study drug (aficamten or placebo) were included in safety analyses. All participants who received ≥1 dose of the study drug and had ≥1 evaluable PK plasma profile were included in the PK analysis set.

The PK analyses were intended to assess single-dose kinetics, multiple-dose (steady state) kinetics, the influence of the CYP2D6 phenotype on absorption and elimination of aficamten, and the influence of food on the absorption and elimination of aficamten. For the SAD cohort, dose proportionality of aficamten was evaluated using a power model on day 1. For the MAD cohort, dose proportionality was evaluated using a power model on day 1 and day 14 or 17. Several considerations were taken into account when assessing dose proportionality of the drug, such as results derived from the power model statistical analysis (e.g., the slope estimate and width of the 2-sided 95% confidence intervals [CIs]), qualitative assessment specific to the PK of the drug, and clinical relevance. For the SAD cohort, the parameters used to assess dose proportionality were area under the plasma drug concentration-time curve (AUC) from time 0 to the time of the last measurable concentration ($AUC_{last}$), AUC from time 0 extrapolated to infinity ($AUC_{inf}$), AUC from time 0 to 24 h ($AUC_{24}$), and maximum plasma concentration ($C_{max}$). For the MAD cohort, the parameters were $AUC_{24}$ and $C_{max}$ on day 1, plus AUC to the end of the dosing period ($AUC_{tau}$) and $C_{max}$ on day 14 or 17. The statistical linear relationship between the ln-transformed PK parameters and the ln-transformed dose was verified by including the quadratic (ln Dose)$^2$ and cubic (ln Dose)$^3$ effects. The statistical linear relationship was established if the quadratic and cubic effects were not statistically significant, using a 5% level of significance, or if the effects were statistically significant, but of such small magnitude that they were not clinically relevant. The dose-proportionality analysis was performed using SAS® PROC MIXED. If a statistical linear relationship was shown and if the 2-sided 95% CIs around the slope estimate parameters included the value of 1 for dose-dependent parameters, then dose proportionality was established.

In the MAD cohort, a steady-state analysis for aficamten was performed on the ln-transformed plasma trough concentration ($C_{trough}$) values using Helmert contrasts. An analysis of variance (ANOVA) model was conducted separately for each dose level; day was included as the fixed effect. Helmert contrasts were developed such that each time-point was compared with the mean of the subsequent time-points. Steady state was established at the time-point where no statistical difference (alpha=5%, 2-sided) was observed with the subsequent time-points.

All participants who received ≥1 dose of study drug and had ≥1 pre-dose and ≥1 post-dose echocardiographic measurement were included in the PD analysis set. Descriptive analyses included absolute reduction in LVEF relative to baseline and categorical LVEF responses (proportions of participants with reduction in LVEF from baseline of ≥5%, ≥10%, and ≥15% and proportions of participants with LVEF <50% and <45%). Descriptive statistics of the echocardiographic parameters were generated using SAS® Version 9.3 or higher.

Dose-response analysis was performed using analysis of covariance (ANCOVA) to identify the least-squares mean difference (aficamten minus placebo). To analyze the impact of drug dose on echocardiographic parameters in the SAD and MAD cohorts, an inferential analysis was conducted on the PD analysis set using linear mixed models for repeated-measures analysis of covariance (ANCOVA). The ANCOVA used baseline value as a covariate, included treatment, time-point, and time-point-by-treatment interaction as fixed effects, and change from baseline as the dependent variable. The unstructured variance-covariance structure was used, and the model accounted for the time-point repeated measures. The ANCOVA analysis was conducted separately for each study part and for each PD parameter. The least-squares means, the difference in least squares means (active minus placebo), and the associated 2-sided 95% CIs were presented for each comparison.

Analyses of concentration 'bin' and exposure-response were also performed using ANCOVA. SAS® PROC MIXED was used for all comparative analyses. An additional inferential analysis was performed in the SAD and MAD cohorts, to evaluate the relationship between concentrations of aficamten and LVEF for participants in the PK/PD analysis set. A concentration bin ANCOVA was conducted using linear mixed models for repeated-measures analyses with concentration bin group as a fixed effect, baseline PD parameters as a covariate, change from baseline as the dependent variable, and a random intercept to adjust for the repeated measures. The unstructured variance-covariance structure was used. Plasma concentrations of aficamten were paired with coincident PD parameters. The ANCOVA compared the change in PD parameters between each bin versus the pooled placebo group. The least-squares means, the difference in least squares means (bin group minus placebo), and the associated 2-sided 95% CIs were presented for each comparison. The ANCOVA analysis was conducted separately for each study part. For all time-points at which both PK data and PD measures were available, the time-points were pooled for the analysis. In each part of the study, aficamten concentrations with time-matched PD data were pooled and sorted in increasing order. From least to greatest, the data were then divided into 5 groups of observations ('bins'), each consisting of 20% of the data points. Each bin was treated as a separate group. Concentration bins consisted of a placebo group and 5 bin groups based on the pool of concentrations from all time-points on aficamten treatment.

The above analysis was then repeated using concentration as a continuous variable to estimate the exposure-response trend. Both a random intercept effect and a random concentration effect were added to the ANCOVA. The estimate of the concentration slope, with corresponding 2-sided 95% CIs, and the ANCOVA analyses were presented for each study part.

For all time-points at which both PK data and PD measures were available, the time points were pooled for the analysis. A nominal significance level of 5% was used for statistical comparisons, without adjustment for multiplicity.

Results

Study Population. A total of 102 participants were enrolled: 57 in the SAD cohorts, 24 in the MAD cohorts, 9 in the CYP2D6-PM cohort, and 12 in the food-effect cohort. All participants completed the study. Mean age ranged between 32 and 40 years across cohorts, and the majority of participants were male (Table 1).

TABLE 1

Baseline Characteristics

| | SAD (n = 57) | MAD (n = 24) | CYP2D6-PM (n = 9) | Food-Effect (n = 12) |
|---|---|---|---|---|
| Age, years | 39.6 (18-55) | 40.4 (28-54) | 32.0 (20-47) | 39.6 (25-51) |
| Male | 41 (72) | 18 (75) | 9 (100) | 9 (75) |
| White race | 52 (91) | 17 (71) | 9 (100) | 11 (92) |
| Hispanic or Latino ethnicity | 42 (74) | 13 (54) | 4 (44) | 8 (67) |
| Weight, kg | 79.4 ± 10.3 | 77.0 ± 9.1 | 84.8 ± 12.0 | 76.4 ± 11.1 |
| Height, cm | 169.0 ± 9.4 | 168.9 ± 10.0 | 177.8 ± 7.8 | 168.8 ± 9.2 |
| BMI, kg/m$^2$ | 27.8 ± 2.7 | 27.0 ± 2.3 | 26.8 ± 3.3 | 26.8 ± 3.0 |
| LVEF, % | 65.8 ± 2.4 | 67.5 ± 1.2 | 61.0 ± 2.6 | 67.2 ± 1.2 |

Values are mean (range), n (%), or mean ± SD. BMI = body mass index; LVEF = left ventricular ejection fraction; MAD = multiple-ascending dose; CYP2D6-PM = cytochrome P450 2D6 poor metabolizer; SAD = single-ascending dose; SD = standard deviation.

For the SAD cohorts, there were no safety concerns that prohibited dose escalation between 1 mg and 25 mg. With the next planned dose (50 mg), 1 participant had a post-dose LVEF <50% (46.2%); however, this did not meet the dose escalation stopping rules and the 75-mg cohort was initiated. The sentinel participant in the 75-mg cohort had LVEF <45% post dose; consequently, no further participants were dosed at 75 mg. As a result, the 50-mg group was expanded, and an additional 5 participants were dosed in this cohort. Following the expansion, 1 participant in the 50-mg dose group experienced LVEF <45%, which was also a decrease of >15%. Therefore, no further participants were dosed at ≥50 mg. The DLRC determined the appropriate dose for the final single-dose cohort was 40 mg.

Following results from the 1-mg to 25-mg SAD cohorts, the first MAD cohort was initiated at 5 mg of aficamten once daily for 14 days. There were no safety concerns, and the next cohort was initiated at 10 mg once daily for 14 days. In this cohort, 2 participants met the stopping criteria based on echocardiography results. The DLRC decided the next treatment level should be 7.5 mg, to better characterize the PK at steady state; thus, the dosing period was extended from 14 to 17 days to ensure PK had reached steady state by the last day of dosing.

Safety and Tolerability. There were no serious AEs, and no participants discontinued the study due to AEs. The TEAEs that were observed were generally mild (grade 1) and no more frequent with aficamten than with placebo for both single-dose and multiple-dose administration (Table 2 and Table 3). Overall, the most common TEAE was headache in both the SAD and MAD cohorts (Table 2 and Table 3).

TABLE 2

Treatment-Emergent Adverse Events in the SAD Cohorts

| | Pooled Placebo (n = 15) | Aficamten SAD Cohort, mg | | | | | | | Total (N = 57) |
|---|---|---|---|---|---|---|---|---|---|
| | | 1 (n = 6) | 3 (n = 6) | 10 (n = 6) | 25 (n = 6) | 40 (n = 6) | 50 (n = 11) | 75 (n = 1) | |
| Participants with any TEAE | 4 (27) | 1 (17) | — | 1 (17) | 5 (83) | 1 (17) | 4 (36) | 1 (100) | 17 (30) |
| Most common TEAEs | | | | | | | | | |
| Headache | 1 (7) | — | — | 1 (17) | 2 (33) | — | 1 (9) | — | 5 (9) |
| Ejection fraction decreased | — | — | — | — | — | 1 (17) | 1 (9) | 1 (100) | 3 (5) |
| Abdominal tenderness | — | — | — | — | 1 (17) | — | 1 (9) | — | 2 (4) |
| Chest pain | — | — | — | — | — | — | 1 (9)* | 1 (100)† | 2 (4) |
| Dyspepsia | — | — | — | — | 1 (17) | — | 1 (9) | — | 2 (4) |
| Flatulence | — | — | — | — | 1 (17) | — | 1 (9) | — | 2 (4) |
| Nausea | — | — | — | — | 2 (33) | — | — | — | 2 (4) |
| Upper abdominal pain | — | — | — | — | 2 (33) | — | — | — | 2 (4) |
| Upper respiratory tract infection | 2 (13) | — | — | — | — | — | — | — | 2 (4) |

Values are n (%). Most common TEAEs based on preferred terms, reported in ≥2 participants in the total cohort.
*'Bubbling sensation to the left chest' consistent with a gastrointestinal association rather than a cardiac association.
†Onset approximately 60 h post dose.
SAD = single-ascending dose;
TEAE = treatment-emergent adverse event.

TABLE 3

Treatment-Emergent Adverse Events in the MAD Cohorts

| | Aficamten MAD Cohorts | | | | |
|---|---|---|---|---|---|
| | Pooled Placebo (n = 6) | 5 mg qd × 14 Days (n = 6) | 7.5 mg qd × 17 Days (n = 6) | 10 mg qd × 14 Days (n = 6) | Total (N = 24) |
| Participants with any TEAE | 1 (17) | 1 (17) | — | 2 (33) | 4 (17) |
| TEAEs | | | | | |
| Headache | 1 (17) | — | — | 1 (17) | 2 (8) |
| Chapped lips | — | 1 (17) | — | — | 1 (4) |
| Cough | — | 1 (17) | — | — | 1 (4) |
| Feeling hot | 1 (17) | — | — | — | 1 (4) |
| Nausea | 1 (17) | — | — | — | 1 (4) |
| Salivary hypersecretion | — | 1 (17) | — | — | 1 (4) |
| Upper respiratory tract infection | — | — | — | 1 (17) | 1 (4) |
| Vomiting | 1 (17) | — | — | — | 1 (4) |

Values are n (%). TEAEs based on preferred terms, reported in ≥1 participant in the total cohort.
MAD = multiple-ascending dose; qd = once daily; TEAE = treatment-emergent adverse event.

Echocardiogram-related AEs of decreased ejection fraction <45% based on the study echocardiogram expert assessment were reported in 3 participants: 1 each in the SAD 40-mg, 50-mg, and 75-mg cohorts (Table 4). All were grade 1, and all resolved at the next echocardiogram assessment (within 2.5 to 4.6 h). The single participant who received 75 mg of aficamten had LVEF of 34.6% at 1.5 h post dose, which was a reduction in LVEF of 31.5% and led to concluding escalation of doses in the SAD portion of the study as discussed above. At the following assessment 2.5 h later, LVEF had returned to 51.9%. No AEs of decreased ejection fraction <45% were reported in the MAD, CYP2D6-PM, or food-effect cohorts.

In all cohorts, mean safety ECG parameters at the assessed time-points were within normal limits. No clinically notable changes from baseline were observed among any of the parameters. The QT interval corrected for heart rate using Fridericia's formula (QTcF) did not exceed 450 ms either at baseline or at any assessment during the dosing interval, with the exception of 2 individuals whose baseline QTcF was ≥440 ms and whose QTcF values increased by 3 and 13 ms, respectively. In all cohorts, there were no increases in QTcF interval ≥30 ms, with the exception of 1 participant in the SAD placebo group whose QTcF interval increased by 33 ms on day 5 (427 ms vs. a baseline value of 394 ms). In the cardiodynamic assessments, categorical analysis of ECG parameters revealed no cardiac safety concerns, and there was no evidence of a positive QT effect following single or multiple doses of aficamten.

All vital signs were within normal limits at the post-dose time-points. No clinically significant serum chemistry, hematology, or urinalysis findings were observed during the study.

TABLE 4

Echocardiogram-Related AEs of Decreased Ejection Fraction <45%

| Cohort, Participant | Dose | Grade | Onset* | LVEF Deemed AE† | Outcome‡ |
|---|---|---|---|---|---|
| SAD, 42-year-old white female | 40 mg | 1 (mild) | 1.4 h | 42.2% | Resolved 4.6 h later (6 h after drug dose), with LVEF recorded at 58.4% |
| SAD, 46-year-old white male | 50 mg | 1 (mild) | 1.5 h | 42.1% | Resolved 2.5 h later (4 h after drug dose), with LVEF recorded at 50.2% |
| SAD, 36-year-old white/ Hispanic male | 75 mg | 1 (mild) | 1.5 h | 34.6% | Resolved 2.5 h later (4 h after drug dose), with LVEF recorded at 51.9% |

*Time after drug dose.
†LVEF values for safety assessments were determined by the study cardiologist.
‡In the SAD cohorts, post-dose echocardiograms were performed at 1.5, 4, 6, 24, and 48 h post dose.
AE = adverse event; LVEF = left ventricular ejection fraction; SAD = single-ascending dose.

Pharmacokinetics

Figures 3A, 3B:
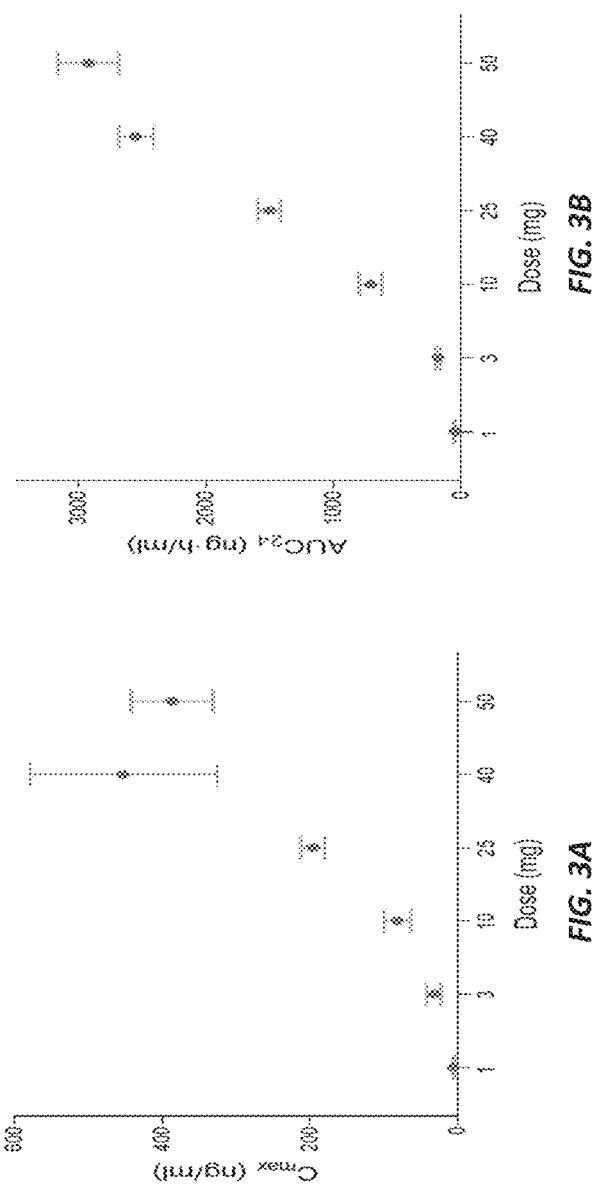
FIG. 3A shows mean (SE) maximum plasma concentration ($C_m$) of aficamten increased in a dose-proportional manner following single oral doses between 1 mg and 50 mg.
FIG. 3B shows exposure ($AUC_{24}$) (B) of aficamten increased in a dose-proportional manner following single oral doses between 1 mg and 50 mg. $AUC_{24}$=area under the plasma drug concentration-time curve from 0 to 24 h; $C_{max}$=maximum plasma concentration; SE=standard error.

Single-dose kinetics. The plasma aficamten profiles were generally well characterized for all dose levels with the exception of the lowest dose of 1 mg (due to concentrations close to the lower limit of quantitation) and the highest dose of 75 mg, which was administered to only 1 participant, as discussed above. Over the dose range of 1 mg to 50 mg, mean maximal plasma concentrations and exposure increased in a dose-proportional manner, as demonstrated by the rise in $C_{max}$ and area under the plasma concentration-time curve from time 0 to 24 h ($AUC_{24}$) with increasing doses (FIGS. 3A-3B and Table 5). Mean clearance and volume of distribution were similar across the doses. Median time to maximum observed concentration occurred between 0.5 and 2.8 h, with a maximum time of 4.0 h across all participants. Mean half-life ranged from 75 to 85 h.

TABLE 5

Summary of Plasma Aficamten Pharmacokinetics Following Single Oral Dose Administration

| | Aficamten SAD Cohort, mg | | | | | | |
|---|---|---|---|---|---|---|---|
| | 1 | 3 | 10 | 25 | 40 | 50 | 75 |
| $C_{max}$ (ng/ml) | 5.8 (38.4) n = 6 | 26.1 (82.4) n = 6 | 70.5 (69.0) n = 6 | 192.6 (23.3) n = 6 | 383.2 (67.9) n = 6 | 359.4 (38.9) n = 11 | 1,220 (—) n = 1 |
| $T_{max}$ (h) | 1.0 (0.5, 4.0) n = 6 | 1.3 (0.5, 2.6) n = 6 | 2.8 (0.5, 3.0) n = 6 | 1.8 (0.5, 4.0) n = 6 | 1.0 (0.5, 1.5) n = 6 | 1.0 (0.5, 2.5) n = 11 | 0.5 (0.5, 0.5) n = 1 |
| $AUC_{24}$ (ng · h/ml) | 50 (20) n = 6 | 174 (27) n = 6 | 679 (35) n = 6 | 1,493 (15) n = 6 | 2,532 (13) n = 6 | 2,833 (26) n = 11 | 4,556 (—) n = 1 |
| $AUC_{inf}$ (ng · h/ml) | — — | 823 (61) n = 5 | 3,434 (24) n = 4 | 7,113 (15) n = 6 | 11,860 (20) n = 5 | 13,740 (35) n = 9 | |
| Vz/F (L) | — | 392.7 ± 122.2 n = 5 | 361.7 ± 108.0 n = 4 | 405.3 ± 56.6 n = 6 | 381.7 ± 66.9 n = 5 | 431.3 ± 122.9 n = 9 | |
| $t_{1/2}$ (h) | — — | 75.1 ± 21.8 n = 5 | 84.7 ± 17.7 n = 4 | 79.8 ± 10.0 n = 6 | 79.2 ± 18.5 n = 4 | 80.4 ± 14.9 n = 9 | |
| CL/F (L/h) | — | 4.2 ± 3.1 n =5 | 3.0 ± 0.7 n = 4 | 3.6 ± 0.5 n =6 | 3.4 ± 0.6 n = 5 | 3.8 ± 1.1 n = 9 | |

$C_{max}$ and AUC values are presented as geometric mean and geometric CV %, $T_{max}$ as median (range), and all other parameters as arithmetic mean ± standard deviation.
$AUC_{24}$ = area under the plasma drug concentration-time curve from time 0 to 24 h;
$AUC_{inf}$ = area under the plasma drug concentration-time curve from time 0 extrapolated to infinity;
CL/F = apparent total body clearance;
$C_{max}$ = maximum plasma concentration;
CV% = percent coefficient of variation;
$t_{1/2}$ = half-life;
$T_{max}$ = time to maximum plasma concentration;
Vz/F = apparent volume of distribution.

Figure 4:
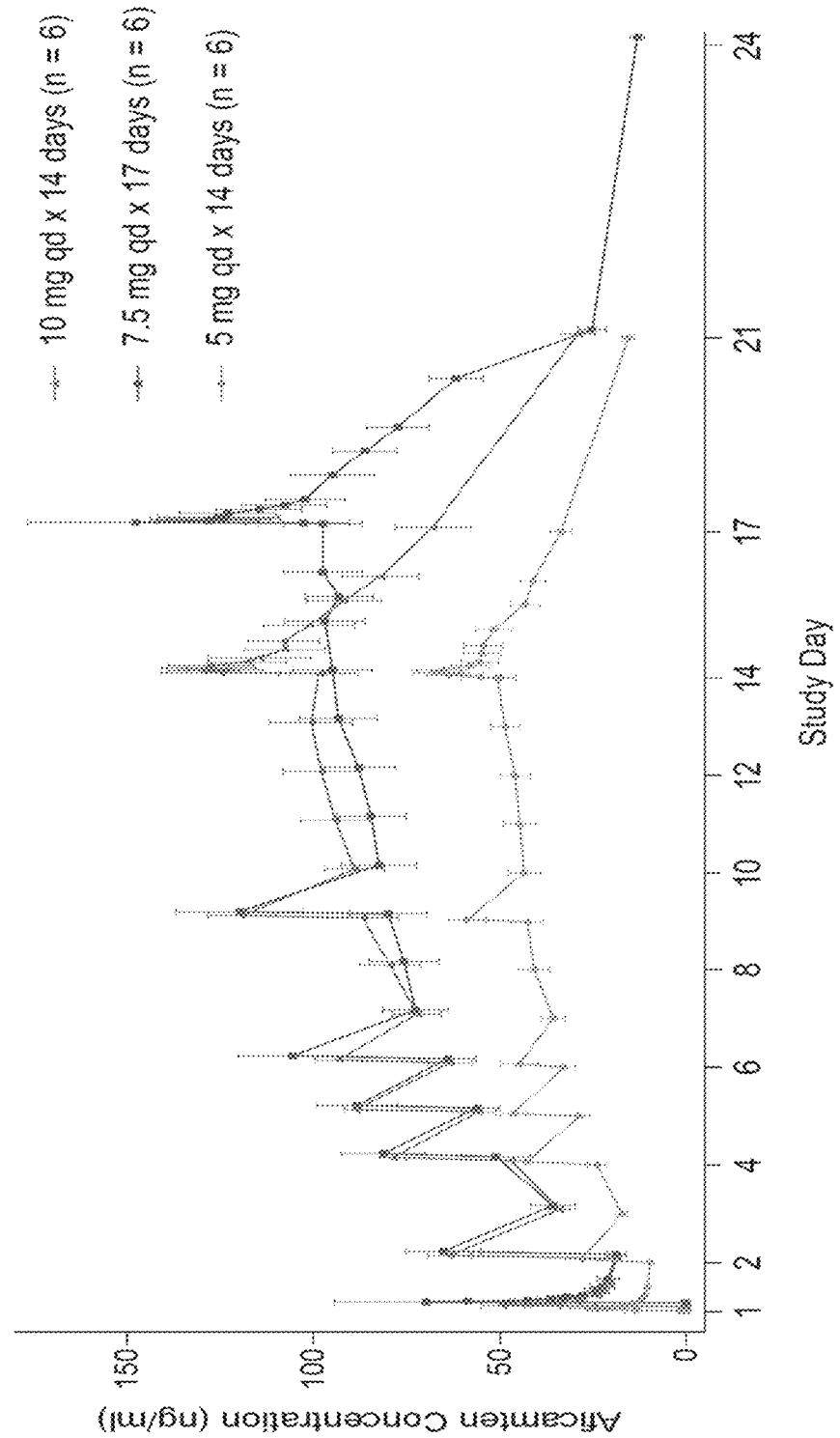
FIG. 4 shows plasma concentration over time with multiple doses of aficamten according to an exemplary clinical trial. Mean (SE) aficamten plasma concentrations are displayed. Data points are offset for clarity. Aficamten plasma concentrations increased between the 5-mg dose and the 2 higher doses; however, by day 2 there was no difference between mean concentrations of the 7.5-mg and 10-mg doses. Clearance was similar for the 5-mg and 10-mg doses, and the accumulation ratio was similar for all 3 doses. For days 7, 8, 10, 11, 12, and 13, only trough measurements are shown. For the 5-mg and 10-mg cohorts, the dosing period was 14 days with a 3-day follow-up. For the 7.5-mg cohort, dosing was extended to 17 days, with a 3-day follow-up, and confirmed that steady state was achieved after 10 to 12 days. SE=standard error.

Multiple-dose kinetics. With once-daily dosing, mean plasma concentrations increased between the 5-mg dose and the 2 higher doses (7.5 mg and 10 mg); however, by day 2 there was little difference between mean concentrations of the 7.5-mg and 10-mg doses (FIG. 4). Plasma PK parameters are displayed in Table 6. By the end of the treatment period (day 14 or 17), the mean plasma concentration was between 2 and 2.5 times that of day 1. Terminal elimination half-life estimates were consistent across doses, ranging between 77 and 86 h. Clearance was similar for the 5-mg and 10-mg doses, and the accumulation ratio was similar for the 3 doses. Consistent with the observed terminal elimination half-life estimates, steady state was achieved after 10 to 12 days (FIG. 4).

TABLE 6

Summary of Plasma Aficamten Pharmacokinetics Following Multiple Oral Dose Administration

| | Multiple-Ascending Dose (MAD) Cohorts | | |
|---|---|---|---|
| | 5 mg qd × 14 Days (n = 6) | 7.5 mg qd × 17 Days (n = 6) | 10 mg qd × 14 Days (n = 6) |
| Day 1 | | | |
| $C_{max}$ (ng/ml) | 28.0 (30.1) | 69.3 (66.5) | 54.4 (25.1) |
| $T_{max}$ (h) | 1.3 (0.5, 2.5) | 0.8 (0.5, 1.5) | 1.0 (1.0, 2.5) |
| $AUC_{24}$ (ng · h/ml) | 278 (21) | 551 (33) | 547 (11) |
| Day 14/17 | | | |
| $C_{max,ss}$ (ng/ml) | 69.0 (23) | 147.6 (39.5) | 141.2 (19.7) |
| $T_{max,ss}$ (h) | 2.8 (1.5, 4.0) | 1.0 (0.5, 5.0) | 2.5 (0.5, 3.0) |
| $AUC_{tau}$ (ng · h/ml) | 1320 (23) | 2518 (26) | 2632 (23) |
| $t_{1/2}$ (h) | 86.4 ± 11.9 | 76.9 ± 14.5 | 79.8 ± 14.1 |
| $CL_{ss}/F$ (h) | 3.9 ± 0.9 | 3.1 ± 0.7 | 3.9 ± 0.8 |
| $RA_{,AUC}$ | 4.8 ± 0.2 | 4.6 ± 0.7 | 4.9 ± 0.9 |

$AUC_{24}$, $C_{max}$, $AUC_{tau}$, and $C_{max,ss}$ values are presented as geometric mean and geometric CV %, $T_{max}$ and $T_{max,ss}$ values as median (range), and all other parameters as arithmetic mean ± standard deviation. $AUC_{24}$ = area under the plasma drug concentration-time curve from time 0 to 24 h; $AUC_{tau}$ = AUC to the end of the dosing period; $CL_{ss/F}$ = apparent total body clearance after oral administration (at steady state); $C_{max}$ = maximum plasma concentration; $C_{max,ss}$ = maximum plasma concentration at steady state; CV % = percent coefficient of variation; $RA_{,AUC}$ = accumulation ratio calculated from $AUC_{tau}$ at steady and following a single dose; $t_{1/2}$ = half-life; $T_{max}$ = time to maximum plasma concentration; $T_{max,ss}$ = time to reach maximum plasma concentration following drug administration at steady state.

CYP2D6 poor metabolizer cohort. In CYP2D6-PMs, mean half-life was prolonged to 110 h, compared with 85 h in extensive metabolizers (i.e., the 10-mg SAD cohort); however, no increase in AUC was observed in this group, with geometric mean $AUC_{24}$ of 495 ng·h/ml (geometric percent coefficient of variation [CV %]19) (Table 7), compared with 679 ng·h/ml (geometric CV % 35) in extensive metabolizers (Table 5). The CYP2D6-PMs did not appear to have reduced clearance that resulted in a clinically meaningful difference in exposures.

TABLE 7

Summary of Plasma Aficamten Pharmacokinetics in the CYP2D6 Poor Metabolizer Cohort

| PK Parameter | CYP2D6 Poor Metabolizers (n = 7) |
|---|---|
| $C_{max}$ (ng/ml) | 57.3 (55.0) |
| $T_{max}$ (h) | 1.0 (0.5, 4.0) |
| $AUC_{24}$ (ng · h/ml) | 495 (19) |
| $AUC_{inf}$ (ng · h/ml) | 2966 (46) |
| $t_{1/2}$ (h) | 110.2 ± 47.3 |

TABLE 7-continued

Summary of Plasma Aficamten Pharmacokinetics in the CYP2D6 Poor Metabolizer Cohort

| PK Parameter | CYP2D6 Poor Metabolizers (n = 7) |
|---|---|
| CL/F (L/h) | 3.6 ± 1.4 |
| Vz/F (L) | 506.0 ± 84.4 |

Aficamten dosage was 10 mg. AUC and $C_{max}$ values are presented as geometric mean and geometric CV %, $T_{max}$ values as median (range), and all other parameters as arithmetic mean ± standard deviation. $AUC_{24}$ = area under the plasma drug concentration-time curve from time 0 to 24 h; $AUC_{inf}$ = AUC from time 0 extrapolated to infinity; CL/F = apparent total body clearance; $C_{max}$ = maximum plasma concentration; CV % = percent coefficient of variation; PK = pharmacokinetic; $t_{1/2}$ = half-life; $T_{max}$ = time to maximum plasma concentration; Vz/F = apparent volume of distribution.

Effect of food. The PK parameters of aficamten in the food-effect cohort are displayed in Table 8. When taken with food, the $C_{max}$ of aficamten increased by approximately 30% and the time to maximum observed concentration was reduced (1.5 vs. 2.3 h). However, food had little effect on AUC, with geometric mean $AUC_{24}$ (geometric CV %) in the fasted state of 601 (33) ng·h/ml versus 631 (25) in the fed state.

TABLE 8

Summary of Plasma Aficamten Pharmacokinetics in the Food-Effect Cohort

| PK Parameter | Fasted (n = 10)* | Fed (n = 12)† |
|---|---|---|
| $C_{max}$ (ng/ml) | 50.6 (47.2) | 65.0 (69.5) |
| $T_{max}$ (h) | 2.3 (0.6, 6.0) | 1.5 (0.5, 6.0) |
| $AUC_{24}$ (ng · h/ml) | 601 (33) | 631 (25) |
| $AUC_{inf}$ (ng · h/ml) | 3674 (24) | 3413 (32) |
| $t_{1/2}$ (h) | 84.4 ± 16.4 | 78.0 ± 8.1 |
| CL/F (L/h) | 2.8 ± 0.6 | 3.1 ± 0.9 |
| Vz/F (L) | 345.7 ± 133.7 | 339.7 ± 100.4 |

Aficamten dosage was 10 mg in each cohort.
*n = 4 for $AUC_{inf}$, $t_{1/2}$, CL/F, and Vz/F.
†n = 7 for $AUC_{inf}$, $t_{1/2}$, CL/F, and Vz/F.
AUC and $C_{max}$ values are presented as geometric mean and geometric CV %, $T_{max}$ as median (range), and all other parameters as arithmetic mean ± standard deviation. $AUC_{24}$ = area under the plasma drug concentration-time curve from 0 to 24 h; $AUC_{inf}$ = AUC from time 0 extrapolated to infinity; CL/F = apparent total body clearance; $C_{max}$ = maximum plasma concentration; CV % = percent coefficient of variation; $t_{1/2}$ = half-life; $T_{max}$ = time to maximum plasma concentration; Vz/F = apparent volume of distribution.

Pharmacodynamics

Figure 5A:
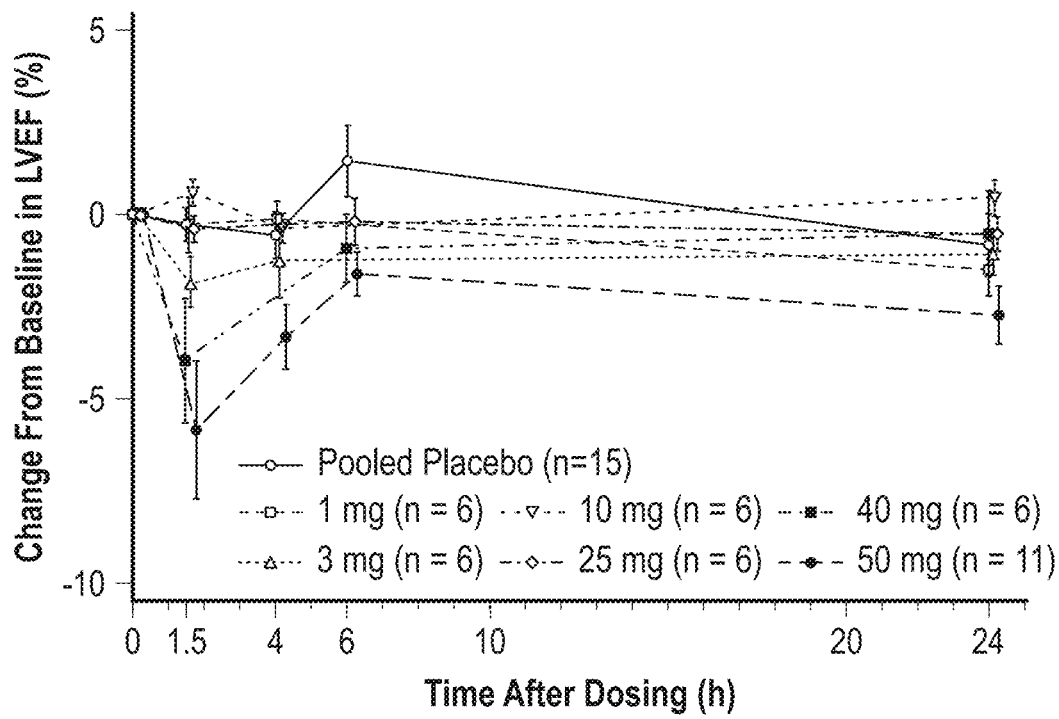
FIG. 5A shows SAD cohorts and FIG. 5B shows MAD cohorts for an exemplary aficamten clinical trial. Mean (SE) change from baseline in LVEF is displayed. Data points are offset for clarity. In both the SAD and MAD cohorts, reductions in LVEF within the target range (5% to 15% reduction) were observed. In the SAD cohorts, there were generally small decreases in LVEF, with mean maximum reduction of 5.8% in the 50-mg group (at 1.5 h post dose). In the MAD cohort, the greatest mean reduction in LVEF from baseline occurred in the 10-mg group (mean change of 5.0% 1.5 h after dosing on day 14). LVEF=left ventricular ejection fraction; MAD=multiple-ascending dose; qd, once daily; SAD=single-ascending dose; SE=standard error.
Figure 5B:
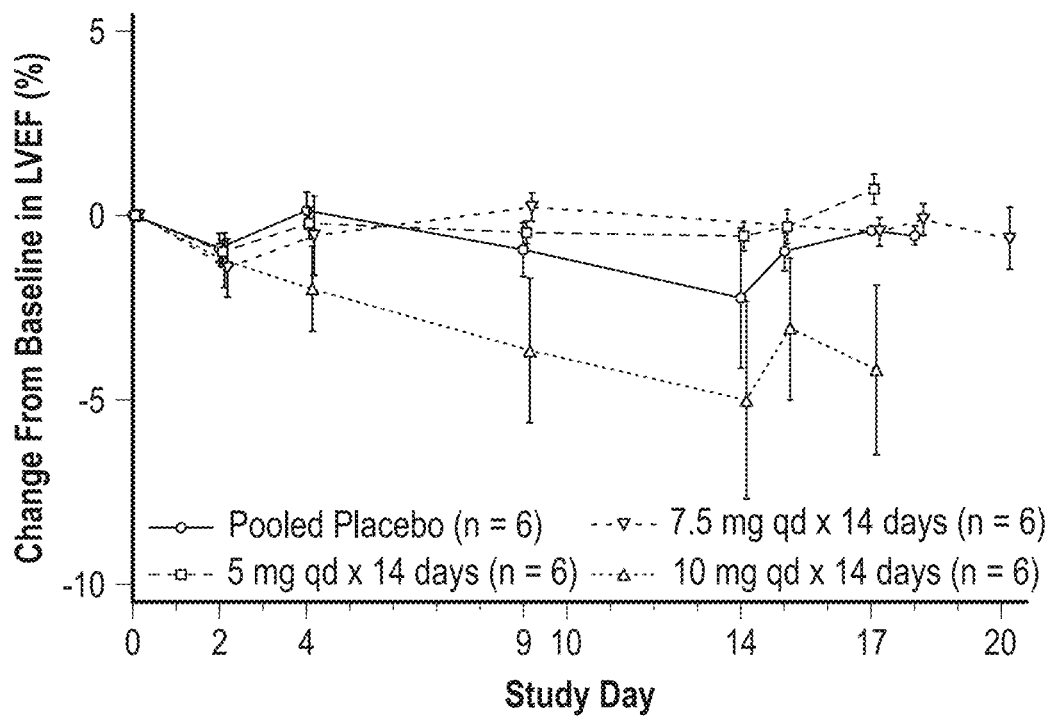

Left ventricular ejection fraction. At baseline, mean LVEF ranged from 61.0% to 67.5% across cohorts (Table 1). In the SAD cohorts, mean decreases in LVEF were observed in the groups receiving the highest doses of aficamten (FIG. 5A). Maximum mean reduction from baseline was seen in the 50-mg cohort at 1.5 h post dose (least-squares mean difference 5.5%, p=0.0001). LVESV and LVEDV were statistically significantly increased by 8.1 and 6.6 mL, respectively (Table 9). Other echocardiographic parameters such as stroke volume, cardiac output, cardiac time intervals, and measures reflective of diastolic function did not significantly change (Table 9). The single participant who received 75 mg of aficamten exhibited reduction in LVEF of 31.5% at 1.5 h post dose, which resolved 2.5 h after onset but led to concluding escalation of doses in the SAD portion of the study, as discussed above. In the MAD cohorts, a clear decrease in LVEF emerged as dosing continued in the 10-mg cohort (FIG. 5B). The largest mean maximum percent reduction from baseline, of 5.0%, was seen in the 10-mg cohort at 1.5 h post dose on day 14 (FIG. 5B). The placebo-corrected reduction of 3.2% (least-squares mean difference) did not reach statistical significance (p=0.21), likely due to the lack of statistical power in this small group comparison.

TABLE 9

The table compares the placebo data of echocardiographic parameters at baseline and 1.5 h (the time of the echocardiogram closest to peak of plasma concentrations of aficamten) to those at 50 mg of aficamten (the highest well tolerated single dose).

| | Placebo (n = 15) | | | | | | 50 mg (n = 11) | | | | | | p value |
|---|---|---|---|---|---|---|---|---|---|---|---|---|---|
| | Baseline | | 1.5 h | | CFB | | Baseline | | 1.5 h | | CFB | | CFB v |
| | Mean | SD | Mean | SD | Mean | SD | Mean | SD | Mean | SD | Mean | SD | CFB |
| Heart rate (bpm) | 61.6 | 5.6 | 61.4 | 7.6 | −0.2 | 5.6 | 61.7 | 11.5 | 62.3 | 10.6 | 0.5 | 5.8 | NS |
| LVEF (%) | 66 | 2 | 65.8 | 2 | −0.3 | 1.8 | 66.3 | 3.8 | 60.5 | 7.3 | −5.8 | 6.1 | 0.003 |
| LV ESV (mL) | 32 | 5.5 | 31.1 | 5.5 | −0.9 | 3.6 | 31.6 | 6.8 | 39.7 | 10.4 | 8.1 | 8.4 | 0.001 |
| LV EDV (mL) | 93.6 | 15.2 | 90.6 | 14.4 | −3 | 8.1 | 93.2 | 13.2 | 99.8 | 13.4 | 6.6 | 10.6 | 0.016 |
| LV SV (mL) | 56.7 | 6.3 | 56.1 | 9.7 | −0.6 | 6.8 | 58.9 | 8 | 52.6 | 10.5 | −6.2 | 7.6 | NS |
| LV CO (mL) | 3470 | 299 | 3450 | 655 | −21.4 | 538 | 3580 | 597 | 3240 | 681 | −346 | 498 | NS |
| IVCT (msec) | 46.9 | 2.4 | 46.9 | 6.4 | 0.4 | 5.9 | 42.3 | 1.6 | 42.6 | 1.8 | 0.4 | 2.9 | NS |
| IVRT (msec) | 72.1 | 10.6 | 73.9 | 7 | 1.9 | 11.3 | 68.7 | 3 | 69.3 | 3.3 | 0.5 | 3.8 | NS |
| LV ET (msec) | 332 | 32.2 | 324 | 26.3 | −6.9 | 12.5 | 344 | 35.1 | 328 | 34.1 | 1.9 | 12.8 | NS |
| LAV (mL) | 36 | 8.4 | 35.3 | 9.3 | −1 | 7.6 | 35.7 | 9.9 | 35.7 | 7.2 | 0 | 4.7 | NS |
| E (cm/sec) | 73.6 | 6.7 | 68.2 | 8.2 | −5.3 | 5.7 | 66.7 | 14.7 | 64 | 14.7 | −2.7 | 4.5 | NS |
| A (cm/sec) | 49.4 | 11.4 | 47.7 | 10.3 | −1.7 | 5.6 | 52 | 12.8 | 54.5 | 17.5 | 2.5 | 6.6 | NS |
| e' lateral (cm/sec) | 12.7 | 2.5 | 12.3 | 2.7 | −0.7 | 1.5 | 11.5 | 3.1 | 10.2 | 2.4 | −1.3 | 1.6 | NS |
| E/A ratio | 1.6 | 0.4 | 1.5 | 0.4 | −0.1 | 0.2 | 1.3 | 0.1 | 1.2 | 0.2 | −0.1 | 0.5 | NS |
| E/e' ratio | 6 | 1.2 | 5.8 | 1.3 | −0.1 | 0.7 | 6.3 | 2.8 | 6.8 | 3.3 | 0.5 | 1.5 | NS |

A = peak A wave velocity,
bpm = beat per minute,
CFB = change from baseline,
CO = cardiac output,
E = peak E wave velocity,
EDV = end-systolic volume,
ESV = end-systolic volume,
ET = ejection time,
e' lateral = tissue doppler velocity of the lateral wall,
IVCT = isovolumic contraction time,
IVRT = isovolumic relaxation time,
LAV = left atrial volume,
LVEF = left ventricular ejection fraction,
NS = not significant (p > 0.05),
SD = Standard deviation,
SV = stroke volume Categorical LVEF responses. In the SAD cohorts, absolute reductions in LVEF of ≥5% from baseline were observed in 1 of 15 participants in the placebo cohort (7%), 1 of 6 (17%) in the 3-mg cohort, 2 of 6 (33%) in the 40-mg cohort, 7 of 11 (64%) in the 50-mg cohort, and 1 of 1 (100%) in the 75-mg cohort, while no participants in the 1-, 10-, or 25-mg cohorts had a reduction ≥5%. Absolute reductions in LVEF of ≥10% occurred in 1 of 6 participants (17%) in the 40-mg cohort, 2 of 11 (18%) in the 50-mg cohort, and 1 (100%) in the 75-mg cohort. Reduction in LVEF to <50% was observed for 2 of 11 participants (18%) in the 50-mg cohort (48.2% and 45.5% per core laboratory assessment), and 1 of 1 (100%) in the 75-mg cohort. Only the participant in the 75-mg cohort experienced LVEF <45%.

In the MAD cohort, absolute reduction in LVEF of ≥5% from baseline was observed in 4 participants: 1 of 6 participants (17%) receiving placebo, 1 of 6 (17%) receiving 7.5 mg of aficamten once daily, and 2 of 6 (33%) receiving 10 mg of aficamten once daily. Of these, reductions were ≥10% in the 2 participants in the 10-mg cohort. Reduction in LVEF to <50% was not observed in any of the MAD cohorts per core laboratory assessment.

Figure 6A:
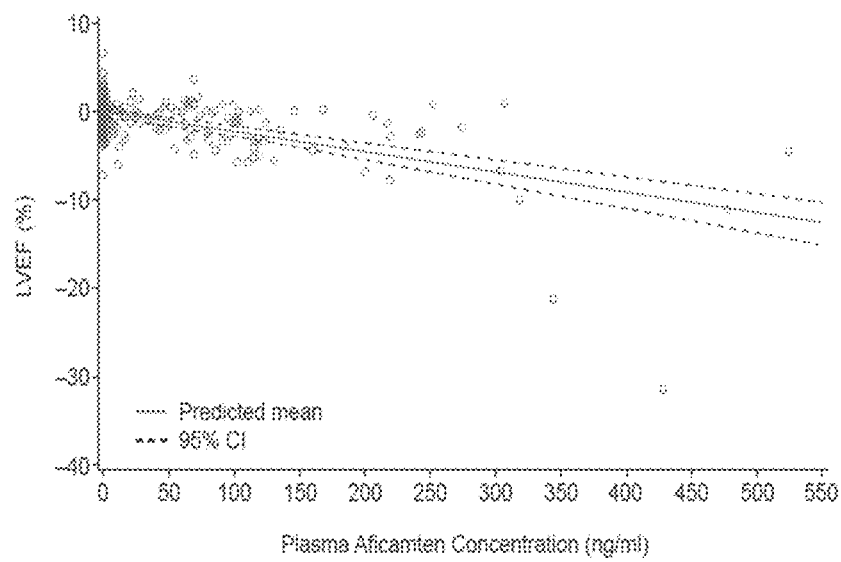
FIG. 6A shows analysis of the SAD cohorts according to an exemplary clinical trial, and shows that, as the plasma concentration of aficamten increased, there was a trend toward a decrease in LVEF.
Figure 6B:
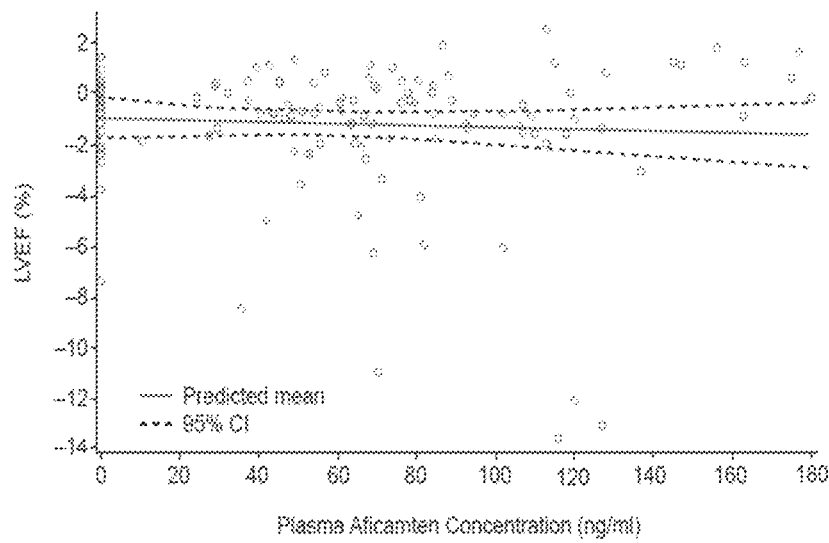
FIG. 6B shows analysis of the MAD cohorts from an exemplary clinical trial, and shows minimal suppression of LVEF in most participants at plasma aficamten concentrations of ≤180 ng/ml. CI=confidence interval; LVEF=left ventricular ejection fraction; MAD=multiple-ascending dose; SAD=single-ascending dose.

Relationship of Plasma Concentration to Change in LVEF. The PK/PD relationship for aficamten is illustrated by plotting the plasma concentration of aficamten versus change in LVEF for the SAD and MAD cohorts (FIG. 6A and FIG. 6B). In the SAD cohort, as plasma concentration of aficamten increased, there was a trend toward a decrease in LVEF. The relationship of LVEF to the plasma concentration of aficamten was statistically significant, both in the bin concentration analysis for the highest plasma concentration bin (122 to 524 ng/ml, p<0.0001) and in the concentration-slope analysis (p=0.0027). In the MAD cohorts, the relationship of LVEF to plasma aficamten did not reach statistical significance in the bin concentration analysis or the linear regression analysis, likely due to the more limited range of plasma concentrations explored and the small group sizes.

Discussion

This phase 1, first-in-human study has established the doses (up to 50 mg as a single oral dose or up to 10 mg following multiple doses) at which aficamten was both physiologically effective at reducing LVEF and was well tolerated in healthy participants, identifying pharmacologically active doses that will serve as starting doses for a study in patients with HCM. In addition, single oral doses of 10 mg were well tolerated among individuals with the CYP2D6-PM phenotype and there was no significant effect of food on the PK of aficamten. Collectively, these observations support the continued development of aficamten for patients with HCM and provide a roadmap for phase 2 studies.

Safety of aficamten. No serious AEs were observed in the study and all participants completed intended dosing as planned. Generally, AEs were mild and similar in frequency between participants treated with aficamten and placebo. Importantly, there were no associated symptoms or adverse changes in vital signs for participants whose LVEF fell below 50% and the LVEF in these cases returned to baseline within 24 h. This study was not intended to find a maximum tolerated dose and hence dose escalation stopped once a clear PD effect was observed in the SAD and MAD portions of the study; thus, a dose that was not tolerated due to AEs was not identified.

Effect on LVEF. In the SAD cohorts, a dose of 50 mg produced a mean reduction in LVEF of 5.8% while in the MAD cohort, 10 mg once daily for 14 days produced a mean absolute reduction in LVEF of approximately 5%. The proportion of participants with absolute reductions in LVEF of ≥5% from baseline increased as the dose increased; up to 64% of participants in the 50-mg SAD cohort and 33% in the 10-mg MAD cohort had absolute reductions in LVEF of ≥10% from baseline. In the SAD cohorts, where the broadest range of exposures of aficamten was explored, there was a statistically significant decrease in LVEF as plasma concentrations of aficamten increased. Thus, the study achieved its secondary objective of identifying a pharmacologically active dose and describing its PK/PD relationship.

Three participants had decreases in LVEF to <50% that were rapidly reversible upon study drug discontinuation. Following a single dose of 50 mg, 2 (18%) participants experienced LVEF <50% (48.2% and 45.5%). After a single dose of 75 mg, 1 participant experienced reduction of LVEF to 34.1%. In all cases, the event was noted approximately 1.5 h after dosing, and LVEF recovered to >50% by 4 to 6 h after dosing. The SAD results informed dose selection for the other portions of the study, and there were no echocardiographic AEs in the MAD, CYP2D6-PM, or food-effect cohorts.

Implications of PK results. Aficamten demonstrated linear kinetics over the dose range of 1 mg to 50 mg; half-life was independent of concentration, and clearance was independent of dose. Steady state was achieved by the end of day 10 with the 10-mg dose and by the end of day 12 with the 5-mg and 7.5-mg doses. There was no effect of food suggestive of a need to alter dosing. These findings support once-daily dosing in either the fasted or fed state.

The relationship between plasma concentration and LVEF suggests a broad therapeutic index, which will facilitate optimization of individual doses in patients with HCM, who are expected to be titrated through an escalating range of doses until the desired PD effect is achieved. In addition, the half-life of aficamten (75 to 85 h following a single dose; 77 to 86 h following multiple doses) and observed reversibility of effect offers a potential advantage in that steady state is achieved within 2 weeks and excessive effects on LVEF are readily reversed. Conclusions. Aficamten demonstrated a favorable safety profile in healthy participants, without serious AEs or meaningful changes in laboratory tests, ECGs, or health assessments. Any decreases in LVEF to values <50% were reversible within 6 h following single doses. Pharmacologically active doses of aficamten that may serve as starting doses for a study in patients with HCM were identified.

Example 2

A multi-center, randomized, placebo-controlled, double-blind, dose finding phase 2 clinical trial of CK-274 in patients with symptomatic obstructive HCM (oHCM) was conducted. The primary objective of the trial was to determine the safety and tolerability of CK-274. The secondary objectives were to describe the concentration-response relationship of CK-274 on the resting and post-Valsalva left ventricular outflow tract gradient as measured by echocardiography during 10 weeks of treatment, to describe the dose response relationship of CK-274, and to evaluate the plasma concentrations of CK-274 in patients with oHCM. Seventeen investigative sites in North America and Europe screened for patients to enroll in Cohorts 1 and 2. A third cohort (Cohort 3) was also studied to evaluate the safety and efficacy of CK-274 in combination with disopyramide, a class IA antiarrhythmic drug.

The first two cohorts (Cohort 1 and Cohort 2) excluded patients receiving disopyramide. Cohort 3 included patients receiving disopyramide. Within each of the first two cohorts, patients were randomized 2:1 to active or placebo treatment and received up to three escalating doses of CK-3773274 or placebo based on echocardiographic guidance. In the third cohort, all patients received up to three escalating doses of CK-3773274 based on echocardiographic guidance. Overall, the treatment duration was 10 weeks with a 4-week follow-up period after the last dose.

Since patient characteristics vary substantially in this disease, individualized dose titration to a pharmacodynamics (PD) response (reduction of the LVOT-G to <30 mmHg with preservation of LVEF >50%) was employed to maximize efficacy and safety.

Patients were eligible to be included in the study only if all the following criteria apply: 1. Able to comprehend and willing to sign an informed consent form (ICF) and willing to comply with all study procedures and restrictions for the duration specified in the Schedule of Activities; 2. Males and females between 18 and 85 years of age at screening; 3. Body weight was ≥45 kg at screening; 4. Diagnosed with oHCM per the following criteria: (a) as LV hypertrophy and non-dilated LV chamber in the absence of other cardiac disease; and (b) had minimal wall thickness ≥15 mm (minimal wall thickness ≥13 mm was acceptable with a positive family history of HCM or with a known disease-causing gene mutation); 5. Adequate acoustic windows for echocardiography; 6. Had LVOT-G during screening as follows for Cohorts 1 and 2: (a) resting gradient ≥50 mmHg; or (b) resting gradient ≥30 mmHg and <50 mmHg with post-Valsalva LVOT-G ≥50 mmHg; or as follows for Cohort 3: persistent resting LVOT obstruction (≥30 mmHg) and provoked LVOT obstruction (≥50 mmHg); 7. Left ventricular ejection fraction (LVEF) ≥60% at screening; 8. New York Heart Association (NYHA) Class II or III at screening; 9. Patients on beta-blockers, verapamil, diltiazem, or ranolazine should have been on stable doses for >4 weeks prior to randomization and anticipate remaining on the same medication regimen during the study; 10. Male patients were eligible to participate if they agreed to the following during the study and for at least 10 weeks after the last dose: (a) refrain from donating sperm; plus either (b)(i) be abstinent from heterosexual intercourse as their preferred and usual lifestyle (abstinent on a long term and persistent basis) and agree to remain abstinent; or (b)(i) must agree to use a male condom and, when his female partner is a woman of childbearing potential, have his female partner use a highly effective method of contraception; 11. A female patient was eligible to participate if she is not pregnant or breastfeeding, and at least one of the following conditions applies: (a)(i) is not a woman of childbearing potential, or (a)(ii) is a woman of childbearing potential and using a highly effective method of contraceptive during the study and for at least 4 weeks after the last dose; and (b) a woman of childbearing potential must have a negative pregnancy test (urine or serum as required by local regulations) within 3 days before the first dose of study intervention; 12. Able to complete all screening procedures; and 13. Taking stable doses of disopyramide for >4 weeks prior to screening (Cohort 3 only).

Patients were excluded from the study if any of the following criteria apply: 1. Aortic stenosis or fixed subaortic obstruction; 2. Known infiltrative or storage disorder causing cardiac hypertrophy that mimics oHCM (e.g., Noonan syndrome, Fabry disease, amyloidosis); 3. History of left ventricular (LV) systolic dysfunction (LVEF <45%) at any time during their clinical course; 4. Documented history of current obstructive coronary artery disease (>70% stenosis in one or more epicardial coronary arteries) or documented history of myocardial infarction; 5. Has been treated with septal reduction therapy (surgical myectomy or percutaneous alcohol septal ablation) or has plans for either treatment during the study period; 6. Prior treatment with cardiotoxic agents such as doxorubicin or similar; 7. For Cohorts 1 and 2: Has been treated with disopyramide or antiarrhythmic drugs that have negative inotropic activity within 4 weeks prior to screening, and for Cohort 3: Has been treated with an antiarrhythmic drug other than disopyramide that has negative inotropic activity within 4 weeks prior to screening; 8. Has any ECG abnormality considered by the investigator to pose a risk to patient safety (e.g., second degree atrioventricular block type II); 9. Paroxysmal atrial fibrillation or flutter documented during the screening period; 10. Paroxysmal or permanent atrial fibrillation requiring rhythm restoring treatment (e.g., direct-current cardioversion, ablation procedure, or antiarrhythmic therapy) ≤6 months prior to screening, except that this exclusion does not apply if atrial fibrillation has been treated with anticoagulation and adequately rate-controlled for >6 months; 11. History of syncope or sustained ventricular tachyarrhythmia with exercise within 6 months prior to screening; 12. Implantable cardioverter defibrillator (ICD) placement within 3 months prior to screening or planned ICD placement during the study; 13. History of appropriate ICD shock for life-threatening ventricular arrhythmia within six months prior to screening; 14. Recipient of a major organ transplant (e.g., heart, lung, liver, bone marrow, renal) or anticipated transplantation within 12 months from randomization); 15. Hepatic impairment defined by a total bilirubin (TBL) ≥1.5× the upper limit of normal (ULN), or alanine aminotransferase (ALT) or aspartate aminotransferase (AST) ≥3×ULN at screening, except that patients with documented Gilbert syndrome and TBL ≥1.5×ULN due to unconjugated hyperbilirubinemia, without other hepatic disease, were permitted; 16. History or evidence of any other clinically significant disorder, malignancy, active infection, other condition, or disease that, in the opinion of the investigator or the Medical Monitor, would pose a risk to patient safety or interfere with the study evaluation, procedures, or completion; 17. Hemoglobin <10.0 g/dL at screening; 18. Estimated glomerular filtration rate (eGFR) <30 mL/min/1.73 m² (by the modified Modification of Diet in Renal Disease equation) at screening; 19. Currently participating in another investigational device or drug study or received an investigational device or drug <1 month (or 5 half-lives for drugs, whichever is longer) prior to screening; 20. Has received prior treatment with CK-3773274 or is currently receiving mavacamten; 21. Has a known hypersensitivity to any excipients in CK-3773274 Tablets, Film-Coated.

In each cohort, a patient received up to three escalating doses of CK-3773274 as shown in Table 11. Each patient received Dose 1 once daily for 2 weeks. At Week 2, the patient had an echocardiogram 2 hours following administration of their dose. Patients up-titrated to Dose 2 if either of the following conditions were met on echocardiography: (1) resting LVOT-G ≥30 mmHg and the biplane LVEF ≥50%; or (2) resting LVOT-G<30 mmHg, post-Valsalva LVOT-G ≥50 mmHg, and the biplane LVEF ≥50%. Otherwise, the patient remains on Dose 1. If LVEF is <50% at Week 2, the patient was down-titrated to placebo. The dose-adjustment algorithm is shown below in Table 10.

After 2 more weeks on the assigned dose (i.e., Week 4), each patient had an echocardiogram 2 hours following administration of their dose. Patients were escalated to the next higher dose if either of the following conditions were met on echocardiography: (1) resting LVOT-G ≥30 mmHg and the biplane LVEF ≥50%; or (2) resting LVOT-G<30 mmHg, post-Valsalva LVOT-G ≥50 mmHg, and the biplane LVEF ≥50%. Otherwise, the patient remained on the same dose. If LVEF was <50% at Week 4, the patient was returned to a prior dose level or to placebo if the patient was on Dose 1.

After 2 more weeks on the assigned dose (i.e., Week 6), each patient had an echocardiogram 2 hours following administration of their dose. If LVEF was <50% at Week 6, the patient was down-titrated to a prior dose level or to placebo if the patient was on Dose 1.

TABLE 10

Dose Adjustment Algorithm

| Biplane LVEF | | LVOT Gradient | Action |
|---|---|---|---|
| <40% | | | Permanent discontinuation |
| <50% | | | Dose reduce to next lower dose or placebo (if on lowest dose) |
| ≥50% | and | Resting LVOT gradient < 30 mmHg AND Valsalva LVOT gradient < 50 mmHg | Dose unchanged |
| ≥50% | and | Rest LVOT gradient ≥ 30 mmHg AND/OR Valsalva LVOT gradient ≥ 50 mmHg | Dose escalate to next dose level |

If at any time, a patient's dose was down-titrated to placebo, then they remained on placebo for the duration of the study.

TABLE 11

Dosing Scheme

| Cohort | Dose 1 | Dose 2 | Dose 3 |
|---|---|---|---|
| Cohort 1 | 5 mg | 10 mg | 15 mg |
| Cohort 2 | 10 mg | 20 mg | 30 mg |
| Cohort 3 | 5 mg | 10 mg | 15 mg |

Baseline characteristics of patients in Cohort 1, Cohort 2, and Cohort 3 are shown in Table 12 and Table 13.

TABLE 12

Baseline Characteristics of Patients in Phase 2 Clinical Trial

| Characteristic | Cohort 1 (N = 21) | Cohort 2 (N = 20) | Cohort 3 (N = 13) |
| --- | --- | --- | --- |
| Age (Years), Mean (SD) [Range] | 56.7 (12.1) [33, 69] | 57.0 (13.0) [35, 78] | 59.4 (14.4) [23, 82] |
| Female, n (%) | 10 (47.6) | 13 (65.0) | 7 (53.8) |
| BMI (kg/m2), Mean (SD) [Range] | 29.1 (5.3) [20.2, 39.9] | 30.3 (6.6) [22.3, 48.4] | 30.1 (6.2) [22.7, 41.2] |
| NYHA Class, n (%) | | | |
| Class II | 16 (76.2) | 12 (60.0) | 5 (38.5) |
| Class III | 5 (23.8) | 8 (40.0) | 8 (61.5) |
| Beta Blocker Use, n (%) | 16 (76.2) | 16 (80.0) | 11 (84.5) |
| LVEF at Screening (%), Mean (SD) | 72.9 (7.9) | 71.8 (7.0) | 69.9 (7.1) |
| LVOT-G, Rest at Screening (mmHg), Mean (SD) | 61.0 (28.4) | 67.1 (30.4) | 52.3 (21.7) |
| LVOT-G, Valsalva at Screening (mmHg), Mean (SD) | 88.2 (24.6) | 93.0 (35.1) | 97.1 (36.4) |
| NT-proBNP (pg/mL), Geometric Mean (CV %) | 368.5 (255.0) | 573.8 (145.5) | 1050.6 (147.3) |

TABLE 13

Baseline Demographic and Clinical Characteristics of Patients in Phase 2 Clinical Trial, Cohorts 1 and 2

| Characteristics | Pooled Placebo (N = 13) | Cohort 1 (N = 14) | Cohort 2 (N = 14) | Pooled Aficamten (N = 28) |
| --- | --- | --- | --- | --- |
| Age, y | 57 ± 10 | 54 ± 14 | 59 ± 14 | 57 ± 14 |
| Female, n (%) | 8 (62) | 4 (29) | 11 (79) | 15 (54) |
| Race, white, n (%) | 12 (92) | 14 (100) | 14 (100) | 28 (100) |
| BMI, kg/m$^2$ | 29 ± 6 | 30 ± 5 | 30 ± 6 | 30 ± 6 |
| NYHA FC, n (%) | | | | |
| Class II | 11 (85) | 10 (71) | 7 (50) | 17 (61) |
| Class III | 2 (15) | 4 (29) | 7 (50) | 11 (39) |
| NT-proBNP, pg/mL, Geometric Mean (% CV) | 395 (227) | 344 (254) | 695 (124) | 520 (189) |
| High sensitivity cardiac troponin I, ng/ml (% CV) | 15 (416) | 8 (496) | 10 (115) | 9 (306) |
| Basal interventricular septal wall thickness, mm (SD) | 15 (3) | 18 (3) | 16 (3) | 17 (3) |
| Posterior wall thickness, mm (SD) | 12 (2) | 13 (2) | 12 (2) | 12 (2) |
| LAVI, mL/m$^2$ (SD) | 31.4 (7.5) | 31.9 (9.2) | 33.0 (7.2) | 32.5 (8.1) |
| LVED, mm (SD) | 39 (3) | 39 (5) | 39 (4) | 39 (4) |
| LVEF, % (SD) * | 74 (6) | 71 (8) | 72 (8) | 72 (8) |
| LVOT gradient at rest, mmHg (SD) * | 70 (28) | 52 (23) | 70 (34) | 61 (30) |
| LVOT gradient with Valsalva, mmHg (SD) * | 93 (27) | 83 (19) | 96 (40) | 89 (31) |
| Lateral E/e' ratio, Mean (SD) | 17.4 (10.0) | | | 13.8 (6.3) |
| Lateral e' (cm/s), Mean (SD) | 5.8 (2.1) | | | 6.7 (2.3) |
| LAVI (mL/m$^2$), Mean (SD) | 31.4 (7.5) | | | 32.5 (8.1) |
| LVMI (g/m$^2$), Mean (SD) | 103.3 (25.1) | | | 109.8 (28.6) |
| Presence of MR, n (%) | 11 (84.6%) | | | 26 (92.9%) |
| Presence of Eccentric MR, n (%) | 3 (25.0%) | | | 12 (42.9%) |
| Presence of SAM, n (%) | 12 (92.3%) | | | 24 (85.7%) |
| Medications | | | | |
| Beta-blocker, n (%) | 11 (85) | 10 (71) | 11 (79) | 21 (75) |
| Calcium channel-blocker, n (%) | 2 (15) | 5 (36) | 2 (14) | 7 (25) |

* = derived from individual investigator site echocardiographic assessments.

BMI = body mass index; CV = coefficient of variation; LVEF = left ventricular ejection fraction; LA = left atrium; LVED = left ventricular end diastolic dimension; LVOT = left ventricular outflow tract; NT-proBNP = N-terminal pro B-type natriuretic peptide; NYHA FC = New York Heart Association functional class.

Echocardiograms obtained every 2 weeks and 2 weeks after the last dose were analyzed for several key structural and physiologic metrics and N-terminal prohormone of brain natriuretic peptide (NT-proBNP).

Initial results from the clinical study included data from two sequentially conducted cohorts, Cohort 1 (n=21) and Cohort 2 (n=20) which randomized treatment of patients 2:1 to CK-274 or placebo. Patients received up to three escalating doses of CK-274 once daily (5, 10, 15 mg in Cohort 1 and 10, 20, 30 mg in Cohort 2) or placebo. Patients had an echocardiogram after two weeks of treatment at each dose to determine potential up-titration to the next higher dose. Overall, treatment duration for each patient in the study was 10 weeks with an echocardiogram conducted 2 weeks after the last dose.

Figure 7:
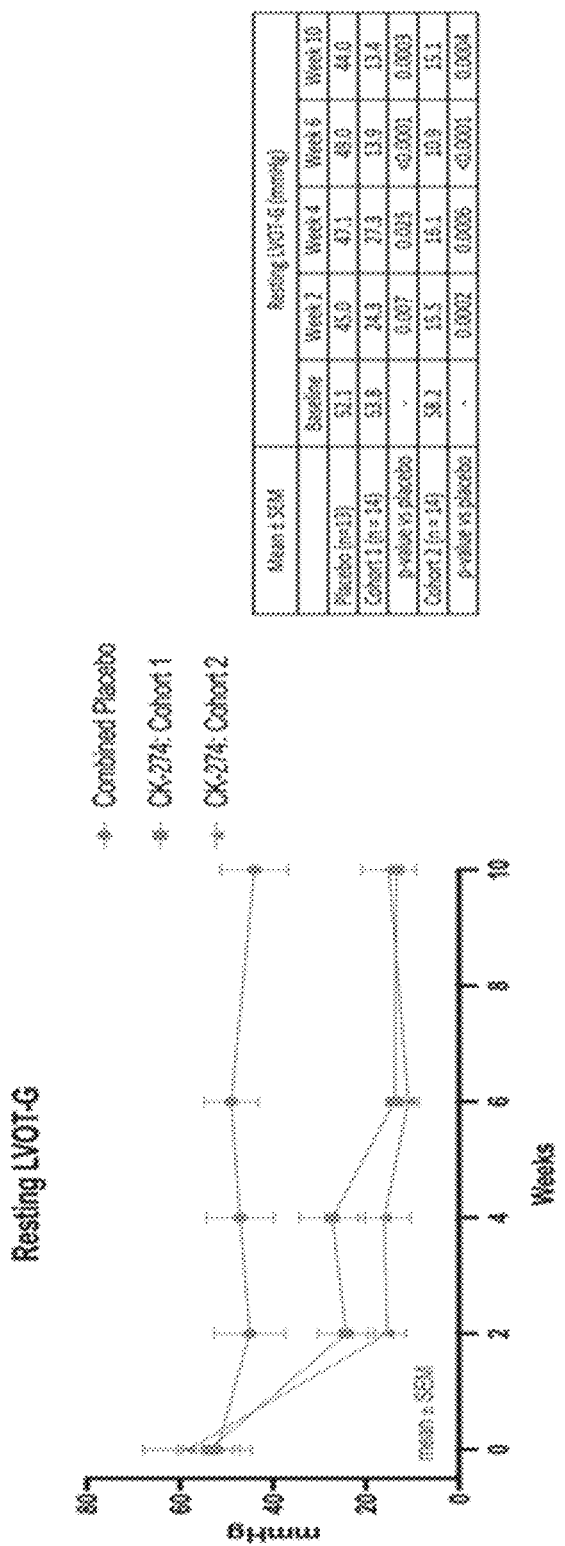
FIG. 7 shows resting LVOT-G for treatment and placebo cohorts according to an exemplary clinical trial for CK-274 (aficamten).

For patients on CK-274 in Cohort 1 (n=14), the average resting LVOT-G changed from 53.8 mmHg at baseline to 13.4 mmHg at 10 weeks; for patients on CK-274 in Cohort 2 (n=14) the average resting LVOT-G changed from 58.2 mmHg at baseline to 15.1 mmHg at 10 weeks; and for patients in the combined placebo group (n=13) the average resting LVOT-G changed from 52.1 at baseline to 44.0 mmHg at 10 weeks (FIG. 7, p=0.0003 for Cohort 1, p=0.0004 for Cohort 2 in comparison to placebo at 10 weeks).

Figure 8:
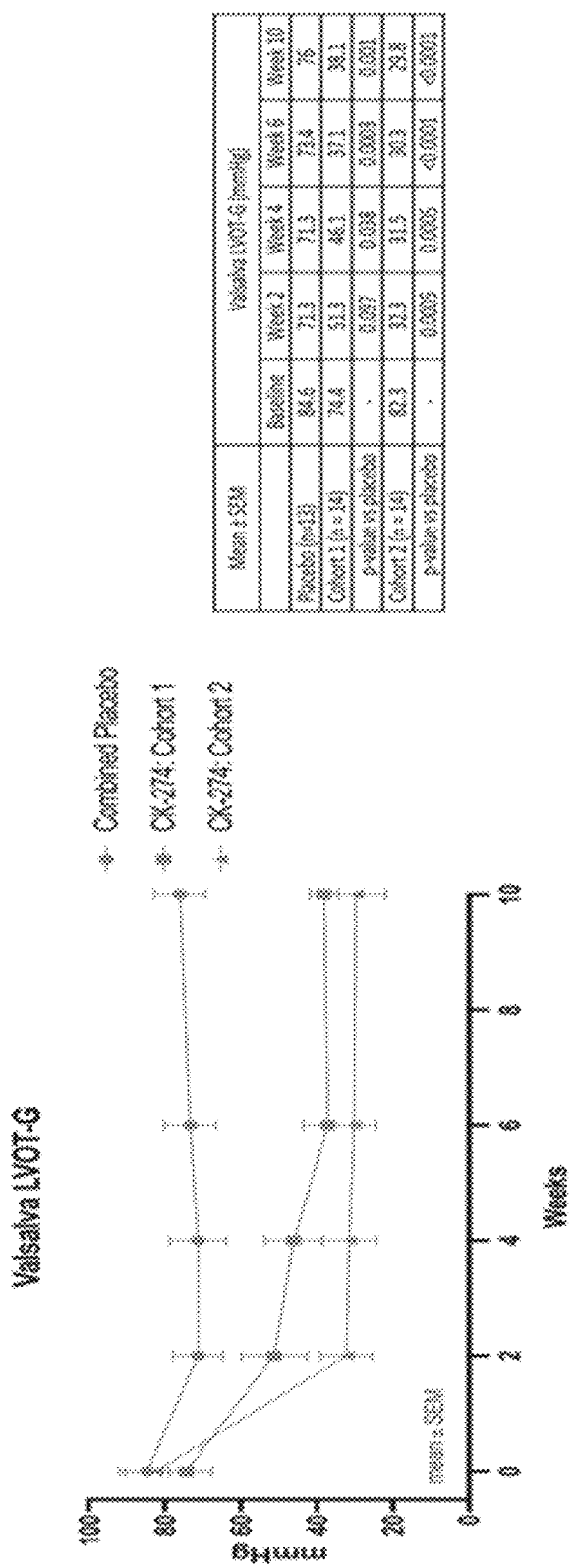
FIG. 8 shows post-Valsalva LVOT-G for treatment and placebo cohorts according to an exemplary clinical trial for CK-274 (aficamten).

For patients on CK-274 in Cohort 1 (n=14) the average Valsalva LVOT-G changed from 77.4 mmHg at baseline to 38.1 mmHg at 10 weeks; for patients on CK-274 in Cohort 2 (n=14) the average Valsalva LVOT-G changed from 82.3 mmHg at baseline to 29.8 mmHg at 10 weeks; and for patients in the combined placebo group (n=13) the average Valsalva LVOT-G changed from 84.6 at baseline to 76.0 mmHg at 10 weeks (FIG. 8; p=0.001 for Cohort 1, p<0.0001 for Cohort 2 in comparison to placebo at 10 weeks).

The average ejection fraction for patients on CK-274 in Cohort 1 (n=14) changed from 72.8% at baseline to 67.3% at 10 weeks; for patients on CK-274 in Cohort 2 (n=14) the average ejection fraction changed from 75.4% at baseline to 64.1% at 10 weeks, and for patients in the combined placebo group (n=13) the average ejection fraction changed from 74.5% at baseline to 74.9% at 10 weeks (p=0.01 for Cohort 1, p=<0.0001 for Cohort 2 in comparison to placebo at 10 weeks).

Overall, the incidence of adverse events was similar between treatment arms. Treatment with CK-274 in the study was well tolerated with adverse events reported as mild or moderate in severity. There were no treatment related serious adverse events reported by investigators.

No patients who received CK-274 in Cohort 1 had an LVEF <50%. In Cohort 2, one patient with an LVEF at baseline of 58% was up titrated to 20 mg of CK-274 and experienced transient LVEF reduction to <50% (remaining above 40%) requiring down titration. No interruptions or discontinuations of treatment with CK-274 occurred in any patients across both cohorts.

The distribution of patients across doses of CK-274 in the study (Cohorts 1 and 2) is shown in Table 14. The distribution of patients across doses of CK-274 in Cohort 3 of the study is shown in Table 15.

TABLE 14

| | | Final Dose Achieved (N) | | | | | |
|---|---|---|---|---|---|---|---|
| | | Cohort 1 | | | Cohort 2 | | |
| | Placebo | 5 mg | 10 mg | 15 mg | 10 mg | 20 mg | 30 mg |
| Cohort 1 + 2 (N = 41) | 13 | 4 | 5 | 5 | 9 | 4 | 1 |

TABLE 15

| | | Final Dose Achieved (N) | | | | |
|---|---|---|---|---|---|---|
| | | 5 mg | 10 mg | 15 mg | 20 mg | 30 mg |
| N = 13 | Cohort 3 | 1 | 6 | 6 | | |

Secondary results from the clinical study included data from Cohort 3 (n=13). All patients received up to three escalating doses of CK-274 once daily (5, 10, 15 mg). Patients had an echocardiogram after two weeks of treatment at each dose to determine potential up-titration to the next higher dose. Overall, treatment duration for each patient in the study was 10 weeks with an echocardiogram conducted 2 weeks after the last dose. Efficacy endpoints included resting and provoked LVOT gradients, NYHA class, and NT-proBNP.

In Cohort 3, 13 patients were enrolled (59±14 years of age; 54% female) with NYHA class II (n=5) and III (n=8). Compared with Cohorts 1 and 2, patients in Cohort 3 had similar demographics, LVEF and severity of obstruction, but were more symptomatic and had higher baseline NT-proBNP. Cohort 3 patients had symptomatic obstructive HCM and a resting or post-Valsalva left ventricular outflow tract gradient (LVOT-G) of ≥50 mmHg, and had previously been treated with disopyramide and, in the majority, a beta-adrenergic blocker. All patients received up to three escalating doses of aficamten once daily (5, 10, 15 mg), titrated based on echocardiographic guidance, as discussed above. Overall treatment duration was 10 weeks with a 4-week follow up period after the last dose. In total, thirteen patients were enrolled and all patients completed the study on treatment.

Results from Cohort 3 showed that substantial reductions in the average resting LVOT-G as well as the post-Valsalva LVOT-G (defined as resting gradient <30 mmHg and post-Valsalva gradient <50 mmHg) were achieved. These clinically relevant decreases in pressure gradients were achieved with only modest decreases in average left ventricular ejection fraction (LVEF); there were no patients whose LVEF fell below the prespecified safety threshold of 50%.

New York Heart Association functional class was improved in the majority of patients participating in Cohort 3 of the trial. Pharmacokinetic data were similar to those observed in Cohorts 1 and 2. In addition, the safety and tolerability of aficamten were consistent with no treatment interruptions and no serious adverse events attributed to treatment reported by the investigators.

CK-274 in combination with disopyramide may present a treatment option for the most severe and treatment refractory oHCM patients.

Results after 10 weeks of therapy

Figure 9:
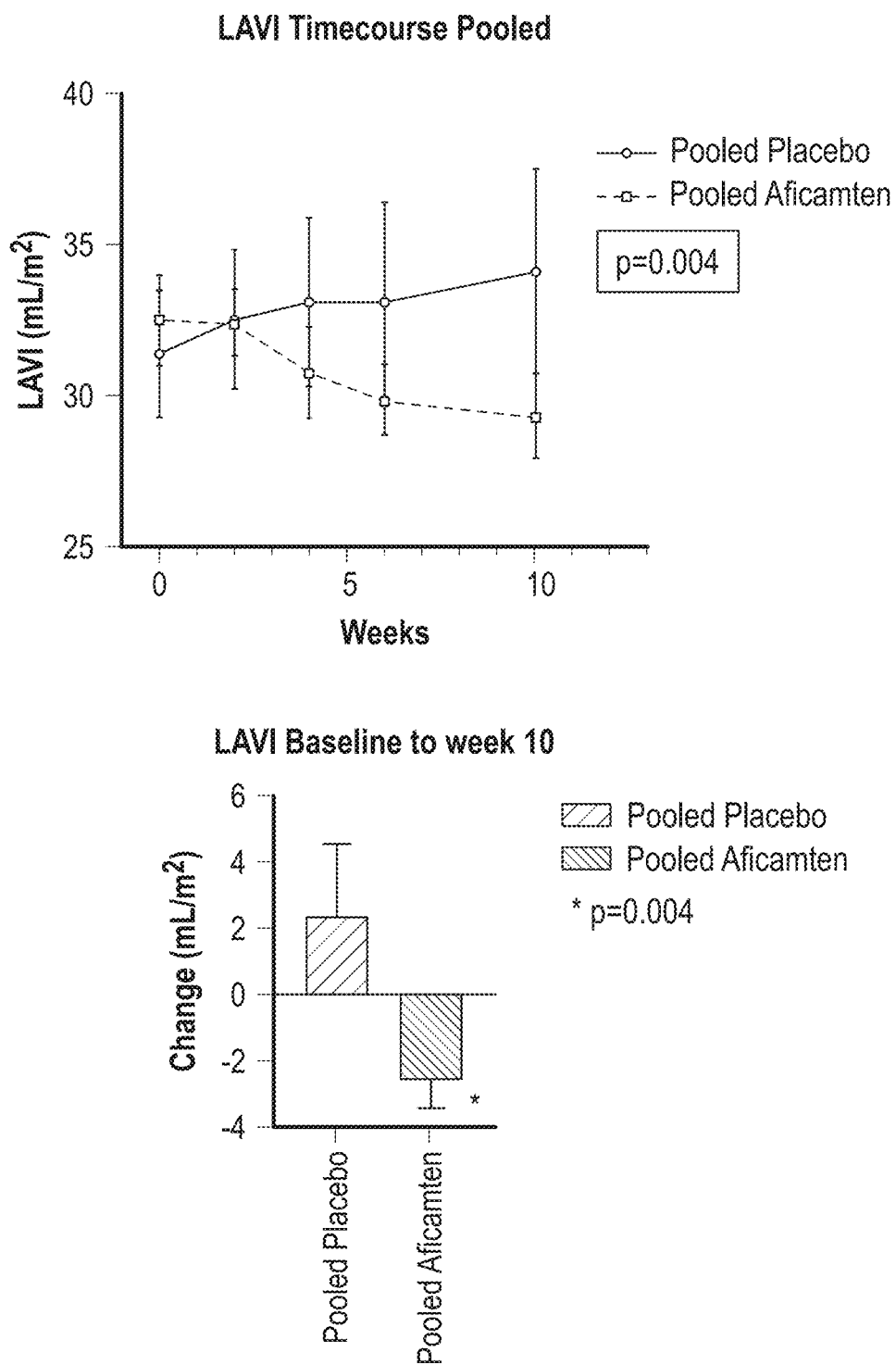
FIG. 9 shows left arterial volume index (LAVI) changes for treatment and placebo cohorts according to an exemplary clinical trial for CK-274.
Figure 10:
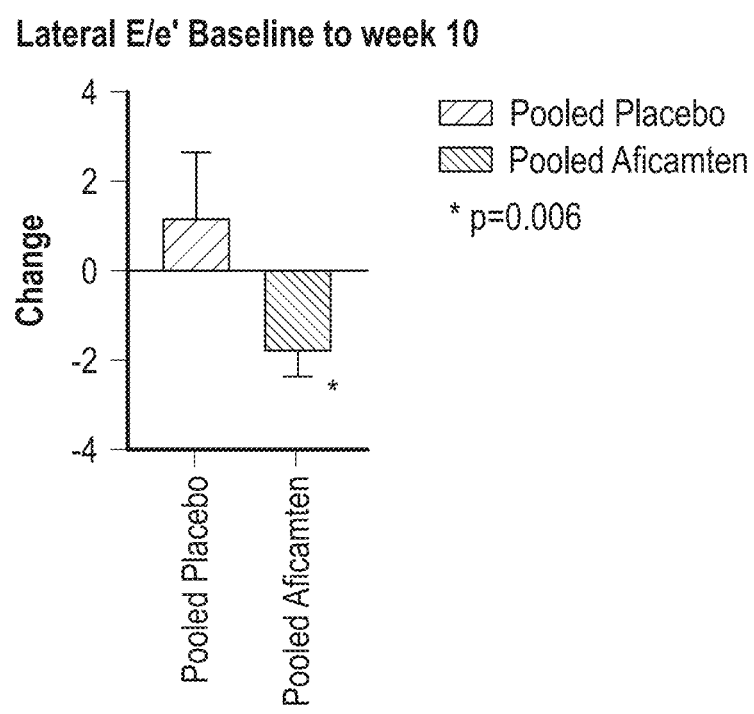
FIG. 10 shows changes to lateral E/e' ratio for treatment and placebo cohorts according to an exemplary clinical trial for CK-274 (aficamten).
Figure 11:
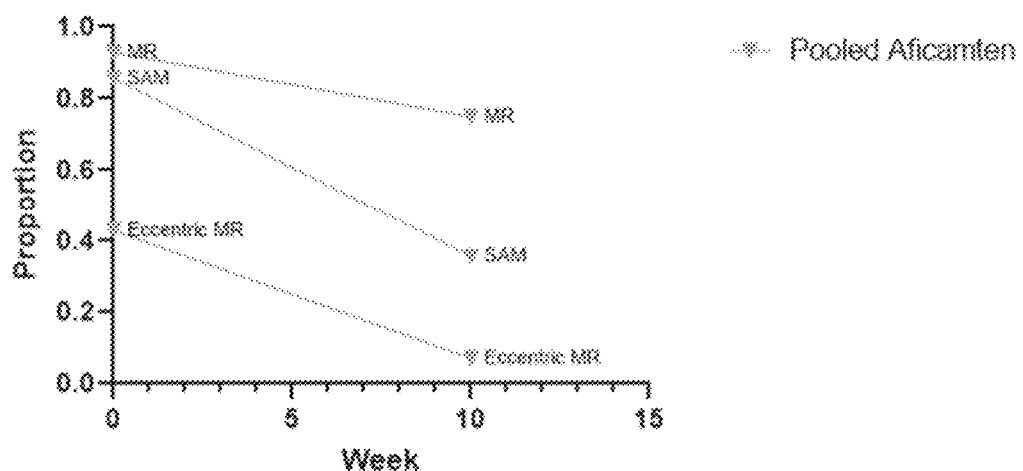
FIG. 11 shows changes to mitral valve characteristics, including mitral regurgitation (MR), eccentric MR, and systolic anterior motion (SAM), for treatment and placebo cohorts according to an exemplary clinical trial for CK-274 (aficamten).
Figure 11:
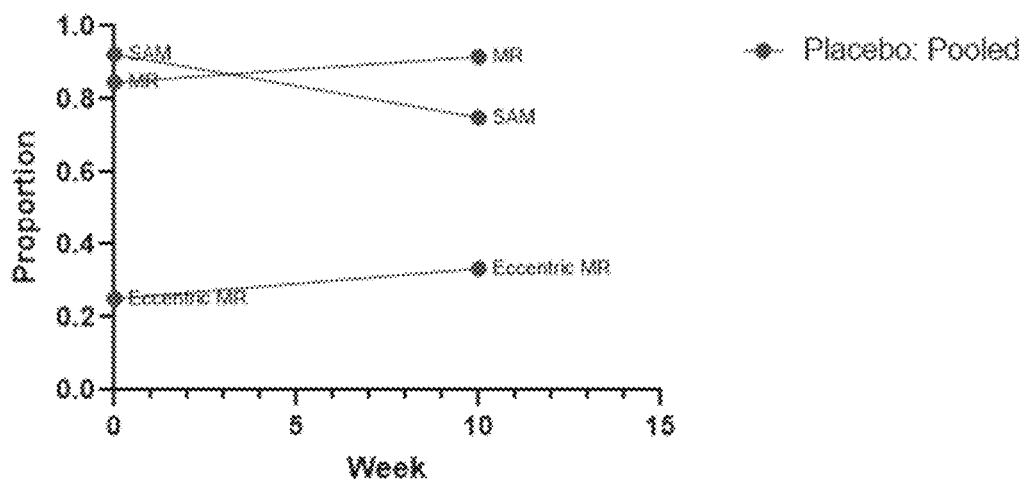

There was no significant difference at baseline in the key echocardiographic metrics and NT-proBNP values between aficamten and placebo. Compared to placebo, patients on aficamten had a trend toward reduction in mean left ventricular mass index (LVMI) (−4.8 g/m² (±2.4) vs 3.3 g/m² (±3.6); mean difference: 8.1 g/m², p=0.063 value). Indices of left ventricular (LV) filling pressures improved in the aficamten treated group including left atrial volume index (LAVI) (−2.9 mL/m² (±1.5) vs 2.2 mL/m² (±1.5), P=0.004) (FIG. 9); e' (0.5 cm/s (±0.4) vs −0.5 cm/s (±0.3), p=0.03), and lateral E/e' (−2.0 (±1.1) vs 1.8 (±0.8), p=0.006) (FIG. 10) from baseline to week 10. Similarly, a reduction relative to baseline in the categorical assessment of systolic anterior motion of the mitral valve leaflet (SAM; −50% vs −17.3%) (FIG. 11) and frequency of eccentric mitral regurgitation (MR; −35.8% vs+13.3%) (FIG. 11) was observed in the aficamten versus placebo, respectively, at week 10. There was a significantly greater reduction in NT-proBNP with aficamten versus placebo (geometric least squares mean ratio 0.38 (0.25-0.56), p=0.0002) at week 10.

Figure 12:
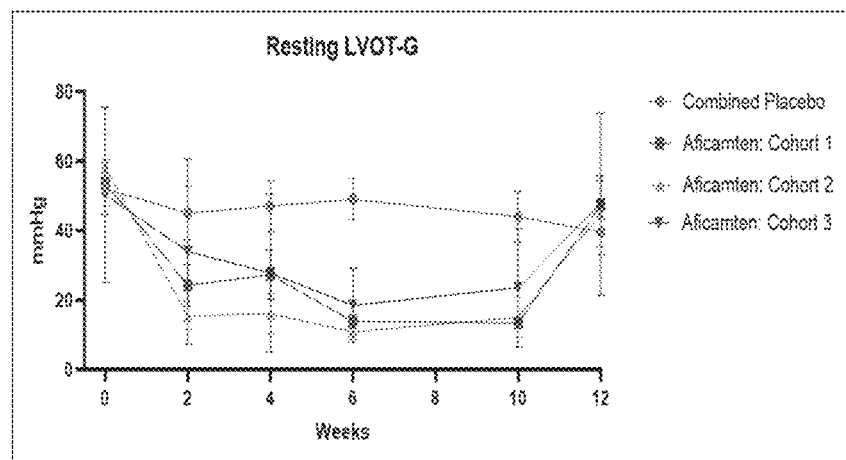
FIG. 12 shows changes to resting LVOT-G for treatment and placebo cohorts according to an exemplary clinical trial for CK-274 (aficamten).
Figure 13:
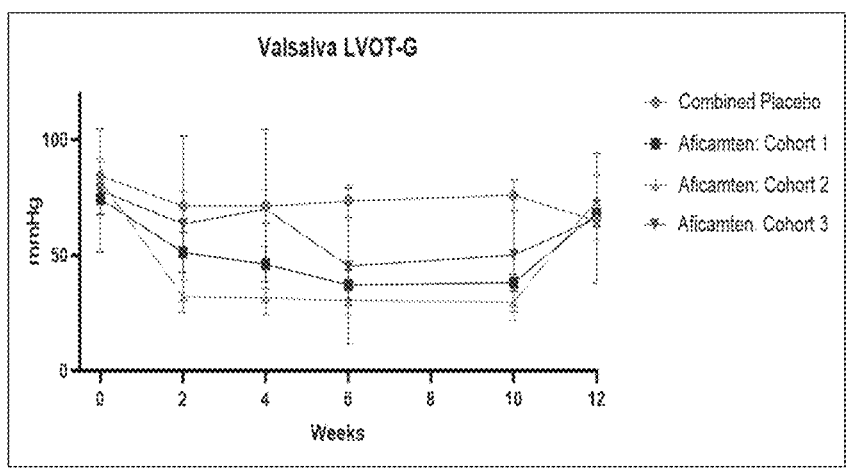
FIG. 13 shows changes to resting Valsalva LVOT-G for treatment and placebo cohorts according to an exemplary clinical trial for CK-274 (aficamten).
Figure 14:
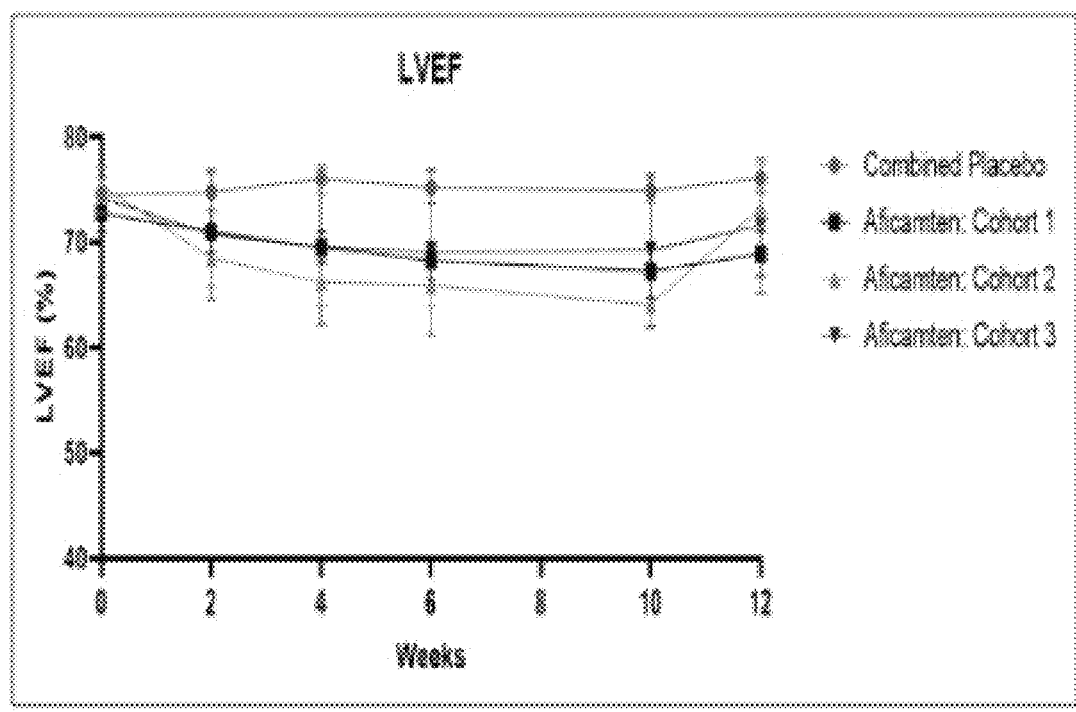
FIG. 14 shows changes to LVEF for treatment and placebo cohorts according to an exemplary clinical trial for CK-274 (aficamten).
Figure 15:
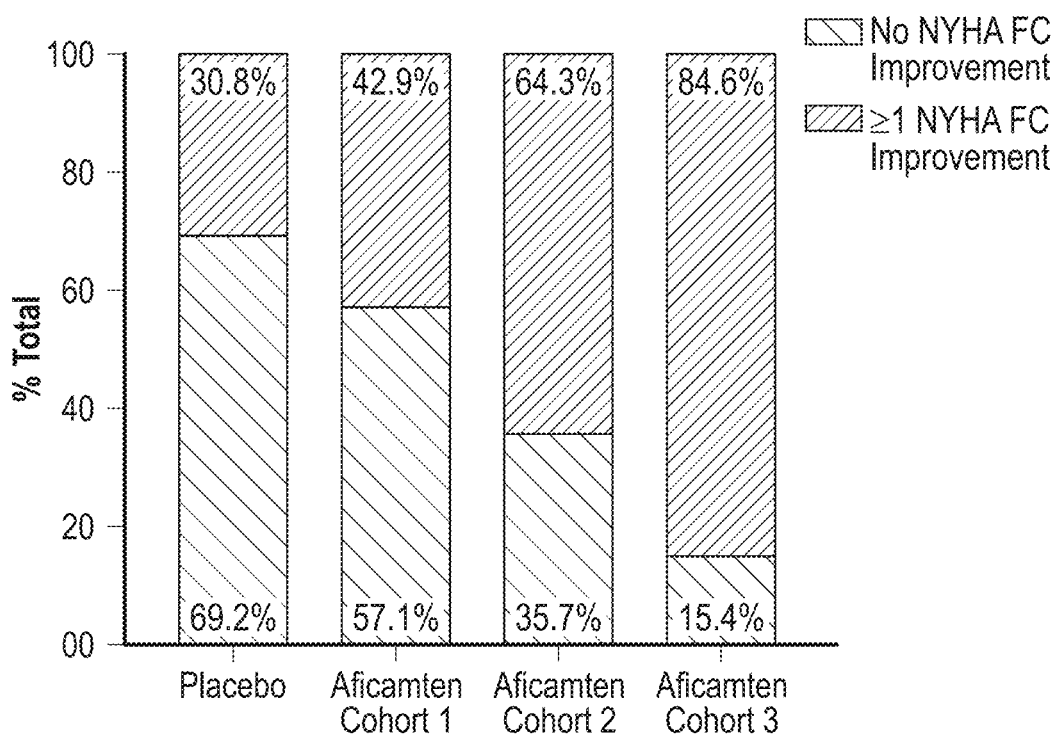
FIG. 15 shows NYHA functional class response for treatment and placebo cohorts according to an exemplary clinical trial for CK-274 (aficamten).
Figure 16:
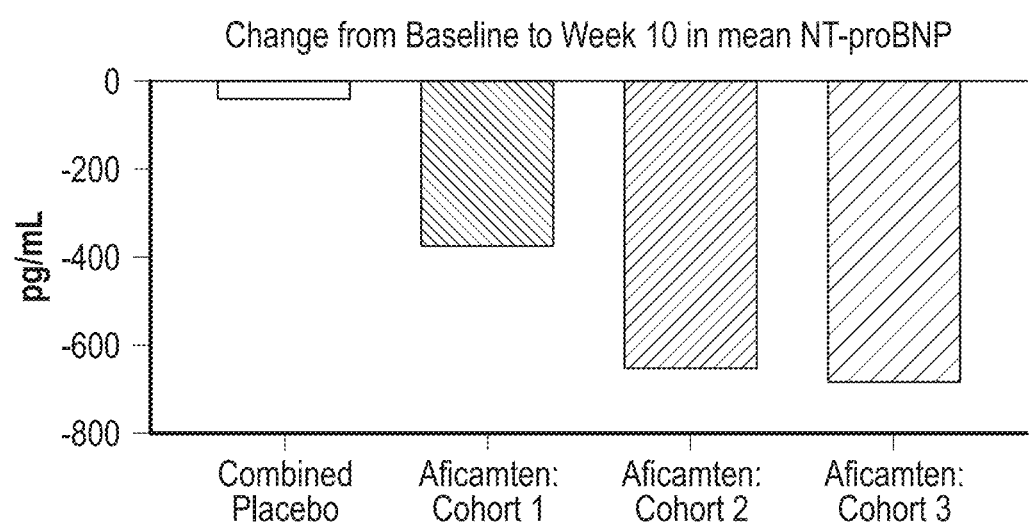
FIG. 16 shows changes in mean NT-proBNP for treatment and placebo cohorts according to an exemplary clinical trial for CK-274 (aficamten).

FIG. 12 shows changes to resting LVOT-G for treatment and placebo cohorts. FIG. 13 shows changes to resting Valsalva LVOT-G for treatment and placebo cohorts. Effect on LVOT-G was mostly attenuated with CK-274 treatment in patients treated with disopyramide (Cohort 3) when compared with Cohort 1 patients (same CK-274 dose). FIG. 14 shows changes to LVEF for treatment and placebo cohorts. FIG. 15 shows NYHA functional class response for treatment and placebo cohorts. FIG. 16 shows changes in mean NT-proBNP for treatment and placebo cohorts.

The safety profile for all three treatment cohorts is presented in Table 16, In Cohort 3, six moderate adverse events were recorded, including pneumonia, pertussis, lung mass, back pain, shortness of breath, and orthopnea. One adverse event of asymptomatic atrial fibrillation in patient with known prior history was recorded. The remaining adverse events included gastrointestinal symptoms (a known side effect of disopyramide) and other adverse events seen in Cohorts 1 and 2 (headaches, dizziness). Overall safety profile in Cohort 3 supports the combined use of CK-274 and disopyramide.

TABLE 16

Safety Profile for Patients Treated with CK-274 in a Phase 2 Clinical Trial

| | Cohort 1 N (%) | Cohort 2 N (%) | Cohort 3 N (%) | Total |
|---|---|---|---|---|
| Patients Randomized | 21 (100) | 20 (100) | 13 (100) | 54 (100) |
| Patients with at least one TEAE | 17 (81) | 15 (75) | 9 (69) | 41 (75.9) |
| Patients with TESAEs | 2 (9.5) | 0 | 0 | 2 (3.7) |
| Patients with fatal TEAEs | 0 | 0 | 0 | 0 |
| Patients with TEAEs leading to drug interruption or termination | 0 | 0 | 0 | 0 |
| Patients with AEs related to study drug (per investigator) | 3 (14.3) | 1 (5.0) | 2 (15.4) | 6 (11.1) |
| TEAE of LVEF <50% (Core Lab) | 0 | 2 (10) | 0 | 2 (3.7) |

These findings indicate that aficamten treatment resulted in salutary early cardiac remodeling associated with reductions in LVMI, LAVI, lateral E/e', SAM, eccentric mitral regurgitation, and brain natriuretic peptide with increment in e' velocity, and further indicate that aficamten favorably impacts cardiac remodeling in oHCM.

Results for Cohort 1 and Cohort 2

Figure 17:
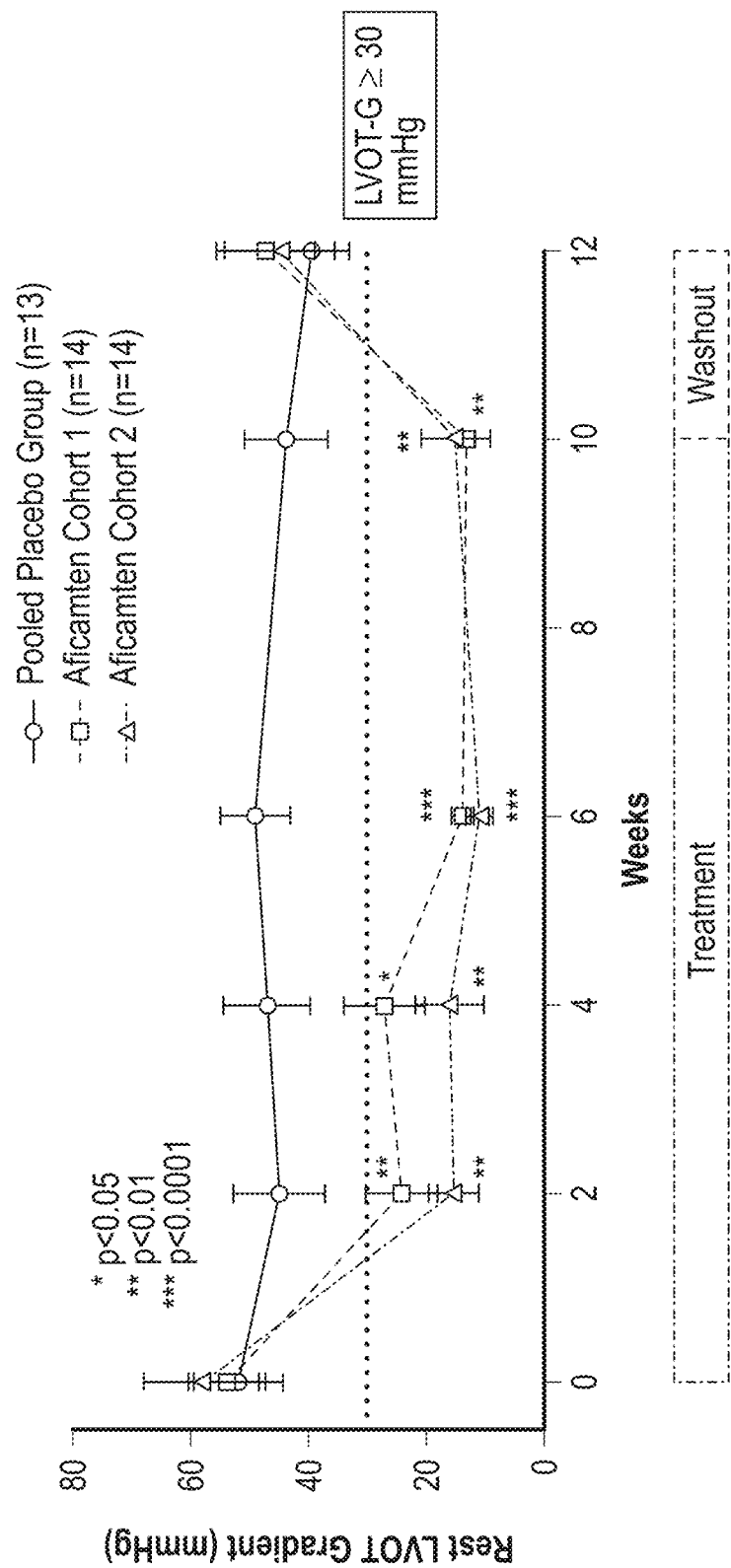
FIG. 17 shows changes to resting LVOT-G for treatment and placebo cohorts according to an exemplary clinical trial for CK-274 (aficamten).
Figure 18:
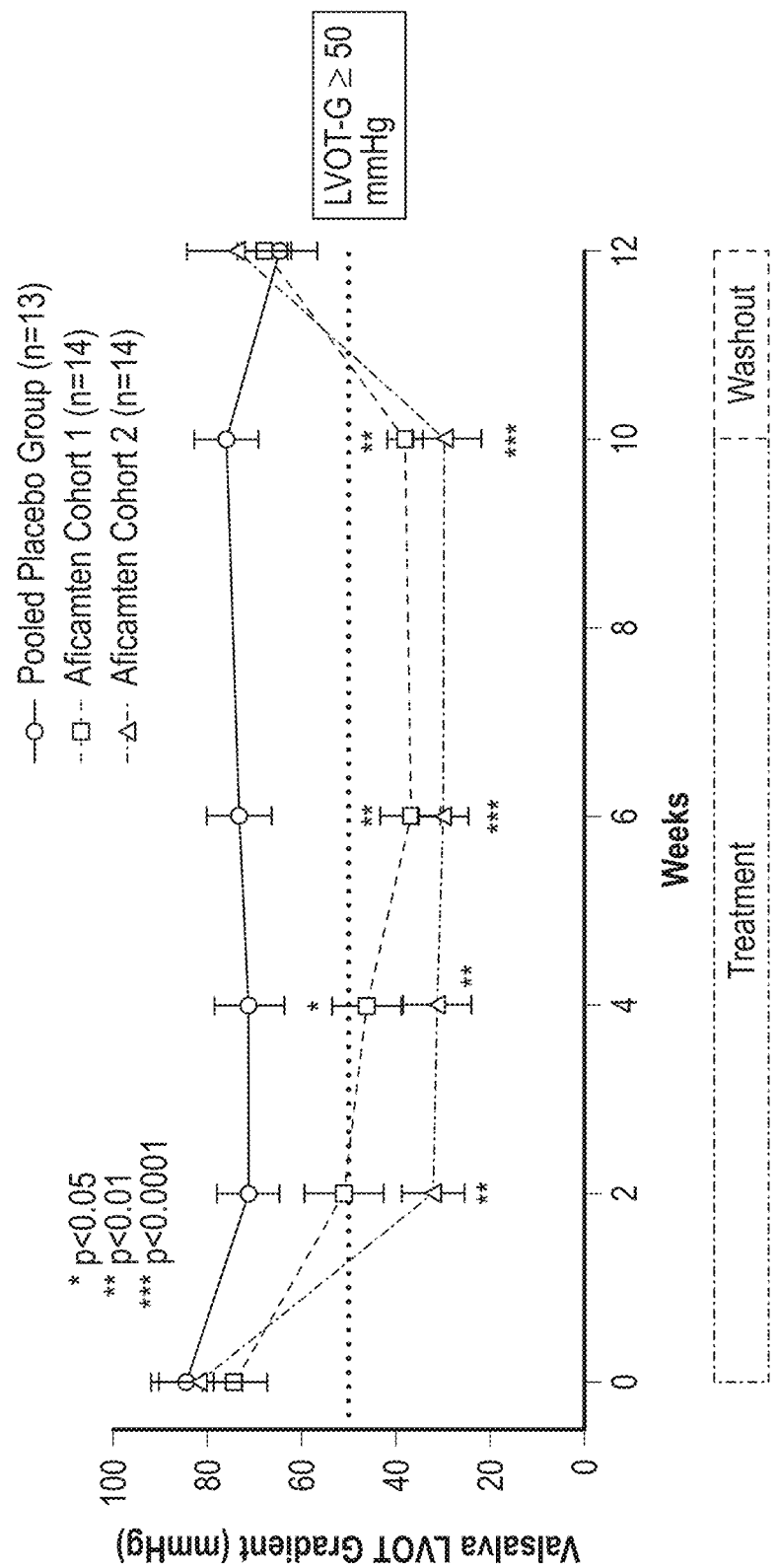
FIG. 18 shows changes to resting Valsalva LVOT-G for treatment and placebo cohorts according to an exemplary clinical trial for CK-274 (aficamten).
Figure 20:
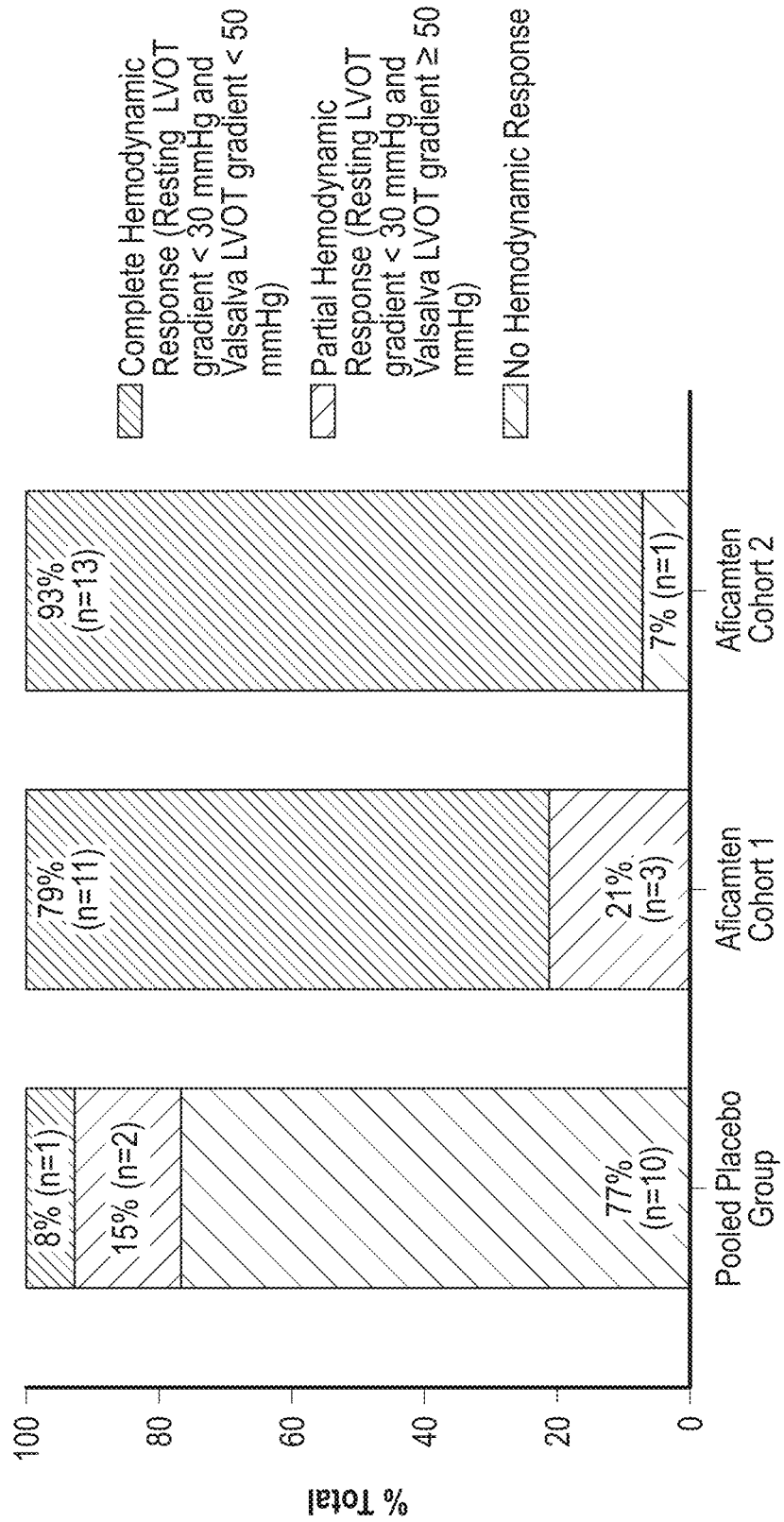
FIG. 20 shows hemodynamic response for treatment and placebo cohorts according to an exemplary clinical trial for CK-274 (aficamten).

With reference to Cohorts 1 and 2, a complete hemodynamic response (resting LVOT gradient <30 mmHg and Valsalva gradient <50 mmHg at Week 10) occurred in 11 out of 14 patients (79%) in aficamten Cohort 1 and 13 out of 14 patients (93%) in aficamten Cohort 2, compared with only 1 out 12 (8%) in the pooled placebo group (FIG. 17, FIG. 18, FIG. 20).

Figure 19:
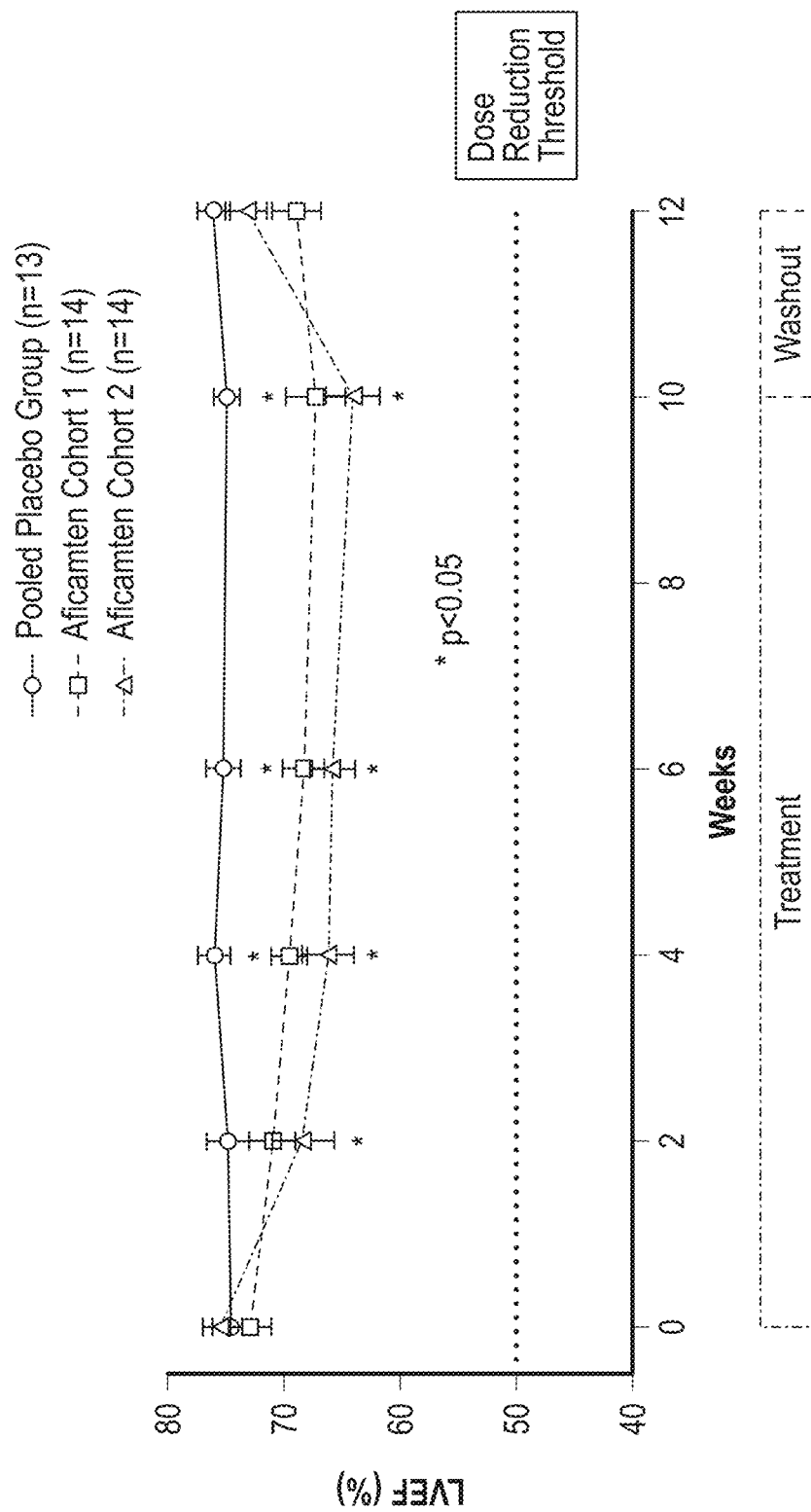
FIG. 19 shows changes to LVEF for treatment and placebo cohorts according to an exemplary clinical trial for CK-274 (aficamten).

Over the treatment period, EF decreased in aficamten Cohort 1 from 73±6% to 67±9% (LSMean difference vs. placebo p=0.007) and in aficamten Cohort 2 from 75±6% to 64±8% (LSMean difference vs. placebo p<0.001), with no change in the placebo group (75±6% to 75±4%; p=0.5). (FIG. 19) Analysis of the relationship between aficamten dose and EF over time revealed a dose-dependent decrease with a mean reduction in EF of −0.6% (SE 0.084) per mg of aficamten.

Figure 21:
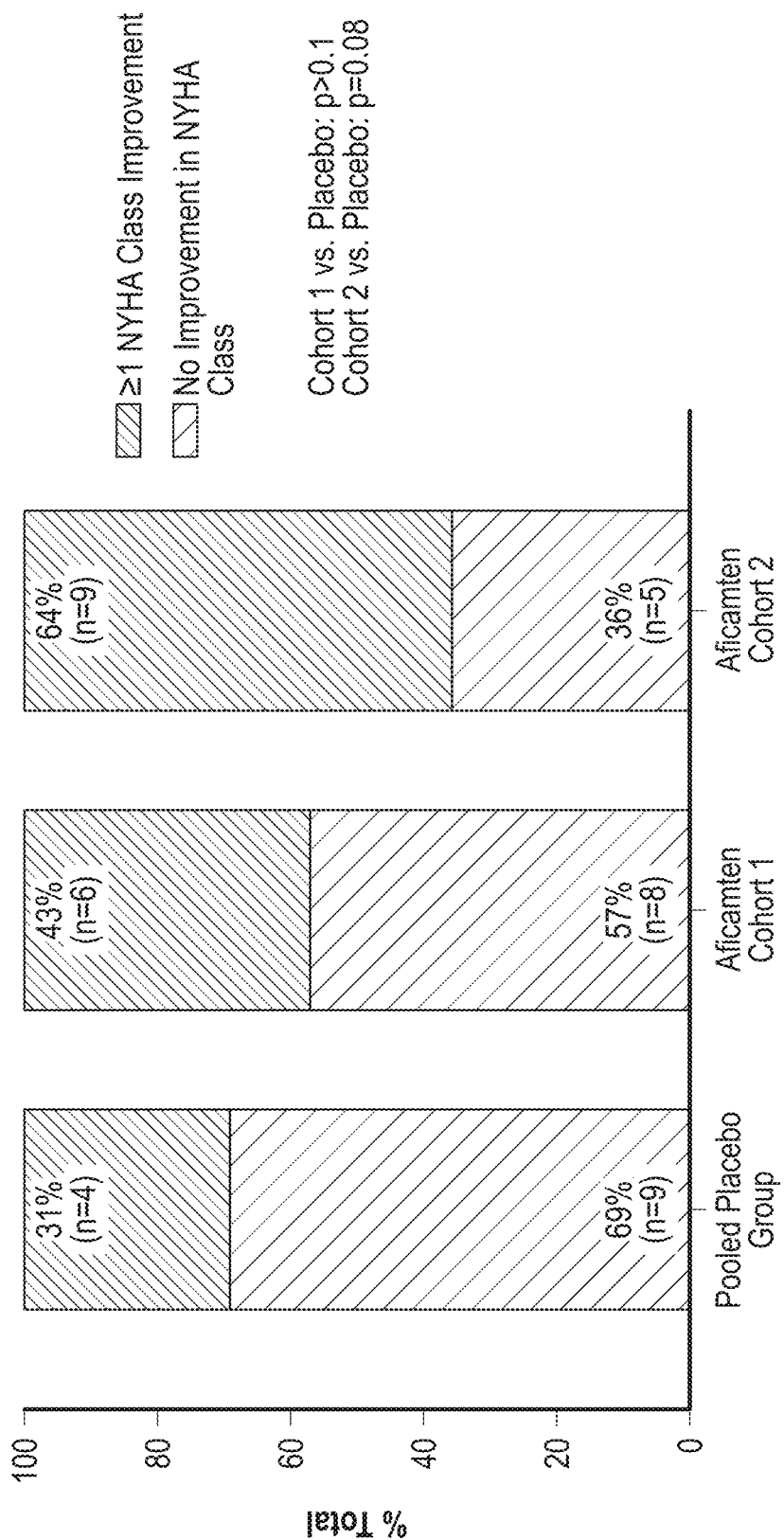
FIG. 21 shows NYHA functional class response for treatment and placebo cohorts according to an exemplary clinical trial for CK-274 (aficamten).
Figure 22:
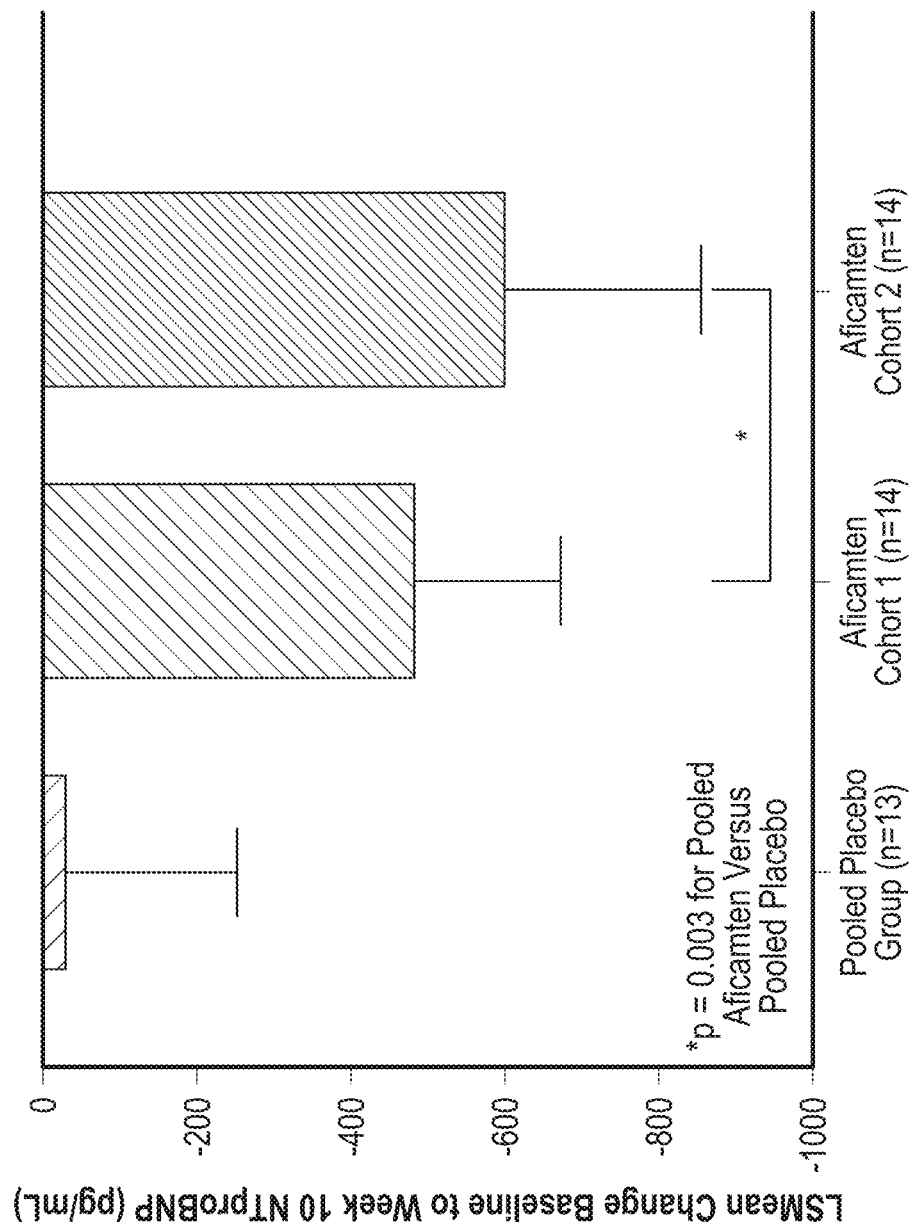
FIG. 22 shows changes in mean NT-proBNP for treatment and placebo cohorts according to an exemplary clinical trial for CK-274 (aficamten).
Figure 24:
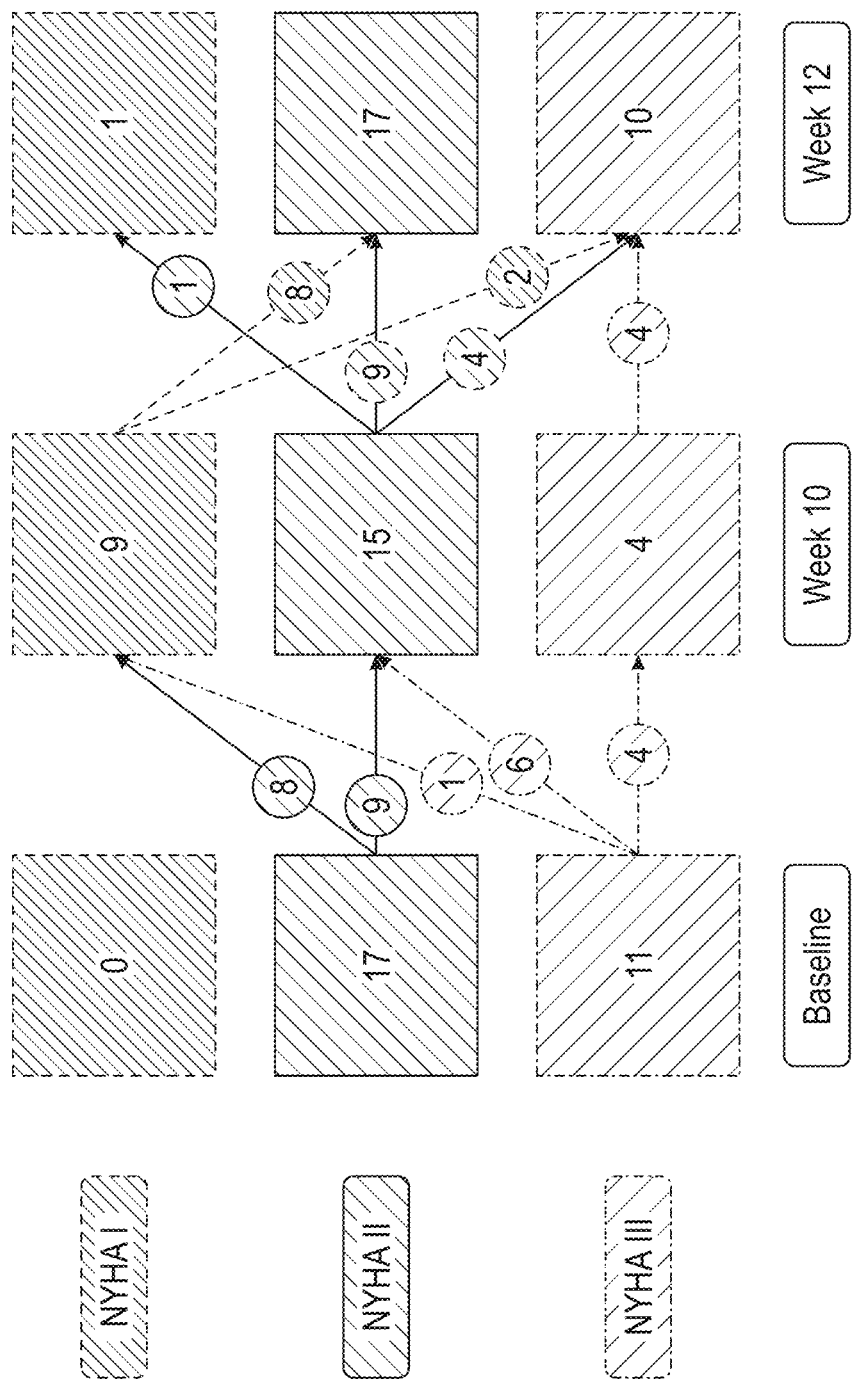
FIG. 24 shows NYHA functional class response for treatment and placebo cohorts according to an exemplary clinical trial for CK-274 (aficamten).
Figure 25:
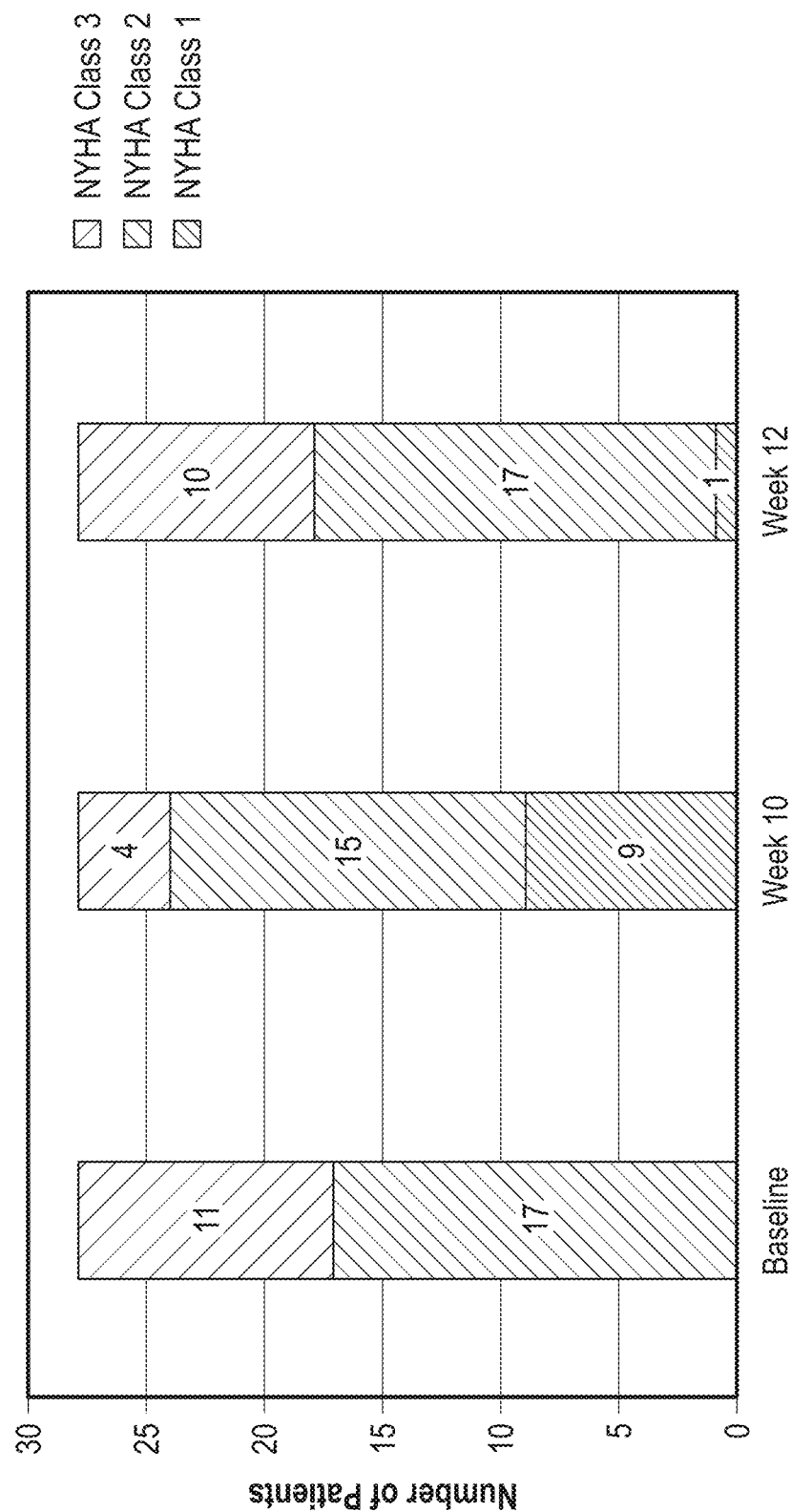
FIG. 25 shows NYHA functional class response for treatment and placebo cohorts according to an exemplary clinical trial for CK-274 (aficamten).

In the pooled aficamten treatment group (Cohorts 1 and 2), 15 of 28 (53%) patients experienced a change in NYHA class of one or more classes (FIG. 21), including: 6 patients who improved from class III to II, 8 from class II to I and one from III to I. (FIG. 24).

Aficamten treatment was associated with a 62% proportional reduction in NT-proBNP levels at Week 10 compared to placebo (p<0.001). Importantly, 25 out of the 27 patients on aficamten (93%) experienced at least some reduction in NT-proBNP levels compared to only 6 of 12 placebo treated patients (50%).

Figure 23:
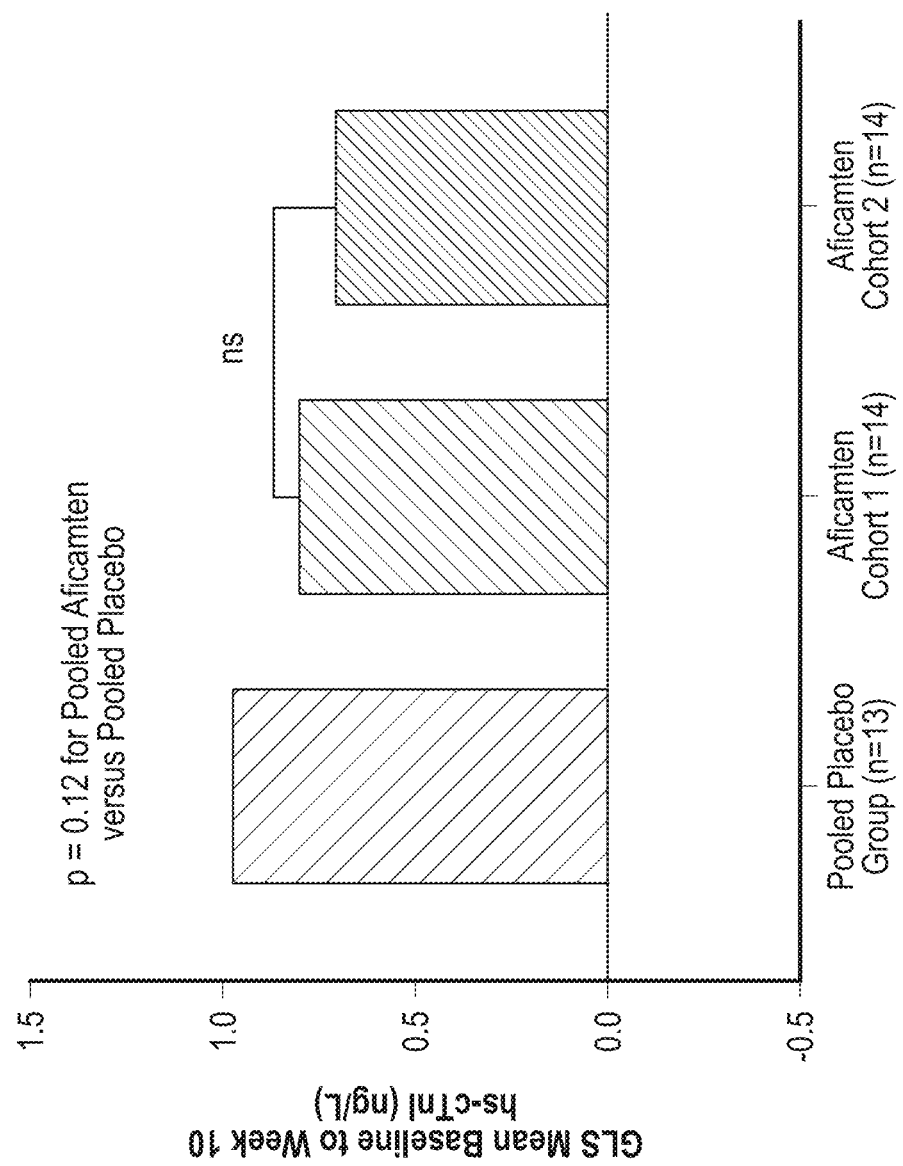
FIG. 23 shows hs-troponin for treatment and placebo cohorts according to an exemplary clinical trial for CK-274 (aficamten).
Figure 37:
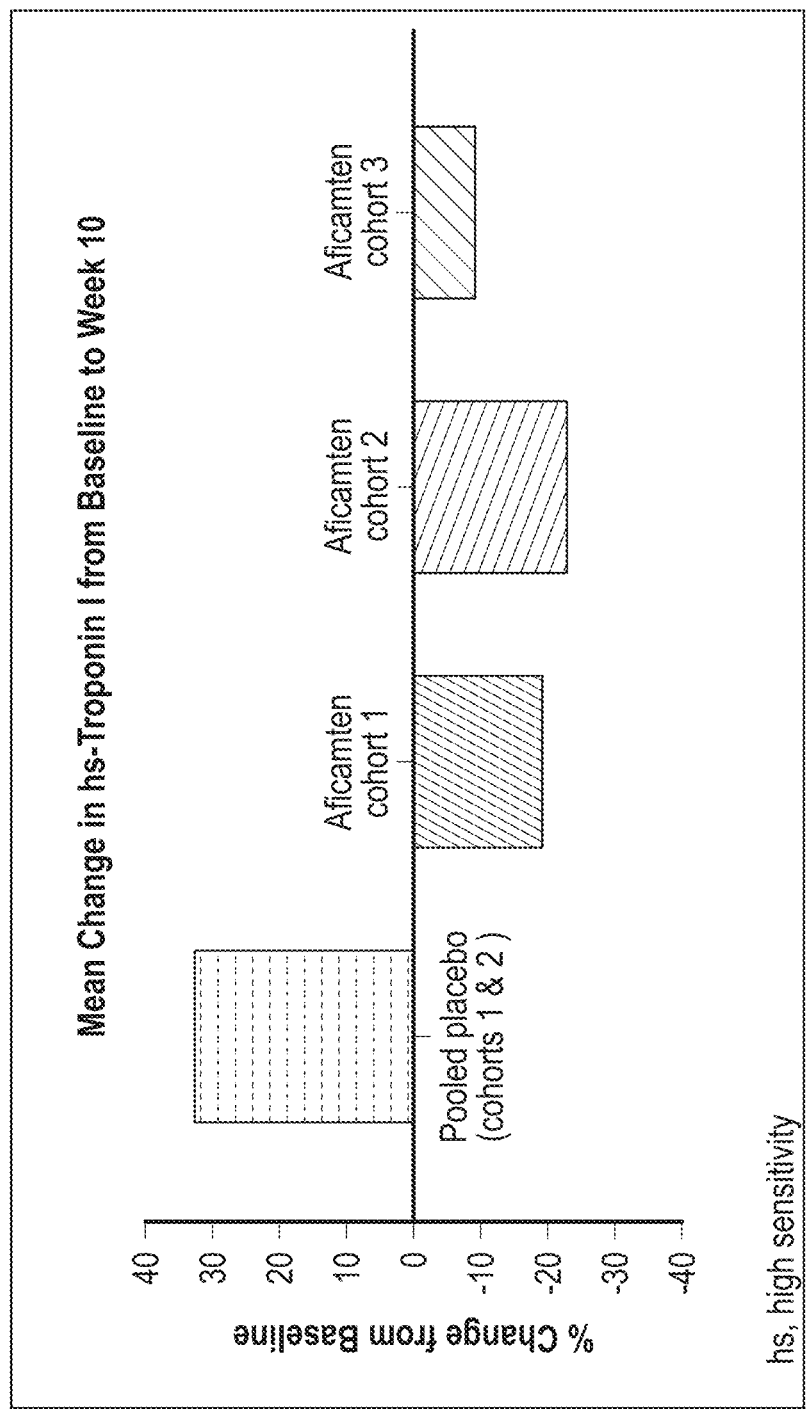
FIG. 37 shows the percent change in hs-troponin I from baseline for treatment and placebo cohorts according to an exemplary clinical trial for CK-274 (aficamten).

Baseline levels of hs-Trop were 17 ng/L (% CV 290) for the pooled aficamten group and 17 ng/L (% CV 290) for pooled placebo. (FIG. 23) At Week 10, patients receiving aficamten in Cohort 1 experienced a 18% relative reduction (p=0.29) compared with pooled placebo, and patients in Cohort 2, a 26% relative reduction (p=0.097) compared with pooled placebo. Change in levels of hs-Troponin I in the pooled placebo groups, as well as patients receiving aficamten in cohort 1, cohort 2, and cohort 3, are shown in FIG. 37.

The early and sustained hemodynamic effect of aficamten was accompanied by marked clinical benefit in heart failure symptoms in most patients. Symptom improvement in NYHA class by one or more classes occurred in more than half of patients treated with aficamten, including 64% in Cohort 2 with most of that improvement resulting in patients transitioning from class II to becoming entirely asymptomatic (class I). It is notable that aficamten converted 7 patients from advanced heart failure symptoms (class III) to less symptomatic status (class II or I).

This robust hemodynamic response is particularly notable since aficamten converted the majority of obstructive HCM patients to gradient levels that are below the current threshold for consideration of septal reduction therapies, such as myectomy or alcohol septal ablation. This is a particularly relevant point since one of the strengths of septal reduction therapy is the opportunity to convert patients with advanced limiting symptoms (class III) to asymptomatic or mildly symptomatic status.

Aficamten was also associated with marked reductions in NT-proBNP and hs-troponin, underscoring that the compound may result in other potential downstream pathophysiologic benefits including decreases in LV wall stress and reduction in myocardial injury.

Example 3

An open-label extension clinical trial of CK-274 in patients with symptomatic oHCM was initiated. The primary objective of the trial was to determine the safety and tolerability of CK-274 over a 5 year period.

Patients who completed the study as described in Example 2 and had not developed atrial fibrillation were eligible to enroll in the study. Echo-guided dose titration based on site reads was managed by the investigator and could occur at any time during the trial, as described below.

Study Design

Each patient received Dose 1 of CK-274 once daily for 2 weeks. At Week 2, each patient had a truncated echocardiogram 2 hours following administration of their dose. Patients were up-titrated to Dose 2 if either of the following conditions were met on echocardiography: (1) resting LVOT-G ≥30 mmHg and the biplane LVEF ≥50%; or (2) resting LVOT-G<30 mmHg, post-Valsalva LVOT-G ≥50 mmHg, and the biplane LVEF ≥50%. Otherwise, the patient remained on 5 mg of CK-274. If LVEF was <50%, treatment was discontinued. If LVEF was <40%, treatment is interrupted.

Figure 26:
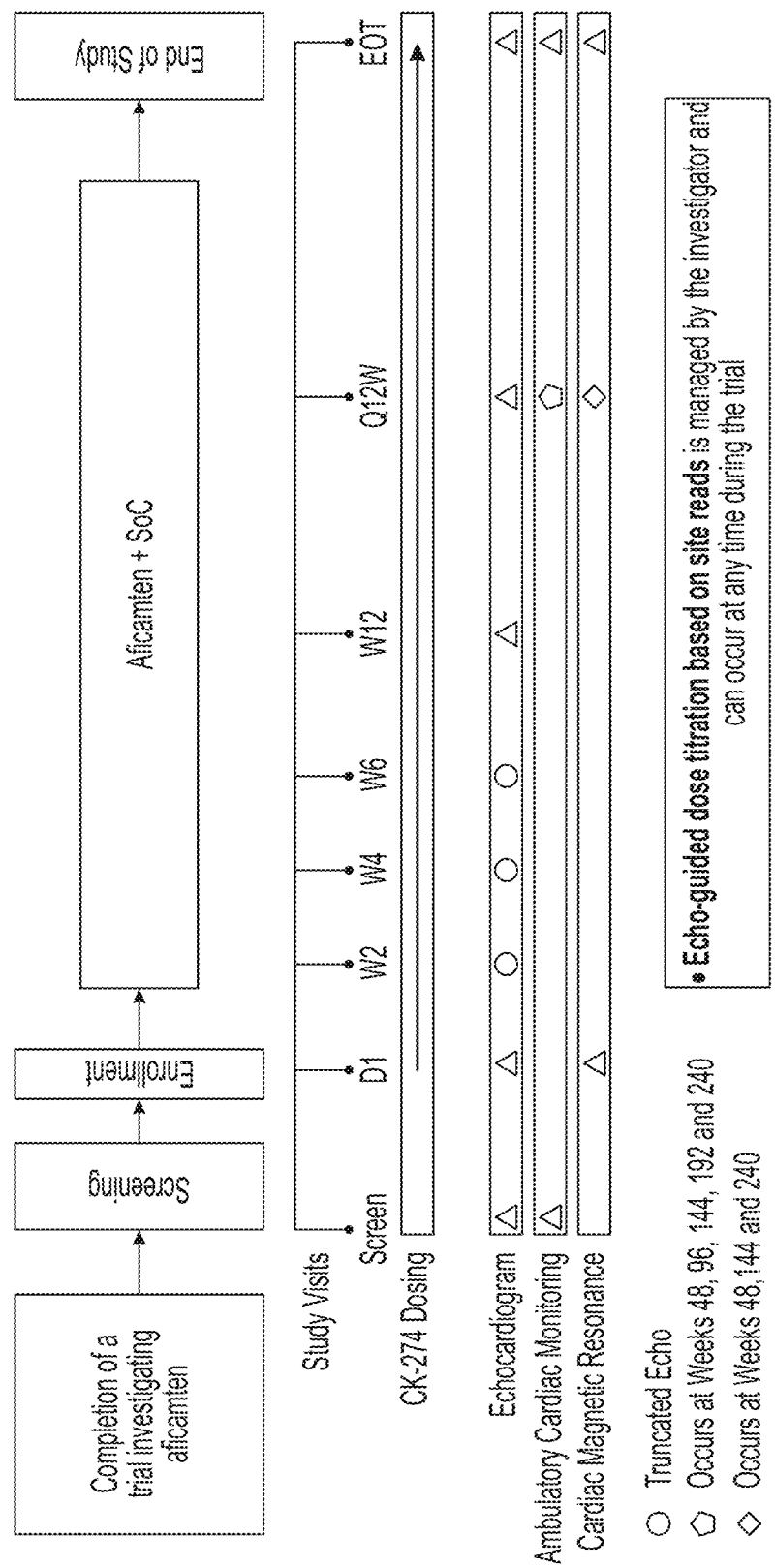
FIG. 26 shows the design of an open label extension of an exemplary clinical trial for CK-274 (aficamten).

At Weeks 4, 6, 12, and every 12 weeks thereafter, each patient had an echocardiogram or truncated echocardiogram 2 hours following administration of their dose (a truncated echocardiogram at weeks 4 and 6; and an echocardiogram at week 12 and every 12 weeks thereafter) to determine whether additional dose titration is needed (see Table 17 and Table 18). Ambulatory cardiac monitoring is performed on weeks 48, 96, 144, 192 and 240. Cardiac magnetic resonance is monitored at weeks 48, 144 and 240. (See FIG. 26). Baseline characteristics for the patients enrolled in the open-label extension study are shown in Table 19.

TABLE 17

Dose Adjustment Algorithm

| Biplane LVEF | LVOT Gradient | Action |
|---|---|---|
| <40% | | Permanent discontinuation |
| <50% | | Dose reduce to next lower dose, or discontinuation if on lowest dose |
| ≥50% | and Resting LVOT gradient < 30 mmHg AND Valsalva LVOT gradient < 50 mmHg | Dose unchanged |
| ≥50% | and Rest LVOT gradient ≥ 30 mmHg AND/OR Valsalva LVOT gradient ≥ 50 mmHg | Dose escalate to next dose level |

TABLE 18

Dosing Scheme

| Dose 1 | Dose 2 | Dose 3 | Dose 4 |
|---|---|---|---|
| 5 mg | 10 mg | 15 mg | 20 mg |

TABLE 19

Baseline characteristics for open-label extension study

| Baseline Characteristics | N = 38 |
|---|---|
| Age (Years), Mean (SD) [Range] | 59.9 (13.0) [23-82] |
| Female, n (%) | 22 (57.9%) |
| BMI (kg/m2), Mean (SD) [Range] | 30.1 (6.5) [22-51] |

TABLE 19-continued

Baseline characteristics for open-label extension study

| Baseline Characteristics | N = 38 |
|---|---|
| NYHA Class, n (%) | |
| Class II | 18 (47.4%) |
| Class III | 20 (52.6%) |
| Positive family history of HCM, n (%) | 9 (23.7%) |
| Background HCM Therapy, n (%) | |
| Beta Blocker | 30 (78.9%) |
| Calcium Channel Blocker | 11 (28.9%) |
| Disopyramide | 10 (26.3%) |
| LVEF* at Screening (%), Mean (SD) [Range] | 69.7 (4.1) [60-78] |
| LVOT-G*, Rest at Screening (mmHg), Mean (SD) [Range] | 47.0 (26.6) [10-95] |
| LVOT-G*, Valsalva at Screening (mmHg), Mean (SD) [Range] | 81.1 (29.1) [23-150] |
| NT-proBNP (pg/mL), Geometric Mean (% CV) [Range] | 628.1 (163.7) [70-8333] |
| Cardiac Troponin I (ng/L), Geometric Mean (% CV) [Range] | 13.8 (287.5) [3.4-2017] |
| Duration on Treatment in Weeks, Mean (SD) [Range] | 25.7 (11.7) [5-47] |

Preliminary Results

Figure 27:
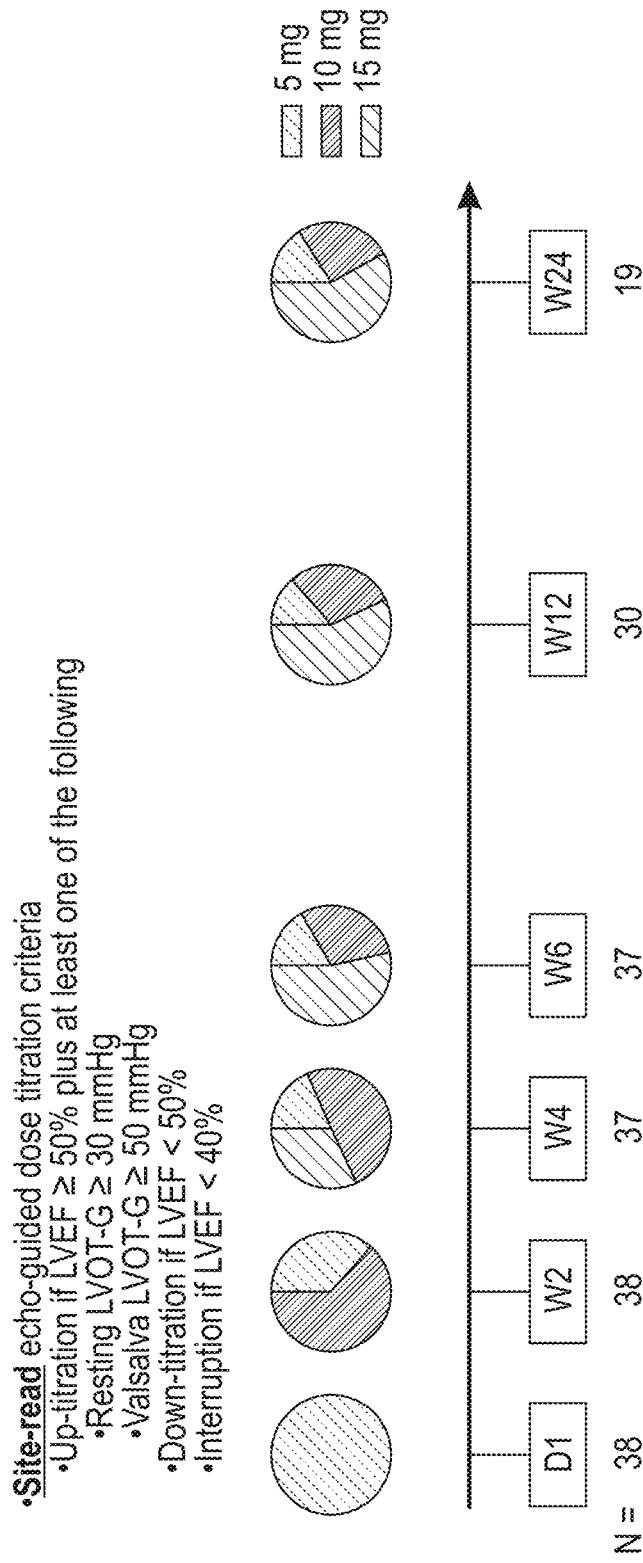
FIG. 27 shows the distribution of patients across doses over time in the open label extension of an exemplary clinical trial for CK-274 (aficamten).
Figure 28:
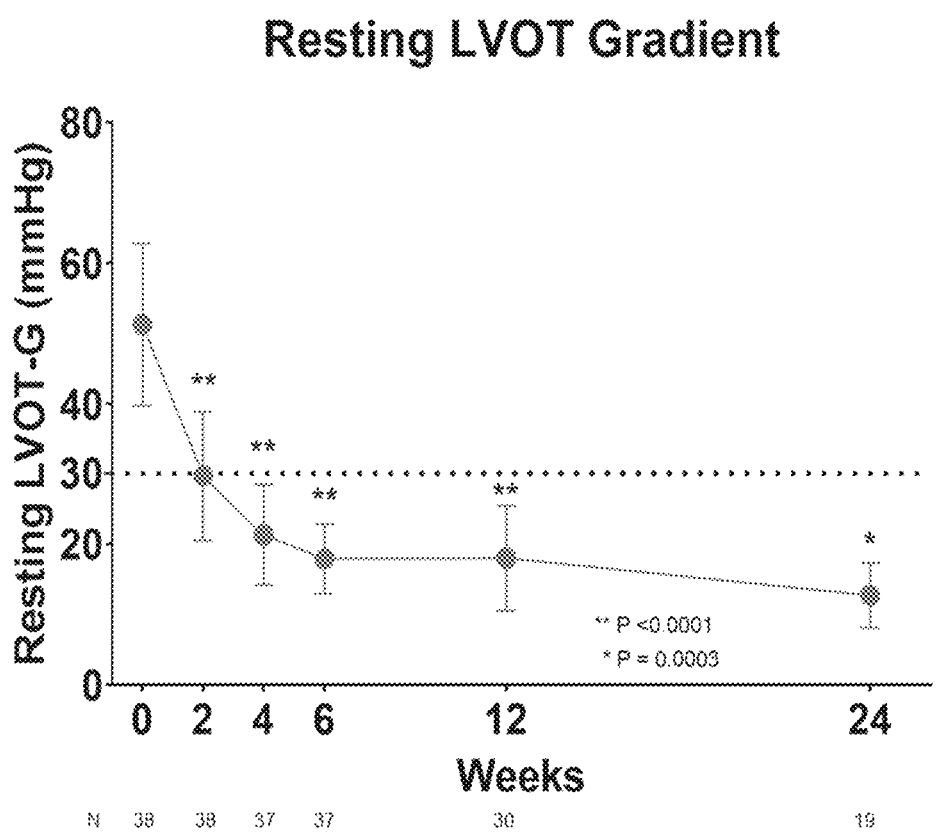
FIG. 28 shows resting LVOT-G for patients in the open label extension of an exemplary clinical trial for CK-274 (aficamten).
Figure 29:
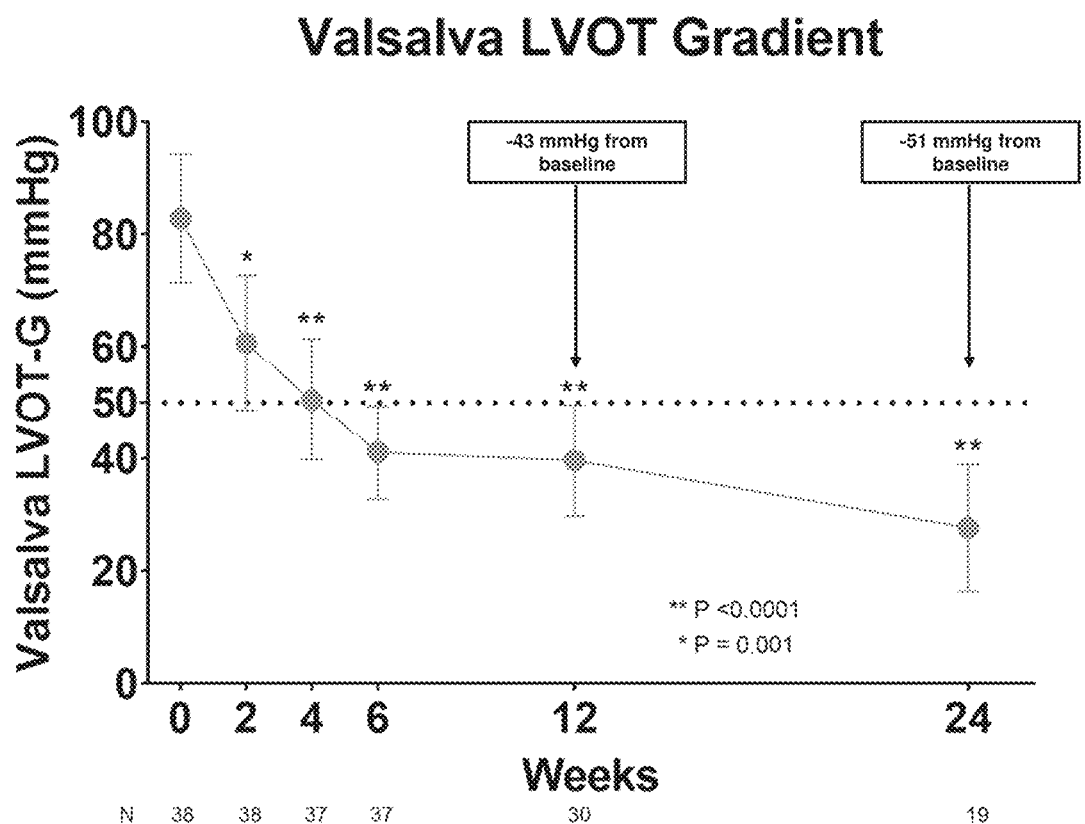
FIG. 29 shows post-Valsalva LVOT-G for patients in the open label extension of an exemplary clinical trial for CK-274 (aficamten).
Figure 30:
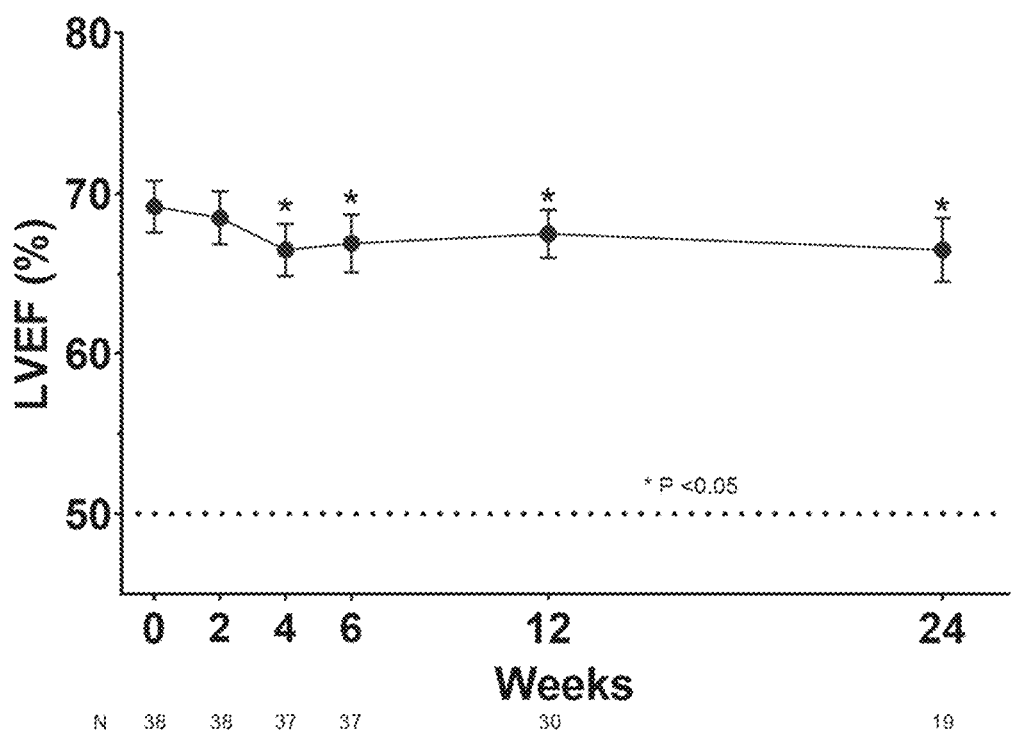
FIG. 30 shows changes to LVEF for patients in the open label extension of an exemplary clinical trial for CK-274 (aficamten).
Figure 31:
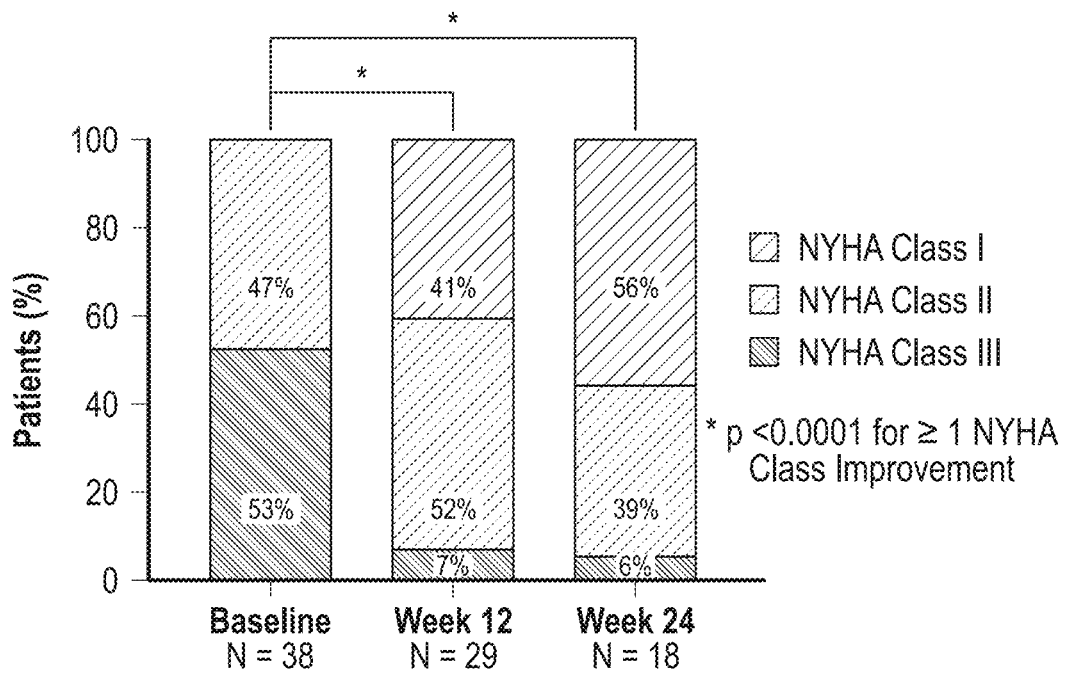
FIG. 31 shows NYHA functional class distribution at various time points for patients in the open label extension of an exemplary clinical trial for CK-274 (aficamten).

Preliminary results are shown in FIGS. 27-34. FIG. 27 shows the distribution of patients across doses over time. At the time of data collection, 38 patients had enrolled in the trial, and all 38 patients had reached at least week 2 of dosing; 37 of the 38 patients had reached at least week 6 of dosing; 30 of the 38 patients had reached at least week 12 of dosing; and 19 of the 38 patients had reached at least week 24 of dosing. The percentage of patients receiving each dose level (5, 10, or 15 mg) at each time point is shown in FIG. 27. Significant reduction in resting LVOT-G and Valsalva LVOT-G over time based on echocardiographic data from site reads of these patients is shown in FIG. 28 and FIG. 29; significant and sustained reduction in LVOT gradients was identified at Weeks 2-24. In addition, minimal and stable reductions in LVEF were noted through Week 24, as shown in FIG. 30.

At baseline, 53% of patients were NYHA class III, and 47% of patients were NYHA class II.

Figure 32:
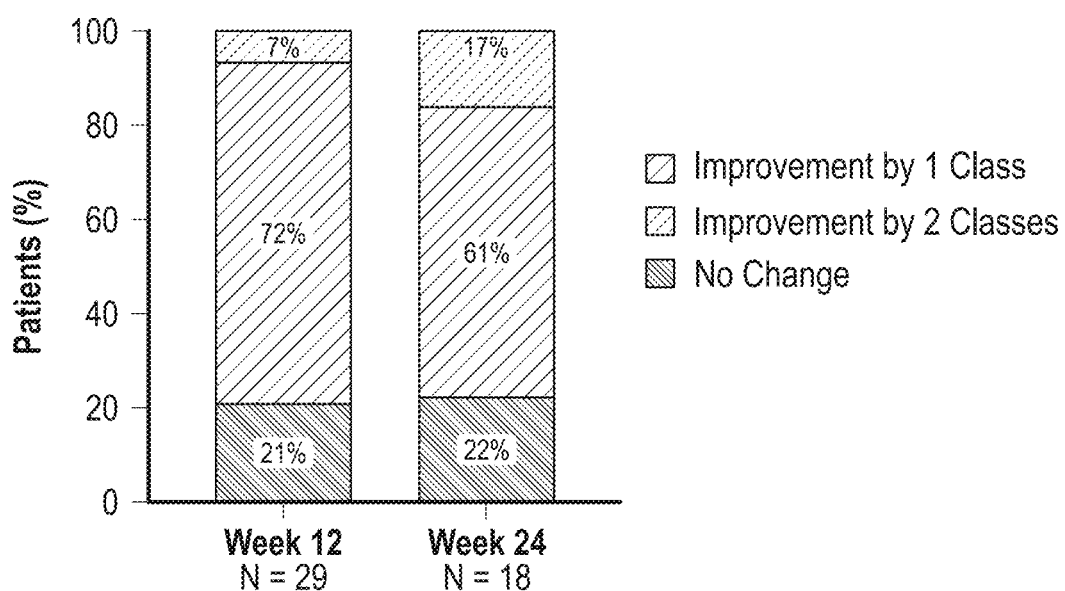
FIG. 32 shows NYHA functional class response for at various time points for patients in the open label extension of an exemplary clinical trial for CK-274 (aficamten).

Of the patients that had reached at least week 12 of dosing: at week 12, only 7% of patients were NYHA class III; 52% of patients were NYHA class II; and 41% of patients were NYHA class I (FIG. 31). 72% of patients had experienced an improvement by one NYHA class, and 7% of patients improved by two NYHA classes relative to baseline (FIG. 32).

Of the patients that had reached at least week 24 of dosing: at week 24, only 6% of patients were NYHA class III; 39% of patients were NYHA class II; and 56% of patients were NYHA class I (FIG. 31). 61% of patients had experienced an improvement by one NYHA class, and 17% of patients had experienced an improvement by two NYHA classes relative to baseline (FIG. 32).

No patients in the study showed worsening in NYHA class from baseline.

Preliminary Safety

TABLE 20

|  | N = 38 |
| --- | --- |
| Patients with at Least One TEAE | 28 (74%) |
| Patients with at Least One Related TEAE | 8 (21%) |
| Patients with at Least One TESAE | 2 (5%) |
| Patients with at Least One Severe TEAE | 1 (3%) |
| Patients with TEAE Leading to Drug Interruption | 1 (3%) |
| Patients with TEAE Leading to Dose Reduction | 2 (5%) |

TEAE: Treatment Emergent Adverse Event
TESAE: Treatment Emergent Serious Adverse Event
Cardiac AEs: Atrial fibrillation (2); Angina pectoris (1); Bradycardia (1); Decreased ejection fraction (1); Mitral valve stenosis (1); QTc prolongation (1)

One patient with LVEF <50% and TESAE had a history of alcohol induced atrial fibrillation prior to study with reduced LVEF <50%. On 15 mg of CK-274, recurrent episode of alcohol induced atrial fibrillation with similar reduction of LVEF to 47%; CK-274 was down-titrated. The patient subsequently developed worsening atrial fibrillation and had a failed cardioversion; CK-274 was interrupted. This patient is back in sinus rhythm on amiodarone, abstinent from alcohol, with LVEF 60% with evidence of obstruction and has restarted CK-274 at dose 1 (5 mg).

One patient experienced temporary down-titration due to Investigator concern about QTc prolongation in a subject with abnormal baseline EKG. Temporary aficamten down-titration was performed pending core-lab QTc interpretation. It was confirmed that the QTc was normal, and aficamten was subsequently increased.

One subject with Severe TESAE showed altered mental status prior to planned cardioversion for worsening atrial fibrillation on DOAC (direct-acting oral anticoagulants), leading to hospitalization. MRI showed presumed embolic stroke. Patient was subsequently diagnosed with congenital cardiac abnormality (secundum atrial septal defect). No CK-274 down-titration or interruption was needed.

Kansas City Cardiomyopathy Questionnaire (KCCQ)

Participants' health status was assessed with the KCCQ prior to starting aficamten in the OLE and at 12 and 24 weeks of treatment. Change in KCCQ scores from baseline, including OSS=overall summary score, CSS=clinical summary score, TSS=total symptom score, PLS=physical limitation score, SLS=social limitation score, QoL=quality of life, were determined. Patients were categorized with worsened (≤−5 points), unchanged (−5 to <5 points), small improvement (5 to <10 points), moderate to large improvement (10 to <20 points), and large to very large improvement (≥20 points) relative to baseline.

Figure 35:
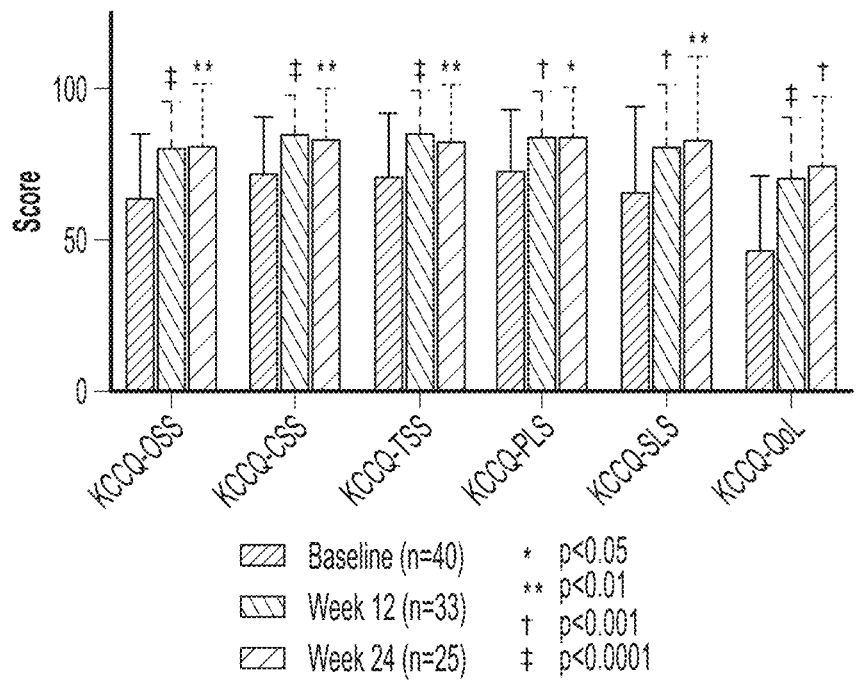
FIG. 35 shows changes in KCCQ scores from baseline for patients in the open label extension of an exemplary clinical trial for CK-274 (aficamten).
Figure 36:
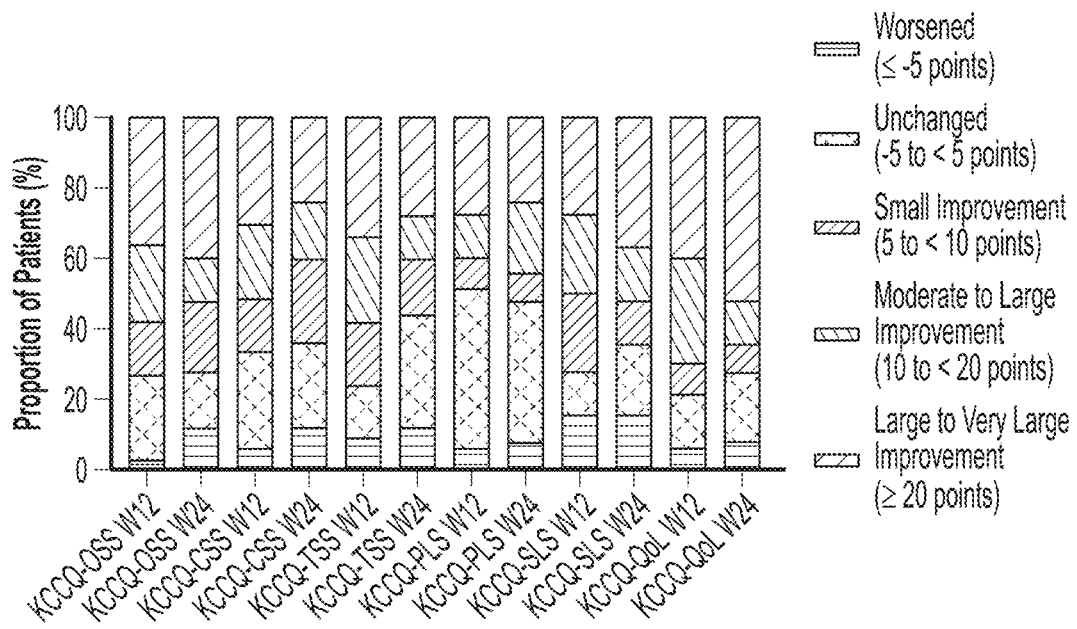
FIG. 36 shows proportion of patients with various levels of changes in KCCQ scores from baseline for patients in the open label extension of an exemplary clinical trial for CK-274 (aficamten).

The results display the marked improvements in KCCQ scores among OLE participants at 12 weeks that were sustained to 24 weeks. The proportion of participants with clinically-important improvement (≥5 points on the Overall Summary Score) was 72.7% at Week 12 and 72.0% at Week 24. Very large clinical improvements (≥20 points) were seen in 36.4% at Week 12 and 40.0% at Week 24 (FIG. 35, FIG. 36). Treatment with CK-274 resulted in a marked and sustained improvement in all KCCQ domain scores for up to 6 months.

Conclusions

Figure 33:
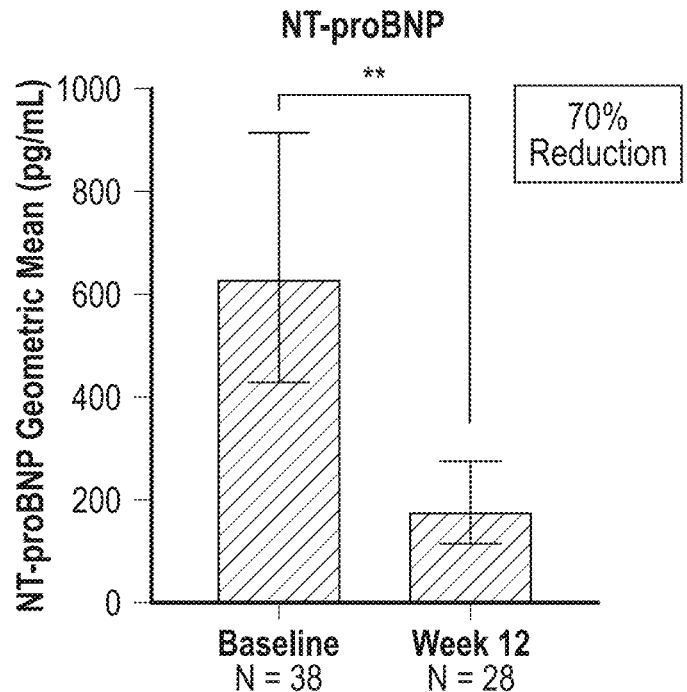
FIG. 33 shows changes in mean NT-proBNP for patients in the open label extension of an exemplary clinical trial for CK-274 (aficamten).
Figure 34:
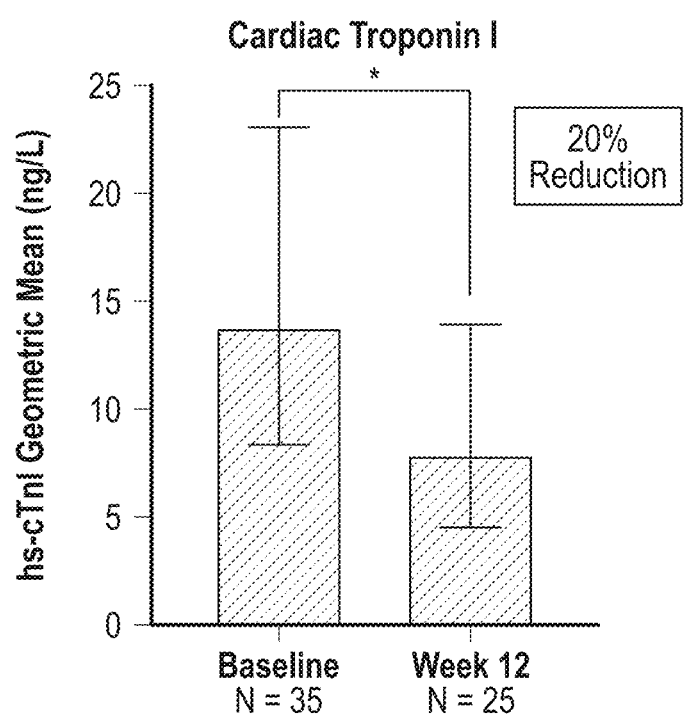
FIG. 34 shows changes in mean cardiac troponin I for patients in the open label extension of an exemplary clinical trial for CK-274 (aficamten).

In this open label extension study of patients with obstructive HCM treated with background medical therapy, including disopyramide in some cases: CK-274 was associated with significant and sustained reductions in LVOT gradients (FIG. 28 and FIG. 29) and substantial improvement in heart failure symptoms (about 80% of patients had NYHA class improvement of one or more classes) (FIG. 31 and FIG. 32), as well as significant reduction in cardiac biomarkers (NT-proBNP and hs-cTnI) (FIG. 33 and FIG. 34). CK-274 was well tolerated, with no events of LVEF <50% attributed to CK-274. These data demonstrate that the treatment effect of CK-274 is durable for up-to 6 months.

Example 4

The following example describes a phase 3, multi-center, randomized, double-blind, placebo-controlled trial to evaluate the efficacy and safety of CK-3773274 (also referred to as CK-274 or aficamten) in adults with symptomatic hypertrophic cardiomyopathy and left ventricular outflow tract obstruction. This trial evaluates the effects of treatment with CK-3773274 over a 24-week period on cardiopulmonary exercise capacity and health status in patients with symptomatic oHCM. This trial is intended to establish the efficacy and safety of CK-3773274 with respect to improvements in exercise capacity and patient symptoms, as well as reduction in left ventricular outflow tract gradient (LVOT-G) in patients with oHCM.

This is a Phase 3 randomized, placebo-controlled, double-blind, multi-center trial in patients with symptomatic oHCM. Approximately 270 eligible patients are randomized in a 1:1 ratio to receive CK-3773274 or placebo. Doses of 5, 10, 15, or 20 mg or matching placebo are administered in an escalating manner using echocardiography to guide dose titration. Randomization is stratified by use of beta-blockers and CPET exercise modality.

The trial comprises three periods. The screening period is up to 6 weeks in duration. The double-blind placebo-controlled treatment period lasts 24 weeks. Following the final dose of CK-3773274, there is a 4-week safety follow-up period. CK-3773274 is administered orally once daily. During the initial six weeks of the treatment period, CK-3773274 doses are individually titrated at Weeks 2, 4, and 6 using echocardiography. Dose escalation at the Weeks 2, 4, and 6 visits occur only if a patient has a post-Valsalva LVOT-G ≥30 mmHg and a biplane LVEF ≥55%. An echocardiogram is performed at each subsequent visit during the trial and the dose down-titrated if necessary. The primary endpoint of $pVO_2$ is measured by CPET at screening and at end of treatment (Week 24). If applicable, patients continue taking background HCM medications consistent with regional clinical practice guidelines during the trial.

A CMR imaging sub-study is open to approximately 40 patients who consent to participate.

The main mitigation strategy is facilitated by an individualized dose titration scheme based on each patient's PD response to CK-3773274 with application of pre-specified echocardiographic criteria, including LVEF thresholds for dose escalation, down-titration, and drug discontinuation.

Patients enrolled in this trial are required to have an LVEF ≥60% prior to randomization, as confirmed by the central echocardiography laboratory. A low starting dose of 5 mg and a maximum dose of 20 mg were chosen as these were found to be well-tolerated in the Phase 2 study (CY 6021) of patients with oHCM and effective at reducing the LVOT-G without adversely impacting overall LVEF. Dose escalation is performed on an individualized basis only if the following criteria are met: both post-Valsalva LVOT-G ≥30 mmHg and biplane LVEF ≥55%. Importantly, in contrast to CY 6021, the lower limit of LVEF for dose escalations is increased from 50% to 55% to provide a safety margin from the threshold of LVEF (<50%) that will trigger dose reduction. If the LVEF is <50% at any time, the dose of CK-3773274 will be down-titrated, and if the LVEF is <40% at any time, CK-3773274 will be temporarily interrupted.

The primary objective of this trial is to evaluate the effect of CK-3773274 on exercise capacity in patients with symptomatic oHCM. The indicated endpoint is a change in peak oxygen uptake ($pVO_2$) by cardiopulmonary exercise testing (CPET) from baseline to Week 24.

A secondary objective of this trial is to evaluate the effect of CK-3773274 on patient health status, as determined by changes in the Kansas City Cardiomyopathy Questionnaire-Clinical Summary Score (KCCQ-CSS) from baseline to Week 12 and Week 24.

A further secondary objective of this trail is to evaluate the effect of CK-3773274 on New York Heart Association (NYHA) Functional Classification, as determined by the proportion of patients with ≥1 class improvement in NYHA Functional Class from baseline to Week 12 and Week 24.

A further secondary objective is to evaluate the effect of CK-3773274 on post-Valsalva left ventricular outflow tract gradients (LVOT-G), as determined by change in post-Valsalva LVOT-G from baseline to Week 12 and Week 24, and the proportion of patients with post-Valsalva LVOT-G<30 mmHg at Week 12 and Week 24.

A further secondary objective is to evaluate the effect of CK-3773274 on exercise capacity, as determined by change in total workload during CPET from baseline to Week 24.

To evaluate the safety and tolerability profile of CK-3773274 in patients with symptomatic oHCM, the following are recorded: (1) incidence of reported major adverse cardiac events (cardiovascular [CV]death, cardiac arrest, non-fatal stroke, non-fatal myocardial infarction, CV hospitalization); (2) incidence of new onset persistent atrial fibrillation; (3) incidence of appropriate implantable cardiac defibrillator (ICD) discharges and aborted sudden cardiac death; (4) incidence of left ventricular ejection fraction (LVEF) <50%; and (5) incidence of treatment emergent adverse events.

An exploratory objective of this trial is to evaluate the effect of CK-3773274 on exercise capacity and functional class, as determined by comparing with baseline, the number of patients at Week 24 achieving either (1) change from baseline of ≥1.5 mL/kg/min in $pVO_2$ AND ≥1 class improvement in NYHA Functional Class; or (2) Change from baseline of ≥3.0 mL/kg/min in $pVO_2$ AND no worsening of NYHA Functional Class.

A further exploratory objective of this trial is to evaluate the effect of CK-3773274 on patient response over time, as determined by (1) proportion of patients with improvement in KCCQ-CSS >5 points at Weeks 12 and 24; (2) proportion of patients with resting LVOT-G<30 mmHg, post-Valsalva LVOT-G<50 mmHg, and NYHA Functional Class I at Weeks 12 and 24; and (3) proportion of patients with resting LVOT-G<30 mmHg, post-Valsalva LVOT-G<50 mmHg, and ≥1 class improvement in NYHA Functional Class at Weeks 12 and 24.

A further exploratory objective of this trial is to evaluate the effect of CK-3773274 on other CPET parameters, as determined by changes from baseline to Week 24 in: (1) ventilator efficiency (VE/VCO$_2$ slope); (2) circulatory power (VO$_2$×systolic BP); and (3) ventilator anaerobic threshold (VAT).

A further exploratory objective of this trial is to evaluate the effect of CK-3773274 on health status and health-related quality of life as measured by PRO questionnaire, as determine by changes from baseline to Week 24 in individual responses to the EuroQol 5-dimension 5-level instrument (EQ-5D-5L).

A further exploratory objective of this trial is to evaluate the effect of CK-3773274 on cardiac function and structure, as determined by change from baseline to Week 24 in echocardiographic measurements of cardiac structure and of systolic function including: LVEF, left ventricular end-systolic and end-diastolic volumes (LVESV and LVEDV, respectively), and left atrial volume.

A further exploratory objective of this trial is to evaluate the effect of CK-3773274 on biomarker levels, as determined by changes from baseline values in NT-pro-BNP, hs-cardiac-TnI and other biomarkers through Week 24

A further exploratory objective of this trial is to evaluate the effect of CK-3773274 on left ventricular mass, function, and structure by cardiac magnetic resonance (CMR) imaging, as determined by changes from baseline to Week 24 in CMR measurements of left ventricular (LV) mass index, LVEF, septal and free wall thickness, left arterial volume index, LVESV, and LVEDV.

A further exploratory objective of this trial is to assess the pharmacokinetics of CK-3773274 and its metabolites, as determined by pharmacokinetic parameters through Week 24.

Overall Design. This is a Phase 3, randomized, placebo-controlled, double-blind, multi-center trial in patients with symptomatic oHCM. Approximately 270 eligible patients are randomized in a 1:1 ratio to receive CK-3773274 or placebo. Randomization will be stratified by use of beta-blockers (yes or no) and CPET exercise modality (treadmill or bicycle) and implemented in the Interactive Web Response System (IWRS). A cap on the number of patients taking beta-blockers and will not exceed approximately 70% of total enrollment. The number of patients with persistent atrial fibrillation at screening is also capped at approximately 15%, and the number of patients using the bicycle CPET exercise modality will be capped at approximately 50% as well.

CK-3773274 is administered orally once daily with or without food. During the initial six weeks of the treatment period, CK-3773274 doses are individually titrated at Weeks 2, 4, and 6 using echocardiography. Dose escalation at Weeks 2, 4, and 6 occur only if a patient has a post-Valsalva LVOT-G ≥30 mmHg and a biplane LVEF ≥55%. Echocardiograms are performed at each subsequent visit during the trial and the dose down titrated if necessary. The primary endpoint of $pVO_2$ is measured by CPET at screening and at end of treatment (Week 24). If applicable, patients continue taking background HCM medications consistent with regional clinical practice guidelines during the trial.

All patients are followed according to the Schedule of Activities (SoA) from randomization through the date of their final visit irrespective of whether the patient is continuing to receive CK-3773274, unless the patient has discontinued prematurely from the trial or withdrawn consent. An early discontinuation visit is performed for patients that discontinue prematurely from the trial.

This trial is designed to provide data supporting the clinical efficacy and safety of CK-3773274 in patients with symptomatic oHCM and an LVOT-G >50 mmHg post-Valsalva. Reduction of the LVOT-G is expected to correlate with improvement in the patients' symptoms, health status and exercise capacity. Since patient characteristics vary substantially in this disease, individualized dose titration to a PD response (reduction of the post-Valsalva LVOT-G to <30 mmHg with preservation of LVEF ≥55%) is being employed to maximize efficacy and safety. The eligibility criteria are designed to enable enrollment of a patient population representative of the general population of patients with oHCM while ensuring the safety of the patients in this trial. A placebo control and double-blinded approach are being employed in this trial to avoid bias in data collection, including the safety assessments and PD measures that comprise the primary and secondary endpoints.

Patients are eligible to be included in the trial only if all the following criteria apply: (1) Able to comprehend and willing to sign an ICF and willing to comply with all trial procedures and restrictions for the duration specified in the Schedule of Activities. (2) Males and females between 18 and 85 years of age, inclusive, at screening. (3) Body mass index <35 kg/m². (4) Diagnosed with HCM per the following criteria: (a) has LV hypertrophy and non-dilated LV chamber in the absence of other cardiac disease, and (b) has an end-diastolic LV wall thickness as measured by the echocardiography core laboratory of: ≥15 mm in one or more myocardial segments OR ≥13 mm in one or more wall segments and a known-disease-causing gene mutation or positive family history of HCM. (5) Has resting LVOT-G ≥30 mmHg and post-Valsalva LVOT-G ≥50 mmHg during screening as determined by the echocardiography core laboratory. (6) LVEF ≥60% at screening as determined by the echocardiography core laboratory. (7) New York Heart Association (NYHA) Functional Class II or III at screening. (8) Hemoglobin ≥10 g/dL at screening. (9) Respiratory exchange ratio (RER) ≥1.05 and $pVO_2$ <80% predicted on the screening CPET per the core laboratory. (10) Patients on beta-blockers, verapamil, or diltiazem should have been on a stable regimen for ≥6 weeks prior to randomization and anticipate remaining on the same medication regimen during the trial. (11) Male patients are eligible to participate if they agree to the following during the trial and for at least 4 weeks after the last dose of CK-3773274: (a) Refrain from donating sperm, plus (b) either (i) be abstinent from heterosexual intercourse as their preferred and usual lifestyle (abstinent on a long term and persistent basis) and agree to remain abstinent, or (ii) must agree to use a male condom and, when his female partner is a woman of childbearing potential, have his female partner use a highly effective method of contraception. (12) a female patient is eligible to participate if she is not pregnant, breastfeeding or planning to donate eggs, and at least one of the following conditions applies: (a) is not a woman of childbearing potential (WOCBP), or is a WOCBP and using a highly effective method of contraception and male partner agrees to use a condom, during the trial and for at least 4 weeks after the last dose of CK-3773274, and (b) a WOCBP must have a negative pregnancy test (urine or serum as required by local regulations) at Day 1, prior to the first dose of study CK-3773274. (13) Able to complete all screening procedures.

Patients will be excluded from the trial if any of the following criteria apply: (1) Significant valvular heart disease (per investigator judgment), including moderate-severe valvular aortic stenosis and/or regurgitation, or moderate-severe mitral regurgitation not due to systolic anterior motion of the mitral valve. (2) Documented history of current obstructive coronary artery disease (>70% stenosis in one or more epicardial coronary arteries) or documented history of myocardial infarction. (3) Known or suspected infiltrative, genetic or storage disorder causing cardiac hypertrophy that mimics oHCM (e.g., Noonan syndrome, Fabry disease, amyloidosis). (4) Prior treatment with cardiotoxic agents such as doxorubicin or similar. (5) History of LV systolic dysfunction (LVEF <45%) or stress cardiomyopathy at any time during their clinical course. (6) Has any ECG abnormality considered by the investigator to pose a risk to patient safety (e.g., second degree atrioventricular block type II). (7) Documented paroxysmal atrial fibrillation during the screening period. (8) Paroxysmal or permanent atrial fibrillation requiring rhythm restoring treatment (eg, direct-current cardioversion, atrial fibrillation ablation procedure, or antiarrhythmic therapy) ≤6 months prior to screening. (This exclusion does not apply if atrial fibrillation has been treated with anticoagulation and adequately rate-controlled for >6 months.) (9) History of syncope or sustained ventricular tachyarrhythmia with exercise within 6 months prior to screening. (10) ICD placement within 3 months prior to screening or planned ICD placement during the trial. (11) History of appropriate ICD discharge for life-threatening ventricular arrhythmia within 6 months prior to screening. (12) Has been treated with septal reduction therapy (surgical myectomy or percutaneous alcohol septal ablation) or has plans for either treatment during the trial period. (13) Inability to exercise on a treadmill or bicycle (e.g., orthopedic limitations). (14) Documented room air oxygen saturation reading <90% at screening. (15) Hepatic impairment defined by a total bilirubin (TBL) ≥1.5× the upper limit of normal (ULN), or alanine aminotransferase (ALT) or aspartate aminotransferase (AST) ≥3×ULN at screening. Patients with documented Gilbert syndrome and TBL ≥1.5×ULN due to unconjugated hyperbilirubinemia, without other hepatic impairment, are permitted. (16) Recipient of a major organ transplant (eg, heart, lung, liver, bone marrow, renal) or anticipated transplantation within 12 months from randomization. (17) History or evidence of any other clinically significant disorder, malignancy, active infection, other condition, or disease that, in the opinion of the investigator or the Medical Monitor, would pose a risk to patient safety or interfere with the trial evaluation, procedures, or completion. (18) Estimated glomerular filtration rate (eGFR) <30 mL/min/1.73 m² (by the modified Modification of Diet in Renal Disease equation) at screening. (19) Currently participating in another investigational device or drug trial or received an investigational device or drug <1 month (or 5 half-lives for drugs, whichever is longer) prior to screening. Other investigational procedures while participating in this trial are not permitted. (20) Has received prior treatment with CK-3773274 or mavacamten. (21) Any known hypersensitivity to excipients in study drug tablets.

Exclusion Criteria for CMR sub-study include (1) inability to tolerate CMR, (2) has an ICD, or (3) has a cardiac pacemaker.

Dose modifications and scheduled dose titrations. Patients randomized to CK-3773274 may receive up to four escalating doses of CK-3773274 over the initial 6 weeks of the trial as outlined in Table 21. Patients receiving CK-3773274 start at a dose of 5 mg once daily (Dose 1) and may escalate through doses of 10, 15, and 20 mg once daily if they continue to meet the escalation criteria or will stop at their current dose when escalation criteria are not met.

TABLE 21

Echocardiogram Criteria for Scheduled Dose Titrations

| Biplane LVEF | Post-Valsalva LVOT-G | Action |
|---|---|---|
| <50% | | Reduce Dose[a] |
| ≥50%-55% | | No Dose Change |

TABLE 21-continued

Echocardiogram Criteria for Scheduled Dose Titrations

| Biplane LVEF | | Post-Valsalva LVOT-G | Action |
|---|---|---|---|
| ≥55% | and | <30 mmHg | No Dose Change |
| ≥55% | and | ≥30 mmHg | Increase Dose |

*aOnce a patient's CK-3773274 dose is down titrated, no further escalation is permitted. If LVEF <50% on 5 mg, the patient will receive placebo.*

After randomization, each patient receives Dose 1 (5 mg) once daily for two weeks. At the Week 2 visit, the patient has an echocardiogram 2 hours following administration of their dose of CK-3773274. Patients will up-titrate to Dose 2 (10 mg) if the following conditions are met on echocardiography: Post-Valsalva LVOT-G ≥30 mmHg, and the biplane LVEF ≥55%. Otherwise, the patient will remain on Dose 1, except that if LVEF is <50% at Week 2, the IWRS will assign the patient to placebo.

After two more weeks on the assigned dose, at the Week 4 visit each patient has an echocardiogram 2 hours following administration of their dose of CK-3773274. Patients will up-titrate to the next higher dose if the following conditions are met on echocardiography: Post-Valsalva LVOT-G ≥30 mmHg, and the biplane LVEF ≥55%. Otherwise, the patient will remain on the same dose, except that if LVEF is <50% at Week 4, the IWRS will assign the patient to the prior dose level or to placebo if the patient was on Dose 1

After 2 more weeks on the assigned dose, at the Week 6 visit each patient has an echocardiogram 2 hours following administration of their dose of CK-3773274. Patients will up-titrate to the next higher dose if the following conditions are met on echocardiography: post-Valsalva LVOT-G ≥30 mmHg, and the biplane LVEF ≥55%. Otherwise, the patient will remain on the same dose, except that if LVEF is <50% at Week 6, the IWRS will assign the patient to the prior dose level or to placebo if the patient was on Dose 1.

After two additional weeks on the assigned dose, at the Week 8 visit each patient has an echocardiogram 2 hours following administration of their dose of CK-3773274 to ensure the LVEF is ≥50%. If the LVEF is <50% at Week 8, the IWRS will assign the patient to the next lower dose or to placebo if the patient was on Dose 1.

After Week 6, no further dose escalations may occur. During the course of the study, for safety reasons, dose reductions may occur at scheduled or unscheduled visits. Dose reductions is determined by the IWRS system based on echocardiography results. After Week 8, dose reductions are based on echocardiogram results from the initial scheduled or unscheduled visits. If the LVEF is <50%, then the IWRS assigns the patient to the next lower dose or to placebo if the patient was on Dose 1. The IWRS will not further reduce the dose for at least seven days after the previous reduction.

Cardiopulmonary Exercise Testing (CPET). All patients undergo CPET with gas-exchange analysis and the methodology will be standardized across all participating sites, as described in the CPET manual. Testing includes continuous ECG monitoring by trained personnel and be performed in an area that is equipped for cardiopulmonary resuscitation. Treadmill is the preferred modality for exercise testing. For CPET laboratories that do not perform treadmill testing, cycle ergometry is an acceptable alternative. Exercise protocols for both modalities are provided in the CPET manual. Patients must use the same testing modality for all exercise tests during the trial. Whenever possible, CPET is administered by the same trial personnel using the same equipment and performed after the other trial procedures on that visit day (including echocardiogram, KCCQ, EQ-5D-5L, CGI, PGI-C, NYHA class, SAQ-7, vital signs, ECG, blood sampling, IP administration). Patients naïve to exercise protocols will be familiarized with the technique during screening.

All CPET testing is symptom-limited and patients will be strongly encouraged to achieve maximal exertion and an RER ≥1.05. The reason(s) for termination of sub-maximal exercise tests will be documented. A test is identified as being maximal effort if the RER is ≥1.05.

The Week 24 CPET should be performed at approximately the same time of day (eg, morning, mid-day, afternoon) as the baseline CPET at screening, at a consistent time after the last dose of beta-blocker and IP. Whenever possible, patients should perform exercise testing between three and ten hours after taking beta blocking agents.

If a life-threatening arrhythmia, early ischemia, severe hypotension or other serious finding is identified by the investigator during CPET, the patient will be asked to stop the exercise test, and his/her physicians will be notified of the results. If the patient is performing the screening test, s/he will not be randomized to the trial. Enrolled patients who have a non-life-threatening event or finding that stops the test can resume testing when it is safe to do so and after appropriate treatment, per the investigator.

Echocardiography. Echocardiography is done during screening and prior to dosing on Day 1. Echocardiography is also performed 2 hours after dosing in the clinic on Weeks 2, 4, 6, 8, 12, 16, 20, 24, and 28.

Certified sonographers will perform echocardiography using standard high-quality, high-fidelity machines. Whenever possible, the same sonographer will perform all studies for a single patient. Echocardiograms will be performed after the patient has been resting in a supine position for at least 10 minutes and in accordance with the echocardiography manual. Instructions for the performance of the Valsalva maneuver and imaging the LVOT-G will also be included in the echocardiography manual.

When echocardiograms are scheduled at the same time as blood draws, vital signs, and/or ECGs, the order of evaluation will be vital signs, ECGs, blood draw and echocardiogram. The blood draw should be obtained at the scheduled time point and the echocardiograms will follow.

Echocardiographic parameters to be measured at least include the left ventricular parameters (resting left ventricular outflow tract pressure gradient (LVOT-G), post-Valsalva LVOT-G, LVEF, LVFS, global longitudinal strain (GLS), left ventricular end diastolic diameter (LVEDD), left ventricular end diastolic volume (LVEDV), left ventricular end systolic diameter (LVESD), left ventricular end systolic volume (LVESV), left ventricular cardiac output (LVCO), LV Stroke Volume, LVOT velocity time integral (VTI), interventricular septum thickness (IVST), isovolumic contraction time (IVCT), IVRT, E/E, ratio (septal and lateral), and left atrial volume (LAV)) in addition to right heart function metrics detailed in the echocardiography protocol.

Unscheduled echocardiograms may be obtained when clinically indicated, for example to assess an AE or follow-up a clinically significant change in a prior echocardiogram, as determined by the investigator. Results will be interpreted by the unblinded Echo Cardiologist at the investigational site.

All echocardiograms (including unscheduled) will be sent to the core laboratory for interpretation. On-site interpretation of LVEF and LVOT-G will be used for dose escalation and reduction decisions via IWRS. The core laboratory quantification of the echocardiograms will be used for all statistical analyses.

Cardiac Magnetic Resonance. A CMR imaging sub-study will assess the effects of administration of CK-3773274 dosing on cardiac morphology, function, and fibrosis in approximately 40 oHCM patients who are eligible and consent to participate. CMR will be performed during screening period and Week 24. Patients with eGFR <30 mL/min/1.73 m² or an allergy to gadolinium may have a non-contrast CMR.

What is claimed is:

1. A method of treating obstructive hypertrophic cardiomyopathy (oHCM) in a patient in need thereof, comprising:
administering to the patient a first daily dose of Compound 1,

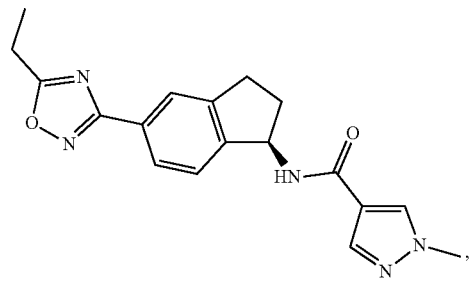

(Compound 1)

or a pharmaceutically acceptable salt thereof, for a first time period, wherein the first daily dose is about 5 mg and the first time period is about 2 weeks; and
based on one or more components of a first echocardiogram for the patient acquired after the first time period, administering to the patient a second daily dose of Compound 1, or a pharmaceutically acceptable salt thereof, for a second time period, wherein the second time period is about 2 weeks, wherein the one or more components of the first echocardiogram comprises a LVEF and a post-Valsalva LVOT-G, and
wherein the second daily dose of Compound 1, or the pharmaceutically acceptable salt thereof, is about 10 mg when the LVEF of the first echocardiogram is at or above 55% and the post-Valsalva LVOT-G of the first echocardiogram is at or above 30 mmHg, or wherein the second daily dose of Compound 1, or the pharmaceutically acceptable salt thereof, is the same as the first daily dose of Compound 1, or the pharmaceutically acceptable salt thereof, when either of the following conditions are met on the first echocardiogram: (1) the LVEF is at or above 50% and below 55%; or (2) the LVEF is at or above 55% and the post-Valsalva LVOT-G is below 30 mmHg.

2. The method of claim 1, wherein the second daily dose of Compound 1, or the pharmaceutically acceptable salt thereof, is administered to the patient for the second time period, the method further comprising, based on one or more components of a second echocardiogram for the patient acquired after the second time period and the second daily dose of Compound 1, or the pharmaceutically acceptable salt thereof, administering to the patient a third daily dose of Compound 1, or the pharmaceutically acceptable salt thereof for a third time period, wherein the third time period is about 2 weeks;
wherein the one or more components of the second echocardiogram comprises a LVEF and a post-Valsalva LVOT-G, and
wherein the third daily dose of Compound 1, or the pharmaceutically acceptable salt thereof, is greater than the second daily dose of Compound 1 when the LVEF of the second echocardiogram is at or above 55% and the post-Valsalva LVOT-G of the second echocardiogram is at or above 30 mmHg, wherein the third daily dose is about 10 mg or about 15 mg, or
wherein the third daily dose of Compound 1, or the pharmaceutically acceptable salt thereof, is lower than the second daily dose of Compound 1, or the pharmaceutically acceptable salt thereof, or the administering of Compound 1, or the pharmaceutically acceptable salt thereof, to the patient is terminated, when the LVEF of the second echocardiogram is below 50%, or
wherein the third daily dose of Compound 1, or the pharmaceutically acceptable salt thereof, is the same as the second daily dose of Compound 1, or the pharmaceutically acceptable salt thereof, when either of the following conditions are met on the second echocardiogram: (1) the LVEF is at or above 50% and below 55%; or (2) the LVEF is at or above 55% and the post-Valsalva LVOT-G is below 30 mmHg.

3. The method of claim 2, wherein the administering of Compound 1, or the pharmaceutically acceptable salt thereof, to the patient is terminated when the LVEF of the second echocardiogram is below 50% and the second daily dose of Compound 1, or the pharmaceutically acceptable salt thereof is the same as the first daily dose of Compound 1.

4. The method of claim 2, wherein the third daily dose of Compound 1, or the pharmaceutically acceptable salt thereof, is the same as the first daily dose of Compound 1, or the pharmaceutically acceptable salt thereof, when the second daily dose of Compound 1, or the pharmaceutically acceptable salt thereof, is higher than the first daily dose of Compound 1, or the pharmaceutically acceptable salt thereof, and the LVEF of the second echocardiogram is below 50%.

5. The method of claim 2, wherein the first daily dose of Compound 1, or the pharmaceutically acceptable salt thereof, is about 5 mg of Compound 1, the second daily dose of Compound 1, or the pharmaceutically acceptable salt thereof, is about 5 mg or about 10 mg of Compound 1, and the third daily dose of Compound 1, or the pharmaceutically acceptable salt thereof, is about 5 mg, about 10 mg, or about 15 mg of Compound 1.

6. The method of claim 2, wherein the third daily dose of Compound 1, or the pharmaceutically acceptable salt thereof, is administered to the patient for the third time period, the method further comprising, based on one or more components of a third echocardiogram for the patient acquired after the third time period and the third daily dose of Compound 1, or the pharmaceutically acceptable salt thereof, administering to the patient a fourth daily dose of Compound 1, or a pharmaceutically acceptable salt thereof, for a fourth time period, wherein the one or more components of the third echocardiogram comprises a LVEF and a post-Valsalva LVOT-G, and:
wherein the fourth daily dose of Compound 1, or the pharmaceutically acceptable salt thereof, is greater than the third daily dose of Compound 1 when the LVEF of the third echocardiogram is at or above 55% and the post-Valsalva LVOT-G of the third echocardiogram is at or above 30 mmHg, wherein the fourth daily dose is about 10 mg or about 15 mg or about 20 mg, or wherein the fourth daily dose of Compound 1, or the pharmaceutically acceptable salt thereof, is lower than the third daily dose of Compound 1, or the pharmaceutically acceptable salt thereof, or the administering of Compound 1, or the pharmaceutically acceptable salt thereof, to the patient is terminated, when the LVEF of the third echocardiogram is below 50%, or wherein the fourth daily dose of Compound 1, or the pharmaceutically acceptable salt thereof, is the same as the third daily dose of Compound 1, or the pharmaceutically acceptable salt thereof, when either of the following conditions are met on the third echocardiogram: (1) the LVEF is at or above 50% and below 55%; or (2) the LVEF is at or above 55% and the post-Valsalva LVOT-G is below 30 mmHg.

7. The method of claim 6, wherein the administering of Compound 1, or the pharmaceutically acceptable salt thereof, to the patient is terminated when the LVEF of the third echocardiogram is below 50% and the third daily dose of Compound 1, or the pharmaceutically acceptable salt thereof, is the same as the first daily dose of Compound 1, or the pharmaceutically acceptable salt thereof.

8. The method of claim 6, wherein:
the fourth daily dose of Compound 1, or the pharmaceutically acceptable salt thereof, is the same as the second daily dose of Compound 1, or the pharmaceutically acceptable salt thereof, when the third daily dose of Compound 1, or the pharmaceutically acceptable salt thereof, is higher than the second daily dose of Compound 1, or the pharmaceutically acceptable salt thereof, and the LVEF of the third echocardiogram is below 50%; or the fourth daily dose of Compound 1, or the pharmaceutically acceptable salt thereof, is the same as the first daily dose of Compound 1, or the pharmaceutically acceptable salt thereof, when the third daily dose of Compound 1, or the pharmaceutically acceptable salt thereof, is the same as the second daily dose of Compound 1, or the pharmaceutically acceptable salt thereof, and the LVEF of the third echocardiogram is below 50%.

9. The method of claim 6, wherein the first daily dose of Compound 1, or the pharmaceutically acceptable salt thereof, is about 5 mg of Compound 1, the second daily dose of Compound 1, or the pharmaceutically acceptable salt thereof, is about 10 mg of Compound 1, the third daily dose of Compound 1, or the pharmaceutically acceptable salt thereof, is about 15 mg of Compound 1, and the fourth daily dose of Compound 1, or the pharmaceutically acceptable salt thereof, is about 20 mg of Compound 1.

10. The method of claim 6, wherein the fourth time period is about 2 weeks.

11. The method of claim 1, wherein the patient is administered disopyramide or another antiarrhythmic medication during the treatment with Compound 1, or the pharmaceutically acceptable salt thereof.

12. The method of claim 1, wherein the patient has not been treated with disopyramide or an antiarrhythmic drug that has negative inotropic activity within 4 weeks prior to treatment with Compound 1, or the pharmaceutically acceptable salt thereof.

13. The method of claim 1, wherein the patient is a CYP2D6 poor metabolizer.

14. The method of claim 1, wherein the method does not include taking a blood sample of the patient.

15. The method of claim 1, wherein the method results in one or more of the following: improvement in mitral regurgitation, improvement in cardiac relaxation, beneficial cardiac remodeling, reverse cardiac remodeling, beneficial cardiac structural remodeling, beneficial cardiac functional remodeling, reversal of adverse cardiac remodeling, reduction in mean left ventricular mass index (LVMI), improvement in left ventricular (LV) filling pressures, reduction in left atrial volume index (LAVI), reduction in the categorical assessment of systolic anterior motion of the mitral valve leaflet, reduction in systolic anterior motion of the mitral valve leaflet, reduction in the frequency of eccentric mitral regurgitation, reduction in mitral regurgitation, reduction in lateral E/e', reduction in lateral E/E, reduction in brain natriuretic peptide (BNP) and reduction in N-terminal prohormone of brain natriuretic peptide (NT-proBNP); or wherein the method results in one or more of the following: improvement in exercise capacity, improvement in peak oxygen uptake, improvement in peak oxygen uptake (pVO2) by cardiopulmonary exercise testing (CPET), improvement in Kansas City Cardiomyopathy Questionnaire Overall Summary Score (KCCQ-OSS), Kansas City Cardiomyopathy Questionnaire Clinical Summary Score (KCCQ-CSS), improvement in quality of life, improvement in quality of life as measured by PRO questionnaire, improvement in NYHA Functional Classification by one or more class(es), improvement in post-Valsalva left ventricular outflow tract gradient (LVOT-G), and improvement in total workload during CPET.

16. The method of claim 15, wherein the method results in one or more of:
(a) change from baseline of ≥3.0 mL/kg/min in pVO2 and no worsening of NYHA Functional Class;
(b) improvement in KCCQ-OSS or KCCQ-CSS by at least 5 points, at least 10 points, or at least 20 points; or
(c) LVOT-G <30 mmHg, post-Valsalva LVOT-G <50 mmHg, and improvement in NYHA Functional Class by one or more class(es).

17. The method of claim 1, wherein administration of Compound 1, or the pharmaceutically acceptable salt thereof, is stopped when the LVEF is below 50%.

18. The method of claim 15, wherein the method results in change from baseline of >1.5 mL/kg/min in pVO2 and improvement in NYHA Functional Class by one or more class(es).

19. The method of claim 1, wherein the LVEF of the first echocardiogram is a biplane LVEF.

20. The method of claim 2, wherein the LVEF of the second echocardiogram is a biplane LVEF.

21. The method of claim 6, wherein the LVEF of the third echocardiogram is a biplane LVEF.

* * * * *

UNITED STATES PATENT AND TRADEMARK OFFICE
CERTIFICATE OF CORRECTION

Page 1 of 1

PATENT NO. : 12,370,179 B1
APPLICATION NO. : 18/909401
DATED : July 29, 2025
INVENTOR(S) : Fady Malik et al.

It is certified that error appears in the above-identified patent and that said Letters Patent is hereby corrected as shown below:

In the Claims

At Column 90, Claim number 18, Line number 51, delete ">1.5" and insert -- ≥1.5 --.

Signed and Sealed this
Eighteenth Day of November, 2025

John A. Squires
*Director of the United States Patent and Trademark Office*